US011903958B2

(12) United States Patent
Payne et al.

(10) Patent No.: US 11,903,958 B2
(45) Date of Patent: Feb. 20, 2024

(54) THERAPEUTIC AGENTS AND METHODS OF PRODUCING SAME

(71) Applicant: GLYCOSYNNOVATIONS PTY LTD, Cloverdale (AU)

(72) Inventors: Alan David Payne, Fremantle (AU); Bruno Basic, Kriftel (DE); Shifaza Mohamed, Victoria Park (AU); Deirdre Roma Coombe, Wembly Downs (AU)

(73) Assignee: GLYCOSYNNOVATIONS PTY LTD, Cloverdale (AU)

( * ) Notice: Subject to any disclaimer, the term of this patent is extended or adjusted under 35 U.S.C. 154(b) by 223 days.

(21) Appl. No.: 16/341,777

(22) PCT Filed: Oct. 12, 2017

(86) PCT No.: PCT/AU2017/051102
§ 371 (c)(1),
(2) Date: Apr. 12, 2019

(87) PCT Pub. No.: WO2018/068090
PCT Pub. Date: Apr. 19, 2018

(65) Prior Publication Data
US 2021/0386770 A1 Dec. 16, 2021

Related U.S. Application Data

(60) Provisional application No. 62/407,109, filed on Oct. 12, 2016.

(51) Int. Cl.
*A61K 31/7056* (2006.01)
*A61K 47/54* (2017.01)
(Continued)

(52) U.S. Cl.
CPC ...... *A61K 31/7056* (2013.01); *A61K 31/7034* (2013.01); *A61K 47/545* (2017.08);
(Continued)

(58) Field of Classification Search
None
See application file for complete search history.

(56) References Cited

U.S. PATENT DOCUMENTS

2011/0046982 A1    2/2011   Arya et al.

FOREIGN PATENT DOCUMENTS

CN    104045673 A    9/2014
WO    2005/061523 A1    7/2005
(Continued)

OTHER PUBLICATIONS

André et al., "'Fluorinated Carbohydrates as Lectin Ligands: Biorelevant Sensors with Capacity to Monitor Anomer Affinity in 19F-NMR-Based Inhibitor Screening" European Journal of Organic Chemistry (2012) pp. 4354-4364 DOI: 10.1002/ejoc.201200397 (Year: 2012).*
(Continued)

*Primary Examiner* — Eric Olson
(74) *Attorney, Agent, or Firm* — Seed IP Law Group LLP

(57) ABSTRACT

The present invention relates generally to the field of glycanics and its application to the generation of glycoconjugates for therapeutic use. The present invention also relates to process for the preparation of glycoconjugates.

13 Claims, 11 Drawing Sheets

(51) Int. Cl.
| | |
|---|---|
| A61P 29/00 | (2006.01) |
| A61K 31/7034 | (2006.01) |
| C07H 19/056 | (2006.01) |
| C07H 15/00 | (2006.01) |
| C07H 15/26 | (2006.01) |

(52) U.S. Cl.
CPC .............. *A61P 29/00* (2018.01); *C07H 15/00* (2013.01); *C07H 15/26* (2013.01); *C07H 19/056* (2013.01)

(56) References Cited

FOREIGN PATENT DOCUMENTS

| WO | 2005/100374 A1 | 10/2005 |
|---|---|---|
| WO | 2010/037179 A1 | 4/2010 |
| WO | 2010/037180 A1 | 4/2010 |

OTHER PUBLICATIONS

Alix et al., "Click chemistry' in Cu(I)-zeolites: a convenient access to glycoconjugates" Tetrahedron vol. 64 pp. 8922-8929 (Year: 2008).*

Morotti et al., "Semi-Synthesis of new glycosidic triazole derivatives of dihydrocucurbitacin B" Tetrahedron Letters vol. 56 pp. 303-307 http://dx.doi.org/10.1016/j.tetlet.2014.11.049 (Year: 2015).*

Supplemental data for Morotti et al., "Semi-Synthesis of new glycosidic triazole derivatives of dihydrocucurbitacin B" Tetrahedron Letters vol. 56 pp. 303-307 http://dx.doi.org/10.1016/j.tetlet.2014.11.049 (Year: 2015).*

Nobrega et al., "Conformational study of the hydroxymethyl group in alpha-D-mannose derivatives" Tetrahedron: Asymmetry vol. 14 pp. 2793-2801 DOI: 10.1016/S0957-4166(03)00623.2 (Year: 2003).*

Mayato et al., "Experimental Evidence on the hydroxymethyl group conformation in alkyl beta-D-mannopyranosides" Tatrahedron: Asymmetry vol. 15 pp. 2385-2397 doi: 10/1016/j.tetasy.2004.06.019 (Year: 2004).*

Daly et al., "Synthesis and Biological Evaluation of a Library of Glycoporpohyrin Compounds" Chemistry: A European Journal vol. 18 pp. 14671-14679 DOI: 10/1002/chem.201202064 (Year: 2012).*

Daly et al., "Synthesis and Biological Evaluation of a Library of Glycoporpohyrin Compounds" Chemistry: A European Journal vol. 18 supplementary data DOI: 10/1002/chem.201202064 (Year: 2012).*

Cepkova et al., "Pharmacotherapy of Acute Lung Injury and the Acute Respiratory Distress Syndrome", 2006, J Intensive Care Med., vol. 21, No. 3, pp. 119-143.

Kellish et al., "Multivalent Amino Sugars to Reconize Different TAR RNA Conformations", Aug. 1, 2014, Medchemcomm, vol. 5, No. 8, pp. 1235-1246.

Lander et al., "The Elusive Funcatons of Proteoglycans: In Vivo Veritas", Jan. 24, 2000, The Journal of Cell Biology, vol. 148, No. 2, pp. 227-232.

Maclaren et al., "Emerging Role of Anticoagulants and Fibrinolytics in the Treatment of Acute Respiratory Distress Syndrome", Jun. 2007, Pharmacotherapy, vol. 27, No. 6, pp. 860-873.

Ordanini et al., "Designing nanomolar antagonists of DC-SIGN-mediated HIV infection: ligand presentation using molecular rods", 2015, Chem. Commun., vol. 51, pp. 3816-3819.

Perez-Balderas et al., "Click Multivalent Homogeneous Neoglycoconjugates—Synthesis and Evaluation of Their binding Affinities", 2009, Eur. J. Org. Chem., pp. 2441-2453.

Tran et al., "Synthesis and Assessment of Glycosaminoglycna Priming Activity of Cluster-xylosied for Potential Use as Proteoglycan Mimetics", 2013, ACS Chem. Biol., vol. 8, pp. 949-957.

Wildhagen et al., "Nonanticoagulant heparin prevents histone-mediated cytotoxicity in vitro and improves survival in sepsis", Feb. 13, 2014, Blood, vol. 123, No. 7, pp. 1098-1101.

Yao et al., "Adaptable synthesis of C-lactosyl glycoclusters and their binding properties with galectin-3", 2014, Org. Biomol. Chem., vol. 12, pp. 8180-8195.

International Search Report with Written Opinion and Preliminary Report on Patentability for PCT/AU2017/051102, dated Dec. 4, 2017.

* cited by examiner

A

B

A

B

A

B

A.

B.

A.

B.

THERAPEUTIC AGENTS AND METHODS OF PRODUCING SAME

This application is associated with and claims priority from U.S. Provisional Patent Application No. 62/407,109, filed on 12 Oct. 2016, entitled "Therapeutic agents and methods of producing same", the entire contents of which, are incorporated herein by reference, in their entirety.

BACKGROUND

Field

The present invention relates generally to the field of glycanics and its application to the generation of glycoconjugates for therapeutic use. The present invention also relates to process for the preparation of glycoconjugates.

Description of Related Art

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

Glycosaminoglycans (GAGs), the glycanic moiety of proteoglycans, are ubiquitous and play pivotal roles in many biological processes within the human body. For example, GAGs are considered the critical biological structure which enables immobilization of biological regulators such as chemokines, cytokines, growth factors and chemotactic agents on extracellular matrices and cell surfaces. However, in relation to some cytokines, GAG interaction can contribute to physiologically adverse processes such as inflammation, cancer metastasis and various immunological reactions with counter productive outcomes.

Currently, one of the best known GAGs is the heparin family of sulfated polysaccharides which bind to three-dimensional motifs on proteins and which also have anti-coagulant activity.

Given their ability to bind to and modulate activity of biological regulators, GAGs have been proposed as potential therapeutic agents.

However, GAGs are a heterogenous group of molecules [Conrad (1998) Heparin binding proteins. Academic Press, San Diego; Lander and Selleck (2000) *J. Cell Biol.* 148(2): 227-232], often being synthesized with incomplete modifications to chains of repeating saccharide units. In addition, the protein binding characteristics of a particular GAG are largely determined by the sulfation pattern of the saccharide chains. The sulfation patterns of GAGs are complex especially with respect to the positioning of 6-O-sulfates. Consequently, not all GAG molecules are identical. Similarly, not all molecules in a preparation of GAGs from a particular cell or tissue are identical; rather such preparations represent a family of molecules. Hence, the GAGs themselves do not represent the most ideal therapeutic agent, especially in terms of isolating a particular GAG or fraction of GAGs from a heterogenous mixture.

Furthermore, accessing quantities of these complex oligosaccharides from natural sources necessitates repeated purification by chromatography and due to the similarity of many of these oligosaccharides, homogeneous samples are difficult to obtain.

The synthetic chemical production of GAGs is also not commercially attractive. For example, the generation of one particular synthetic pentasaccharide which was selective for a target protein, required approximately 40 chemical steps.

Whilst the concept of modulating the activity of biological regulators such as chemokines, cytokines, growth factors and chemotactic agents using a relatively non-toxic GAG has appeal, there is a need to be able to generate alternative compounds which are functional GAG mimetics in terms of binding to and modulating the activity of the biological regulators.

SUMMARY

The present invention is predicated in part on the identification of a process for the synthesis of a glycoconjugate which binds to and modulates the activity of a selected biological regulator such as but not limited to a chemokine, cytokine, growth factor or chemotactic agent associated with a cellular signaling pathway. Conveniently, glycoconjugates are generated in a manner which enables rapid synthesis with an ability to scale-up synthetic production. The manner of generation includes a modular approach which minimizes the number of synthetic chemical steps required. Additionally, glycoconjugates are generated as single chemical entities of high purity when compared with previous approaches utilized in the art. As indicated above, the glycoconjugates are synthesized in a modular manner enabling the ready generation of a library of molecules to an array of biological regulators. The glycoconjugates of the present invention have similar binding properties to GAGs and are referred to herein as "functional GAG mimetics", however, the glycoconjugates of the present invention are homogeneous, pure and readily synthesized. This is a significant improvement on the synthesis of GAGs themselves.

It is proposed that the glycoconjugates enabled herein are useful in the prophylaxis and/or treatment of disease conditions such as but not limited to inflammatory conditions including allergic diseases; osteoarthritis; cancer treatment; and treatment of infection by a pathogenic agent including, but not limited to, *Mycobacterium tuberculosis*, an influenza-type A virus associated with human flu or bird flu and human immunodeficiency virus (HIV). Examples of particular diseases include asthma; allergic respiratory disease; allergic rhinitis; subepithelial fibrosis in airway hyperresponsiveness; chronic sinusitis; perennial allergic rhinitis; allergic bronchopulmonary aspergillosis in cystic fibrosis patients; COPD; eosinophilic bronchitis; bronchiectasis; bronchospasm; bronchial constriction; bronchial hyperreactivity; and bronchial hypertrophy.

In an embodiment taught herein is a compound of formula (I):

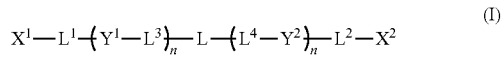

wherein

L is a bond or an optionally substituted divalent linker;

$L^1$ and $L^2$ are each independently selected from a bond and an optionally substituted divalent linker, $L^3$ and $L^4$ are each independently selected from a bond and an optionally substituted divalent linker; $X^1$ and $X^2$ are each a capping sugar, wherein each of $X^1$ and $X^2$ is independently selected from an optionally substituted monosaccharide, a disaccharide, a trisaccharide, a tetrasaccharide and a pentasaccharide or a compound derived from an optionally substituted monosaccharide, a disaccharide, a trisaccharide, a tetrasaccharide or a pentasaccharide;

$Y^1$ and $Y^2$ are each a connecting sugar, wherein each $Y^1$ and $Y^2$ is independently selected from an optionally substituted monosaccharide, a disaccharide, a trisaccharide, a tetrasaccharide and a pentasaccharide, or a compound derived from an optionally substituted monosaccharide, a disaccharide, a trisaccharide, a tetrasaccharide or a pentasaccharide; and n is an integer from 0 to 3.

Also taught herein is a process for the preparation of a compound of formula (I), comprising:
   i) providing a divalent linker,
   ii) conjugating at least two equivalents of a capping sugar via the divalent linker;
   to form a compound of formula (I).

Further taught herein is a process for the preparation of a compound of formula (I), comprising:
   (i) providing a divalent linker,
   (ii) conjugating at least two equivalents of a connecting sugar via the divalent linker to form a conjugate intermediate; and
   (iii) conjugating with at least two equivalents of a capping sugar via the conjugate intermediate; to form a compound of formula (I).

Additionally taught herein is a process for the preparation of a compound of formula (I), comprising:
   (i) providing a capping sugar,
   (ii) conjugating the capping sugar with a connecting sugar to form a conjugate intermediate; and
   (iii) conjugating with at least two equivalents of the conjugate intermediate via a divalent linker;
   to form a compound of formula (I).

These processes advantageously provide for the rapid assembly of glycoconjugates as single chemical entities, in relatively few chemical steps and in high purity. This rapid assembly is in part due to a modular synthetic approach to the generation of glycoconjugates.

Further taught herein is an agent which binds to the same target site on a biological regulator to which a glycoconjugate generated by the present process binds. Such an agent may be synthesized as part of a chemical library or may be a purified natural product.

By "biological regulator" means a chemokine, cytokine, growth factor or chemotactic agent. The biological regulator may be a peptide, polypeptide or protein. The term "biological mediator" is encompassed by the term "biological regulator" and may be used interchangeably.

Enabled herein is a method for generating libraries of glycoconjugates and methods for identifying glycoconjugates which bind to and modulate the activity of a particular biological regulator. The glycoconjugates produced according to the process described herein have utility in treating any disease associated with or exacerbated by the activity of the biological regulator, including the interaction between a biological regulator and its receptor or involved in activation of a signaling pathway or between a virus and a cell. As indicated above, the biological regulator may be a chemokine, cytokine, growth factor or chemotactic agent. The glycoconjugates are useful inter alia in the treatment of inflammatory or allergic disease conditions and metastatic cancers and infection by pathogenic agents such as bacteria, viruses or parasites.

Further contemplated herein is a method of treatment of a mammalian subject comprising the administration of a glycoconjugate as defined herein or a glycoconjugate mimetic thereof.

In an embodiment, the mammal is a human.

Further taught herein is a pharmaceutical composition comprising a glycoconjugate as defined herein and one or more pharmaceutically acceptable carriers, diluents and/or excipients.

Further taught herein is the use of a glycoconjugate as defined herein or a glycoconjugate mimetic thereof in the manufacture of a medicament for the treatment of a mammalian subject in need of therapy. In a related embodiment enabled herein is a glycoconjugate as defined herein or a glycoconjugate mimetic thereof for use in the treatment of a mammalian subject in need of therapy. In an embodiment, the mammal is a human.

Further enabled herein is a method for generating a medicament for treating a disease condition in a subject, the method comprising producing a range of glycoconjugates according to the method of the subject invention and screening each glycoconjugate for an ability to interact with or modulate the activity of a biological regulator as herein defined associated with the disease or condition. A glycoconjugate which interacts with a regulator is identified and is used in the manufacture of the medicament.

DETAILED DESCRIPTION

Figure 1:
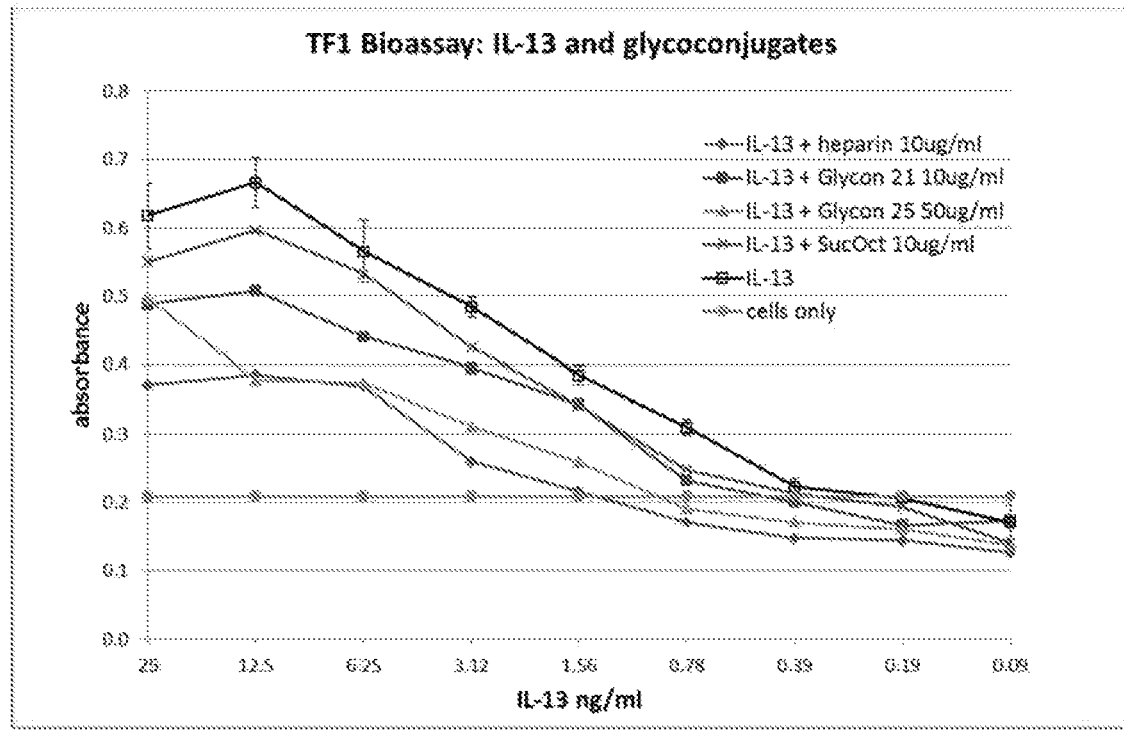
FIG. 1 is a graphical representation showing a TF1 bioassay with recombinant human IL-13. A: IL-13 is titrated from 25 ng/ml-0.9 ng/ml and the inhibitors: heparin, sulphated glycoconjugates: 21, and sucrose octasulfate are held at 10 µg/ml, but glycoconjugate 25 was used at 50 µg/ml. The IL-13 dependent cell proliferation is shown as absorbance at 490 nm. B: data from 5 independent experiments are displayed as an average of the % inhibition of cell proliferation at 4 ng/ml IL-13 and either 2.5 µg/ml or 10 µg/ml of inhibitor for heparin, sucrose octasulfate and glycoconjugate 21, glycoconjugate 25 was used at 12.5 µg/ml. Mean and standard deviation are shown.
Figure 1:
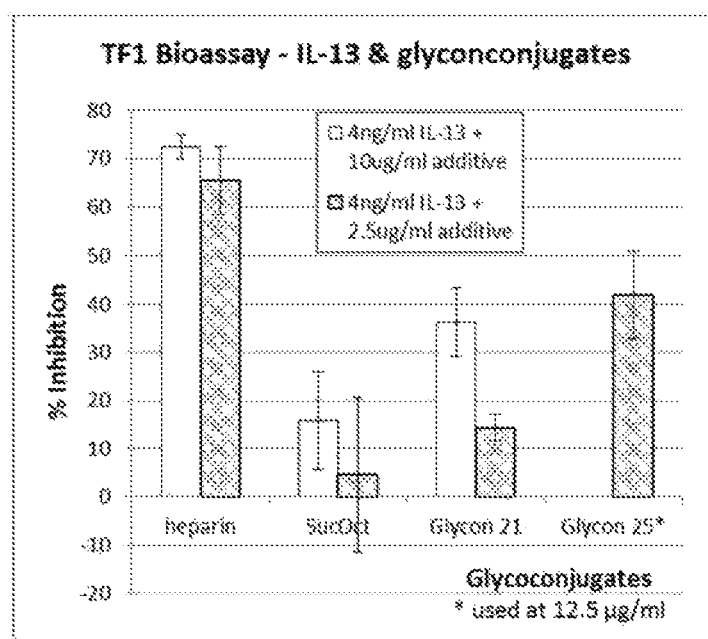

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the subject specification, the singular forms "a", "an" and "the" include plural aspects unless the context clearly dictates otherwise. Thus, for example, reference to "a biological regulator" includes a single biological regulator, as well as two or more biological regulators; reference to "an agent" includes a single agent, as well as two or more agents; reference to "the disclosure" includes a single and multiple aspects taught by the disclosure; and so forth. Aspects taught and enabled herein are encompassed by the term "invention". All such aspects are enabled within the width of the present invention. Any variants and derivatives contemplated herein are encompassed by "forms" of the invention.

The present invention relates generally to glycoconjugates which bind to and modulate the activity of a target biological regulator. Furthermore, the present invention relates to a glycanics approach for generating glycoconjugates in a manner which enables rapid synthesis and an ability to scale-up production resulting in a highly homogeneous preparation of a glycoconjugate.

As used in the specification, the term "biological regulator" means a chemokine, cytokine, growth factor or chemotactic agent. The term "biological mediator" is encompassed by the term "biological regulator" and may be used interchangeably.

Enabled herein is a process for preparing a glycoconjugate which targets a selected biological regulator. The biological regulator may include a peptide, polypeptide or protein.

As used in the specification, the term "glycoconjugate" refers to a composite compound which comprises saccharides or a compound derived therefrom joined by one or more linkers. The glycoconjugates can be considered as GAG mimetics in terms of functionality.

Accordingly, one aspect of the invention is directed to a compound of formula (I):

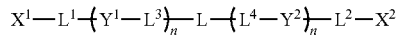

wherein

L is a bond or a divalent linker;

$L^1$ and $L^2$ are each independently selected from a bond and a divalent linker;

$L^3$ and $L^4$ are each independently selected from a bond and a divalent linker;

$X^1$ and $X^2$ are each a capping sugar, wherein each of $X^1$ and $X^2$ is independently selected from an optionally substituted monosaccharide, a disaccharide, a trisaccharide, a tetrasaccharide and a pentasaccharide or a compound derived from an optionally substituted monosaccharide, a disaccharide, a trisaccharide, a tetrasaccharide or a pentasaccharide;

$Y^1$ and $Y^2$ are each a connecting sugar, wherein each $Y^1$ and $Y^2$ is independently selected from an optionally substituted monosaccharide, a disaccharide, a trisaccharide, a tetrasaccharide and a pentasaccharide, or a compound derived from an optionally substituted monosaccharide, a disaccharide, a trisaccharide, a tetrasaccharide or a pentasaccharide; and n is an integer from 0 to 3.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, hydroxyl, acyl, amino, alkyl, alkenyl, alkynyl, aryl, alkoxy, alkylamino, alkenylamino, alkylheterocyclyl, cycloalkyl, cycloalkenyl, cycloalkylamino, cycloalkenylamino, arylamino, heteroaryl, heterocyclyl, heteroarylamino, heterocyclylamino, aminoarylamino, aminoheteroarylamino, aminoheterocyclylamino, tetrahydropyridinylamino, azetidinyl, pyrrolidinyl, piperidinyl, piperazinyl, morpholinyl, azetidinylamino, pyrrolidinylamino, piperidinylamino, piperazinylamino, azetidinylcarbonylamino, pyrrolidinylcarbonylamino, piperidinylcarbonylamino, piperazinylcarbonylamino, alkoxy, alkenyloxy, alkynyloxy, cycloalkoxy, cycloalkenyloxy, aryloxy, heteroaryloxy, heterocyclyloxy, aminoalkoxy, aminoalkenyloxy, aminoalkynyloxy, aminocycloalkoxy, aminocycloalkenyloxy, aminoaryloxy, aminoheteroaryloxy, azetidinyloxy, pyrrolidinyloxy, piperidinyloxy or piperazinyloxy.

"Acyl" means an R—C(=O)— group in which the R group may be an alkyl, cycloalkyl, heterocycloalkyl, aryl or heteroaryl group as defined herein. Examples of acyl include acetyl and benzoyl.

"Alkyl" as a group or part of a group refers to a straight or branched aliphatic hydrocarbon group, including a $C_1$-$C_{18}$ alkyl, including a $C_1$-$C_8$ alkyl, and including $C_1$-$C_6$ alkyl unless otherwise noted.

"Alkylene" refers to divalent alkyl groups having from 1 to 10 carbon atoms including from 1 to 6 carbon atoms, and including 1 to 3 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

"Alkenyl" means an aliphatic hydrocarbon group containing at least one carbon-carbon double bond and which may be straight or branched, including a $C_2$-$C_{10}$ alkenyl, including a $C_2$-$C_8$ alkenyl, including preferably $C_2$-$C_6$ alkenyl. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkynyl" means an aliphatic hydrocarbon group containing a carbon-carbon triple bond and which may be straight or branched, including a $C_2$-$C_{10}$alkynyl, including a $C_2$-$C_8$alkynyl, including $C_2$-$C_6$alkynyl.

"Alkoxy" as a group or part of a group refers to an alkyl-O— group in which alkyl is as defined herein. In an embodiment the alkoxy is a $C_1$-$C_{10}$alkoxy. Examples include, but are not limited to, methoxy and ethoxy.

"Aryl" refers to an unsaturated aromatic carbocyclic group having a single ring (e.g. phenyl) or multiple condensed rings (e.g. naphthyl or anthryl), including from 6 to 14 carbon atoms. Examples of aryl groups include phenyl, naphthyl and the like.

"Aryloxy" refers to an aryl-O— group in which the aryl is as defined herein. In an embodiment, the aryloxy is a $C_6$-$C_{10}$aryloxy.

"Cycloalkyl" refers to a saturated monocyclic or fused or spiro polycyclic, carbocycle including from 3 to 10 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane.

"Cycloalkenyl" refers to a non-aromatic monocyclic or multicyclic ring system containing at least one carbon-carbon double bond and including from 5-10 carbon atoms per ring. Exemplary monocyclic cycloalkenyl rings include cyclopentenyl, cyclohexenyl or cycloheptenyl.

"Cycloalkoxy" refers to a cycloalkyl-O— group in which cycloalkyl is as defined herein. In an embodiment, the cycloalkoxy is a $C_3$-$C_{10}$cycloalkoxy. Examples include, but are not limited to, cyclopropanoxy and cyclobutanoxy.

"Heteroalkyl" as a group or part of a group refers to a straight or branched aliphatic hydrocarbon group, including a $C_1$-$C_{10}$ heteroalkyl, including a $C_1$-$C_8$ heteroalkyl, including $C_1$-$C_6$ heteroalkyl unless otherwise noted, wherein one or more carbons in the aliphatic chain has been replaced by a heteroatom selected from S, O, P and N. Exemplary heteroalkyls include alkyl ethers, secondary and tertiary alkyl amines, amides, alkyl sulfides, and the like.

"Heteroalkenyl" refers to an aliphatic hydrocarbon group containing at least one carbon-carbon double bond and which may be straight or branched, including a $C_2$-$C_{10}$ alkenyl, including a $C_2$-$C_8$ heteroalkenyl, including a $C_2$-$C_6$ heteroalkenyl, wherein one or more carbons in the aliphatic chain has been replaced by a heteroatom selected from S, O, P and N. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Heteroalkynyl" refers to an aliphatic hydrocarbon group containing a carbon-carbon triple bond and which may be straight or branched, including a $C_2$-$C_{10}$heteroalkynyl, including a $C_2$-$C_8$ heteroalkynyl, including a $C_2$-$C_6$heteroalkynyl, wherein one or more carbons in the aliphatic chain has been replaced by a heteroatom selected from S, O, P and N.

"Heteroaryl" either alone or part of a group refers to groups containing an aromatic ring (including a 5, 6, 9, 10 or 11 membered aromatic ring) having one or more heteroatoms as ring atoms in the aromatic ring with the remainder of the ring atoms being carbon atoms. Suitable heteroatoms include nitrogen, oxygen and sulphur. Examples of a heteroaryl group include triazole, thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl, and includes benzofused heteroaryl, such as benzothiophene, benzofuran, benzimidazole, benzoxazole, benzothiazole, benzisothiazole, and naphtho[2,3-b]thiophene.

"Heterocyclyl" or "heterocyclic" refers to a saturated monocyclic, bicyclic, or polycyclic ring containing at least one heteroatom selected from nitrogen, sulfur, oxygen, including from 1 to 3 heteroatoms in at least one ring. Each ring including from 3 to 11 membered rings, including 4 to 7 membered rings and 9 to 11 membered rings. Examples of suitable heterocyclyl substituents include aziridinyl, oxiranyl, thiiranyl, azetidinyl, oxetanyl, thistanyl, pyrrolinyl, pyrrolidinyl, pyrazolidinyl, imidazolidinyl, tetrahydrofuryl, tetrahydrothiofuranyl, piperidinyl, thiazolidinyl, piperazinyl, tetrahydropyridinyl, morpholino, thiomorpholinyl, 1,3-diazapane, 1,4-diazapane, 1,4-oxazepane, and 1,4-oxathiapane, and includes benzofused compounds such as indiny, isoindolinyl, oxoisoindolinyl, isoquinolinyl, and quinolinyl.

In an embodiment, the connecting and capping sugars are independently selected from optionally substituted mono, di, tri, tetra and pentasaccharides, or compounds derived from a mono, di, tri, tetra or pentasaccharide. In an embodiment, the connecting and capping sugars are selected from glucose, fructose, galactose, mannose, sucralose, sucrose, lactose, lactulose, trehalose, maltose, neamine, kanamycin A, isomaltotriose, nigerotriose, maltotriose, acarbose, maltotetraose, stachyose melezitose, maltotriulose, raffinose, kestose, glucuronic acid, iduronic acid, glucosamine, heptulose, pentose, galactosamine, glucosamine and compounds derived therefrom. In an embodiment, the connecting and/or capping sugars are selected from sucralose or mannose.

Furthermore, in an embodiment one or more connecting and/or capping sugars are compounds derived from mono, di, tri, tetra or pentasaccharides, including amino sugars. As used herein, the term "amino sugar" refers to a saccharide or sugar molecule wherein at least one hydroxyl group is replaced with an amino group. The amino sugars may be naturally occurring amino sugars or synthetic amino sugars prepared by any suitable methods known in the art. In an embodiment, the amino sugar is selected from optionally substituted galactosamine, glucosamine and derivatives thereof, such as N-acetylglucosamine or N-acetylgalactosamine.

The glycoconjugates may also be "optionally modified". For example, the connecting and/or the capping sugars may be "optionally modified" before or after conjugation. In an embodiment, the connecting and/or the capping sugars are modified prior to conjugation to facilitate conjugation. Examples of such modifications include but are not limited to chain shortening, chain extension, exchange (trans-glycosylation), N-acetylation, functional group protection (such as the protection of alcohols as a benzylic ester) and functional group interconversion (such as the conversion of a primary alcohol to an azide or the conversion of an alkenic moiety to an epoxide). Whilst some saccharides may of themselves possess functionality which facilitates the conjugation of 2 or more such compounds, other saccharides may be modified prior to conjugation to facilitate conjugation. Even those saccharides which possess functionality which facilitates the conjugation may also be modified to facilitate conjugation via a different type of linking group. Hydrolysis of one or more glycosidic linkages to expose the reducing terminus of a reducing sugar as a reactive handle is an example of a modification which facilitates conjugation.

Additionally, or alternatively, in an embodiment the connecting and/or the capping sugars are modified before or after conjugation to enhance or modify the biological activity and/or binding affinity of the resultant glycoconjugates for target proteins. In an embodiment, the connecting and/or the capping sugars are modified by, for example, but not limited to, sulfation, phosphorylation, oxylation, functional group interconversion, and/or attachment of side chains. Accordingly, in an embodiment, the connecting and/or the capping sugars are persulfated, non-sulfated, or semi-sulfated, perphosphorylated, non-phosphorylated or semi-phosphorylated. In an embodiment, the connecting sugars and/or capping sugars are persulphated or semi-sulphated. In an embodiment, the connecting and/or capping sugars are persuflated. In an embodiment, the connecting and/or capping sugars are perphosphorylated.

Chemical sulfation may be achieved by any suitable means of sulfation known in the art. In an embodiment, sulfation is selective sulfation. In another embodiment, sulfation is by global sulfation to provide a persulfated product. For example, sulfation of a glycoconjugate with pyridine sulfur trioxide provides persulfated product. Chemical sufation of related heparin-type oligosaccharides has been studied. Some degree of selectivity is achieved, for example, by using varied reaction conditions and the reactivity of certain hydroxyl groups has been determined (see Ogamo et al. (1989) *Carbohydr. Res.* 193:165-172). Furthermore, some selectivity in sulfation is achieved by first per-sulfating then selectively de-sulfating certain positions. For example, in an embodiment a glycoconjugate is sulfated by treating the glycoconjugate with a sulfur trioxide source, such pyridine sulfur trioxide complex.

Chemical phosphorylation may be achieved by any suitable means of phosphorylation known in the art. In an embodiment, phosphorylation is selective phosphorylation. In another embodiment, phosphorylation is by global phosphorylation to provide a perphosphorylated product. For example, in an embodiment a glycoconjugate is phosphorylated by treating the glycoconjugate with a phosphate source, such phosphoric acid, phosphoryl chloride, diphenyl phosphorochloridate or salts of inorganic phosphate. Alternatively, glycoconjugates may be phosphorylated enzymatically.

As described above, such modifications may be used to enhance or alter the biological activity and/or binding affinity of the resultant glycoconjugates. In an embodiment, modification may, for example, provide a glycoconjugate having a net negative charge (an anionic conjugate), a net positive charge (a cationic conjugate), or a net neutral charge. In an embodiment, the glycoconjugate is an anionic glycoconjugate.

As used herein, the term "anionic" describes the net negative charge of a material. It will be understood that a given negatively charged material may have one or more positively charged counterions associated with it, or vice versa. In solution, a negatively charged material may have dissociated from one or more positively charged counterions with which it is associated. As used herein, the term "anionic" is used to describe a property of that material and not the overall complex with one or more counterions which will typically render the complex neutral. It is understood that certain functional groups are negatively charged, neutral or positively charged at varying values of pH. Whether a material is anionic will be determined based on the sum of these charges. Accordingly, at a given pH, if a material has one positively charged functional group and two negatively charged functional groups, then the material has a net negative charge and is anionic as the term is used in the context of the present invention. In an embodiment, the glycoconjugates of the present invention have a net negative charge in aqueous solution at a pH of 5. Modification, including sulfation and/or phosphorylation and/or oxylation of the connecting and/or the capping sugar for example, may provide a glycoconjugate having a net negative charge.

As used herein the terms "linker" or "linking group" refers to a multivalent group that covalently links 2 or more materials. In an embodiment, the or each linking group, L, $L^1$, $L^2$, $L^3$ and $L^4$, may be any suitable multivalent group. In an embodiment, the or each linking group, L, $L^1$, $L^2$, $L^3$ and $L^4$, is each independently a divalent linking group. In an embodiment, the or each linking group is independently a divalent group selected from alkylene, alkenylene, alkynylene, arylene, acyl, carbocyclylene, heterocyclylene, heteroarylene, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio.

In an embodiment, the or each linking group, L, $L^1$, $L^2$, $L^3$ and L, are each independently a divalent linker selected from $C_1$-$C_{18}$ alkylene, $C_2$-$C_{18}$ alkenylene, $C_2$-$C_{18}$ alkynylene, $C_6$-$C_{18}$ arylene, $C_1$-$C_{18}$ acylene, $C_3$-$C_{18}$ carbocyclylene, $C_2$-$C_{18}$ heterocyclylene, $C_3$-$C_{18}$ heteroarylene, $C_1$-$C_{18}$ alkyloxy, $C_2$-$C_{18}$ alkenyloxy, $C_2$-$C_{18}$ alkynyloxy, $C_6$-$C_{18}$ aryloxy, $C_1$-$C_{18}$ acyloxy, $C_3$-$C_{18}$ carbocyclyloxy, $C_2$-$C_{18}$ heterocyclyloxy, $C_3$-$C_{18}$ heteroaryloxy, $C_1$-$C_{18}$ alkylthio, $C_2$-$C_{18}$ alkenylthio, $C_2$-$C_{18}$ alkynylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_3$-$C_{18}$ alkylalkenyl, $C_3$-$C_{18}$ alkylalkynyl, $C_7$-$C_{24}$ alkylaryl, $C_2$-$C_{18}$ alkylacyl, $C_4$-$C_{18}$ alkylcarbocyclyl, $C_3$-$C_{18}$ alkylheterocyclyl, $C_4$-$C_{18}$ alkylheteroaryl, $C_2$-$C_{18}$ alkyloxyalkyl, $C_3$-$C_{18}$ alkenyloxyalkyl, $C_3$-$C_{18}$ alkynyloxyalkyl, $C_7$-$C_{24}$ aryloxyalkyl, $C_2$-$C_{18}$ alkylacyloxy, $C_4$-$C_{18}$ alkylcarbocyclyloxy, $C_3$-$C_{18}$ alkylheterocyclyloxy, $C_4$-$C_{18}$ alkylheteroaryloxy, $C_2$-$C_1$m alkylthioalkyl, $C_3$-$C_{18}$ alkenylthioalkyl, $C_3$-$C_{18}$ alkynylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_4$-$C_{18}$ alkylalkenylalkyl, $C_4$-$C_{18}$ alkylalkynylalkyl, $C_8$-$C_{24}$ alkylarylalkyl, $C_3$-$C_{18}$ alkylacylalkyl, $C_{13}$-$C_{24}$ arylalkylaryl, $C_{14}$-$C_{24}$ arylalkenylaryl, $C_{14}$-$C_{24}$ arylalkynylaryl, $C_{13}$-$C_{24}$ arylacylaryl, $C_7$-$C_{18}$ arylacyl, $C_9$-$C_{18}$ arylcarbocyclyl, $C_8$-$C_{18}$ arylheterocyclyl, $C_9$-$C_{18}$ arylheteroaryl, $C_8$-$C_{18}$ alkenyloxyaryl, $C_8$-$C_{18}$ alkynyloxyaryl, $C_{12}$-$C_{24}$ aryloxyaryl, $C_7$-$C_{18}$ arylacyloxy, $C_9$-$C_{18}$ arylcarbocyclyloxy, $C_8$-$C_{18}$ arylheterocyclyloxy, $C_9$-$C_{18}$ arylheteroaryloxy, $C_7$-$C_{18}$ alkylthioaryl, $C_8$-$C_{18}$ alkenylthioaryl, $C_8$-$C_{18}$ alkynylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, and $C_9$-$C_{18}$ arylheteroarylthio.

In an embodiment, the or each linking group, L, $L^1$, $L^2$, $L^3$ and $L^4$, are each independently selected from $C_1$-$C_{12}$ alkylene, $C_2$-$C_{12}$ alkenylene, $C_2$-$C_{12}$ alkynylene, $C_5$-$C_{18}$ arylene, $C_3$-$C_{18}$ heteroarylene, $C_3$-$C_{12}$ carbocyclyl, $C_2$-$C_{18}$ heterocyclylene, $C_6$-$C_{18}$ alkylarylene, $C_4$-$C_{18}$ arylheteroarylene, $C_4$-$C_{18}$ alkylcarbocyclylene, and $C_3$-$C_{18}$ alkylheterocyclylene, $C_6$-$C_{18}$ arylacyl, $C_1$-$C_{12}$ alkyloxy, $C_2$-$C_{18}$ alkenyloxy, $C_2$-$C_{18}$ alkynyloxy, $C_8$-$C_{18}$ aryloxy, acyl, acyloxy, $C_1$-$C_{18}$ alkylthio, $C_2$-$C_{18}$ alkenylthio, $C_2$-$C_{18}$ alkynylthio, $C_8$-$C_{18}$ arylthio, acylthio, sulfonyl, sulfoxyl, $C_1$-$C_{18}$ alkylamino, $C_2$-$C_{18}$ alkenylamino, $C_2$-$C_{18}$ alkynylamino, $C_8$-$C_{18}$ arylamino, and acylamino.

In the lists above defining multivalent groups from which the or each linking group may be selected, each alkylene, alkenylene, alkynylene, arylene, carbocyclylene, heteroarylene, and heterocyclylene moiety may be optionally substituted as hereinbefore described. For avoidance of any doubt, where a given linking group contains two or more of such moieties (e.g. alkylaryl), each of such moieties may be optionally substituted with one, two, three or more optional substituents as herein defined.

In the lists of possible linking groups defined above, where a given linking group contains two or more subgroups, for example the subgroups may be listed in the format [subgroup A][subgroup B] as in alkylaryl, or [subgroup A][subgroup B][subgroup C] as in aryloxyalkyl, the order of the subgroups as they are listed above is not intended to be limited to the order in which they are presented. Thus, a linking group with two subgroups defined as [subgroup A][subgroup B], such as alkylaryl, is intended to also be a reference to a linking group with two subgroups defined as [subgroup B][subgroup A], such as arylalkyl.

The or each linking group may be branched and/or optionally substituted. Where the or each linking group comprises an optionally substituted alkyl moiety, an optional substituent includes where a —$CH_2$— group in the alkyl chain is replaced by a group selected from —O—, —S—, —NRa—, —C(O)— (i.e. carbonyl), —C(O)O— (i.e. ester), and —C(O)NRa— (i.e. amide), where Ra is selected from hydrogen, alkyl, alkenyl, alkynyl, aryl, carbocyclyl, heteroaryl, heterocyclyl, arylalkyl, and acyl.

Linking groups preferably do not interact with the GAG receptor. Linking groups may affect the geometry, size, flexibility or rigidity, hydrophilicity and hydrophobicity of the glycoconjugate without adversely affecting its ability to bind to a target protein. Accordingly, linking groups include those chosen to enhance or modify a given biological effect. In this regard, linking groups can be considered as a "framework" on which connecting and capping sugars are arranged in order to orient the glycoconjugate to produce a multibinding agent. Knowledge of the structure-activity relationship between a GAG (or GAGs) to be mimicked and/or congeners and/or structural information about ligand-receptor complexes (e.g., from X-ray crystallography, NMR) may influence the choice of linking group.

Different orientations of glycoconjugates of the present invention can be achieved through the choice of linker.

For example, in an embodiment, desired orientations of the glycoconjugates may be achieved through the use of mono- or polycyclic linking groups, including aryl and heteroaryl groups, or structures incorporating one or more unsaturated carbon-carbon bonds (i.e., alkenes and alkynes). In an embodiment, the inclusion of cyclic groups (e.g., aryl, heteroaryl, cycloalkyl, heterocycles, etc.) imparts rigidity on the glycoconjugate. In an embodiment, the cyclic group is a six- or ten-membered ring. The cyclic group may be an aromatic group (for example phenyl or naphthyl) or a heteroaryl group (triazole). In still another embodiment, the linker comprises an alkene or an alkyne.

In still another embodiment, the flexibility of the linking group is reduced by the inclusion of ancillary groups which are rigid and/or bulky. The presence of rigid or bulky groups may hinder free rotation about bonds in the linking group. Examples of rigid groups are those groups whose conformational flexibility is restrained by the presence of rings and/or multiple bonds, for example, aryl, heteroaryl, cycloalkyl and/or heterocyclic.

Rigidity may also be imparted by internal hydrogen bonding. Examples of bulky groups include large atoms and/or ions (e.g., iodine, sulfur, metal ions, etc.), polycyclic groups (including aromatic groups and non-aromatic groups) and groups comprising one or more alkenic and/or alkynic bonds.

Alternatively, for example, a less rigid glycoconjugate may be required. In an embodiment, a flexible orientation is achieved through the use of a flexible linker, such as structures incorporating one or more saturated carbon-carbon bonds (i.e., alkyl, heteroalkyl). In an embodiment, the linker comprises a $C_1$-$C_{18}$ alkyl, or $C_1$-$C_{18}$ heteroalkyl.

The identification of an appropriate framework geometry may be an important consideration in the construction of a glycoconjugates of the present invention. Systematic spatial searching strategies can be used to aid in the identification of a desired framework for GAG mimetics. Accordingly, molecular design may aid in the design of the glycoconjugates of the present invention.

Examples of suitable linking groups are shown below:

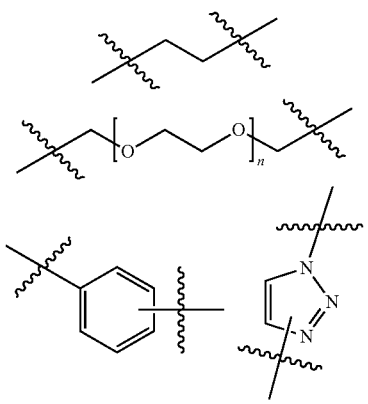

The linking groups shown above may further form part of a larger linking group, such that the spatial arrangement of the ligand domains is substantially determined by the substitution pattern of, for example, a phenylene group in the above linking groups.

Similarly to the connecting and/or the capping sugars, the linking groups may be "optionally modified" before or after conjugation. The linking groups, including L, $L^1$, $L^2$, $L^3$ and $L^4$ of a compound of formula (I), may be modified prior to conjugation to facilitate conjugation. Where any one of $L^1$, $L^2$, $L^3$ and $L^4$ are independently a linker, these may be individual chemical entities which are conjugated with one or more connecting or capping sugars, and/or one or more L of formula (I). For example, in an embodiment, the linking groups $L^1$ and $L^2$ are derived from glycol.

Alternatively, $L^1$, $L^2$, $L^3$ and $L^4$ are each independently formed by conjugation of one or more capping and/or connecting sugars, for example. Specifically, functional groups on each of the capping and/or connecting sugars prior to conjugation can form any one of the linking groups ($L^1$ to $L^4$) in a compound of Formula (I). For example, in an embodiment, the linking groups $L^1$ and $L^2$ are each triazoles formed by reaction of an alkyne with an azide. In one embodiment, the capping sugars, $X^1$ and/or $X^2$, are modified to comprise an alkyne functional group and the connecting sugars, $Y^1$ and/or $Y^2$, are modified to comprise an azide functional group. The capping sugar ($X^1$) is subsequently conjugated with the connecting sugar ($Y^1$) by reaction of the alkyne with the azide to form a triazole linking group ($L^1$). Similarly, the capping sugar ($X^2$) is subsequently conjugated with the connecting sugar ($Y^2$) by reaction of the alkyne with the azide to form a triazole linking group ($L^2$). In another embodiment, the capping sugars, $X^1$ and/or $X^2$, are instead modified to comprise an azide functional group and the connecting sugars, $Y^1$ and/or $Y^2$, are modified to comprise an alkyne functional group which may be similarly conjugated by the resultant triazole linking groups ($L^1$ and/or $L^2$).

For example, in one embodiment, the glycoconjugate of formula (I) comprises a linker L which is derived from polyethylene glycol, $L^1$ and $L^2$ are each linkers derived from a triazole and the connecting sugars are derived from mannose (top) or sucralose (bottom), which are then further conjugated to additional connecting sugars and/or capping sugars (represented by R' below).

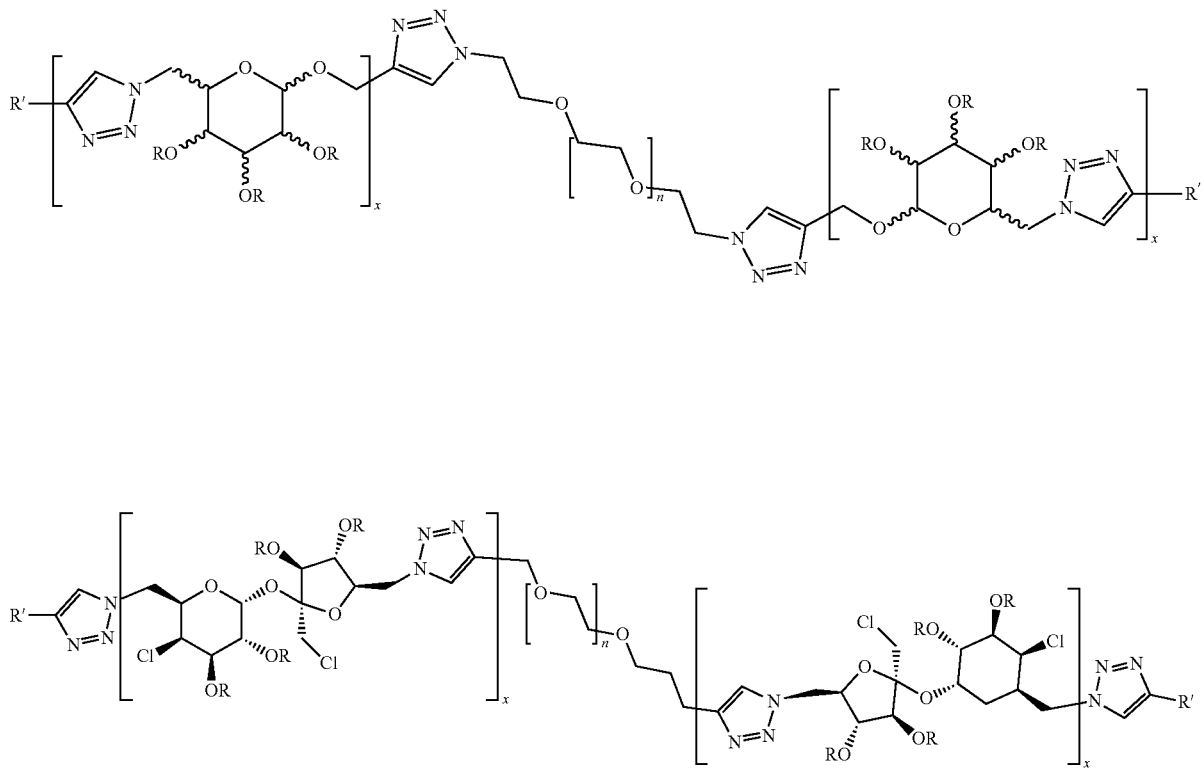

R = SO$_3$M (where M = Li, Na, K, etc.)
R' = monosacchardie, disaccharide, trisaccharide Linking groups may also comprise one or more ancillary groups which may, for example, modulate the solubility of the multibinding agent (in water, fats, lipids, biological fluids, etc.), hydrophobicity, hydrophilicity, linker flexibility, antigenicity, molecular size, molecular weight, in vivo half-life, in vivo distribution, biocompatability, immunogenicity, stability, and the like.

Examples of groups that enhance the water solubility/hydrophilicity of the linking group are poly(ethylene glycol), alcohols, polyols (e.g. glycerin, glycerol propoxylate and saccharides such as mono-, oligo- and polysaccharides), carboxylates, polycarboxylates (e.g. polyglutamic acid, polyacrylic acid, etc.), amines, polyamines (e.g. polylysine, poly(ethyleneimine), etc). In an embodiment, the ancillary group used to improve water solubility/hydrophilicity is a polyether. In an embodiment, the ancillary group is a poly (ethylene glycol).

Lipophilic ancillary groups may be incorporated into the linking group in order to enhance the lipophilicity and/or hydrophobicity of the anionic conjugates. Examples of such groups are optionally substituted alkyl, aryl and heteroaryl groups.

Examples of glycoconjugates include, but are not limited to the following octomer comprising a glycol linker (L), mannose connecting sugars and sucralose capping sugars.

As indicated above, in these examples R also includes the group SO$_3$M where M is Li, Na K and the like. Still other examples include, but are not limited to the following hexamers, comprising either a glycol linker or an alkyl linker (L), mannose connecting sugars and sucralose capping sugars.

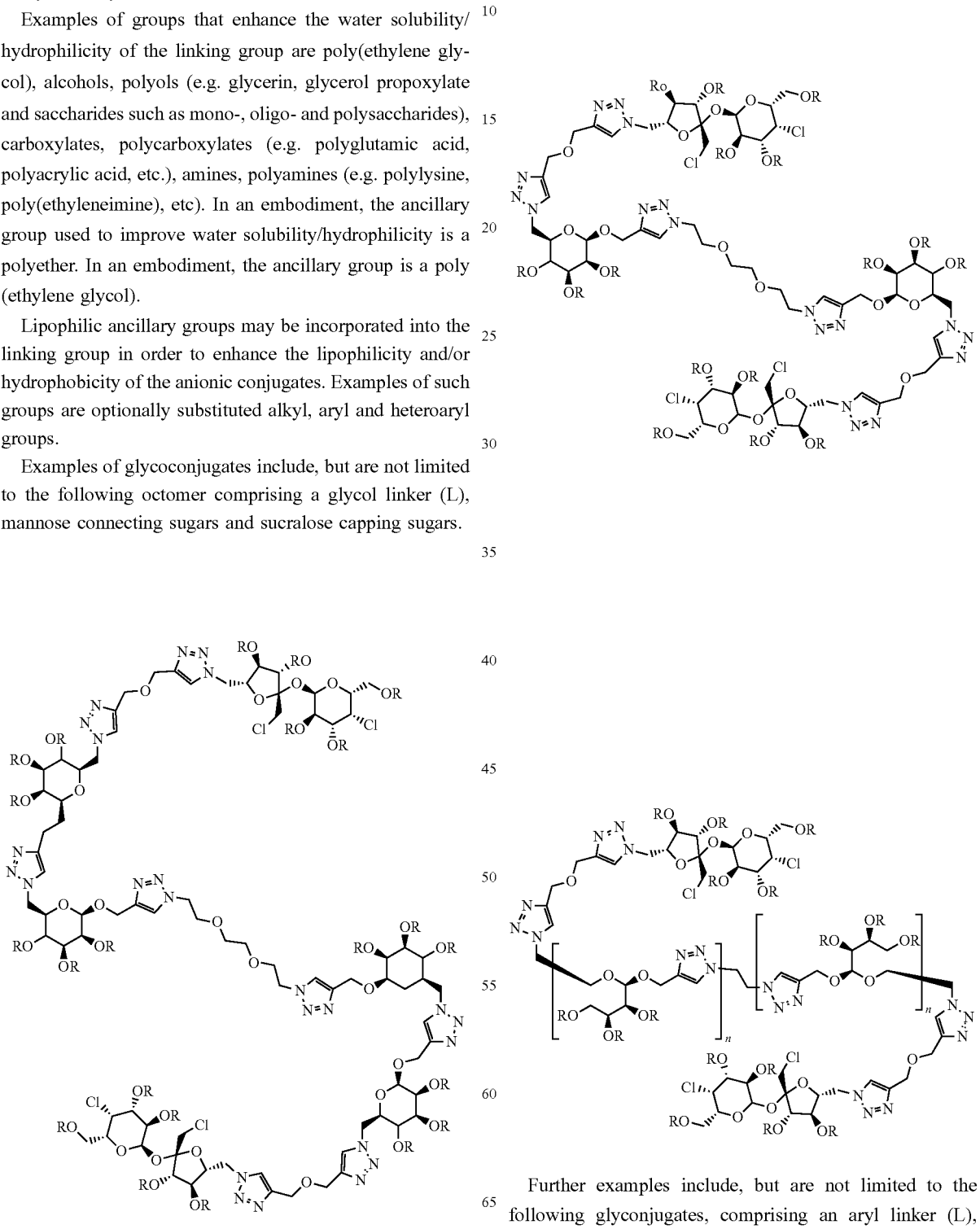

Further examples include, but are not limited to the following glycoconjugates, comprising an aryl linker (L), mannose connecting sugars and sucralose capping sugars.

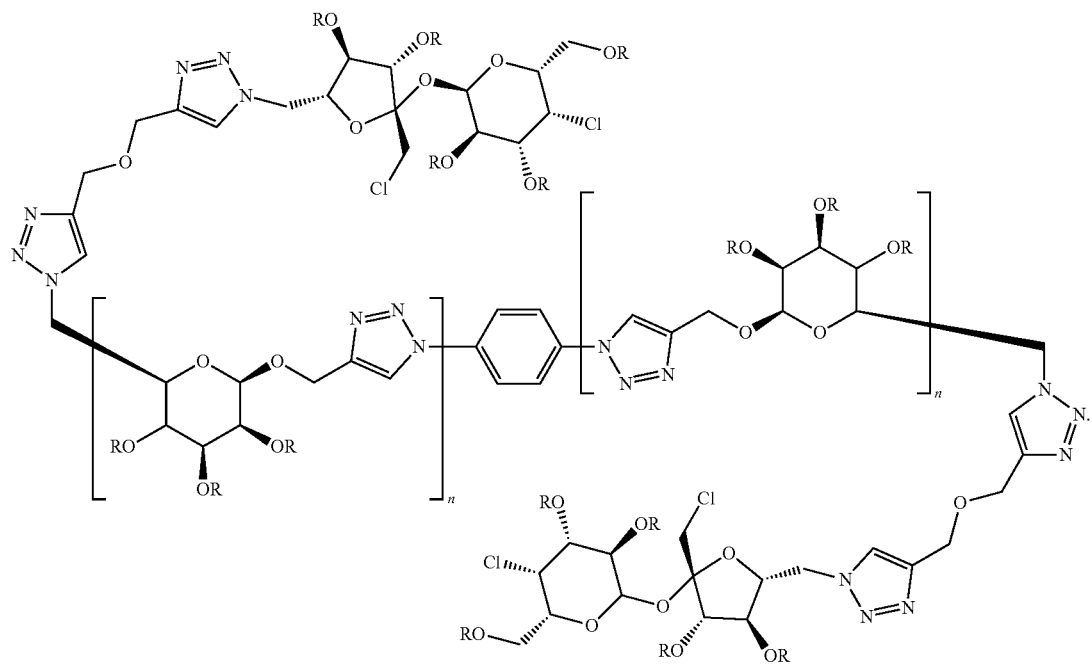

In another aspect, the present invention provides the preparation of optionally substituted mono, di, tri, tetra and/or pentasaccharides as building blocks for glycoconjugates. As previously described mono, di, tri, tetra and/or pentasaccharides may be modified for use as capping and/or connecting sugars to facilitate conjugation. In an embodiment, capping and connecting sugars comprising at least one reactive position or handle for conjugation are envisaged. For example, in an embodiment, the connecting sugars are selected from modified monosaccharides and disaccharides, such as mannose and sucralose derivatives, comprising alkyne and/or azide functional groups and/or groups that can be converted to azide functional groups.

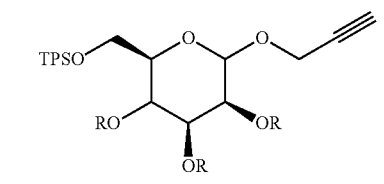

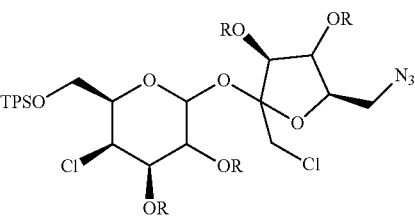

In an embodiment, the capping sugars are selected from modified monosaccharides and disaccharides, such as the following mannose and sucralose derivatives, comprising alkyne functional groups.

With respect to formula (I) compounds disclosed herein the following combinations of any or more of (i) to (x) are contemplated:
 (i) L is phenylene; or
  L is methylene; or
  L is ethylene;
  L is dimethylene ether; or
  L is ethylene glycol; or
  L is triethylene glycol; or
  L is bis(triazolyl)dimethylether;
 (ii) $L^1$ is dimethylene ether; or
  $L^1$ is triazolyl; or
  $L^1$ is methylene triazolyl, or
  $L^1$ is ethylene triazolyl, or
  $L^1$ is methoxy triazolyl, or
  $L^1$ is methoxymethylene triazolyl, or
  $L^1$ is methoxymethylene(triazolyl)methylene(triazolyl); or
  $L^1$ is bis(triazolyl)dimethylether, or
  $L^1$ is bis(methylene)triazolyl; or
  $L^1$ is bis(methoxy)triazolyl;

(iii) $L^2$ is dimethylene ether; or
$L^2$ is triazolyl; or
$L^2$ is methylene triazolyl, or
$L^2$ is ethylene triazolyl, or
$L^2$ is methoxy triazolyl, or
$L^2$ is methoxymethylene triazolyl, or
$L^2$ is methoxymethylene(triazolyl)methylene(triazolyl); or
$L^2$ is bis(triazolyl)dimethylether; or
$L^2$ is bis(methylene)triazolyl; or
$L^2$ is bis(methyoxy)triazolyl;
(iv) $L^3$ is methylene; or
$L^3$ is triazolyl; or
$L^3$ is methylene triazolyl; or
$L^3$ is ethylene triazolyl, or
$L^3$ is bis(methylene)triazolyl;
(v) $L^4$ is methylene; or
$L^4$ is triazolyl; or
$L^4$ is methylene triazolyl; or
$L^4$ is ethylene triazolyl, or
$L^4$ is bis(methylene)triazolyl;
(vi) $X^1$ is sucralose or a derivative thereof; or
$X^1$ is mannose or a derivative thereof;
(vii) $X^2$ is sucralose or a derivative thereof; or
$X^2$ is mannose or a derivative thereof;
(viii) $Y^1$ is sucralose or a derivative thereof; or
$Y^1$ is mannose or a derivative thereof;
(ix) $Y^2$ is sucralose of a derivative thereof; or
$Y^2$ is mannose or a derivative thereof;
(x) n is 0; or
n is 1; or
n is 2; or
n is 3.

In a further aspect, the present invention provides a process for the preparation of a compound of formula (I), comprising:
i) providing a divalent linker,
ii) conjugating at least two equivalents of a capping sugar via the divalent linker;
to form a compound of formula (I).

For example, in an embodiment, at least two equivalents of a capping sugar, such as a sucralose or a derivative thereof is conjugated via a divalent linker to provide a glycoconjugate for formula (I).

In other aspects, the present invention provides a process for the preparation of a compound of formula (I), comprising:
(i) providing a divalent linker,
(ii) conjugating at least two equivalents of a connecting sugar via the divalent linker to form a conjugate intermediate; and
(iii) conjugating with at least two equivalents of a capping sugar via the conjugate intermediate;
to form a compound of formula (I).

For example, in an embodiment, at least two equivalents of a connecting sugar such as mannose or a derivative thereof, is conjugated via a divalent linker to provide an intermediate conjugate. Subsequently, at least two equivalents of a capping sugar such as sucralose or a derivative thereof is conjugated via the intermediate conjugate to provide a glycoconjugate of formula (I).

In other aspects, the present invention provides a process for the preparation of a compound of formula (I), comprising:
(i) providing a capping sugar,
(ii) conjugating the capping sugar with a connecting sugar to form a conjugate intermediate; and
(iii) conjugating with at least two equivalents of the conjugate intermediate via a divalent linker;
to form a compound of formula (I).

For example, in an embodiment, at least two equivalents of a capping sugar, such as sucralose or a derivative thereof, is conjugated with a connecting sugar, such a mannose or a derivative thereof, to provide an conjugate intermediate. Subsequently, at least two equivalents of the conjugate intermediate is conjugated via a divalent linker to provide a glycoconjugate of formula (I).

Conjugation may be achieved by any means known in the art. The term "conjugation" as used herein to refers to covalent or other form of linking two or more molecules or components. For example, conjugation of capping, connecting and/or linkers may be achieved by standard chemical reactions known in the art, including but not limited to, azide-alkyne click chemistry, metathesis (including cross metathesis and ring closing metathesis), substitution (including nucleophilic substitution and electrophilic substitution), addition (including, cycloaddition, electrophilic addition and nucleophilic addition), alkylation, amination, esterification, amidation and combinations thereof.

The process of the present invention advantageously provides the rapid assembly of glycoconjugates as single chemical entities. In one embodiment, the process may be considered a modular synthesis which is amenable to scale up and provides a glycoconjugate in relatively few chemical steps and/or in high purity and homogeneity.

In one embodiment, the process for preparation of glycoconjugates is a modular "inside out" synthetic approach. The "inside out" synthetic approach for the preparation of glycoconjugates provides, with each step, the glycoconjugates are assembled in at least two directions. Such an approach may increase the speed and/or ease of preparation of glycoconjugates. Such an approach may also reduce the overall number of synthetic steps required to assemble a glycoconjugate.

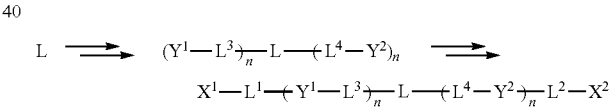

In an embodiment, the "inside out" synthetic approach provides glycoconjugates of formula (I) which are symmetrical about the central linker (L). For example, in an embodiment, the glycoconjugates are considered to be a palindrome, wherein the capping sugars $X^1$ and $X^2$ are each the same mono, di, tri, tetra or pentasaccharide or a derivative thereof. Furthermore, in an embodiment, the connecting sugars $Y^1$ and $Y^2$ are each the same mono, di, tri, tetra or pentasaccharide or a derivative thereof. The $X^1$, $X^2$, $Y^1$ and $Y^2$ may also comprise one or more sulfate groups, phosphate groups, oxylate groups or combinations thereof.

In one embodiment, the process for preparation of glycoconjugates is a modular "outside in" synthetic approach. The "outside in" synthetic approach for the preparation of glycoconjugates provides a modular, convergent synthesis. That is, portions of the target glycoconjugate are synthesized first prepared. Subsequently, the individual portions are conjugated about a central linker (L) to form the target glycoconjugate. Such an approach may increase the speed and/or ease of preparation of glycoconjugates. Such an approach may also reduce the overall number of synthetic steps required to assemble a glycoconjugate.

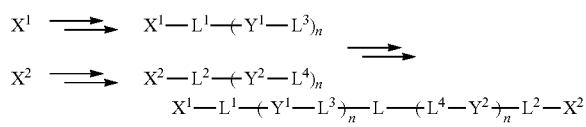

In an embodiment, the "outside in" synthetic approach provides glycoconjugates of formula (I) which are symmetrical about the central linker (L). For example, in an embodiment, the glycoconjugates are considered to be a palindrome, wherein the capping sugars $X^1$ and $X^2$ are each the same mono, di, tri, tetra or pentasaccharide or a derivative thereof. Furthermore, in an embodiment, the connecting sugars $Y^1$ and $Y^2$ are each the same mono, di, tri, tetra or pentasaccharide or a derivative thereof. The $X^1$, $X^2$, $Y^1$ and $Y^2$ may also comprise one or more sulfate groups, phosphate groups, oxylate groups or combinations thereof.

In another embodiment, the "outside in" synthetic approach provides glycoconjugates of formula (I) which are non-symmetrical about the central linker (L), for example, wherein the capping sugars $X^1$ and $X^2$ are different mono, di, tri, tetra or pentasaccharide or a derivative thereof. Furthermore, in an embodiment, the connecting sugars $Y^1$ and $Y^2$ are different mono, di, tri or pentasaccharide or a derivative thereof. The modular convergent nature of the "outside-in" synthetic approach provides for the efficient preparation of non-symmetrical glycoconjugates. As indicated above, $X^1$, $X^2$, $Y^1$ and $Y^2$ may also comprise one or more sulfate groups, phosphate groups, oxylate groups or combinations thereof.

In a further embodiment, glycoconjugates are prepared by a combination of the "inside out" and "outside in" synthetic approaches. Such an approach may increase the speed and/or ease of preparation of glycoconjugates and may also reduce the overall number of synthetic steps required to assemble a glycoconjugate.

In an embodiment, the connecting and capping sugars are conjugated by triazole linking groups $L^1$ and $L^2$ formed by reaction of an alkyne with an azide. As previously described, in an embodiment, the capping sugars, $X^1$ and/or $X^2$, are modified prior to conjugation to comprise an alkyne functional group and the connecting sugars, $Y^1$ and/or $Y^2$, are modified prior to conjugation to comprise an azide functional group. The capping sugars ($X^1$ and/or $X^2$) are subsequently conjugated with the connecting sugars ($Y^1$ and/or $Y^2$) by reaction of the alkyne with the azide to form triazole linking groups ($L^1$ and $L^2$). The inverse reactivity is also contemplated. Such reactivity is applicable to both the "inside out" synthetic approach and the "outside-in" approach.

In an embodiment, the connecting and capping sugars are conjugated by alkenyl linking groups, comprising an aliphatic hydrocarbon group containing at least one carbon-carbon double bond, such as an ethylenyl linker. In such an embodiment, the alkenyl linking groups, $L^1$ and $L^2$, are formed by cross metathesis. For example, prior to conjugation, the capping and connecting sugars, $X^1$, $X^2$, $Y^1$ and/or $Y^2$, are each modified to comprise an alkene functional group. The capping sugars ($X^1$ and/or $X^2$) are subsequently conjugated with the connecting sugars ($Y^1$ and/or $X^2$) by cross metathesis to form alkenyl linking groups ($L^1$ and $L^2$). Such reactivity is applicable to both the "inside out" synthetic approach and the "outside-in" approach.

The term "equivalent" as used herein in reference to the process, would be understood by a person skilled in the art.

Unless otherwise defined, the term "equivalent" in reference to the process is a unit of measurement which indicates the approximate relative amount of a given substance in moles.

In an embodiment, functional groups on any one of the capping sugars, connecting sugars and/or linkers may optionally be protected with one or more protecting groups to facilitate conjugation. The term "protecting group" refers to any group which when bound to one or more hydroxyl, thiol, amino or carboxyl groups of the compounds prevents reactions from occurring at these groups and which protecting group can be removed by conventional chemical or enzymatic steps to re-establish the hydroxyl, thio, amino or carboxyl group. The particular removable protecting group employed is not critical and examples of removable hydroxyl protecting groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in Greene and Wuts (1991), "Protective Groups in Organic Synthesis" $2^{nd}$ Ed., John Wiley and Sons, N.Y. The term "blocking group" is considered to be functionally equivalent to a protecting group and either term may be used in this context.

In an embodiment, one or more hydroxyl groups of the capping and/or connecting sugars may be protected with an acetate protecting group. In another embodiment, one or more hydroxyl groups of the capping and/or connecting sugars may be protected with a benzyl protecting group.

The glycoconjugates enabled herein bind to and modulate the activity of biological regulators, such as chemokines, cytokines, growth factors or chemotactic agents, associated with various physiological processes and hence are useful in the treatment or prophylaxis of diseases inflammatory disorders, such as allergic disorders, osteoarthritis, anaphylaxis, asthma, allergic respiratory disease, allergic rhinitis, subepithelial fibrosis in airway hyperresponsiveness, chronic sinusitis, perennial allergic rhinitis, allergic bronchopulmonary aspergillosis in cystic fibrosis patients, COPD, ARDS/ALI, eosinophilic bronchitis, bronchiectasis, bronchospasm, bronchial constriction, bronchial hyperreactivity, bronchial hypertrophy and bronchial inflammation, metastatic cancers; and infection by a pathogenic agent including, but not limited to, *Mycobacterium tuberculosis*, the agent that causes tuberculosis, and human immunodeficiency virus (HIV), the agent that causes AIDS.

In an embodiment, the disease treated includes inflammatory diseases, such as allergic diseases; osteoarthritis; metastatic cancers; and infection by a pathogenic agent including, but not limited to, *Mycobacterium tuberculosis*, the agent that causes tuberculosis, and an influenza-type A virus associated with human or bird flu and human immunodeficiency virus (HIV), the agent that causes AIDS. Examples of diseases include asthma, allergic respiratory disease, allergic rhinitis, subepithelial fibrosis in airway hyperresponsiveness, chronic sinusitis, perennial allergic rhinitis, allergic bronchopulmonary aspergillosis in cystic fibrosis patients, COPD, eosinophilic bronchitis, bronchiectasis, bronchospasm, bronchial constriction, bronchial hyperreactivity, and bronchial hypertrophy.

As used herein, the term "bronchial spasm" means an involuntary spasm of the breathing tubes of a patient. Bronchial constriction is both a term and a medical condition which is interchangeable with "bronchial spasm" in its use with respect to the purposes of this application. As used herein, the term "bronchial inflammation" refers to an inflammation of the breathing tubes of a patient. In addition, allergic syndromes, for example asthma, may be initiated by common cold viruses, especially the rhinovirus and the compounds disclosed can be used for treating infections in the upper respiratory passages, such as cold and flu and those from rhinovirus and coronaviruses. Bronchial constriction is also a symptom of anaphylaxis and the compounds disclosed may be used for treating anaphylaxis.

Anaphylaxis is a serious, rapid-onset, allergic reaction that can cause death. Life-threatening upper airway obstruction, bronchospasm and/or hypotension characterizes severe anaphylaxis. There are about 100,000 episodes each year in the USA, of which approximately 1% result in death and about 66% are new cases. In most cases a specific trigger can be described but about 20% of cases are designated as idiopathic. Epinephrine has been accepted as the treatment of choice for many years, but it has been described as under utilized and not always effective (Golden (2007) $Curr.$ $Opin.$ $Allergy$ $Clin.$ $Immunol.,$ 7:331-336). The physicians' preference is for treatment with corticosteroids and anti-histamines despite little evidence for their efficacy during acute disease. Anti-histamines may help with histamine-mediated pathology, but not with effects arising from other mediators and may have limited efficacy in preventing ongoing mast cell and basophil activation. Like anti-histamines, corticosteroids have been suggested to play a role in disease management despite there being little clinical trial evidence for their efficacy, but their suggested use is on the basis that early administration of corticosteroids in patients with acute asthma is beneficial (El-Shanawany et al. (2008) $Clin.$ $Exp.$ $Immunol.$ 153:1-9). Corticosteroids will not be effective during acute disease because their actions require protein synthesis and hence their activities are delayed.

Anaphylaxis involves the activation of mast cells and/basophils. It is most commonly triggered by exposure to insect venoms, foods, medications and allergen immunotherapy injections through a mechanism involving IgE and the high affinity receptor for IgE on mast cells and basophils. IgE synthesized in response to allergen exposure becomes fixed to IgE receptors (FceRI) on the surface of mast cells and basophils. Receptor aggregation by IgE causes cell activation, pre-formed mediator release (including histamine, tryptases (including β-tryptase), carboxypeptidase A, TNF-α and chymase) and triggering of the immediate hypersensitivity response. Preformed granule mediators are released by exocytosis within minutes. Synthesis of arachidonic acid metabolites including prostaglandins and leukotrienes, and platelet activating factor (PAF) similarly occurs in minutes, whereas synthesis and release of biological regulators, inflammatory cytokines and chemokines, may take hours and these mediators contribute to the late phase of a biphasic anaphylactic reaction. The biological regulators released include IL-5, IL-4, IL-13, granulocyte (G) colony stimulating factor (CSF), macrophage (M)-CSF, GM-CSF, IL-1β, IL-3, IL-6, IL-8, IL-10, IL-16, IL-18 and IL-22. Generally these regulators cause the recruitment and activation of additional cells including basophils, eosinophils and Th2 cells (Ogawa and Grant (2007) $Immunol.$ $Allergy$ $Clin.$ $N.$ $Am.,$ 27:249-260). In some patients described as having idiopathic anaphylaxis, FcεRI receptors may be aggregated through autoimmune mechanisms in the absence of IgE (Simons (2008) $J.$ $Allergy$ $Clin.$ $Immunol.$ 121:S402-7) and there is some evidence of an alternative pathway involving IgG and the IgG receptor. This latter pathway does not trigger histamine release; rather PAF is the main early mediator (Peavy and Metcalfe (2008) $Curr.$ $Opin.$ $Allergy$ $Clin.$ $Immunol.,$ 8:310-314).

In the early phase of anaphylaxis, histamine stimulates vasodilation and increases vascular permeability, heart rate, cardiac contraction and glandular secretion. Prostaglandin D2 is a bronchoconstrictor, pulmonary and coronary vasoconstrictor, and a peripheral vasodilator. Leukotrienes also promote bronchoconstriction and increased vascular permeability, as well as promoting airway remodelling. PAF similarly causes bronchoconstriction and increased vascular permeability. TNF-α activates neutrophils, recruits other effector cells, and enhances chemokine synthesis, which leads to further inflammatory cell recruitment. These overlapping and synergistic effects contribute to the overall pathophysiology of anaphylaxis that variably presents with generalized urticaria and angioedema, bronchospasm, and other respiratory symptoms, hypotension, cardiovascular symptoms (including fainting), and nausea as well as other gastrointestinal symptoms (Peavy and Metcalfe (2008) supra). IL-4 is a key cytokine in the late phase of anaphylaxis and as well as stimulating and maintaining Th2 cell proliferation and switching B cells towards IgE synthesis, the most rapid and dramatic effect of this cytokine on anaphylaxis is to markedly enhance the responsiveness of targeted cells to vasoactive mediators including histamine, serotonin, PAF and cysteinyl leukotrienes (Ogawa and Grant (2007) supra).

Allergic rhinitis and allergic asthma are diseases that involve an inflammatory response. They have similar underlying etiology and are characterized by a marked inflammatory cell infiltrate comprising eosinophils, mast cells, T-lymphocytes and cells of the monocytic lineage. The adhesion molecules, P-selectin, MAC-1 (CD11b/CD18) and PECAM-1 play an important role in the extravasation of leukocytes and are likely to be involved in the inflammatory process. Further, the eotaxin family of chemokines (i.e. CCL11, CCL24 and CCL26) plays a key role in these diseases as they are the prime chemotactic factors stimulating eosinophil and CD4+ T lymphocyte infiltration. There is a growing realization that asthma and allergic rhinitis are components of a single inflammatory airway disease. This conclusion is supported by epidemiological data showing that more than 80% of persons with allergic asthma have allergic rhinitis, and that up to 50% of patients with allergic rhinitis have asthma (Gelfand (2004) $J.$ $Allergy$ $Clin.$ $Immunol,$ 114:S135-138; Passalacqua et al. (2004) $Curr.$ $Opin.$ $Allergy$ $Clin.$ $Immunol.$ 4:177-183). Moreover, longitudinal and follow-up studies have shown that rhinitis usually precedes asthma and is a risk factor for asthma. Allergic rhinitis increases the risk of developing asthma by at least three-fold and correct treatment of allergic rhinitis with intranasal steroids has a favorable effect on bronchial symptoms, significantly reducing the rate of hospital admittance and emergency department visits for asthma exacerbation (Passalacqua et al. (2004) supra).

Allergic diseases are considered to be either "acquired-type allergy" mediated by activated Th2 cells and antigen-specific IgE, or "innate-type allergy" induced without activation of the acquired immune system. The contribution of airway epithelial cells is increasingly being implicated in allergic diseases as they sense exposure to pathogens or allergens via pattern recognition receptors (PRRs) and can activate dendritic cells (DCs). Triggering of these PRRs on airway epithelial cells leads to the release of pro-Th2 cytokines such as thymic stromal lymphopoietin (TSLP), GM-CSF, IL-1alpha, IL-25, IL-18 and IL-33 by the epithelial cells and some immune cells. These cytokines both activate DCs to initiate Th2 responses and stimulate Th2 cells to enhance Th2 immunity. In addition, they also stimulate innate type 2 cells including basophils, mast cells, eosinophils, and group 2 innate lymphoid-like cells (ILC2s). IL-25, IL-33 and TSLP strongly trigger ILC2s to produce IL-5 and IL-13. Whereas IL-18 and IL-33 stimulate mast cells and basophils to secrete IL-4, IL-6, IL-9 and IL-13 without crosslinking of the IgE receptor, Fcε receptor I (FcεRI). Thus, Th2 cytokines are produced in the absence of allergen and IgE antibody and these cytokines trigger "innate-type allergy" (Yoshimoto (2014) *Allergol. Internat.* 63 Suppl 1:3-11).

The development of "acquired-type allergy" occurs following the crosslinking of FcεRI on basophils and mast cells by antigen specific IgE. This causes the release of inflammatory biological regulators (also referenced herein as "mediators") including histamine and the cytokines IL-4 and IL-13. IL-4 initiate the Th2 response and these Th2 cells secrete more IL-4 as well as other Th2 cytokines like IL-5, IL-9, IL-13 and GM-CSF (Yoshimoto (2014) supra). IL-13 together with IL-4 cause B lymphocytes to switch into producing IgE. IL-13 also contributes to the allergic response by triggering mucus formation, airway remodelling and eotaxin production. The latter is important for eosinophil infiltration into the tissues: the lung for asthma and nasal mucosa for allergic rhinitis. IL-5 is the cytokine that is pivotal for eosinophil differentiation, survival and activation, whereas IL-9 contributes to airway eosinophilia, mast cell accumulation, and mucus production in animal asthma models. It is understood that ILC2s are the link between allergen induced epithelial cytokine production and the initiation of the Th2 cell-mediated response (Martinez-Gonalez el al. (2015) *Trends Immunol.* 36:189-195).

A drug targeting IL-33 alleviates/attenuates: airway hyperreactivity (AHR), airway inflammation (eosinophil and neutrophil), mucous secretion and airway remodelling in asthma (Nabe (2014) *J. Pharmacol. Sci.* 126:85-91; Lloyd (2015) *Curr Opin Immunol.* 34:52-58), similarly blocking IL-25 activity significantly reduced levels of IL-5, IL-13 and IgE secretion, eosinophil infiltration and goblet cell hyperplasia in allergic asthma (Ballantyne (2007), *J. Allergy Clin. Immunol.* 120:1324-1331). There is also good evidence that the three cytokines IL-25, IL-33 and TSLP are similarly of pivotal important in allergic rhinitis and this seems also to be true for atopic dermatitis (Matsushita et al. (2015) *Allergol. Internat.* 64: 235e240). Mouse models indicate that IL-33 from epidermal keratinocytes induce ILC2s in the skin and stimulates their production of IL-5, which induces atopic dermatitis with eosinophilic infiltrates. Although atopic dermatitis is frequently associated with increased allergen-specific IgE in the serum, around 20% of patients with atopic dermatitis have no allergen-specific IgE, suggesting that an innate-type atopic dermatitis may also occur as a result of ILC2 stimulation by proallergic cytokines (Yoshimoto (2014) supra).

These allergic-type diseases are a complex mixture of pathologies, involving at least the various cytokines, chemokines and cell adhesion molecules indicated above.

The underlying etiology of chronic obstructive pulmonary disease (COPD) is different from that of allergic inflammatory diseases (Sutherland and Martin (2003) *J Allergy Clin. Immunol.* 112:819-27). COPD involves a chronic inflammatory process affecting peripheral airways and lung parenchyma and inflammation is worse during exacerbations. A major contributory factor to the development of COPD is the inflammatory response to cigarette smoke. The pathological indicators of COPD are destruction of the lung parenchyma (pulmonary emphysema), inflammation of the small peripheral airways (respiratory bronchitis) and inflammation of the central airways. Most patients with COPD have all three pathological conditions (chronic obstructive bronchitis, emphysema and mucus plugging) that exhibit different patterns of inflammation (Adcock and Ito (2005), *Proc. Am. Thorac. Soc.* 2:313-319). The inflammation in stable COPD is characterized by neutrophils, macrophages, T lymphocytes, dendritic cells and B lymphocytes. During COPD exacerbations, there is also a recruitment of eosinophils, particularly during virus-induced severe COPD exacerbations. Alveolar macrophages play a key role in COPD, they are localized to sites of alveolar destruction, and their numbers are positively correlated with disease severity, airway obstruction and degree of alveolar wall damage in emphysema. Airway tissue neutrophils are increased in the large and small airways of COPD patients during exacerbations and in severe COPD, or during infections. Patients with COPD also display either an increase in the CD8+/CD4+ T cell ratio, or an increase in the total numbers of both CD8+ and CD4+ T cells in the airway wall (MacNee (2005) *Proc. Am. Thorac. Soc.* 2:258-266). The bronchioles are obstructed by fibrosis and infiltrated with macrophages and T lymphocytes.

Of the T-lymphocytes, T-helper (Th)-1 and T-cytotoxic (Tc)-1 subtypes, characterized by production of interferon (IFN)-γ, predominate. Many inflammatory mediators are involved in the inflammation associated with COPD. TNFα, IL-1β, granulocyte-macrophage colony-stimulating factor (GM-CSF), and CXCL8 (IL-8) are released by airway epithelial cells exposed to cigarette smoke. Alveolar macrophages are activated by cigarette smoke to release cytokines including TNFα, CXCL8, CCL2 (MCP-1), in addition to leukotriene B4 and oxidants (reactive oxygen species). Neutrophil numbers in sputum and bronchiolar lavage in COPD, and their numbers correlate with disease severity. Chemotactic signals for neutrophil recruitment include leukotriene $B_4$, CXCL1, CXCL2, CXCL3, CXCL5, and CXCL8 (IL-8), the expression of which is increased in COPD, and likely to be derived from alveolar macrophages and epithelial cells. GM-CSF and granulocyte CSF (G-CSF) may increase the survival of neutrophils.

There is increasing evidence of the participation of the inflammasome in COPD and the association of the inflammasome in the activation of proinflammatory cytokines, in particular IL-10 and IL-18 (Caramori et al. (2014) *Internat. J. COPD* 9: 397-412).

Many biological regulators have been implicated in facets of the pathogenesis of COPD. The proinflammatory mediators of these disease processes include leukotriene-B4, IL-8 and other chemokines (e.g. MIP-1α, MCP-1), TNF-α, IL-13 and IL-4 (Barnes (2004), *Pharmacol. Rev.* 56:515-548). It has been suggested that the inhibitory effects of TNF-α and IL-4 on the production of the regulatory cytokine TGF-β by bronchial epithelial cells may contribute to the progression of the inflammatory response. In addition, increased levels of IL-6, IL-1p, TNF-α, and IL-8 have been measured in sputum with further increases during exacerbations. Other proinflammatory biological regulators of importance include IFNγ, IL-5, IL-17, IL-18, IL-22, IL-23, IL-25, IL-32, IL-33 and thymic stromal lymphopoietin (TSLP). It is thought IL-5 maybe involved in COPD exacerbations as in animal models of COPD after exposure to rhinovirus there is increased lung expression of IL-5 (Caramori el al. (2014) supra), although in the general patient population no real increases in mRNA for either IL-4 or IL-5 were detected during exacerbations. However, division of the COPD cohort into patients with disease induced by tobacco smoke (TS-COPD) and those with biomass smoke (BE-COPD) induced disease may reveal the contribution of these Th2 cytokines to COPD pathogenesis. This is because the frequency of Th17 cells in patients with TS-COPD was found to be significantly higher than in patients with BE-COPD and healthy controls. In contrast, patients with BE-COPD had higher levels of Th2 cells than TS-COPD and healthy controls, and serum IL-4 concentrations were higher in BE-COPD than in TS-COPD (Solleiro-Villavicencio et al. (2015) *Clin Immunol*. doi:10.1016/j.clim.2015.07.009). IL-17 is produced predominately by Th17 and Tc17 cells. It induces the release of CXCL1, CXCL8 and GM-CSF from airway epithelial cells and smooth muscle cells to induce neutrophil infiltration. In addition it induces IL-6 expression in bronchial epithelial cells and fibroblasts and IL-17 in association IL-6 trigger production of the mucins MUC5AC and MUC5B from airway epithelial cells. CXCL8 levels are markedly elevated in the suptum of patients with COPD and are correlated with disease severity (Caramori et al. (2014) supra). A monoclonal antibody against CXCL8 improved dyspnea in COPD patients, but did not improve lung function, health status or 6 minute walking distance. It is likely that inhibition of multiple neutrophil chemotactic agents and of other cytokines, e.g. IL-17, will be required for a clinical effect on lung function to be manifest in COPD patients.

Tuberculosis (TB) is a major health issue with around 1.3 million deaths and 9 million new cases annually. TB is an infectious disease transmitted by aerosols containing *Mycobacterium tuberculosis*. *Mycobacterium tuberculosis* does not produce toxins; rather over exuberant inflammatory responses cause tissue damage and disease, and can lead to death as well as drive endogenous re-infection (Cardona, (2010) *Archiv Immunol Et Therap Experimental*. 58:7-14). Controlling the inflammation will help abate the disease process. Active pulmonary TB is characterized by destructive inflammation and the spreading of infection to airway epithelia rendering the individual infectious. In active pulmonary TB, neutrophils and the chemokine/receptor pair: CXCL5/CXCR2, involved in neutrophil recruitment into the lung, are critical for the destructive inflammation as blocking CXCL5 activity eliminates the inflammation. CXCL5 is believed to account for about 60% of neutrophil recruitment. In a mouse model loss of either CXCL5 or CXCR2 was protective against TB and its associated wasting disease and death (Nouailles et al. (2014) *J. Clin. Invest*. 124:1268-1282). Although *M. tuberculosis* multiplies within phagocytic cells, when infected with virulent strains these cells rapidly become necrotic releasing bacilli for more infections. As neutrophils and macrophages undergo necrosis they release extracellular traps (NETs), which cause tissue destruction. Within NETs histones are potent inducers of cytotoxicity, killing alveolar epithelial and endothelial cells. It is known blocking histone-mediated cytotoxicity markedly reduces tissue damage in inflammatory lung disease (Wildhagen et al. (2014) *Blood* 123:1098-1101). A mouse model designed to mimic active TB in immunocompetent patients also showed massive intra-alveolar neutrophil infiltration. When treated with anti-inflammatory drugs lower levels of pro-inflammatory mediators, lower bacillary load, reduced pathology and increased survival were recorded. An effective anti-inflammatory drug in this model was heparin (Marzo et al. (2014) *Tuberculosis* 94:55-64).

In TB activated macrophages containing necrotic cell debris (and bacilli) are drained with the alveolar fluid, to the upper bronchi. As a result bacilli pass into aerosols and cause re-infection via the airway epithelium of the upper bronchi. As *M. tuberculosis* grow in the abundant epithelial cells of the alveoli, these cells are likely to be a significant site of replicating bacilli. HBHA (heparin binding haemagglutinin), expressed by *M. tuberculosis*, is essential for the adhesion of bacilli to epithelia. The lysine-rich C-terminal domain of HBHA binds epithelial heparan sulfate (HS) to mediate adhesion, whilst its coiled-coil domain aggregates the bacilli. Collectively the two HBHA domains enable efficient entry of bacilli into airway epithelia (Pethe et al. (2001) *Nature* 412:190-4).

Disrupting HBHA-HS binding will primarily reduce endogenous re-infection, but initial infection may also be affected.

Acute lung injury (ALI) and acute respiratory distress syndrome (ARDS) are respiratory inflammatory conditions that are associated with high mortality rates. The pathogenesis of ALI and ARDS involve uncontrolled host defense responses that lead to inflammation, endothelial damage, enhanced coagulation, diminished fibrinolysis and fibroproliferation. Pathologically ARDS is characterized by diffuse alveolar damage, alveolar capillary leakage, and protein rich pulmonary oedema leading to the clinical manifestation of poor lung compliance, severe hypoxaemia, and bilateral infiltrates on chest radiograph. The most common risk factor is severe sepsis which can have a pulmonary or a non-pulmonary source. Other risk factors are toxic inhalation, lung contusion, acute pancreatitis, pneumonia, aspiration, pulmonary emboli, near-drowning, reperfusion pulmonary edema, trauma, surgery, burn injury, drug overdose and cardiopulmonary bypass surgery (Han and Mallampalli (2015) *J. Immunol*. 194: 855-860). The incidence of the disease is increasing with approximately 200,000 cases annually in the USA and the mortality rate at 38.5% has not improved for several decades. There are three overlapping phases of the disease: Exudative phase (in first 4-7 days), Proliferative phase ($\geq$7-14 or 21 days) and Fibrotic phase ($\geq$14 or 21 days) (MacLaren and Stringer (2007) *Pharmacotherapy*, 27:860-873).

The initial early phase (exudative phase) is characterized by increased permeability of the endothelial and epithelial barriers of the lung, with accumulation of protein-rich and highly cellular edema fluid in the lung interstitium and alveoli. The edema fluid contains hyaline membranes and a variety of inflammatory cells but neutrophils predominate. Thus the pathological correlate termed: diffuse alveolar damage, consists of hyaline membranes plus at least one of the following: alveolar type I or endothelial cell necrosis, edema, interstitial fibrosis, or prominent alveolar cell type II proliferation. Some patients recover during the first week of the disease, others die during that phase, but some progress into a sub-acute phase of ALI/ARDS that develops 7 or so days after onset. During this sub-acute phase the alveolar space becomes filled with mesenchymal cells, their products and new blood vessels. There is evidence of interstitial and alveolar fibrosis with proliferation of type II cells and destruction of portions of microcirculation in the lungs. In some patients respiratory failure continues beyond 14 days, and this chronic phase is characterized by extensive pulmonary fibrosis with loss of normal alveolar architecture and the progressive development of emphysematous regions in the lung (Cepkova and Matthay (2006) *J. Intensive Care Med.*, 21:119-143).

ARDS is an inflammatory disease characterized by neutrophil and macrophage infiltration and excessive pro-inflammatory cytokine and protease activity in the alveolar space, all of which is associated with alveolar epithelial and capillary endothelial injury (Boyle et al. (2014) *Expert.*

Opin. Biol. Ther., 14:969-981). The initial inflammatory insults (sepsis, trauma, transfusions etc) trigger toll-like receptor (TLR) and nucleotide-binding oligomerization domain-like receptor (NOD-like receptors) signaling pathways to activate alveolar macrophages. These activated cell release pro-inflammatory cytokines including IL-1β, TNF-α, IL-6 and IL-8, which recruit circulating macrophages and neutrophils. Excessive neutrophil numbers and continually activated macrophages damage the alveolar-capillary barrier allowing protein-rich fluid to enter the alveoli, giving rise to the pulmonary edema and interference with gas exchange that characterizes the disease (Han and Mallampalli (2015) supra). Neutrophil influx into the lungs is associated with the severity of ARDS. Biological regulators, and particularly CXCL8 (IL-8) that is produced by both leukocytes and somatic cells, play a key role in neutrophil recruitment and subsequent tissue damage. In particular airway epithelial cells can release CXCL8 from their apical surface and thereby stimulating neutrophil trans-epithelial migration (Shen et al. (2011) Expert. Opin. Biol. Ther. 5:107-114). Neutrophil extracellular traps (NETs) are produced by these activated cells and directly induce the death of lung epithelia and endothelia, in part by the enzymes (elastase, matrix metalloprotease-8 (MMP-8)) and reactive oxygen species (ROS) as well as histones that are contained in the NETs.

ARDS is also characterized by activation of the ubiquitin proteasome system with increased expression of ubiquitin within alveolar (type II) epithelia, and release of ubiquitin proteasome components into lung fluid. Ubiquitination was reported to play an important role in regulating the Na, K-ATPase and epithelial Na⁺ channel functions during ARDS. The Na, K-ATPase is located in the basolateral surface of alveolar type 2 epithelial cells where it contributes to the clearance of lung fluids. During hypoxia, the Na, K-ATPase is internalized and degraded by endocytosis via ubiquitination, resulting in decreased alveolar fluid clearance. Targeting the ubiquitin proteasome system has been suggested as a therapeutic target for ARDS (Han and Mallampalli (2015) supra).

Biological regulator targets for ARDS therapy include CXCL8, IL-1β, IL-17 and TNF-α. Animal studies have suggested that blocking CXCL8 or TNF-α with monoclonal antibodies targeting these molecules attenuated ARDS development and reduced neutrophil infiltration (Boyle et al. (2014) supra). IL-1β is a potent recruiter of neutrophils and increases alveolar-capillary permeability. In addition IL-1β-dependent IL-6 induction initiates fibroblast activity and so contributes to the fibrotic re-modelling stage of ARDS. IL-17 attracts neutrophils to the lungs and acts in synergy with TNF-α to increase selectin expression by endothelial cells to further increase neutrophil recruitment.

In ALI/ARDS local activation of coagulation and disturbances in fibrin turnover occur, lead to excessive alveolar fibrin deposition, which also compromise pulmonary integrity and function. Intraalveolar fibrin accumulation, observed under these conditions, arises from a leakage of plasma proteins (including fibrinogen) into the alveolar space. Tissue factor in association with factor VIIa and inhibition of urokinase by plasminogen activator inhibitor-1 are major factors that are responsible for the procoagulant and antifibrinolytic state in ALI/ARDS (Wygrecka et al. (2008) Thromb. Haemost. 99:494-501). Fibrin itself can increase vascular permeability, influence the expression of inflammatory mediators and alter the migration and proliferation of various cell types. Additionally, fibrin may inactivate pulmonary surfactant and provide a matrix on which fibroblasts can migrate and produce collagen. The application of coagulation inhibitors, like tissue factor pathway inhibitor, active site-inactivated factor VIIa, activated protein C, antithrombin, heparin or hirudin appear to be beneficial in experimental models of acute and chronic lung injury and as a result have attracted interest as possible therapies.

Osteoarthritis (OA) is a degenerative joint disease characterized by articular cartilage degradation which can affect many joints in the body, but is particularly common in weight-bearing joints such as the knee and hip. The loss of cartilage can lead to joint space narrowing, pain, and loss of function and ultimately leads to the need for total joint replacement. Pro- and anti-inflammatory cytokines, have been studied for their associations with the development and progression of OA in humans and in animal models (Mabey and Honsawek (2015) World J Orthop. 6:95-105). As well as pro- and anti-inflammatory roles (for example, interleukin (IL)-6, IL-1β, tumor necrosis factor (TNF)-α, IL-10, IL-13 and IL-4), cytokines also contribute to the pathophysiology of OA through angiogenesis and chemotaxis. IL-1β, IL-6 and TNF-α, are the major pro-inflammatory cytokines involved in OA (Mabey and Honsawek (2015) supra) but also included in this group are IL-15, IL-17, and IL-18. All of these cytokines promote catabolic and destructive processes that lead to cartilage degradation. IL-1β affects causes chondrocytes to synthesize of enzymes of the metalloproteinase (MMP) family, mainly interstitial collagenase (MMP-1), stromelysin-1 (MMP-3), and collagenase 3 (MMP-13), which degrade cartilage. In addition, IL-1β can affect the chondrocytes' production of ADAMTS metalloproteinases, which are responsible for the proteolysis of aggrecan molecules in cartilage. A major role is attributed to ADAMTS-4, whose production is stimulated by both IL-1β and TNFα, while ADAMTS-5 is produced constitutively. TNF-α is the other major cytokine inducing OA pathology. The effect of TNFα generally coincides with the action of IL-1P, and there is a marked synergism between the two cytokines in OA. Thus, TNFα affects the chondrocytes' ability to synthesize proteoglycans, proteins binding proteoglycans, and type II collagen. It also activates chondrocytes to produce MMP-1, MMP-3, MMP-13, and ADAMTS-4. The production of IL-6 in the tissues of an OA joint is usually in response to IL-1β and TNFα and their action on chondrocytes, osteoblasts, macrophages, and adipocytes. Like IL-1β and TNFα, IL-6 causes a decrease in the production of type II collagen and increases the production various MMPs (Nasi et al. (2015) Ann Rheum Dis doi: 10.1136/annrheumdis-2015-207487). IL-6 is the main cytokine, which causes changes in the subchondral bone layer. It promotes the formation of osteoclasts and thus bone resorption. Osteoblasts stimulated by IL-1β, TNFα, and IL-6 may also produce MMPs and so adversely affect cartilage close to the bone in the joint. As well as affecting chondrocytes and synovial cells these inflammatory cytokines affect the immune system cells that migrate to the site of inflammation. Because of these cytokines the immune cells produce excessive inflammatory PGE2, COX-2, phospholipase A2, NO, and free radicals as well as IL-8, CCL5 and more IL-1β, TNFα, and IL-6 in an autocrine fashion (Wojdasiewicz (2014) Mediators Inflamm. 561459 doi: 10.1155/2014/561459).

In accordance with the present invention, the glycoconjugates interact with a number of biological regulators which are responsible, in part or whole, for the conditions discussed above. In an embodiment, the regulator is a chemokine, cytokine, growth factor or chemotactic agent and includes a peptide, polypeptide, protein or glycoprotein.

Suitable biological regulator targets include those that have been described as GAG binding proteins (e.g. heparin, heparin sulphate, chondroitin and hyaluronan). Examples include, but are not limited to: histamine, an interleukin (e.g. IL-1, IL-1α, IL-1β, IL-2, IL-3, IL-4, IL-5, IL-6, IL-7, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38), interferon (e.g. α-interferon, β-interferon, γ-interferon), thymic stromal protein (TSLP), a chemokine-like molecule (CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, CX3CL1, leukotriene B4, MIP-1α, MCP-1) or a growth factor including but not limited to TSLP, G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, M-CSF, NGF, NT 3, NT4, NT5, NT6, NT7, OSM, PBP, PBSF, PDGF, PECAM-1, SCF, TGFα, TGFβ1, TGFβ2, TGFβ, TNFα, TNFβ, TPO, VEGF, GH, insulin and the like; an enzyme (e.g. superoxide dismutase, eosinophilic cationic protein, major basic protein, tryptases, a chymase, elastases, selectins, A Disintegrin And Metalloprotease 4 (ADAM4), ADAM5, phospholipase A2 or prostaglandin endoperoxide); a soluble or cell- or virus-bound receptor (e.g. inositol triphosphate receptor); members of the complement cascade (e.g. C1, C1q, C1-inhibitor, C2, C4, C4b, C4 bp, MASP-1, MASP-2, C3, C3b, Factor D, Factor H, Factor B, properdin, C6, C8, C9); histones or heparin binding haemagglutinin (HBHA).

Enabled herein is an assay or screen for identifying a glycoconjugate that binds to and/or modulates the activity of one or more biological regulators, the assay comprising the steps of:
(a) contacting a biological regulator with a glycoconjugate; and
(b) quantifying the effect of the glycoconjugate on the biological receptor; the glycoconjugate having the following formula (I):

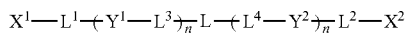

wherein
L is a bond or a linker;
$L^1$ and $L^2$ are each independently selected from a bond and a linker;
$L^1$ and $L^4$ are each independently selected from a bond and a linker;
$X^1$ and $X^2$ are each a capping sugar, wherein each of $X^1$ and $X^2$ is independently selected from an optionally substituted monosaccharide, a disaccharide, a trisaccharide, a tetrasaccharide and a pentasaccharide or a compound derived from an optionally substituted monosaccharide, a disaccharide, a trisaccharide, a tetrasaccharide or a pentasaccharide;
$Y^1$ and $Y^2$ are each a connecting sugar, wherein each $Y^1$ and $Y^2$ is independently selected from an optionally substituted monosaccharide, a disaccharide, a trisaccharide, a tetrasaccharide and a pentasaccharide, or a compound derived from an optionally substituted monosaccharide, a disaccharide, a trisaccharide, a tetrasaccharide or a pentasaccharide; and
n is an integer from 0 to 3.

$X^1$, $X^2$, $Y^1$ and $Y^2$ may also comprise one or more sulfate groups, phosphate groups, oxylate groups or combinations thereof.

In an embodiment, the biological regulator is a chemokine, cytokine, growth factor or chemotactic agent and includes a peptide, polypeptide, protein or glycoprotein. In the method of identifying a glycoconjugate which binds to and/or modulates the activity of a biological regulator, the glycoconjugates may be selected on the basis of one or more physicochemical, pharmacokinetic, biological, and/or physiological properties. Examples of such properties include, but are not limited to, binding affinity, selectivity, toxicity, efficacy, stability, lipophilicity, and/or activity, such as agonism, antagonism and/or inhibition. In another embodiment, the glycoconjugate binds to a chain of a receptor of the biological regulator and, in so doing, modulates that activity of the regulator. For example, the glycoconjugate may modulate the activity of a biological regulator by inhibiting binding of the regulator to a receptor.

In an embodiment, the step of contacting a biological regulator with a glycoconjugate may be carried out in situ, in vitro, or in vivo. For example, the step of contacting a biological regulator with a glycoconjugate may be carried out in a cell or an animal.

The interaction with a biological regulator may be detected by any convenient means such as nuclear magnetic resonance (NMR), mass spectrometry (MS), isothermal titration calorimetry (ITC), dynamic light scattering (DLS), surface plasmon resonance (SPR), dual polarization interferometry (DPI), microscale thermophoresis (MST), gel retardation, filter retardation, affinity co-electrophoresis, bioluminescent resonance energy transfer (BRET) assays, fluoresence resonance energy transfer (FRET) assays, fluorescence polarization (FP) assays, scintillation proximity assays or immobilization to biochips or other surfaces including those coupled with mass spectrometric detection.

The latter may be accomplished by first immobilizing the glycoconjugate to a chip and then adding the biological regulator. Alternatively, the regulator may be immobilized to a chip and used to screen for the ability of a glycoconjugate to bind thereto.

Yet another alternative is to immobilize a GAG, such as heparin, to a solid support and then screen for the ability of an glycoconjugate to inhibit binding of a receptor to the immobilized heparin.

Accordingly, an assay is contemplated herein comprising admixing the biological regulator and the glycoconjugate and screen for the ability of the glycoconjugate to inhibit binding of the regulator to a GAG (e.g. heparin or heparan sulfate) bound to a chip.

In an embodiment, the glycoconjugate binds a biological regulator and, in so doing, inhibits the interaction between the biological regulator and its receptor. In another embodiment, the glycoconjugate binds a chain of a receptor for the biological regulator and, in so doing, inhibits regulator binding and signaling.

There are, of course, any number of other assays, which may be used to screen for interaction between a glycoconjugate and biological regulator or a regulator receptor chain, or used to screen for inhibition of interaction between a regulator and its receptor. Another assay is a filter binding assay. In this assay, one of a glycoconjugate, or a biological regulator is labeled with a reporter molecule capable of providing an identifiable signal such as a fluorescent dye and both molecules are allowed to interact in solution. The resulting mixture is then passed through a filter capable of retarding one of the glycoconjugate or the chemokine or a glycoconjugate-regulator complex.

In an embodiment, for example, the filter is a nitrocellulose filter which retards proteins. In this case, if the glycoconjugate, labeled with a reporter molecule, fails to pass through the filter, then the presence of the reporter signal in the filter indicates binding of the glycoconjugate to the chemokine.

In another embodiment, a GAG is labeled with the reporter molecule and reacted with the biological regulator in the presence of different glycoconjugates. Passage of heparin or heparan sulfate through the filter is indicative of a glycoconjugate that has inhibited the interaction between the heparin/heparan sulfate and the regulator.

Different glycoconjugates will interact with different biological regulators, or different regulators will interact with different glycoconjugates or both. In addition, different glycoconjugates may interact with different biological regulator receptor chains. Accordingly, another assay involves the use of affinity columns carrying immobilized chemokines. The glycoconjugates are then passed through the column and the presence of retardation of the glycoconjugates determined. A salt gradient is conveniently used to elute bound glycoconjugates.

Other examples of assays contemplated by the present invention include functional assays such as whole cell assays to assess cell proliferation (such as shown in Examples 22 to 28). Such functional assays may provide more useful information on the effect of the tested glycoconjugate(s) than pure binding assays.

Once glycoconjugates that bind to a particular ligand have been identified, the glycoconjugate itself may be useful as a therapeutic to inhibit interaction between a biological regulator and a cell surface GAG (e.g. heparin or heparan sulfate) or a receptor for the biological regulator. The regulators are secreted from cells and they may be in the soluble phase or immobilized on an extracellular matrix or attached to a cell surface GAG. The glycoconjugate may also be useful as a therapeutic to modulate interaction between a secreted cellular product and extracellular matrix components or between a cell surface protein and extracellular matrix components, or between a biological regulator and its receptor, both or either of which may be cell surface associated. Alternatively, the glycoconjugate may be used as a target to identify natural products or products from a chemical library that mimic the glycoconjugate in terms of binding to a biological regulator or that inhibits or promotes the interaction between the glycoconjugate and the regulator. These molecules may be antagonists or agonist or chemical analogs of the glycoconjugate. Hence, an "analog" extends to and encompasses any structure which is functionally equivalent in that it binds and/or modulates a chemokine in an analogous manner.

Reference herein to "modulate" or "modulation" extends to and encompasses inhibiting and/or promoting an interaction.

In another aspect, the present invention provides a method of treating or preventing any disease associated with or exacerbated by the activity of a biological regulator in a mammalian subject, including the interaction between a regulator and its receptor such as or involved in activation of a signaling pathway or between a virus and a cell, the method comprising administering to the subject a glycoconjugate as defined herein or a glycoconjugate or glyconjugate mimetic. The glycoconjugates are useful inter alia in the treatment of inflammatory or allergic disease conditions and metastatic cancers and infection by pathogenic agents such as bacteria, viruses or parasites.

In an embodiment, enabled herein is a method of prophylaxis and/or treatment of a disease condition in a subject, the disease condition resulting from interaction between a GAG on a surface of a cell in said host and a biological regulator, or a GAG in the extracellular matrix in the host and a regulator that may or may not be cell associated, or a biological regulator receptor interaction in the host that can be disrupted by a GAG where the protein may be cell associated and the ligand soluble or both regulator and receptor may be cell associated, the method comprising administering to the subject a therapeutically effective amount of a glycoconjugate, produced and identified as defined herein, that interacts with the regulator.

"Subjects" contemplated herein are humans and non-human mammals including laboratory or art accepted test or vehicle animals. "Subjects" include human subjects in need of treatment or prophylaxis.

Also contemplated herein is a method for generating a medicament for treating a disease condition in a subject, the method comprising producing a glycoconjugate or range of glycoconjugates according to the process defined herein, and screening each glycoconjugate for an ability to interact with or modulate the biological regulator. The glycoconjugate that interacts with or modulates the biological regulator is identified and using same or a glycoconjugate mimetic thereof in the manufacture of the medicament.

In an embodiment, the modulation is an inhibition.

Types of biological regulator contemplated herein include those listed above.

Usefully, the present invention further provides compositions comprising a glycoconjugate as herein described. The term "compound" includes "medicament", "agent", "therapeutic", "pharmacologically acceptable compound" and "pharmaceutical composition" and the like. In another embodiment, the composition comprises a pharmaceutically or physiologically acceptable carrier or diluent. A "composition" comprising one or more glycoconjugates (encompassed by the term "a glycoconjugate") includes a single composition or multiple separate compositions each comprising the same or different glycoconjugate(s) for simultaneous or sequential administration or admixed together prior to administration. In an embodiment, a glycoconjugate is for use in the treatment or prevention of conditions or symptoms of conditions promoted or exacerbated by a biological regulator.

Pharmaceutical compositions are conveniently prepared according to conventional pharmaceutical compounding techniques. See, for example, Remington's Pharmaceutical Sciences (1990) 18th Ed., Mack Publishing, Company. These compositions may comprise, in addition to one of the active substances (a glycoconjugate as herein described or mimetic thereof), a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

The glycoconjugates as herein described or compositions comprising same are administered in an effective amount. The terms "effective amount" includes "therapeutically effective amount" and "prophylactically effective amount"

and mean a sufficient amount of active either in a single dose or as part of a series or slow release system which provides the desired therapeutic, preventative, or physiological effect in some subjects. Undesirable effects, e.g. side effects, may sometimes manifest along with the desired therapeutic effect; hence, a practitioner balances the potential benefits against the potential risks in determining an appropriate "effective amount". The exact amount of composition required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine skills or experimentation. The term "treatment" refers to any measurable or statistically significant amelioration in a subject in one or more symptoms of a condition associated with the condition being treated. Prophylactic administration of the compound serves to prevent or attenuate onset of symptoms of a condition to be prevented.

In an embodiment, the disease or disorder is selected from inflammatory diseases, including allergic diseases; osteoarthritis; metastatic cancers; and infection by a pathogenic agent including, but not limited to, *Mycobacterium tuberculosis*, the agent that causes tuberculosis, and an influenza-type A virus associated with human or bird flu and human immunodeficiency virus (HIV), the agent that causes AIDS. Particular diseases include asthma; allergic respiratory disease; allergic rhinitis; subepithelial fibrosis in airway hyperresponsiveness; chronic sinusitis; perennial allergic rhinitis; allergic bronchopulmonary aspergillosis in cystic fibrosis patients; COPD; eosinophilic bronchitis; bronchiectasis; bronchospasm; bronchial constriction; bronchial hyperreactivity; and bronchial hypertrophy.

A "pharmacologically acceptable" composition is one tolerated by a recipient patient. A "pharmaceutically acceptable carrier and/or a diluent" is a pharmaceutical vehicle comprised of a material that is not otherwise undesirable i.e. it is unlikely to cause a substantial adverse reaction by itself or with the active composition. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes.

When the glycoconjugate is suitably protected, it may be orally administered. For oral administration, the compositions can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablets may contain a binder such as tragacanth, corn starch or gelatin; a disintegrating agent, such as alginic acid; and a lubricant, such as magnesium stearate. If desired, tablets may be sugar-coated or enteric-coated by standard techniques. The active composition can be encapsulated to make it stable to passage through the gastrointestinal tract. See for example, International Patent Publication No. WO 96/11698.

For parenteral administration, the composition may be dissolved in a carrier and administered as a solution or a suspension. For transmucosal or transdermal (including patch) delivery, appropriate penetrants known in the art are used for delivering the composition. For inhalation, delivery uses any convenient system such as dry powder aerosol, liquid delivery systems, air jet nebulizers, propellant systems. For example, the formulation can be administered in the form of an aerosol or mist. The compositions may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's Pharmaceutical Sciences (1990) supra. In some embodiments the formulations may be incorporated in lipid monolayers or bilayers such as liposomes or micelles. Targeting therapies known in the art may be used to deliver the agents more specifically to certain types of cells or tissues.

The pharmaceutical forms suitable for injectable use include sterile aqueous solutions (where water soluble), sterile powders for the extemporaneous preparation of sterile injectable solutions and inhalable forms. Such forms are generally stable under the conditions of manufacture and storage. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of surfactants. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the glycoconjugate and carrier/diluent in the required amount in the appropriate solvent followed by sterilization or at least a process to reduce contaminating viruses, bacteria or other biological entities to acceptable levels for administration to a human or animal subject. In the case of sterile powders for the preparation of sterile injectable solutions, suitable methods of preparation include vacuum drying and the freeze-drying technique that yields a powder of active ingredient plus any additionally desired ingredient.

In an embodiment, compositions or preparations according to the present invention are prepared so that an oral dosage unit form contains between about 0.1 μg and 200 mg of active glycoconjugate. Alternative dosage amounts include from about 1 μg to about 1000 mg and from about 10 μg to about 500 mg. These dosages may be per individual or per kg body weight. Administration may be per second, minute, hour, day, week, month or year.

The composition may also be formulated for local or topical administration. Techniques formulation and administration may be found in "Remington's Pharmaceutical Sciences (1990) supra". Thus, for local or topical administration, the subject compositions may be formulated in any suitable manner, including, but not limited to, creams, gels, oils, ointments, solutions, suspensions, powders, mists or aerosols. For transmucosal administration, penetrants appropriate to the barrier to be permeated are used in the formulation. Such penetrants are generally known in the art and include, but are not restricted to, benzalkonium chloride, digitonin, dihydrocytochalasin B5 and capric acid.

The compositions may be in the form of lotions, creams or gels may contain acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, buffering agents, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

In an embodiment, enabled herein is an inhalant pharmaceutical composition. The compositions comprising one or more glycoconjugates of the present invention may be administered to the respiratory tract as a nasal or pulmonary inhalation aerosol or solution for a nebulizer, or as a microfine powder (in an embodiment with particles of the order of 1 to 10 microns in size or less) for insufflation, alone or in combination with an inert carrier such as lactose, or with other pharmaceutically acceptable excipients.

Aerosol formulations include those in which the glycoconjugate is provided in a pressurized pack with a suitable propellant such as a pressurized metered dose inhaler (pMDI). Whilst the propellant may be a chlorofluorocarbon (CFC) such as dichlorodifluoromethane, trichlorofluoromethane, dichlorotetrafluoroethane, the propellant is more preferably a non-chlorofluorocarbon propellant such as carbon dioxide, hydrofluoroalkanes (such as HFA-134a) or another suitable gas. The aerosol may conveniently also contain a surfactant such as lecithin. The dose of the glycoconjugate may be controlled by provision of a metered valve. It has been found that a particle size of approximately 2 to 3 µm is useful for the treatment of asthma, as particles smaller than 1 µm are generally exhaled without delivery to the lung, and particles larger than 10 µm are mostly trapped by oropharyngeal deposition and do not reach the lung. Devices propelled by HFA-134a deliver smaller droplets which penetrate more readily into the bronchial airways. In an embodiment, the delivery of approximately 40% of the inhaled droplets into the lung is desirable and achievable using an pMDI as outlined above. For the treatment of allergic rhinitis the preferred particle size for drug delivery via the nasal passage is 20-80 µm, as smaller particles (less than 10 µm) get carried into the tracheobrachial region, whilst bigger particles (greater than 100 µm) get rapidly cleared from the nasal passageway.

The glycoconjugate may also be provided in a pharmaceutical formulation which forms a gel in the nasal cavity. The glycoconjugate may also be formulated in a powder composition which may be presented in unit dose form for example in capsules or cartridges of e.g. gelatin, or blister packs from which the powder may be administered by means of an inhaler.

As used herein the expression "pharmaceutically acceptable salt" refers to the salt of a given compound, wherein the salt is suitable for administration as a pharmaceutical. For example, such salts may be formed by the reaction of an acid or a base with an amino or a carboxyl group respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "protecting group" refers to any group which when bound to one or more hydroxyl, thiol, amino or carboxyl groups of the compounds prevents reactions from occurring at these groups and which protecting group can be removed by conventional chemical or enzymatic steps to re-establish the hydroxyl, thio, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in Greene and Wuts (1991) supra.

Examples of removable amino blocking (protecting) groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

"Selectivity" or "specificity" in general is a measure of the binding preferences of a ligand for different receptors and/or a measure of the binding preferences of different ligands for a receptor. The selectivity of a ligand with respect to its target receptor relative to another receptor is given by the ratio of the respective values of Kd (i.e., the dissociation constants for each ligand-receptor complex), or in cases where a biological effect is observed below the Kd, selectivity is given by the ratio of the respective EC50 values (i.e. the concentrations that produce 50% of the maximum response for the ligand interacting with the two distinct receptors).

The term "therapeutically effective amount" refers to that amount which is sufficient to effect treatment, as defined above, when administered to a subject, such as a mammal, including a human in need of such treatment. The therapeutically effective amount will vary depending on the subject and disease state being treated, the severity of the affliction and the manner of administration, and may be determined routinely by one of ordinary skill in the art.

The term "treatment" as used herein covers any treatment of a condition or disease in an animal, preferably a mammal, more preferably a human, and includes: (i) preventing the disease or condition from occurring in a subject which may be predisposed to the disease but has not yet been diagnosed as having it; (ii) inhibiting the disease or condition, i.e. arresting its development; (iii) relieving the disease or condition, i.e. causing regression of the condition; or (iv) relieving the conditions caused by the disease, i.e. symptoms of the disease.

It is understood that the compounds of the present invention may exist in one or more stereoisomeric forms (e.g. enantiomers, diastereomers). The present invention includes within its scope all of these stereoisomeric forms either isolated (in for example enantiomeric isolation), or in combination (including racemic mixtures).

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

EXAMPLES

Aspects disclosed herein are further described by the following non-limiting examples.
General Chemistry Procedures Unless stated otherwise, all reactions were conducted in an atmosphere of nitrogen. NMR spectra were collected using a Bruker Ultraspin 400 MHz spectrometer ($^1$H 400 MHz; $^{13}$C 100 MHz). FT-IR spectra were recorded using a Perkin Elmer Spectrum 100 FT-IR spectrometer fitted with a universal ATR sampling accessory. Melting points were measured using a Barnstead 9100 electrothermal melting point apparatus. Optical activity was measured using a Rudolph Research Analytical Autopol I automatic polarimeter. Flash chromatography was conducted using Merck silica gel 60 μm. Reactions were monitored by thin layer chromatography (TLC) using Merck silica gel 60 μm TLC plates with aluminium backing and containing F254 fluorescent indicator. Compounds were visualized on the TLC plates using ultraviolet light followed by staining with potassium permanganate solution containing KMnO$_4$ (1.5 g), K$_2$CO$_3$ (10 g), 10% NaOH solution (1.25 mL) diluted to 200 mL with deionized water or by staining with a solution containing 10% H$_2$SO$_4$ in ethanol.

All organic extracts were dried with anhydrous magnesium sulphate unless otherwise stated and filtered prior to removal of the solvent under reduced pressure. The abbreviations used are as follows: DMF (N,N-dimethylformamide), Ac$_2$O (acetic anhydride), DMSO (dimethylsulfoxide), MeOH (methanol), THF (tetrahydrofuran), PPh$_3$ (triphenylphosphine), NBS (N-bromosuccinimide), DCM (dichloromethane).

Example 1

6'-azideo-6'-deoxysucrndose (1)

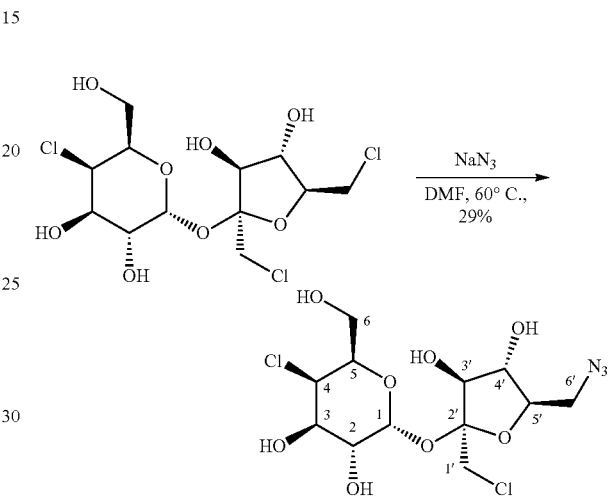

Sucralose (4.069 g, 10.23 mmol) was dissolved in DMF (10 mL) and sodium azide (1.48 g, 22.77 mmol) was added. The reaction mixture was heated at 120° C. for 60 hours. Solvent was removed by reduced pressure. Residue was dissolved in hot 2-propanol and filtered to remove unwanted salts. The filtrate was concentrated under reduced pressure to obtain a brown colored viscous oil. The oil was purified by flash chromatography (eluent, 95:1 ethyl acetate/methanol) to afford 6'-azido-6'-deoxysucralose 1 (1.227 g, 29%) as a pale yellow viscous oil. Compound was unable to be fully characterized by $^1$H NMR.

$^1$H NMR (D$_2$O, 400 MHz): 5.51 (d, 1H, J=4 Hz, H-1), 4.57 (m, 1H, H-4), 4.41-4.48 (m, 2H, H-3', H-5), 4.09-4.25 (m, 3H), 3.93-4.06 (m, 2H), 3.77-3.88 (m, 4H), 3.61-3.67 (dd, 1H).

$^{13}$C NMR (D$_2$O, 100 MHz): 103.4, 92.64, 80.0, 76.0, 74.4, 71.6, 71.2, 70.9, 61.7, 60.6, 52.6, 43.5.

R$_f$=0.76 (95:5 ethyl acetate/methanol)

Example 2

2,3,3',4',6-Penta-O-acetyl sucralose (2)

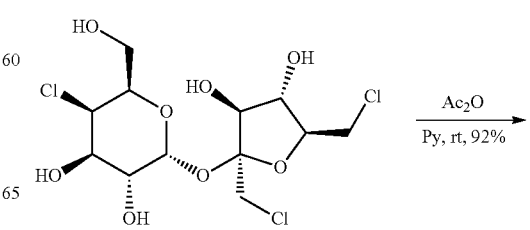

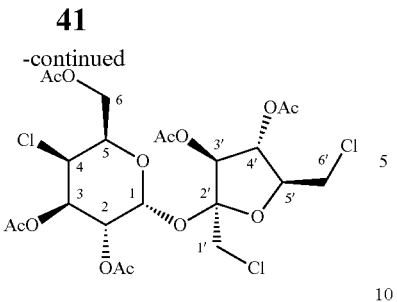

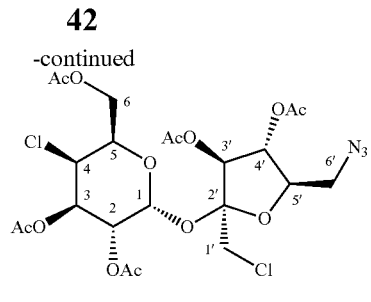

Sucralose (6.125 g, 15.40 mmol) was dissolved in pyridine (80 mL) and acetic anhydride (30 mL) was added. The reaction mixture was stirred at room temperature for 18 hours under nitrogen atmosphere. Pyridine was removed under reduced pressure and the remaining reaction mixture dissolved in ethyl acetate (50 mL). This was washed with HCl (1M, 3×30 mL), brine solution (30 mL), ammonia solution (30%, 1×60 mL), and brine solution (30 mL). Aqueous washings were discarded. The organic extracts were concentrated under reduced pressure to afford 2,3,3',4',6-penta-O-acetyl sucralose 2 (8.616 g, 92%) as a white crystalline powder. Compound was sufficiently pure for subsequent steps.

$^1$H NMR (CDCl$_3$, 400 MHz): 5.69 (d, 1H, J=6.4 Hz, H-3'), 5.67 (m, 1H, H-1), 5.41 (t, 1H, J=6.4 Hz, H-4'), 5.30 (t, 2H, J=1.9 Hz, H-2, H-3), 4.54-4.59 (m, 2H, H-4, H-5), 4.36-4.42 (m, 1H, H-5'), 4.22-4.28 (m, 3H, H-6a, H-6b, H-5'), 3.77 (dd, 2H, J=0.8, 6 Hz, H-6'a, H-6'b) 3.69-3.73 (d, 1H, J=12.0 Hz, H-1'a) 3.57-3.61 (d, 1H, J=12 Hz, H-1'b) 2.00-2.15 (5×AcO).

$^1$H NMR (d$_6$-acetone, 400 MHz): 4.99-5.02 (m, 2H, H-1, H-3'), 4.68-4.75 (m, 2H, H-4', H-3), 4.52-4.57 (dd, J=3.6, 10.8 Hz, H-2), 4.03-4.06 (dd, 1H, J=1.6, 3.6 Hz, H-4), 3.96-4.01 (m, 1H, H-5), 3.54-3.60 (m, 1H, H-5'), 3.51 (d, 2H, J=6 Hz, H-6a, H-6b), 3.16-3.20 (m, 3H, H-6'a, H-6'b, H-1'a) 3.08-3.13 (d, 1H, J=12 Hz, H-1'b), 1.30-1.37 (5x OAc).

$^{13}$C NMR (d$_6$-acetone, 100 MHz): 169.8-169.3 (5×C=O), 104.3 (C, C-2'), 90.9 (CH, C-1), 80.9 (CH, C-5'), 75.8 (CH), 75.7 (CH), 67.9 (CH-5), 67.6 (CH, C-3), 66.7 (CH, C-2), 63.5 (CH$_2$, C-6), 60.1 (CH, C$_4$), 44.5 (2×CH$_2$), 19.9-19.6 (5×CH$_3$).

ATR-FTIR: 2940 (C—H), 1730 (C=O), 1365 (C—C—C), 1215 (C—C(=O)—O), 1055 (C—O—C)

R$_f$=0.42 (1:1 ethyl acetate/petroleum spirits 40-60). $[\alpha]_D^{22.4}$+66.5 (c 1. CH$_3$OH); lit.+66.8 (c 0.9) M.P. 86-90° C.; lit. 92-94° C.

Example 3

2,3,3',4',6-Penta-O-acetyl-6'-azido-6'-deoxysucralose (3)

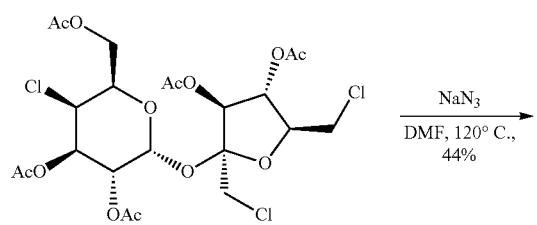

Sucralose pentaacetate 2 (4.025 g, 6.62 mmol) was dissolved in DMF (15 mL) and sodium azide (0.489 g 7.52 mmol) was added. The reaction mixture was heated at 120° C. for 24 hours. Solvent was removed by reduced pressure. The residue was dissolved in a mixture of DCM/water (1:1, 100 mL). The aqueous phase was extracted with DCM (3×50 mL). The organic extracts were combined and washed with copper sulfate solution (3×30 mL) and brine solution (30 mL). The organic extract was dried over magnesium sulfate, and concentrated under reduced pressure to obtain crude material as a yellow viscous oil. The residue was purified by flash chromatography (eluent, 1:1 ethyl acetate/petroleum spirits 40-60) to afford 2,3,3',4',6-penta-O-acetyl-6'-azido-6'-deoxysucralose 3 (1.784 g, 44%) as a faintly yellow viscous oil.

$^1$H NMR (CDCl$_3$, 400 MHz): 5.70 (d, 1H, J=6.8 Hz, H-3'), 5.66 (d, 1H, J=3.6 Hz, H-1), 5.31-5.36 (m, 2H, J=6.8 Hz, H-3, H-4'), 5.25-5.30 (dd, 1 H, J=3.6, 10.8 Hz, H-2), 4.53-4.88 (m, 2H, H-4, H-5), 4.20-4.26 (m, 2H, H-6a H-6b), 4.10-4.17 (td, 1H, J=4.0, 6.8 Hz H-5') 3.68-3.73 (d, 1H, J=12.0 Hz, H-1'a) 3.57-3.65 (m, 2H, H-1'b, H-6'a) 3.49-3.55 (dd, 1H, J=4, 13.2H-6'b) 2.06-2.13 (5×AcO).

$^{13}$C NMR (CDCl$_3$, 100 MHz): 170.3-169.6 (5×C=O), 104.2 (C, C-2'), 90.8 (CH, C-1), 79.6 (CH, C-5'), 75.6 (CH, C-3'), 75.1 (CH, C-4'), 67.9 (CH), 67.7 (CH), 67.0 (CH), 63.5 (CH$_2$, C-6), 58.9 (CH), 52.5 (CH$_2$, C-6'), 44.5 (CH$_2$, C-1'), 20.4-21.0 (5×CH$_3$).

ATR-FTIR: 2961 (C—H), 2103 (N$_3$), 1742 (C=O), 1370 (C—C—C), 1215, (C—C(=O)—O), 1040 (C—O—C) cm$^1$

R$f$=0.55 (1:1 ethyl acetate/petroleum spirits 40-60). $[\alpha]_D^{21.0}$+83.3 (c 1. CH$_3$OH).

Example 4

Prepargyl Triethylene glycol (4)

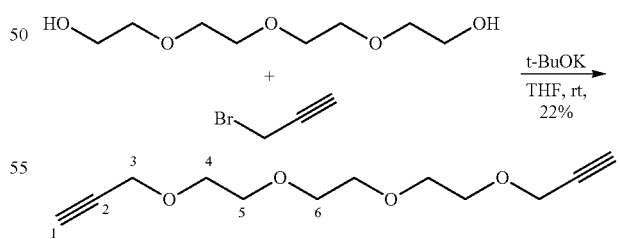

Potassium tert-butoxide (5.098 g, 45.4 mmol) was dissolved in dry THF (30 mL) under nitrogen atmosphere. Triethylene glycol (2.251 g, 14.99 mmol) was dried by co-evaporation with toluene (15 mL) under reduced pressure. The dried triethylene glycol was dissolved in dry THF (5 mL) and added to the reaction mixture. The mixture was allowed to react at room temperature for 1 hour. Propargyl bromide (80%, 4.8 mL, 50.68 mmol) was dissolved in dry THF (30 mL) and added drop-wise to the reaction mixture. It was stirred overnight at room temperature. The mixture was diluted with brine:water (4:1, 100 mL) and extracted with ethyl acetate (3×50 mL). The organic extracts were combined and washed with brine:water (1:1, 40 mL) and brine (80 mL). The organic extract was dried over magnesium sulfate and concentrated under reduced pressure to collect a yellow oil. The oil was purified by flash chromatography (eluent, 40:60 ethyl acetate/petroleum spirits 40-60) to afford propargyl triethylene glycol 4 as a yellow oil (778 mg, 22%).

$^1$H NMR (CDCl$_3$, 400 MHz): 4.15 (d, 2H, J=2.4 Hz, H-3a, H-3b), 3.60-3.67 (m, 6H, H-4a, H-4b, H-5a, H-5b, H-6a, H-6b), 2.4 (t, 1H, J=2.4 Hz, H-1).

$^{13}$C NMR (CDCl$_3$, 100 MHz): 79.6 (CH, C-1), 74.7 (C, C-2), 70.6 (CH$_2$), 70.5 (CH$_2$), 69.0 (CH$_2$), 58.3 (CH$_2$, C-3).

ATR-FTIR: 3257 (C≡C—H), 2871 (C—H), 1089 (C—O—C) cm$^{-1}$

R$_f$=0.25 (3:7 ethyl acetate/petroleum spirits 40-60).

Example 5

Synthesis of Benzoylated Propargyl Mannose (5)

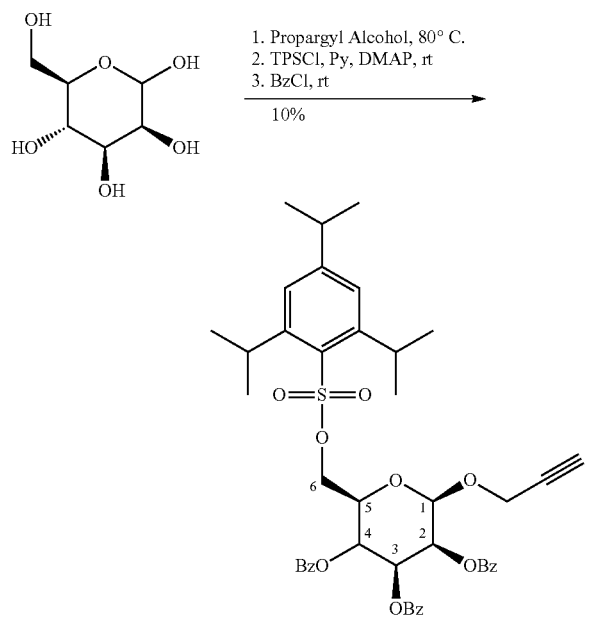

A mixture of mannose (1.8 g, 10 mmol), propargyl alcohol (2.3 ml, 40 mmol), and p-toluenesulfonic acid (172 mg, 1 mmol) was heated to 80° C. for 4 hours. The volatiles were removed. The residue was diluted with ethyl acetate (125 ml) and stirred vigorously overnight. The solvent was decanted and the residue dried to give an oil (1.3 g, 60%).

A solution of the forgoing propargyl mannose (1.283 g, 5.9 mmol) in anhydrous pyridine (10 ml) was cooled to 0° C. under nitrogen. To this 2,4,6-triisopropylbenzene sulfonyl chloride (2.68 g, 8.85 mmol) was added in portions. The solution was allowed to warm to room and stirred for 2 days. The reaction was cooled to 0° C. and benzoyl chloride (2.26 ml, 13.4 mmol) was added dropwise. A few crystals of 4-(dimethylamino)pyridine were added and the reaction mixture stirred for 3 days. The pyridine was removed. The residue was diluted with ethyl acetate (30 ml) and washed with 1M HCl solution (3×30 ml), NaHCO$_3$ solution (3×30 ml), and NaCl solution (3×30 ml), organic layer was dried over anhydrous magnesium sulfate and concentrated under reduced pressure to give a dark colored oil that under high vacuum becomes a brown sugar-like solid. The solid was subjected to flash chromatography using petroleum spirits and ethyl acetate (4:1) to give the title compound 5 (465 mg, 10%).

$^1$H NMR (CDCl$_3$, 400 MHz): 8.09 (dd, 2H, J=1.5, 8.3 Hz, H-Bz), 7.92 (dd, 2H, J=1.5, 8.3 Hz, H-Bz), 7.79 (dd, 2H, J=1.5, 8.3 Hz, H-Bz), 7.63-7.33 (m, 6H, H-Bz), 7.25 (bt, 3H, J=7.9 Hz, H-Bz), 7.14 (s, 2H, H-TIPBS Ar), 5.88 (dd, 1H, J=3.0, 10.2, Hz, H-3), 5.75 (t, 1H, J=10.5 Hz, H-4), 5.68 (dd, 1H, J=1.5, 3.0 Hz, H-2), 5.27 (d, 1H, J=1.5 Hz, H-1), 4.44 (m, 1H, H-5), 4.34 (dd, 2H, J=2.3, 3.8 Hz, H-propargyl CH$_2$), 4.27 (m, 2H, H-6), 4.08 (m, 2H, J=6.8 Hz, H-TIPBS CH), 2.87 (m, 1H, J=7.2 Hz, H-TIPBS CH), 2.49 (t, 1H, J=2.3 Hz, H-propargyl CH), 1.23 (d, 6H, J=7.3 Hz, H-TIPBS CH$_3$), 1.20 (d, 6H, J=7.3 Hz, H-TIPBS CH$_3$), 1.17 (d, 6H, J=6.8 Hz, H-TIPBS CH).

$^{13}$C NMR (CDCl$_3$, 100 MHz): 165.56 (1C, C═O), 165.37 (1C, C═O), 165.30 (1c, C═O), 153.79 (1C, Ar), 150.39 (1C, Ar), 133.57 (2CH, Bz), 133.20 (1CH, Bz), 130.59 (1C, Ar), 129.94 (2CH, Bz), 129.84 (2CH, Bz), 129.72 (2CH, Bz), 129.28 (1C, Ar), 129.71 (1C, Ar), 128.98 (I C, Ar), 128.89 (1C, Ar), 128.64 (2CH, Bz), 128.44 (2CH, Bz), 128.28 (2CH, Bz), 123.79 (2CH, TIPBS-Ar), 95.96 (1CH, C-1), 77.93 (1C, propargyl-C), 75.83 (1CH, propargyl-CH) 70.21 (1CH, C-2), 69.72 (1CH, C-3), 69.61 (1CH, C-5), 67.85 (1CH, C-6), 67.04 (1CH, C-4), 55.13 (1CH$_2$, propargyl-CH$_2$), 34.20 (1CH, TIPBS-CH), 29.69 (2CH, TIPBS-CH), 24.96 (2CH$_3$, TIPBS-CH$_3$), 24.65 (2CH$_3$, TIPBS-CH$_3$), 23.50 (2CH$_3$, TIPBS-CH$_3$).

Example 6

Alternative Synthesis of Benzoylated Prepargyl Mannose (5)

1,2,3,4,6-penta-O-acetyl-D-mannopyranose (6)

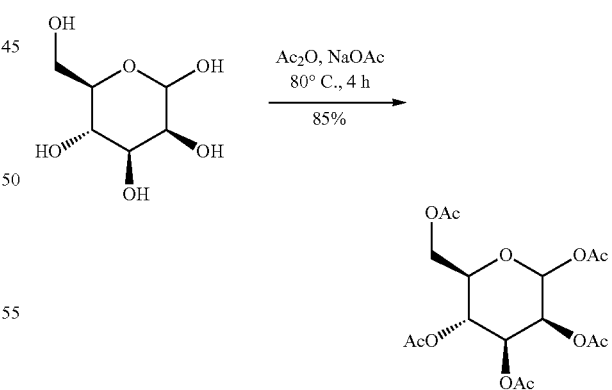

Acetic anhydride (20.7 mL, 160 mmol) was added to a mixture of D-mannose (3.0 g, 10.6 mmol) and sodium acetate (1.6 g, 20 mmol). The reaction mixture was then stirred at 80'C for 4 h. and poured into cold sat. NaHCO$_3$ solution (100 mL). The mixture was then stirred for 1 h, extracted with DCM (2×100 mL), dried (MgSO$_4$) and concentrated under reduced pressure. The pentaacetate 6 (3.5 g, 85%, a/l 1:0.4) was obtained as a colorless oil. The crude material was used in the subsequent step without further purification. $^1$H NMR (CDCl$_3$, 400 MHz): 6.06 (d, 1H, J=1.1 Hz), 5.84 (d, 0.4H, J=1.3 Hz), 5.46 (dd, 0.4H, J=1.1 Hz, J=3.3 Hz), 5.34-5.32 (m, 2H), 5.28 (d, 0.4H, J=9.9 Hz), 5.25-5.22 (m, 1H), 5.11 (dd, 0.4H, J=3.3 Hz, J=10.0 Hz), 4.28 (dd, 0.4H, J=5.4 Hz, J=12.5 Hz), 4.26 (dd, 1H, J=4.9 Hz, J=12.3 Hz), 4.15-3.98 (m, 2.4H), 3.78 (ddd, 0.4H, J=2.4 Hz, J=5.3 Hz, J=7.8 Hz), 2.19 (s, 1.2H, OCH$_3$), 2.16 (s, 3H, OCH$_3$), 2.15 (s, 3H, OCH$_3$), 2.08 (s, 1.3H, OCH$_3$), 2.07 (s, 4H, OCH$_3$), 2.03 (s, 4H, OCH$_3$), 1.99 (s, 4H, OCH$_3$).

Propynyl 2,3,4,6-tetra-O-acetyl-α-D-mannopyranoside (7)

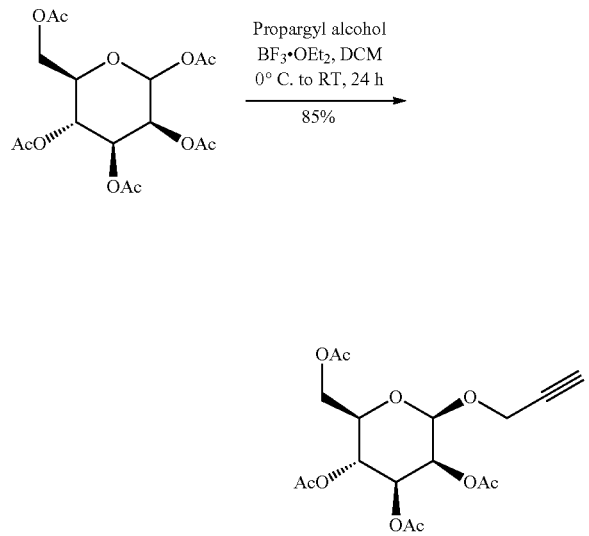

Propargyl alcohol (1.1 mL, 19.2 mmol) was added to a stirred solution of 1,2,3,4,6-penta-O-acetyl-D-mannopyranose 6 (1.5 g, 3.8 mmol) in dry DCM (20 mL). The mixture was cooled to 0° C. and BF$_3$·OEt$_2$ (4.9 mL, 38.4 mmol) was added dropwise. The resulting mixture was stirred for 15 min, brought to r.t., and the stirring was continued for 24 h. The reaction mixture was diluted with DCM (100 mL) and poured into ice-cold sat. NaHCO$_3$ (100 mL) solution. The resulting mixture was stirred until bubbling seized. The organic phase was then separated and washed with (3×50 mL) sat. NaHCO$_3$, water (100 mL), dried (MgSO$_4$) and concentrated under reduced pressure. The crude material was then purified by recrystallizing with Pet.spirit/EtOAc (8:1) to obtain 7 (1.2 g, 85%) as colorless needle like crystals. $^1$H NMR (CDCl$_3$, 400 MHz): 5.33 (dd, 1H, $J_{2,3}$=3.2 Hz, $J_{3,4}$=9.8 Hz, H-3), 5.29 (d, 1H, $J_{3,4}$=$J_{4,5}$=9.3 Hz, H-4), 5.26 (dd, 1H, $J_{1,2}$=1.8 Hz, $J_{2,3}$=3.2 Hz, H-2), 5.01 (d, 1H, $J_{1,2}$=1.8 Hz, H-1), 4.30-4.24 (m, 3H, H-6a, CH$_2$C≡CH), 4.09 (B-ABq, $J_{5,6b}$=2.5 Hz, $J_{6a,6b}$=12.3 Hz, H-6b), 4.00 (ddd, 1H, $J_{4,5}$=9.2 Hz, $J_{5,6}$=2.5 Hz, $J_{5,6a}$=5.3 Hz, H-5), 2.45 (t, 1H, J=2.4 Hz, CH$_2$C≡CH), 2.14 (s, 3H, CH$_3$), 2.09 (s, 3H, CH$_3$), 2.02 (s, 3H, CH$_3$), 1.97 (s, 3H, CH$_3$); $^{13}$C NMR (CDCl$_3$, 100 MHz): 170.6, 169.9, 169.8, 169.7 (4×CH$_3$CO), 96.3 (C-1), 77.9 (OCH$_2$C≡CH), 75.6 (OCH$_2$C≡CH), 69.3 (C-2), 69.0 (C-3), 68.8 (C-4), 66.1 (C-4), 62.3 (C-6), 55.0 (OCH$_2$C≡CH), 20.9, 20.7 (2×), 20.6 (4×CH$_3$CO); HRMS (ESI); m/z [M+Na]$^+$ calculated for C$_{17}$H$_{22}$O$_{18}$Na; found 409.1121.

Propynyl 2,3,4-tri-O-benzoyl-6-2,4,6-triisopropyl-benzene sulfonyl-α-D-mannopyranoside (5)

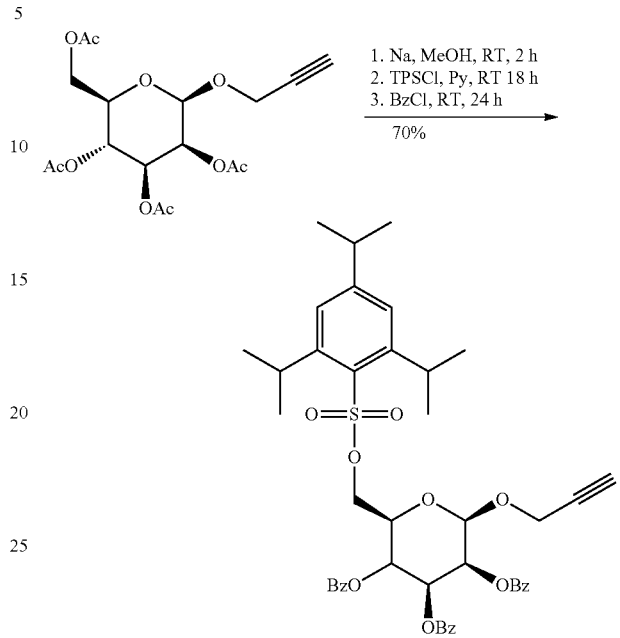

To a solution of mannopyranoside 7 (5.0 g, 13 mmol) in MeOH (50 mL), catalytic amount of sodium metal (~4 mg) was added and the mixture stirred at r.t. for 2 h. The reaction mixture was then neutralized with pre-washed acidic ion exchange resin (IR-120 H$^+$), filtered and concentrated under reduced pressure. The crude material was dissolved in anhydrous pyridine (50 mL) and cooled to 0° C. 2,4,6-triisopropylbenzene sulfonyl chloride (4.7 g, 16 mmol) was added to the reaction mixture and allowed to warm up to r.t., and stirred for 18 h. The reaction mixture was then cooled to 0° C. and benzoyl chloride (5.0 mL, 47 mmol) was added and stirred at r.t. for 24 h. The reaction mixture was concentrated under reduced pressure by co-evaporating the pyridine with toluene. The crude residue obtained was dissolved in EtOAc (100 mL) and washed with 1 M HCl (2×50 mL), sat. NaHCO$_3$ (50 mL), dried (MgSO$_4$) and concentrated under reduced pressure. The crude material was purified by flash column chromatography (Pet.Sp./EtOAc 3:1) on silica gel to afford the mannopyranoside 5 (7.3 g, 70%) as a colorless oil. $^1$H NMR (CDCl$_3$, 400 MHz): 8.06 (dd, 2H, J=1.1 Hz, J=8.1 Hz, H-OBz), 7.90 (dd, 2H, J=0.9 Hz, J=8.1 Hz, H-OBz), 7.78 (dd, 2H, J=1.2 Hz, J=8.3 Hz, H-OBz), 7.62-7.18 (m, 8H, H-OBz), 7.13 (s, 2H, H-OTPS), 5.87 (dd, 1H, $J_{2,3}$=3.3 Hz, $J_{3,4}$=10.0 Hz, H-3), 5.75 (dd, 1H, $J_{3,4}$=$J_{4,5}$=10.0 Hz, H-4), 5.67 (dd, 1H, $J_{1,2}$=1.8 Hz, J, =3.3 Hz, H-2), 5.26 (d, 1H, $J_{1,2}$=1.8 Hz, H-1), 4.47-4.40 (m, 1H, H-5), 4.32 (t, 2H, J=2.9 Hz, CH$_2$C—CH), 4.29-4.25 (m, 2H, H-6), 4.08 (h, 2H, J=6.9 Hz, J=13.3 Hz, J=20.1 Hz, CH-i-pr), 2.86 (p, 1H, J=6.9 Hz, J=13.3 Hz, J=20.1 Hz, CH-i-pr), 2.48 (t, 1H, J=2.4 Hz, CH$_2$C≡CH), 1.22 (s, 3H, CH$_3$), 1.19 (s, 3H, CH$_3$), 1.18 (s, 3H, CH$_3$), 1.17 (s, 3H, CH$_3$), 1.15 (s, 3H, CH$_3$); $^{13}$C NMR (CDCl$_3$, 100 MHz): 165.5, 165.3, 165.2 (3×C=O), 153.8, 150.9, 133.5, 129.9, 129.8, 129.7, 128.6, 128.4, 128.2, 123.7 (Ar-OTPS), 95.9 (C-1), 77.9, 77.2 (OCH$_2$C≡CH), 75.8 (OCH$_2$C≡CH), 70.2 (C-2), 69.7 (C-3), 69.6 (C-5), 67.8 (C-6), 67.0 (C-4), 55.1 (OCH$_2$C—CH), 34.1 (CH-i-pr), 29.6 (CH-i-pr), 24.6, 24.5, 23.4 (6×CH$_3$); HRMS (ESI); m/z [M+Na]$^+$ calculated for C$_{44}$H$_{48}$O$_{11}$NaS; found 819.2844.

Example 7

Synthesis of Acetylated Propargyl Mannose (8)

Propynyl 2,3,4-tri-O-acetyl-6-2,4,6-triisopropylbenzene sulfonyl-α-D-mannopyranoside (8)

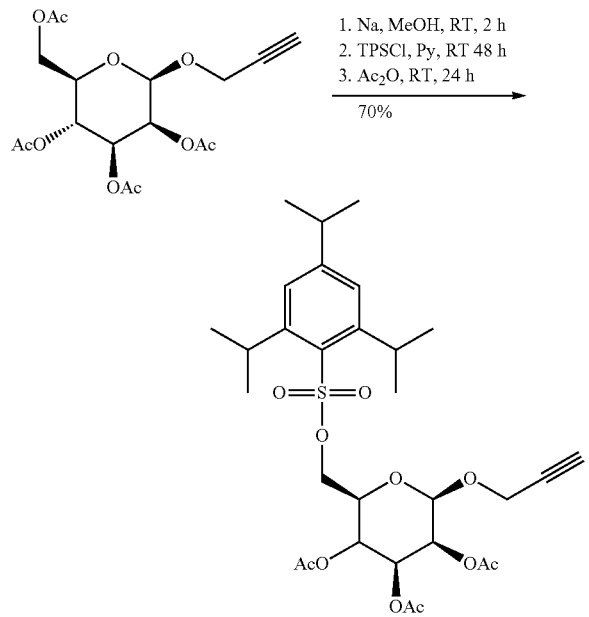

To a solution of mannopyranoside 7 (12.9 g, 33 mmol) in MeOH (200 mL), catalytic amount of sodium metal (~10 mg) was added and the mixture stirred at r.t. for 2 h. The reaction mixture was then neutralized with pre-washed acidic ion exchange resin (IR-120 H$^+$), filtered and concentrated under reduced pressure. The crude material was dissolved in anhydrous pyridine (200 mL) and cooled to 0° C. 2,4,6-triisopropylbenzene sulfonyl chloride (15 g, 50 mmol) was added to the reaction mixture and allowed to warm up to r.t., and stirred for 48 h. The reaction mixture was then cooled to 0° C. and acetic anhydride (12.5 mL) was added and stirred at r.t. for 24 h. The reaction mixture was concentrated under reduced pressure by co-evaporating the pyridine with toluene. The crude residue obtained was dissolved in EtOAc (500 mL) and washed with 1 M HCl (3×500 mL), sat. NaHCO$_3$ (500 mL), dried (MgSO$_4$) and concentrated under reduced pressure.

The crude material was purified by flash column chromatography (Pet.Sp./EtOAc 3:1) on silica gel to afford the mannopyranoside 8 (13.8 g, 70%) as a colorless oil. $^1$H NMR (CDCl$_3$, 400 MHz): 7.19 (s, 2H, Ar-OTPS), 5.32 (dd, 1H, J$_{2,3}$=3.5 Hz, J$_{3,4}$=9.8 Hz, H-3), 5.24 (dd, 1H, J$_{1,2}$=1.7 Hz, J$_{2,3}$=3.5 Hz, H-2), 5.13 (t, 1H, J$_{1,4}$=J$_{4,5}$=9.8 Hz), 4.97 (d, 1H, J$_{1,2}$=1.7 Hz, H-1), 4.20 (dd, J=2.5 Hz, J=3.3 Hz, CH$_2$C≡CH), 4.14-4.07 (m, 5H, H-5, H-6, CH-i-pr), 2.91 (h, 1H, J=6.9 Hz, J=13.6 Hz, J=20.1 Hz, CH-i-pr), 2.43 (t, 1H, J=2.3 Hz, CH$_2$C CH), 2.11 (s, 3H, OCH$_3$), 1.99 (s, 3H, OCH$_3$), 1.97 (s, 3H, OCH$_3$), 1.27 (2×s, 6H, CH$_3$), 1.25 (2×s, 6H, CH$_3$); $^{13}$C NMR (CDCl$_3$, 100 MHz): 169.9, 169.8, 169.7 (3×C=O), 153.9, 150.9, 129.2, 123.8 (Ar-OTPS), 95.8 (C-1), 77.2 (OCH$_2$C≡CH), 78.8 (d, J=214 Hz, OCH$_2$C≡CH), 69.3 (C-5), 69.2 (C-2), 68.7 (C-3), 67.6 (C-6), 66.4 (C-4), 54.8 (OCH$_2$C≡CH), 34.2 (CH-i-pr), 29.7 (CH-i-pr), 24.7 (×2), 23.5 (6×CH$_3$), 20.8, 20.6 (×2) (3×OCH$_3$).

Example 8

2,3,3',4',6-penta-O-acetyl sucralose (9)

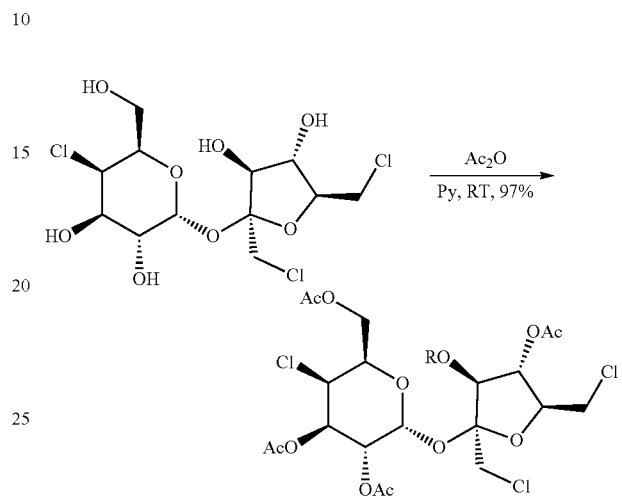

To a stirred solution of sucralose (6.1 g, 15 mmol) in pyridine (80 mL) was added acetic anhydride (15 mL, 100 mmol). The mixture was then stirred at r.t. for 24 h. and concentrated by co-evaporating pyridine with toluene. The crude material was dissolved in EtOAc (100 mL) and washed with 1M HCl (2×100 mL), 5% aq. NaHCO$_3$ (100 mL), brine (50 mL), dried (MgSO$_4$) and concentrated under reduced pressure to obtain a glassy solid. The crude material was recrystallized from toluene to obtain the pentaacetate 9 (8.5 g, 97%) as needle like crystals. $^1$H NMR (CDCl$_3$, 400 MHz): δ=5.67 (d, 1H, J$_{3',4'}$=6.4 Hz, H-3'), 5.65 (d, J$_{1,2}$=2.0 Hz, H-1), 5.29-5.27 (m, 2H, H-2, H-3), 4.58-4.52 (m, 2H, H-4, H-5), 4.27-4.19 (m, 3H, H-5', H-6a, H-6b), 3.75 (dd, 2H, J$_{5',6'}$=6.2 Hz, J$_{6'a,6'b}$=0.7 Hz, H-6'a, H-6'b), 3.69, 3.57 (ABq, 2H, J=12.1 Hz, H-1'), 2.12 (s, 3H, CH$_3$), 2.11 (s, 3H, CH$_3$), 2.09 (s, 3H, CH$_3$), 2.08 (s, 3H, CH$_3$), 2.07 (s, 3H, CH$_3$); $^{13}$C NMR (CDCl$_3$, 100 MHz): δ=170.4, 170.2, 170.0, 169.8, 169.6 (5×COCH$_3$), 104.4 (C-2'), 90.7 (C-1), 80.8 (C-5'), 77.2, 76.1 (C-4'), 75.9 (C-3'), 68.0 (C-2), 67.8 (C-4), 66.9 (C-3), 63.6 (C-6), 59.0 (C-5), 44.5 (C-1'), 43.9 (C-6'), 20.8, 20.7 (×2), 20.5 (5×COCH$_3$).

Example 9

2,3,3',4',6-penta-O-acetyl-6'-azido sucralose (10)

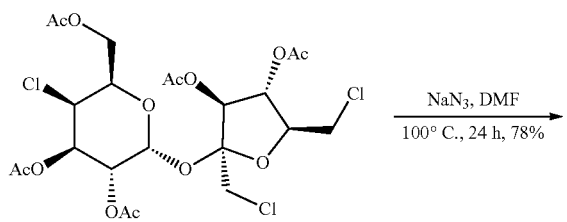

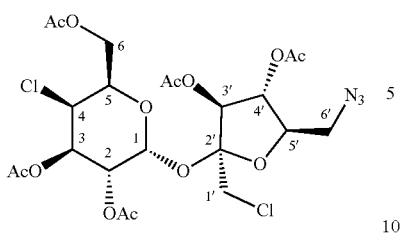

To a solution of 9 (3.8 g, 6.4 mmol) in dry DMF (20 mL), NaN$_3$ (1.3 g, 20 mmol) was added and the mixture was stirred at 100° C. for 24 h. The reaction mixture was then decanted and the residue left in the flask was washed with EtOAc (3×5 mL). The combined organic layer was then concentrated under reduced pressure. The crude material was dissolved in 1:1 DCM/H$_2$O (100 mL). The organic layer was extracted and the aqueous layer was back extracted with DCM (2×10 mL). The combined organic layer was washed with sat. CuSO$_4$ solution (100 mL), brine (50 mL), dried (MgSO$_4$) and concentrated under reduced pressure. The crude material was purified by flash column chromatography (Pet.sp./EtOAc 1:1) to obtain the azide 10 (3.1 g, 78%) as colorless oil. $^1$H NMR (CDCl$_3$, 400 MHz): δ=5.68 (d, 1H, $J_{r-4}$=6.9 Hz, H-3'), 5.64 (d, 1H, $J_{1,2}$=3.6 Hz, H-1), 5.32 (dd, 1H, $J_{2,3}$=10.7 Hz, H-3), 5.32-5.29 (m, 1H, H-4'), 5.25 (dd, 1H, H-2), 4.58-4.49 (m, 2H, H-4, H-5), 4.24-4.20 (m, 2H, H-6a, H-6b), 4.15-4.08 (m, 1H, H-5'), 3.69, 3.58 (ABq, 2H, J=12.1 Hz, H-1'), 3.64-3.56 (m, 1H, H-6'a), 3.50 (dd, 1H, $J_{6a',6b'}$=4.1 Hz, $J_{5,6b'}$=13.3 Hz, H-6b'), 2.10 (s, 3H, CH$_3$), 2.09 (s, 3H, CH$_3$), 2.08 (s, 3H, CH$_3$), 2.06 (s, 3H, CH$_3$), 2.05 (s, 3H, CH$_3$); $^{13}$C NMR (CDCl$_3$, 100 MHz): δ=170.3, 170.1, 170.0, 169.9, 169.7 (5×COCH$_3$), 104.1 (C-2'), 90.8 (C-1), 80.0 (C-5'), 75.6 (C-3'), 75.1 (C-4'), 67.9 (C-3), 67.7 (C-5), 67.0 (C-2), 63.4 (C-6), 58.9 (C-4), 52.5 (C-6'), 44.5 (C-1'), 20.7, 20.6, 20.6, 20.6, 20.4 (5×COCH$_3$); HRMS (ESI); m/z [M+Na]$^+$ calculated for C$_2$H$_{29}$Cl$_2$N$_3$O$_{13}$Na; found 636.0994.

Example 10

6-2,4,6-triisopropylbenzene sulfonyl-6'-azido sucralose (11)

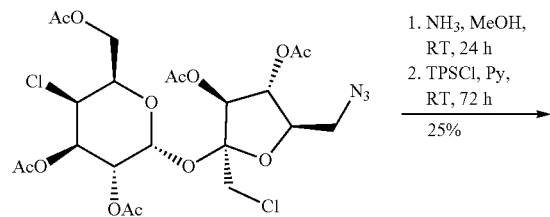

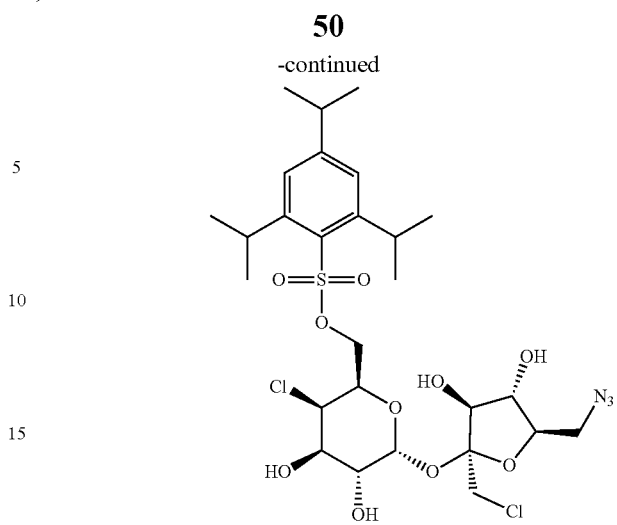

A mixture containing 30% aqueous NH$_3$ (3 mL) and sucralose azide 10 (1.7 g, 2.8 mmol) in MeOH (20 mL) was stirred at r.t. for 24 h. The reaction mixture was concentrated under reduced pressure to afford the polyol as a glassy solid. The crude material was then dissolved in pyridine (10 mL) and 2,4,6-triisopropylbenzene sulfonyl chloride (0.8 g, 2.7 mmol) was added to the mixture and stirred at r.t. for 3 days. The reaction mixture was concentrated under reduced pressure by co-evaporating pyridine with toluene. The crude material was purified by flash column chromatography (EtOAc) on silica gel to obtain compound 11 (0.25 g, 25%) as a colorless oil.

Example 11

2,3,3',4'-tetra-O-acetyl-6-2,4,6-triisopropylbenzene sulfonyl-6'-azido sucralose (12)

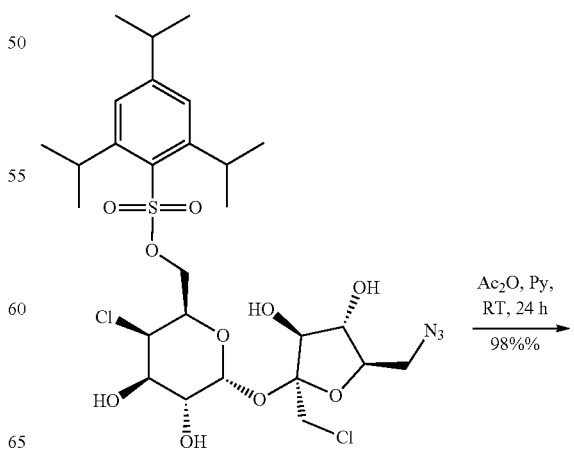

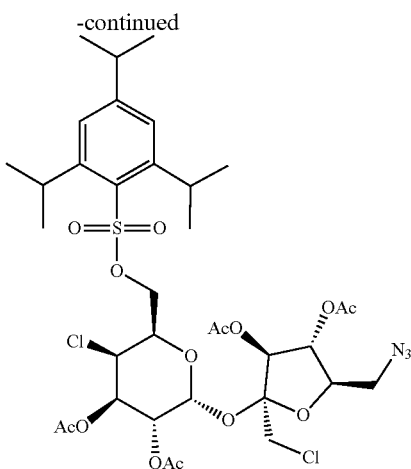

Acetic anhydride (0.3 mL, 3.1 mmol) was added to a mixture of compound 11 (250 mg, 0.6 mmol) in pyridine (10 mL). The mixture was then stirred at r.t. for 24 h. and concentrated under reduced pressure. The crude material was dissolved in EtOAc (50 mL) and washed with 1 M HCl (3×50 mL), sat. NaHCO$_3$ (50 mL), dried (MgSO$_4$) and concentrated under reduced pressure to obtain compound 12 (310 mg, 98%) as a yellow oil. $^1$H NMR (CDCl$_3$, 400 MHz): δ=7.19 (s, 2H, Ar—H), 5.74-5.68 (m, 2H, H-1, H-3'), 5.40-5.34 (m, 2H, H-3, H-4'), 5.25 (dd, 1H, J=3.8 Hz, J=10.7 Hz, H-2), 4.69 (dd, 1H, J=1.1 Hz, J=6.2 Hz, H-4), 4.57 (dd, 1H, J=1.4 Hz, J=3.6 Hz, H-5'), 4.29-4.01 (m, 5H, H-6, H-5, CH-i-Pr), 3.72, 3.58 (ABq, 2H, J=12.1 Hz, H-1'), 3.63-3.58 (m, 2H, H-6'), 2.91 (p, 1H, J=6.9 Hz, J=13.7 Hz, CH-i-pr), 2.16 (s, 3H, OCH$_3$), 2.11 (s, 3H, OCH$_3$), 2.10 (s, 3H, OCH$_3$), 2.08 (s, 3H, OCH$_3$), 1.27, 1.25 (s, 18H, 6×CH$_3$); $^{13}$C NMR (CDCl$_3$, 100 MHz): δ=170.1, 170.0, 169.8, 169.7, 154.1, 151.0, 128.8, 123.9, 104.5, 90.7, 80.3, 75.7, 75.0, 67.9, 67.7, 66.9, 66.8, 58.7, 52.3, 44.5, 34.2, 24.7, 23.5, 20.7, 20.6, 20.5.

Example 12

Acetylated propargyl maltotriose (13)

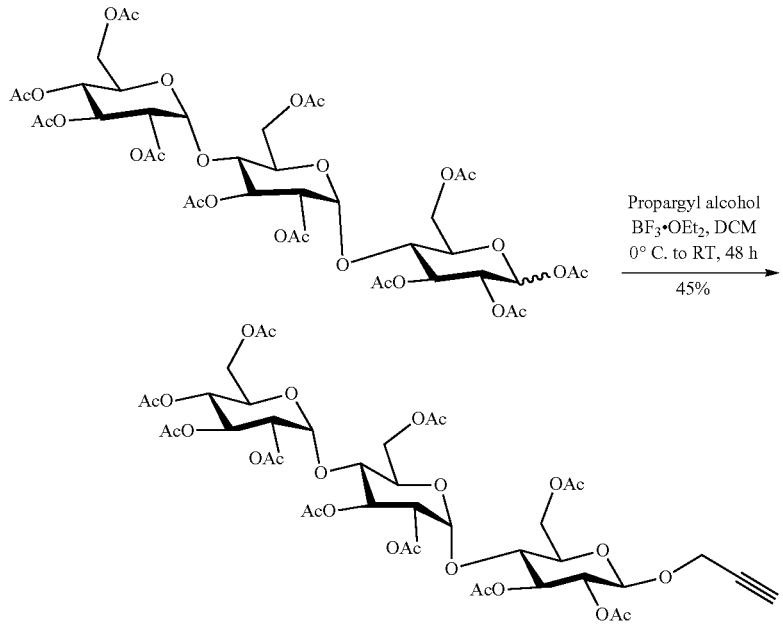

Boron trifluoride diethyl etherate (46 mL) was added dropwise to a mixture of peracetate maltotriose (13.3 g, 13.8 mmol) and propargyl alcohol (8.5 mL, 137 mmol) in dry DCM (500 mL) at 0° C. The mixture was then stirred at r.t. for 48 h. Sat. NaHCO$_3$ (10 mL) was then added to the reaction mixture and stirred for a further 10 min. The organic layer was extracted, dried (MgSO$_4$) and concentrated under reduced pressure. The crude material obtain was purified by flash column chromatography (3:1 EtOAc/Pet.Sp.) to obtain acetylated propargyl maltotriose 13 (6.0 g, 45%) as a glassy solid. $^1$H NMR (CDCl$_3$, 400 MHz): δ=5.43-5.22 (m, 6H), 5.04 (t, 1H, J=10.0 Hz), 4.86-4.76 (m, 3H), 4.71 (dd, 1H, J=4.1 Hz, J=10.4 Hz), 4.51-4.39 (m, 2H), 4.33 (d, 2H, J=2.3 Hz), 4.32-4.13 (m, 4H), 4.06-3.87 (m, 6H), 3.77-3.69 (m, 1H), 2.44 (t, 1H, J=2.4 Hz), 2.15, 2.13, 2.07, 2.02, 2.02, 2.00, 1.98, 1.97 (×2) (s, 3H, 9×CH$_3$); $^{13}$C NMR (CDCl$_3$, 100 MHz): δ=170.6 (×2), 170.5 (×2), 170.3, 170.1, 169.8, 169.7 (×2), 169.4, 97.5, 95.7 (×2), 77.2, 75.5, 75.2, 73.7, 72.5, 72.2, 71.8, 71.7, 70.4, 70.1, 69.4, 68.9, 68.5, 67.9, 62.8, 62.3, 61.4, 60.4, 55.8, 20.9, 20.8, 20.6, 20.5, 14.2; HRMS (ESI); m/z [M+Na]$^+$ calculated for C$_{41}$H$_{54}$O$_{26}$Na; found 385.2792.

Example 13

Acetylated propagyl acarbose (14)

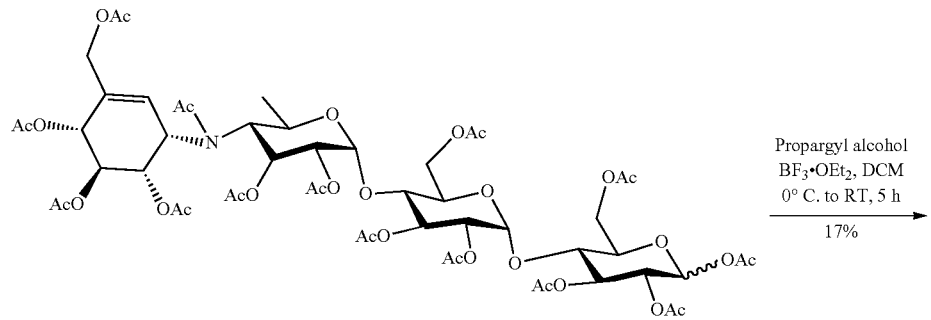

Boron trifluoride diethyl etherate (0.6 mL, 5 mmol) was added dropwise to a mixture of peracetate acarbose (0.6 g, 0.5 mmol) and propagyl alcohol (35 μL, 0.6 mmol) in dry DCM (20 mL) at 0° C. The mixture was then stirred at r.t. for 5 h. Saturated NaHCO$_3$ (10 mL) was then added to the reaction mixture and stirred for a further 10 min. The organic layer was extracted, dried (MgSO$_4$) and concentrated under reduced pressure. The crude material obtain was purified by flash column chromatography (3:1 EtOAc/Pet.Sp.) to obtain propagyl acarbose 14 (0.1 g, 17%) as a glassy solid. $^1$H NMR (CDCl$_3$, 400 MHz): δ=5.95 (d, 1H, J=5.3 Hz), 5.60-5.51 (m, 2H), 5.40-5.31 (m, 1H), 5.31-5.18 (m, 3H), 5.10 (t, 1H, J=10.2 Hz), 4.92 (dd, 1H, J=4.3 Hz, J=10.0 Hz), 4.85-4.69 (m, 4H), 4.67-4.60 (m, 1H), 4.49 (dd, 1H, J=2.9 Hz, J=12.3 Hz), 4.47-4.34 (d, 2H), 4.33 (d, 2H, J=2.3 Hz), 4.29 (dd, R H, J=4.0 Hz, J=12.4 Hz), 4.20-4.14 (m, 1H), 3.99 (t, 1H, J=9.3 Hz), 3.94-3.88 (m, 2H), 3.77-3.67 (m, 2H), 3.57-3.46 (m, 1H), 2.46 (t, 1H, J=2.4 Hz), 2.39 (t, 1H, J=9.9 Hz), 2.16, 2.13, 2.09, 2.04, 2.02, 2.01, 2.00, 1.97, 1.96 (s, OCH$_3$) ppm; $^{13}$C NMR (CDCl$_3$, 100 MHz): δ=171.0, 170.7, 170.6, 170.5, 170.3 (×2), 170.2, 169.9, 169.7, 169.6, 133.9, 128.0, 97.5, 95.8, 95.6, 78.0, 77.2, 75.5, 75.3, 73.3, 72.2 (×2), 71.8 (×2), 71.0, 70.9, 70.7, 70.5, 70.1, 69.8, 69.1, 63.0, 62.7, 62.2, 61.1, 55.8, 52.1, 20.8, 20.7, 20.6, 20.5 (×2), 18.1 ppm.

Example 14

Acetylated 4-pentynyl acarbose (15)

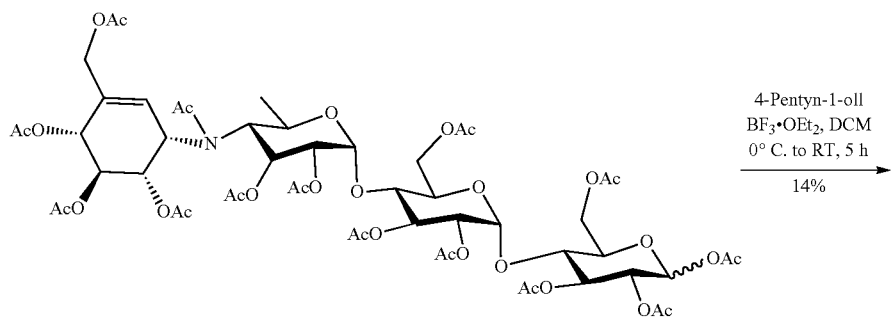

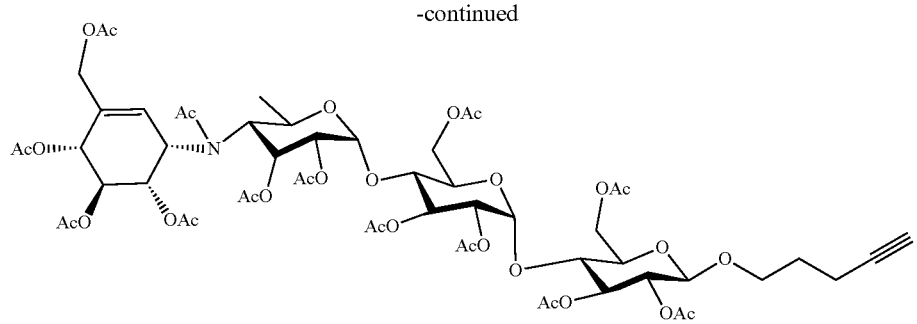

Boron trifluoride diethyl etherate (5 mL, 42 mmol) was added dropwise to a mixture of peracetate acarbose (1.0 g, 0.85 mmol) and 4-pentyn-1-ol (240 µL, 2.55 mmol) in dry DCM (20 mL) at 0° C. The mixture was then stirred at r.t. for 24 h. Saturated NaHCO$_3$ (10 mL) was then added to the reaction mixture and stirred for a further 10 min. The organic layer was extracted, dried (MgSO$_4$) and concentrated under reduced pressure. The crude material obtain was purified by flash column chromatography (3:1 EtOAc/Pet.Sp.) to obtain acetylated 4-pentynyl acarbose 15 (146 mg, 14%) as a glassy solid. $^1$H NMR (CDCl$_3$, 400 MHz): δ=5.96 (d, 1H, J=5.2 Hz), 5.62-5.45 (m, 2H), 5.36 (dd, 1H, J=7.9 Hz, J=10.2 Hz), 5.31-5.19 (m, 2H), 5.17-5.06 (m, 1H), 4.93 (dd, 1H, J=4.0 Hz, J=9.8 Hz), 4.86-4.69 (m, 3H), 4.65, 4.37 (ABq, 2H, J=13.1 Hz), 4.55-4.41 (m, 2H), 4.32 (m, 1H), 4.18 (dd, 1H, J=2.7 Hz, J=12.2 Hz), 4.01-3.88 (m, 3H), 3.78-3.67 (m, 2H), 3.65-3.49 (m, 2H), 2.40 (t, 1H, J=9.9 Hz), 2.23 (dt, 1H, J=2.6 Hz, J=6.9 Hz), 2.16 (s, 3H), 2.14 (s, 3H), 2.10 (s, 3H), 2.04 (s, 3H), 2.02-2.00 (s, 15H), 1.97 (s, 6H), 1.21 (d, 3H, J=6.3 Hz) ppm; $^{13}$C NMR (CDCl$_3$, 100 MHz): δ=170.9, 170.7, 170.6, 170.5, 170.4, 170.3, 170.2, 170.1, 169.9, 169.7 (×2), 134.0, 127.8, 100.4, 95.8, 95.6, 83.3, 77.2, 75.3, 73.5, 72.4, 72.2, 72.0, 71.9, 71.1, 70.8, 70.6, 70.5, 69.9, 69.7, 69.1, 68.8, 68.2, 63.0, 62.9, 62.2, 61.1, 52.2, 28.2, 20.9, 20.8, 20.7, 20.6 (×2), 20.5, 18.1 ppm.

Example 15

Protected Mannose Dimer (16)

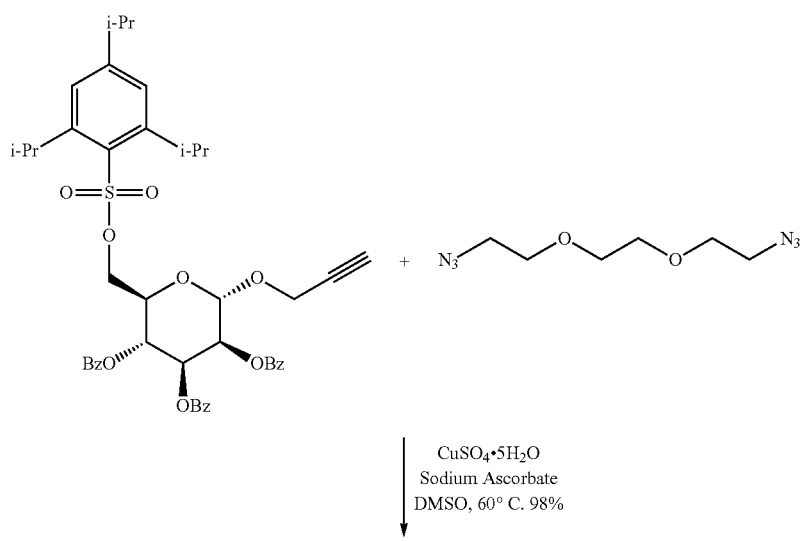

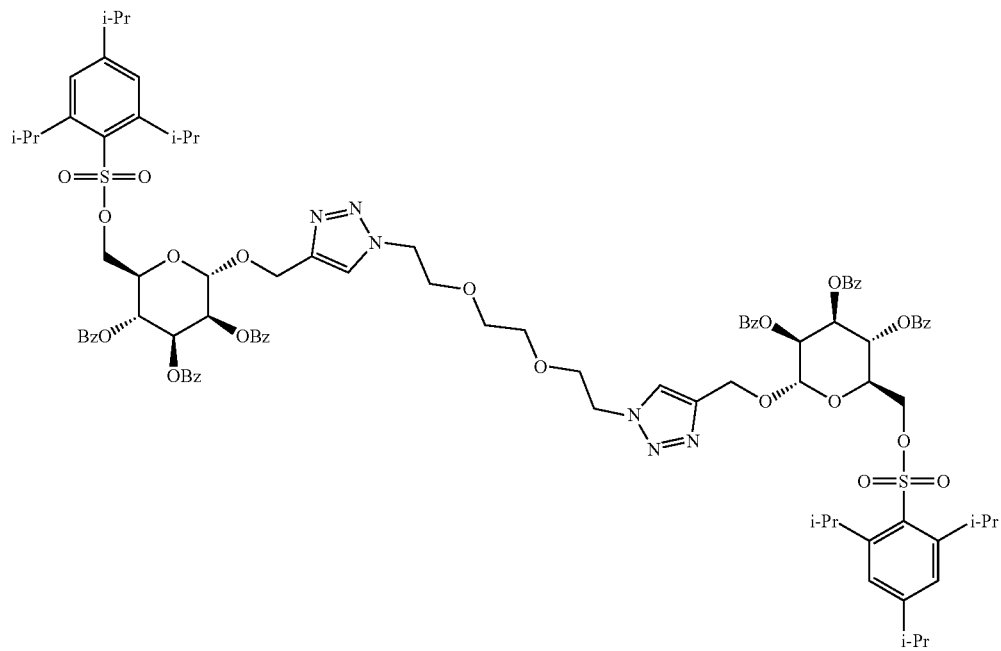

Copper(II) sulfate pentahydrate (72 mg, 0.288 mmol) and sodium ascorbate (171 mg, 0.846 mmol) were added successively to a solution of the mannose precursor 8 (153 mg, 0.192 mmol) and the azide linker (19 mg, 0.096 mmol) in DMSO. The reaction mixture was heated to 60° C. under nitrogen for 3 days. The reaction was allowed to cool and the DMSO removed by placing under a stream of nitrogen. The residue was diluted in ethyl acetate (20 ml) and washed with NaCl solution (3×20 ml). The combined aqueous layers were extracted with ethyl acetate (20 ml). The combined organic extracts were dried over anhydrous magnesium sulfate and concentrated to give the dimer 16 (170 mg, 98%).

$^1$H NMR (CDCl$_3$, 400 MHz): δ=8.05 (dd, 4H, J=1.2, 7.8 Hz, H-Bz), 7.91 (dd, 4H, J=1.2, 7.8 Hz, H-Bz), 7.86 (s, 2H, H-triazole), 7.77 (dd, 4H, J=1.2, 7.8 Hz, H-Bz), 7.62-7.32 (m, 12H, H-Bz), 7.23 (bt, 6H, J=7.6 Hz, H-Bz), 7.13 (s, 4H, H-TIPBS Ar), 5.87 (dd, 2H, J=3.3, 9.8 Hz, H-3), 5.79 (t, 2H, J=9.8 Hz, H4), 5.65 (dd, 2H, J=1.1, 2.7 Hz, H-2), 5.21 (d, 2H, J=1.1 Hz, H-1), 4.95 (d, 2H, J=12.5 Hz, H-propargyl CH$_{2-a}$), 4.79 (d, 2H, J=12.5 Hz, H-propargyl CH$_2$-b), 4.58 (t, 4H, J=4.9 Hz, H-PEG linker CH$_2$), 4.53 (m, 2H, H-5), 4.27 (m, 4H, H-6), 4.09 (m, 4H, J=7.1 Hz, H-TIPBS CH), 3.90 (t, 4H, J=4.9 Hz, H-PEG linker CH$_2$), 3.61 (s, 4H, H-PEG linker CH$_2$), 2.87 (m, 2H, J=7.1 Hz, H-TIPBS CH), 1.22 (d, 12H, J=7.1 Hz, H-TIPBS CH$_2$), 1.19 (d, 12H, J=7.1 Hz, H-TIPBS CH$_3$), 1.15 (d, 12H, J=7.1 Hz, H-TIPBS CH$_3$).

Example 16

Protected Mannose Dimer Bisazide (17)

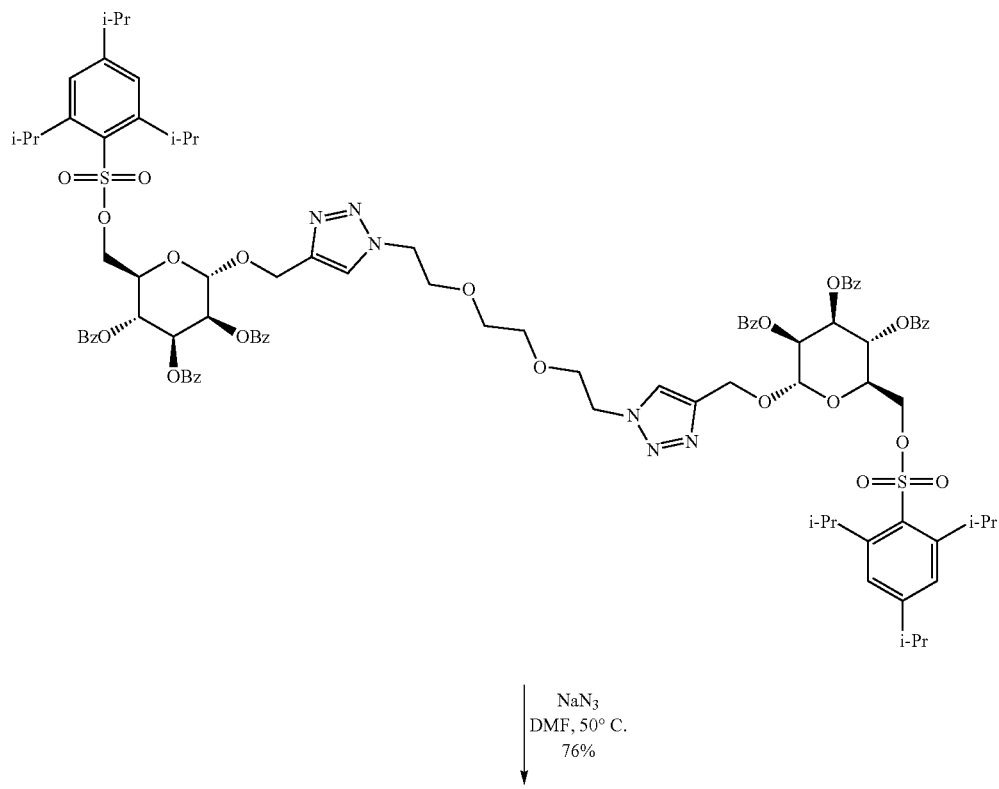

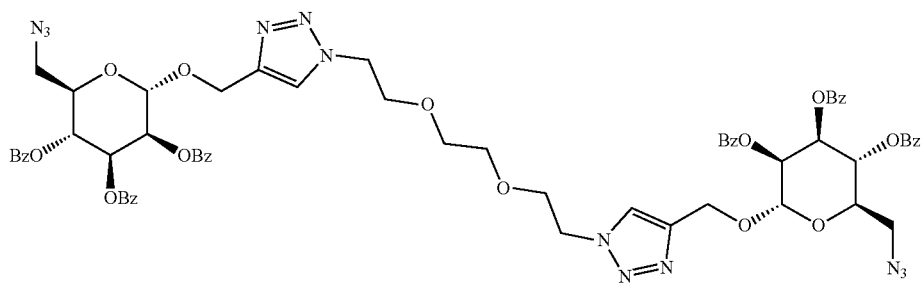

A solution of the dimer 16 (172 mg, 0.0947 mmol) and sodium azide (49 mg, 0.757 mmol) in DMF (3 ml) was stirred and heated to 50° C. overnight. The reaction was allowed to cool and the DMF removed by nitrogen stream. The residue was diluted in DCM (20 ml) and washed with 1M HCl solution (3×20 ml), NaHCO$_3$ solution (3×20 ml), NaCl solution (3×20 ml), CuSO$_4$ solution (3×20 ml), and water (20 ml). The aqueous layers were extracted with DCM (10 ml). The organic extract was dried over anhydrous magnesium sulfate and concentrated under reduced pressure to give the bisazide dimer 17 (96 mg, 76%).

$^1$H NMR (CDCl$_3$, 400 MHz): δ=8.07 (dd, 4H, J=1.6, 8.2 Hz, H-Bz), 7.94 (dd, 4H, J=1.6, 8.2 Hz, H-Bz), 7.83 (s, 2H, H-triazole), 7.78 (dd, 4H, J=1.6, 8.2 Hz, H-Bz), 7.63-7.33 (m, 12H, H-Bz), 7.24 (bt, 6H, J=7.6 Hz, H-Bz), 5.89 (t, 2H, J=9.8 Hz, H-4), 5.83 (dd, 2H, J=3.0, 9.8 Hz, H-3), 5.67 (dd, 2H, J=1.6, 3.3 Hz, H-2), 5.23 (d, 2H, J=161 Hz, H-1), 4.99 (d, 2H, J=12.5 Hz, H-propargyl CH$_{2-a}$), 4.81 (d, 2H, J=12.5 Hz, H-propargyl CH$_2$—), 4.58 (t, 4H, J=4.9 Hz, H-PEG linker CH$_2$), 4.36 (m, 2H, H-5), 3.89 (t, 4H, J=4.9 Hz, H-PEG linker CH$_2$), 3.61 (s, 4H, H-PEG linker CH$_2$), 2.87 (m, 2H, J=7.1 Hz, H-TIPBS CH), 3.50 (bd, 4H, J=4.3 Hz, H-6).

Example 17
Protected Hexamer (18)
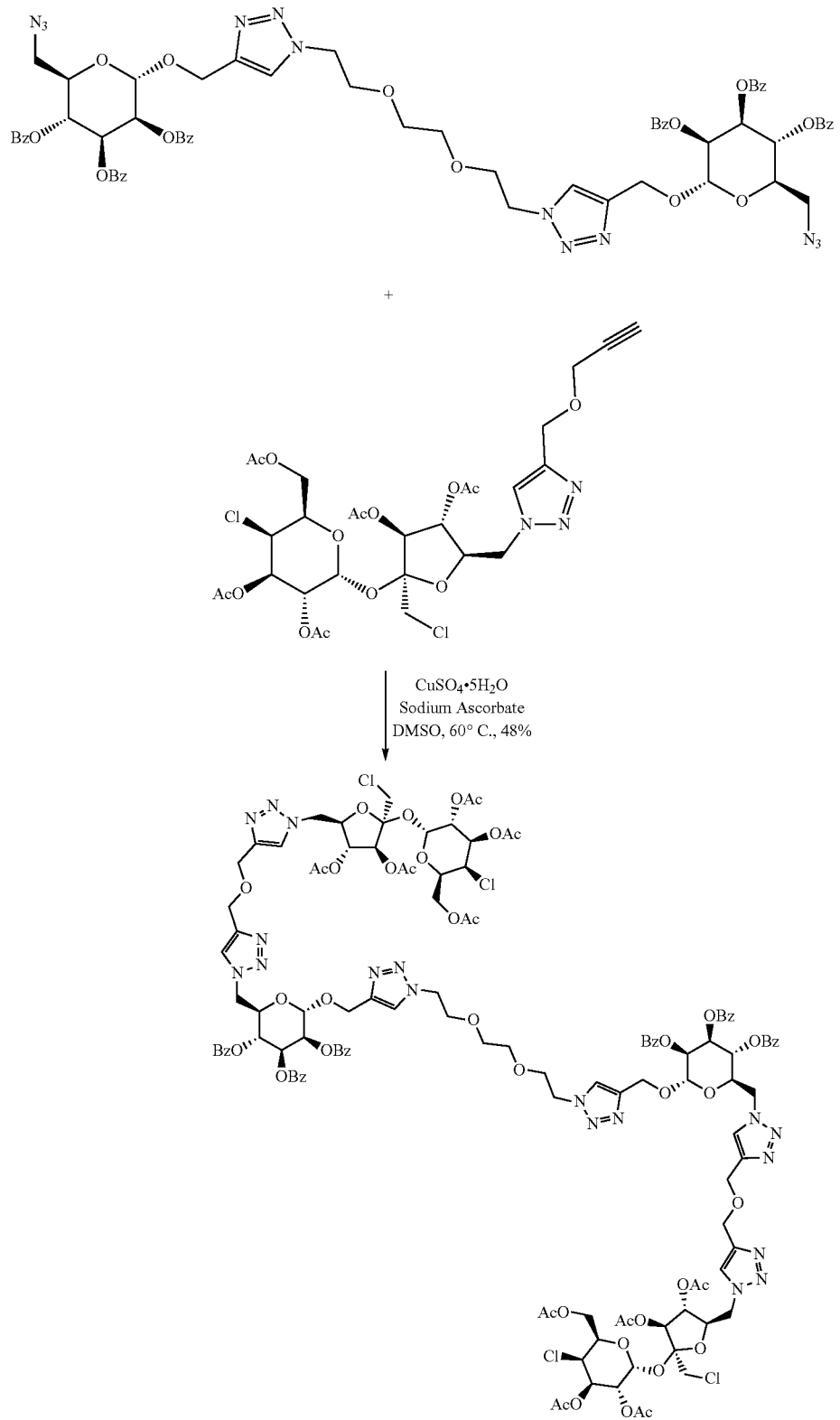

Copper(II) sulfate pentahydrate (23 mg, 0.0936 mmol) and sodium ascorbate (56 mg, 0.281 mmol) were added successively to a solution of the sucralose propargyl ether 26 (44 mg, 0.0624 mmol) and the bisazide dimer 17 (41 mg, 0.0312 mmol) in DMSO (3 ml). The reaction mixture was heated to 60° C. under nitrogen for 3 days. The reaction was allowed to cool and the DMSO removed by nitrogen stream. The residue was diluted in DCM (10 ml) and washed with NaCl solution (2×20 ml). The combined aqueous layers were back extracted with DCM (15 ml). The combined organic extracts were dried over anhydrous magnesium sulfate and concentrated to give the crude hexamer (83 mg, 97%). The oil was precipitated with methanol to give the pure hexamer 18 (41 mg, 48%).

$^{1}$H NMR (CDCl$_{3}$, 400 MHz): δ=8.01-7.96 (m, 8H, H-Bz), 7.92 (s, 2H, H-triazole), 7.77 (s, 2H, H-triazole), 7.75 (d, 4H, J=1.2 Hz, H-Bz), 7.71 (s, 2H, H-triazole), 7.64-7.34 (m, 12H, H-Bz), 7.23 (bt, 6H, J=7.9 Hz, H-Bz), 5.85 (dd, 2H, J=3.4, 10.1 Hz, H-3), 5.73-5.67 (m, 6H), 5.62 (dd, 2H, J=1.7, 3.4 Hz, H-2), 5.39 (t, 2H, J=7.3 Hz), 5.32 (bs, 4H), 5.18 (d, 2H, J=1.7 Hz, H-1), 4.85-4.51 (m, 28H), 4.41 (m, 2H), 4.32-4.18 (m, 6H), 3.87 (t, 4H, J=4.8 Hz, H-PEG linker CH$_{2}$), 3.62 (d, 4H, J=12.1 Hz), 3.60 (s, 4H, H-PEG linker CH$_{2}$), 3.53 (d, 4H, J=12.1 Hz), 2.13 (s, 6H, H-AcO CH$_{3}$), 2.10 (s, 6H, H-AcO CH$_{3}$), 2.08 (s, 6H, H-AcO CH$_{3}$), 2.06 (s, 6H, H-AcO CHs), 2.05 (s, 6H, H-AcO CH$_{3}$).

$^{13}$C NMR (CDCl$_{3}$, 100 MHz): δ=170.40, 170.17, 170.15, 169.99, 169.67, 165.72, 165.33, 165.26, 133.74, 133.69, 133.27, 129.93, 129.83, 129.68, 129.06, 128.87, 128.68, 128.59, 128.55, 128.32, 104.16, 96.73, 90.68, 79.51, 76.73, 75.45, 75.35, 70.50, 70.22, 69.70, 69.49, 69.29, 68.26, 68.01, 67.85, 66.90, 63.98, 63.39, 59.04, 44.68, 29.69, 20.76, 20.68, 20.65, 20.50.

Example 18

Global hydrolysis of Hexamer (19)

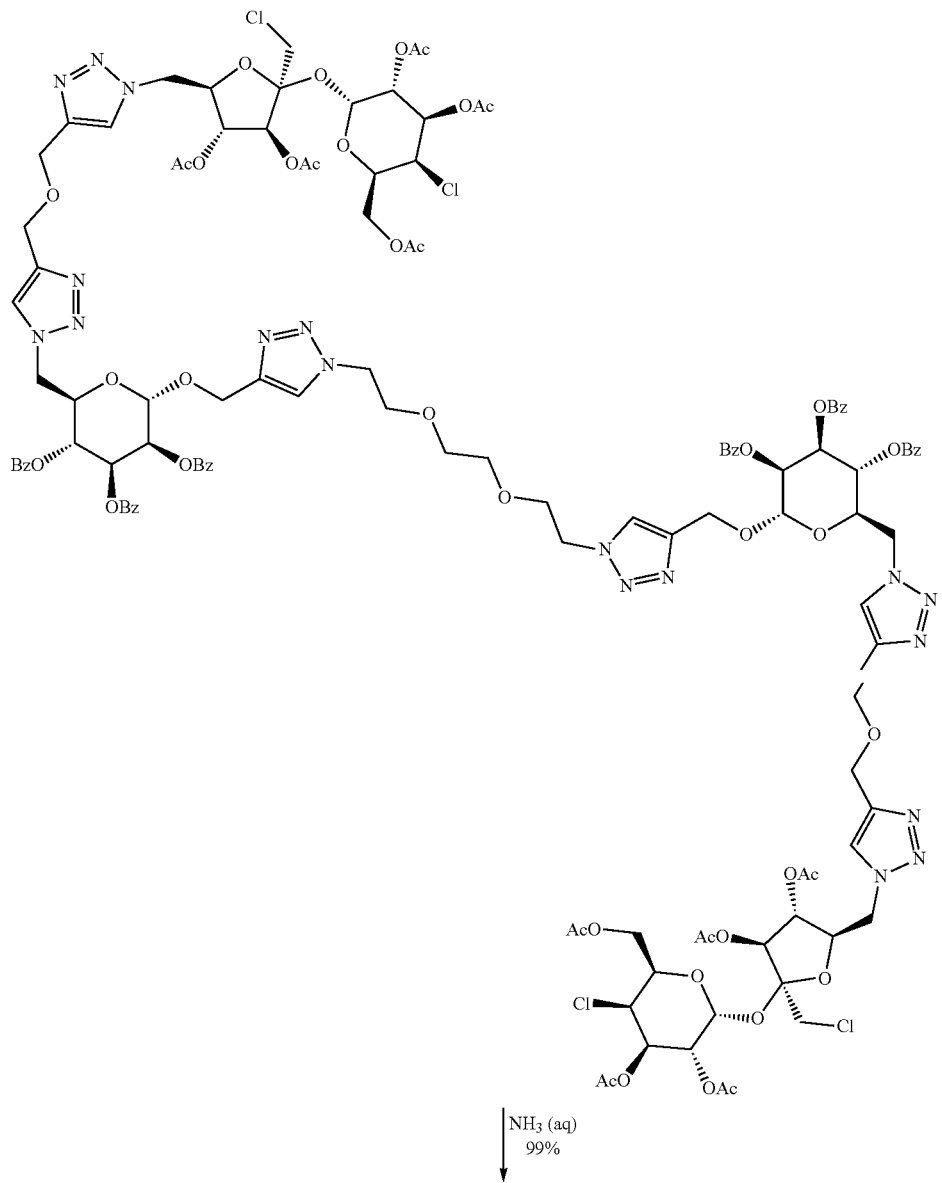

-continued

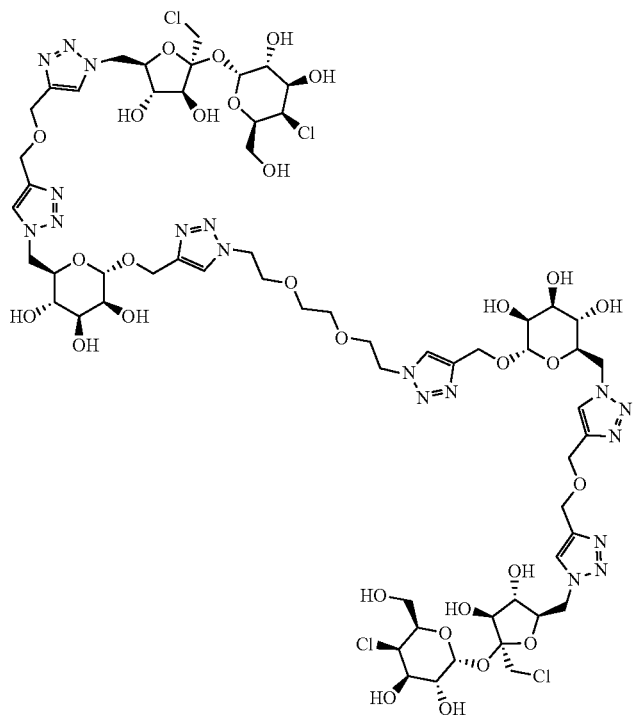

The hexamer 18 (41 mg, 0.015 mmol) was suspended in methanol (3 ml) and 30% ammonia solution (0.5 ml) was added drop-wise. The reaction was stirred overnight. The solvent was removed and the residue diluted in water (10 ml). The aqueous layer was washed with chloroform (4×10 ml) and concentrate under reduced pressure. The sample was dried by co-evaporation with ethanol to give the deprotected hexamer 19 (25 mg, 99%).

$^1$H NMR (D$_2$O, 400 MHz): δ=8.15 (s, 2H, H-triazole), 7.97 (s, 2H, H-triazole), 7.76 (s, 2H, H-triazole), 5.44 (d, 2H, J=4.2 Hz, H-1), 4.87 (bs, 6H), 4.70 (bs, 4H), 4.59 (bs, 6H), 4.54 (d, 2H, J=3.3 Hz), 4.48 (t, 4H, J=4.7 Hz), 4.45-4.38 (m, 4H), 4.34-4.14 (m, 10H), 3.98-3.87 (m, 6H), 3.83-3.74 (m, 10H), 3.71 (s, 4H), 3.63 (t, 2H, J=9.9 Hz), 3.51 (s, 4H).

$^{13}$C NMR (D$_2$O, 100 MHz): δ=143.79 (2C, triazole), 142.93 (2C, triazole), 126.25 (2CH, triazole), 125.62 (2CH, triazole), 125.08 (2CH, triazole), 103.45 (2C, C-2$_{fructose}$), 99.17 (2CH, C-1$_{mannose}$), 92.45 (2CH, C-1$_{gluctose}$), 79.57 (2CH, C-5$_{fructose}$), 75.52 (2CH, C-3$_{fructose}$), 74.85 (2CH, C-4$_{fructose}$), 71.76, 71.57, 70.92, 70.43, 70.27, 69.81, 69.58, 68.63, 68.02, 67.95, 67.50, 63.20, 62.39, 62.25, 61.91, 60.12, 59.25, 52.45, 51.13, 49.99, 43.63 (2CH$_2$, C-1$_{fructose}$).

Example 19

Sulfation of Hexamer (20)

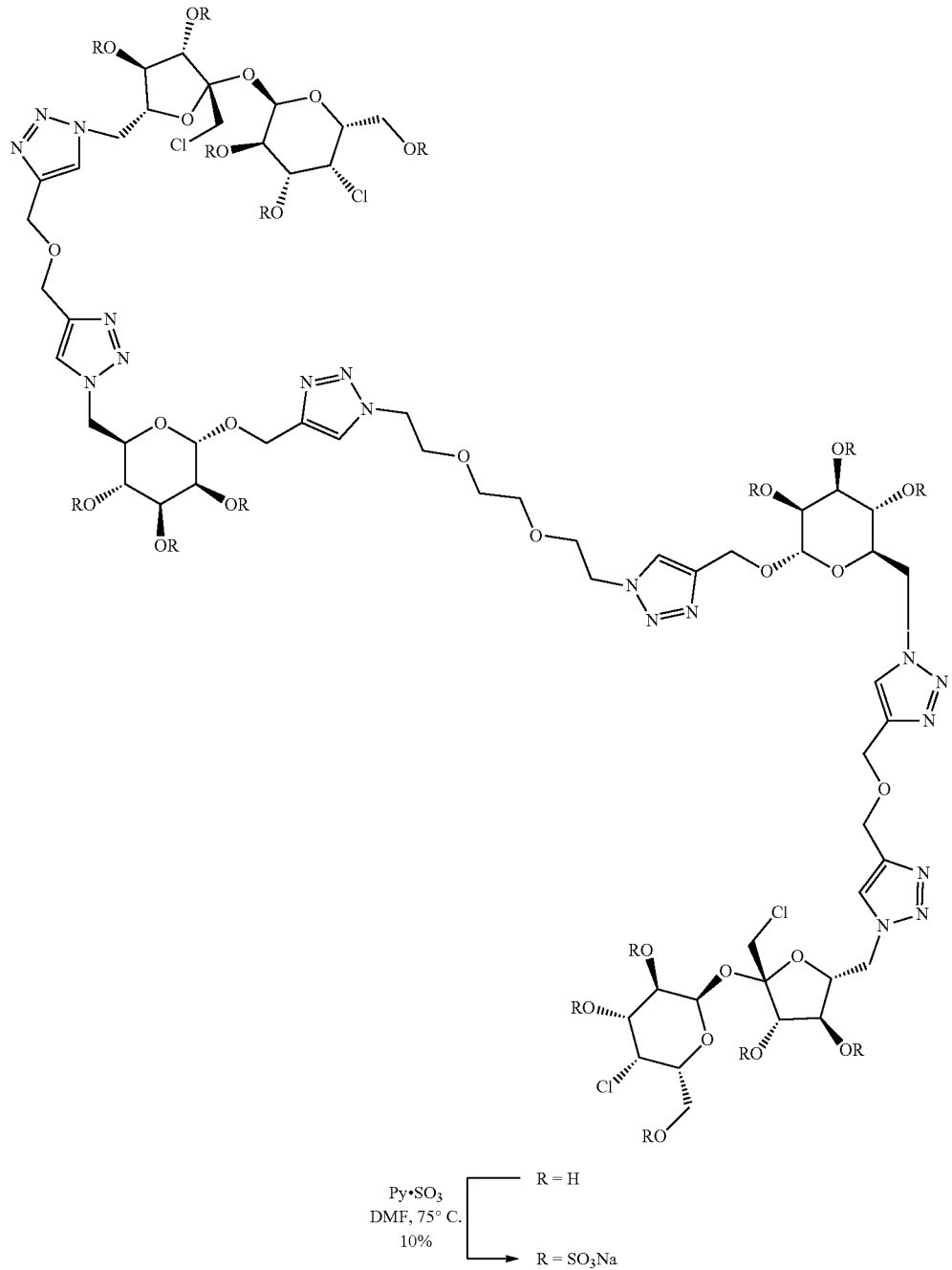

The hexamer 19 (24 mg 0.014 mmol) was dissolved in DMF (3 ml) and treated with freshly prepared pyridine sulfur trioxide complex (363 mg, 2.28 mmol, 10 eq. per OH group on the hexamer). The solution was stirred at 75° C. under nitrogen for 4 days. The solvent was removed by nitrogen stream. The residue was dissolved in water (10 ml) and treated with NaOH (109 mg, 2.74 mmol, 1.2 eq per PySO$_3$). The solution was stirred for 20 minutes under air and washed with ethyl acetate (5×10 ml) to remove the excess pyridine. The solvent was removed leaving a yellowish powder that was dried under high vacuum. The powder was treated with DMF (6×1 ml). The soluble component was taken up leaving behind the unwanted, insoluble simple salts. The DMF was removed and the residue dried under high vacuum. The residue was treated with ACN (6×2 ml). The soluble component was removed. It contained DMF only and was discarded. The insoluble component was dried under high vacuum giving DMF-free sulfated hexamer 20 (4.7 mg, 10%).

$^1$H NMR (D$_2$O, 400 MHz): δ=8.25 (s, 2H, H-triazole), 8.10 (s, 2H, H-triazole), 7.93 (s, 2H, H-triazole), 5.82 (d, 2H, J=3.5 Hz), 5.38 (d, 2H, J=7.6 Hz), 5.24 (d, 2H, J=1.4 Hz), 5.16-5.06 (m, 5H), 5.03-4.93 (m, 10H), 4.89 (m, 6H), 4.71 (s, 5H), 4.60 (t, 4H, J=12.9 Hz), 4.55 (d, 2H, J=10.0 Hz), 4.43 (s, 4H), 4.37-4.23 (m, 6H), 3.99 (d, 2H, J=12.9 Hz), 3.92 (m, 6H), 3.59 (s, 4H).

$^{13}$C NMR (D$_2$O, 100 MHz): δ=143.69 (2C, triazole), 142.85 (2C, triazole), 126.38 (2CH, triazole), 126.20 (2CH, triazole), 125.23 (2CH, triazole), 103.54 (2C, C-2$_{fructose}$), 96.25 (2CH, C-1$_{mannose}$), 90.91 (2CH, C-1$_{gluctose}$), 79.53, 79.46, 78.33, 75.15, 73.52, 72.72, 72.37, 71.33, 70.39, 69.67, 68.78, 68.46, 67.92, 62.27, 60.27, 59.96, 52.76, 50.97, 50.07, 43.90 (2CH$_2$, C-1$_{fructose}$).

Example 20

Protected Mannose Tetramer (21)

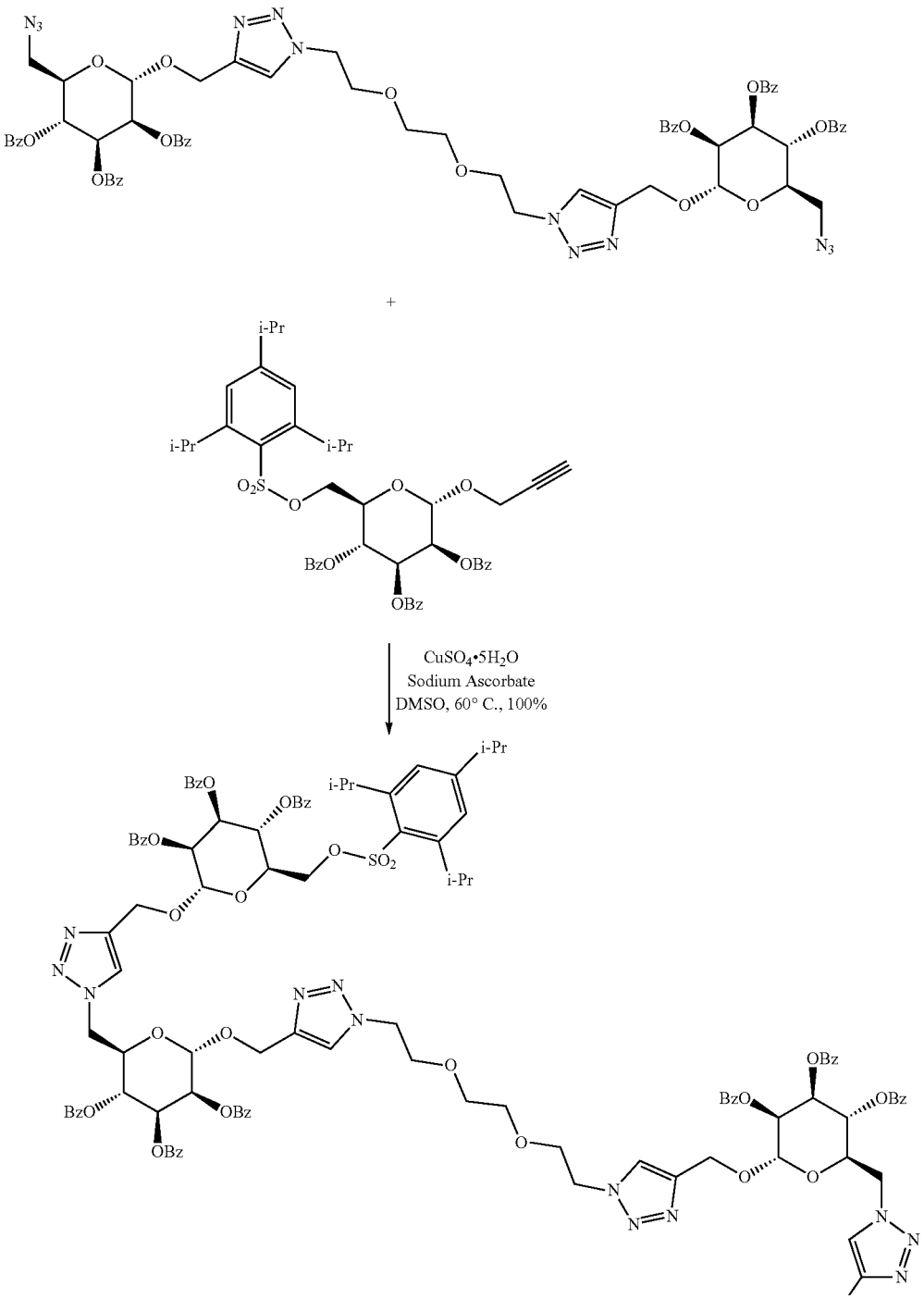

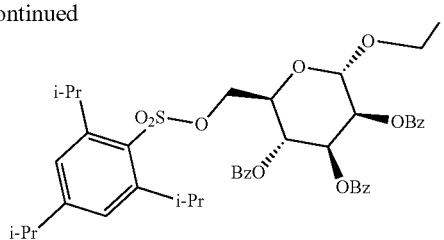

Copper(II) sulfate pentahydrate (31 mg, 0.124 mmol) and sodium ascorbate (74 mg, 0.373 mmol) were added successively to a solution of the mannose 5 (100 mg, 0.125 mmol) and the azide dimer 17 (82 mg, 6.25×10$^{-2}$ mmol) in DMSO (2 ml). The reaction mixture was heated to 60° C. under nitrogen for 3 days. The reaction was allowed to cool and the DMSO removed by nitrogen stream. The residue was diluted in ethyl acetate (10 ml) and washed with NaCl solution (3×10 ml). The combined aqueous layers were extracted with ethyl acetate (10 ml). The combined organic extracts were dried over anhydrous magnesium sulfate and concentrated to give the crude tetramer 21 (177 mg, 100%)

$^1$H NMR (CDCl$_3$, 400 MHz): 8.08 (s, 2H, H-triazole), 8.04-7.96 (m, 12H), 7.90-7.86 (m, 4H), 7.80-7.72 (m, 10H), 7.64-7.30 (m, 28H), 7.25-7.19 (m, 4H), 7.11 (s, 4H, H-TIPBS Ar), 5.88 (dd, 2H, J=3.0, 10.3 Hz), 5.79-5.72 (m, 6H), 5.66 (dd, 2H, J=1.6, 3.4 Hz), 5.56 (t, 2H, J=2.5 Hz), 5.23 (d, 2H, J=1.6 Hz), 5.18 (d, 2H, J=1.6 Hz), 4.93-4.57 (m, 14H), 4.51 (m, 6H), 4.29-4.17 (m, 4H), 4.07 (m, 4H, J=6.7 Hz, H-TIPBS CH), 3.84 (t, 4H, J=5.0 Hz, H-PEG linker CH$_2$), 3.57 (s, 4H, H-PEG linker CH$_2$), 2.85 (m, 2H, J=6.9 Hz, H-TIPBS CH), 1.20 (d, 12H, J=6.9 Hz, H-TIPBS CH$_3$), 1.16 (d, 12H, J=6.9 Hz, H-TIPBS CH), 1.13 (d, 12H, J=6.7 Hz, H-TIPBS CH$_3$).

Example 21

Protected Mannose Tetramer Bisazide (22)

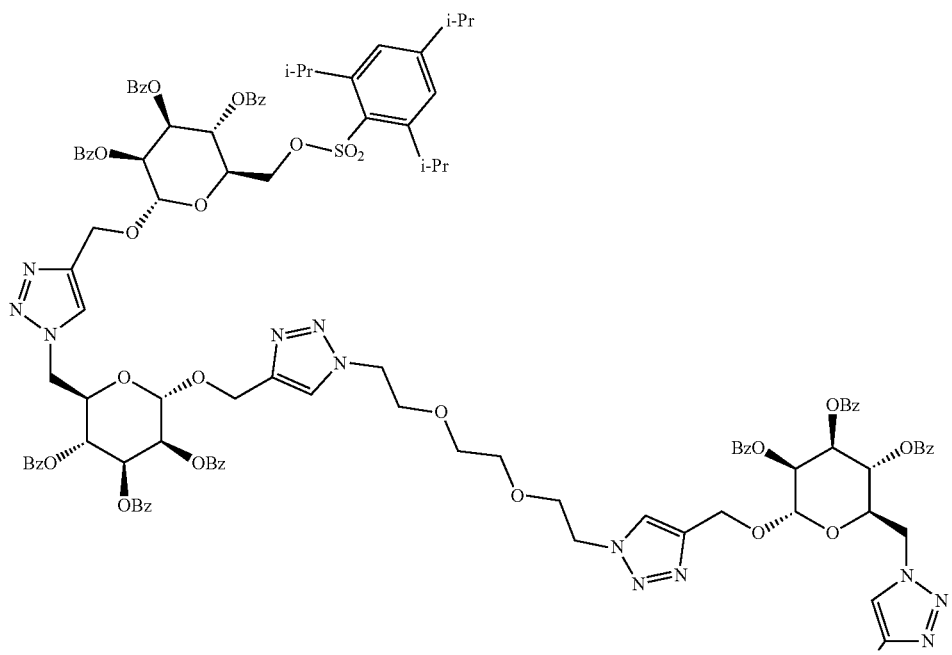

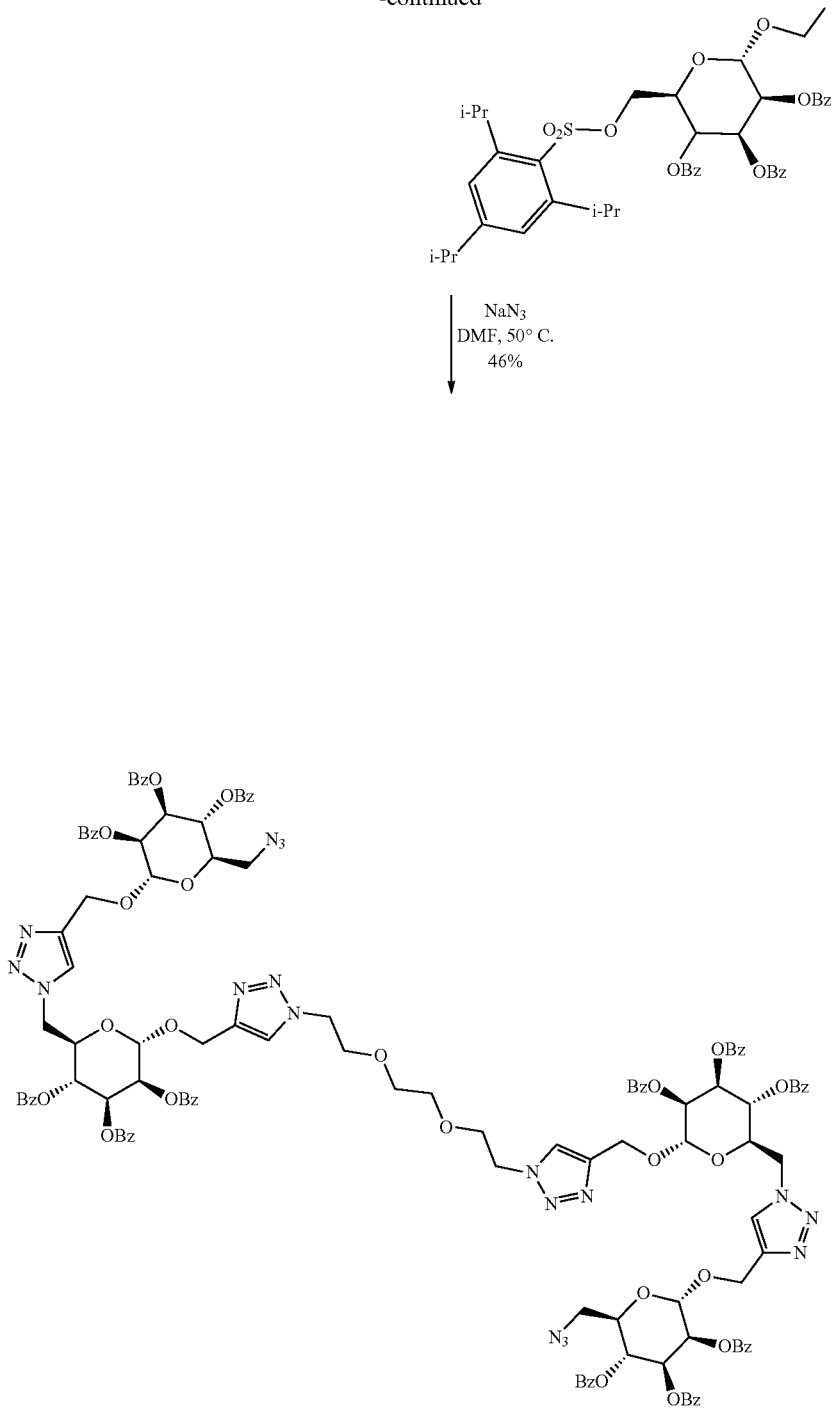

A solution of the tetramer 21 (177 mg, 6.09×10² mmol) and sodium azide (32 mg, 0.492 mmol) in DMF (3 ml) was stirred and heated to 50° C. overnight. The reaction was allowed to cool and the DMF removed by nitrogen stream. The residue was diluted in ethyl acetate (15 ml) and washed with 5% NaHCO$_3$ solution (3×10 ml), CuSO$_4$ solution (3×10 ml), and NaCl solution (3×10 ml). The aqueous layers were extracted with ethyl acetate (15 ml). The organic extract was dried over anhydrous magnesium sulfate and concentrated under reduced pressure to give a crude residue. It was purified by column chromatography using ethyl acetate/petroleum spirits (2:1) as eluent to yield the tetramer 22 (69 mg, 46%).

$^1$H NMR (CDCl$_3$, 400 MHz): δ=8.14-8.04 (m, 6H,), 8.03-7.96 (m, 8H), 7.92 (d, 4H, J=8.0 Hz), 7.74 (m, 8H), 7.65-7.57 (m, 4H), 7.56-7.31 (m, 26H), 7.25-7.20 (m, 8H), 5.97-5.73 (m, 8H), 5.67 (bs, 2H), 5.61 (bs, 2H), 5.22 (bs, 4H), 5.03-4.44 (m, 18H), 4.33 (m, 12H), 3.84 (bs, 4H), 3.57 (bs, 4H), 3.50 (m, 4H).

Example 22
Protected Octomer (23)
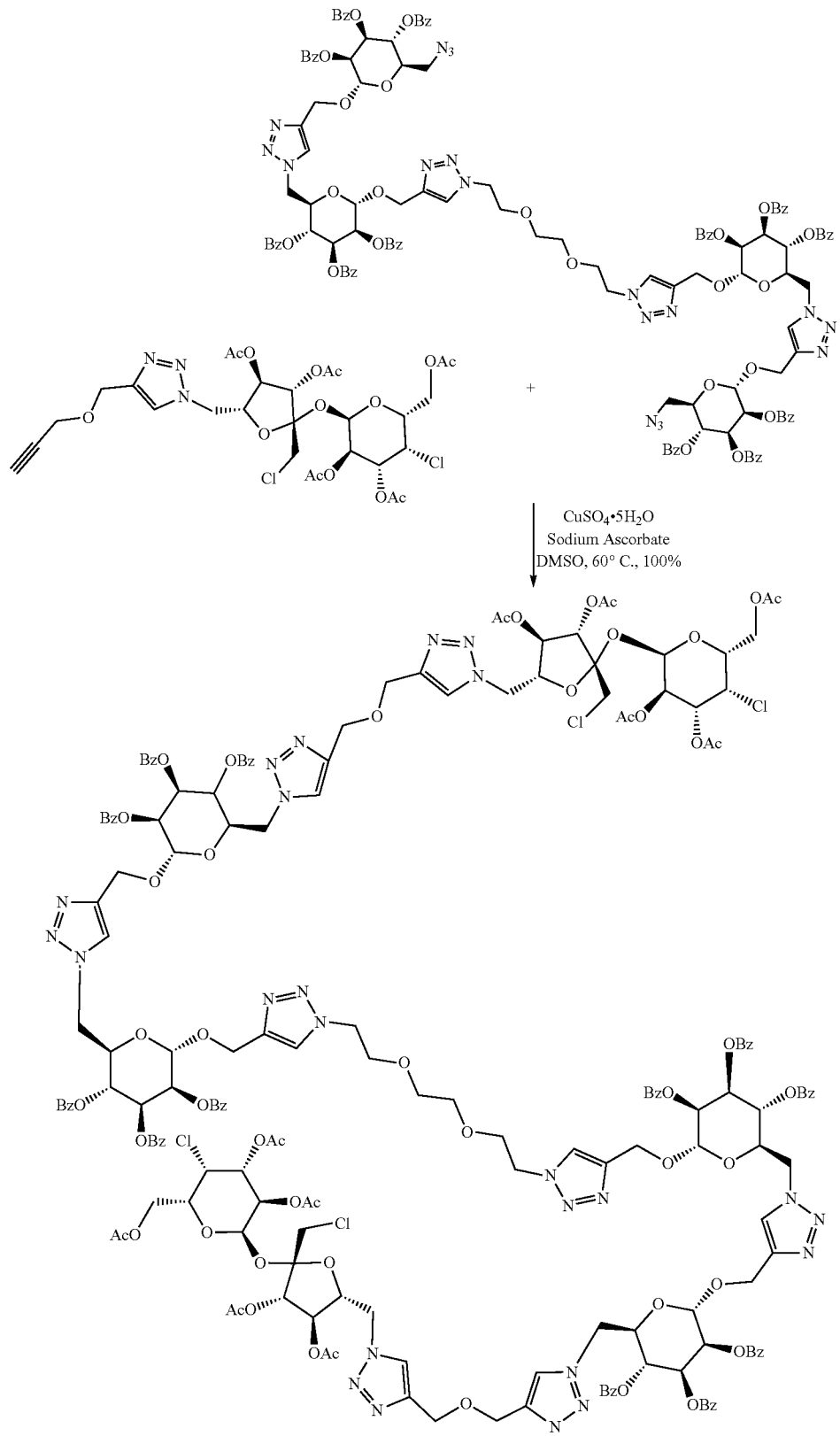

Copper(II) sulfate pentahydrate (14 mg, $5.61 \times 10^{-2}$ mmol, 1 eq per $N_3$ group) and sodium ascorbate (34 mg, 0.172 mmol, 3 eq per $N_3$ group) were added successively to a solution of the sucralose propargyl ether 26 (41 mg, $5.78 \times 10^{-2}$ mmol) and the bisazide tetramer 22 (69 mg, $2.85 \times 10^{-2}$ mmol) in DMSO (3 ml). The reaction mixture was heated to 60° C. under nitrogen for 3 days. The reaction was allowed to cool and the DMSO removed by nitrogen stream. The residue was diluted in ethyl acetate (15 ml) and washed with NaCl solution (3×10 ml) and water (10 ml). The combined aqueous layers were back extracted with ethyl acetate (15 ml). The combined organic extracts were dried over anhydrous magnesium sulphate and concentrated to give the crude hexamer 23 (110 mg, 100%).

$^1$H NMR (CDCl$_3$, 400 MHz): δ=8.25 (bs, 2H, H-triazole), 8.16 (bs, 2H, H-triazole), 8.03-7.90 (m, 20H), 7.80-7.72 (m, 8H), 7.64-6.56 (m, 4H), 7.54-7.43 (m, 12H), 7.43-7.32 (m, 12H), 7.25-7.19 (m, 8H), 5.88 (dd, 2H, J=2.6, 8.6 Hz), 5.82-5.69 (m, 8H), 5.67 (bs, 4H), 5.53 (bs, 2H), 5.42-5.32 (m, 6H), 5.24 (bs, 2H), 5.18 (bs, 2H), 4.89-4.51 (m, 40H), 4.44 (bs, 2H), 4.32-4.19 (m, 4H), 3.88 (bs, 4H), 3.67-3.54 (m, 8H), 2.14 (s, 6H, H-AcO CHs), 2.10 (s, 6H, H-AcO CH$_3$), 2.07 (s, 6H, H-AcO CH$_3$), 2.06 (s, 6H, H-AcO CH$_3$), 2.05 (s, 6H, H-AcO CH$_3$).

Example 23

Global hydrolysis of Octomer (24)

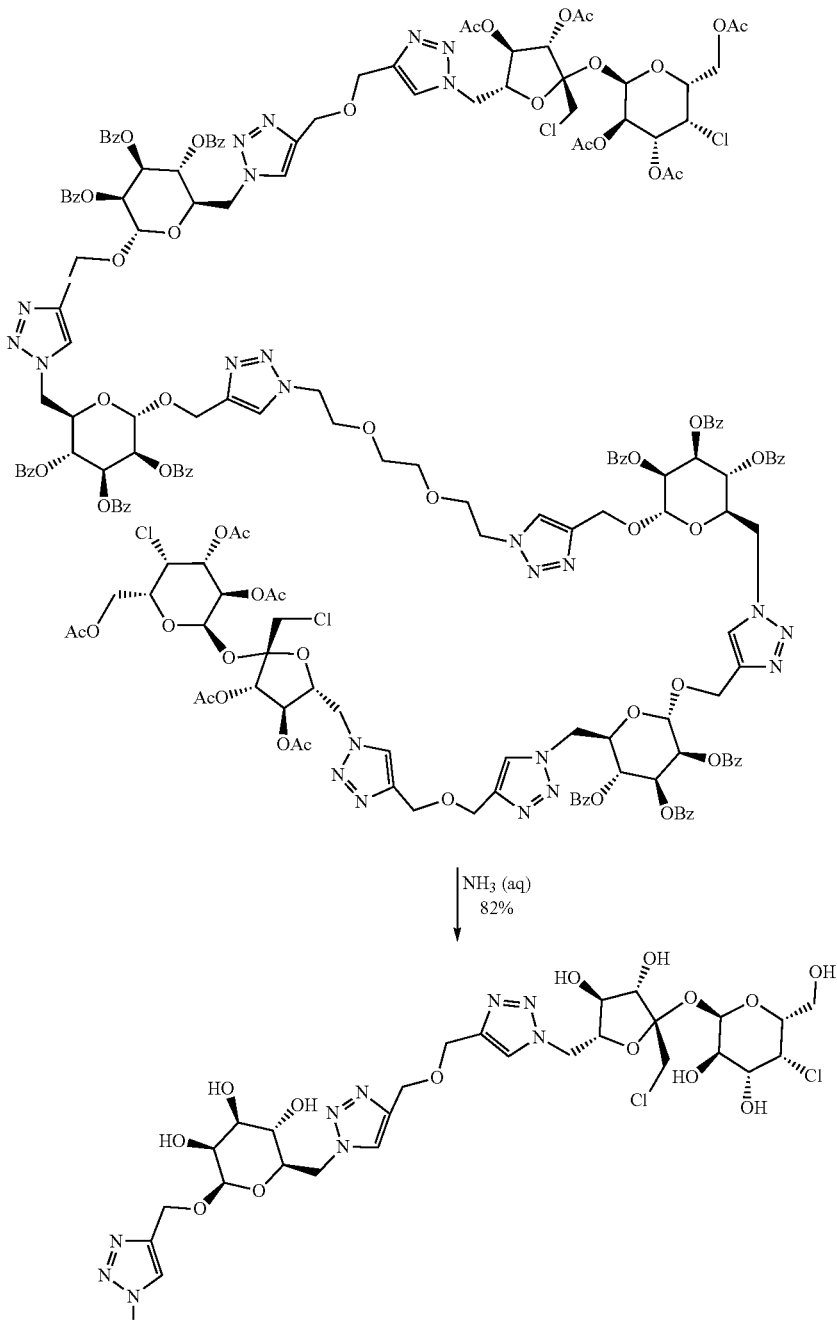

-continued

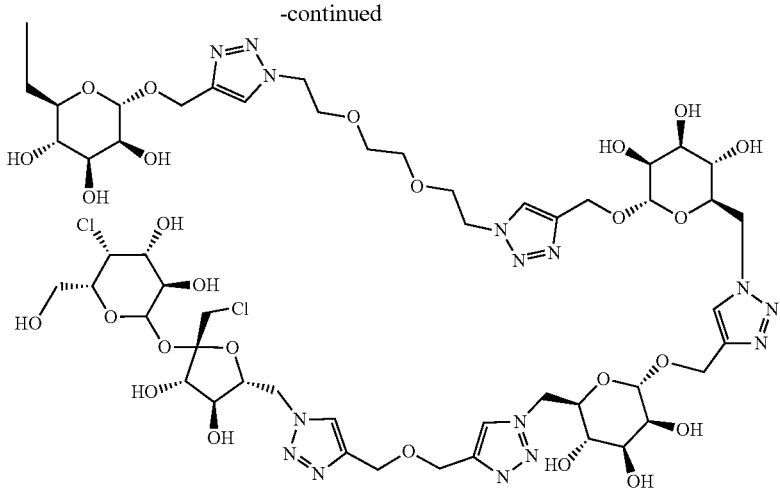

The octomer 23 (110 mg, 2.86×10$^{-2}$ mmol) was dissolved in chloroform (1 ml). The solution was treated with methanol (7 ml) and 30% ammonia solution (1 ml). The reaction was stirred overnight. The solvent was removed, the residue diluted in water (10 ml), filtered through a cotton wool plug, and washed with chloroform (3×10 ml). The solution was concentrated under reduced pressure. The sample was dried under high vacuum to give the deprotected octomer 24 (51 mg, 82%).

$^1$H NMR (320, 400 MHz): δ=8.17 (s, 2H, H-triazole), 7.97 (s, 2H, H-triazole), 7.79 (s, 2H, H-triazole), 7.81 (s, 2H, H-triazole), 5.44 (d, 2H, J=3.3 Hz), 4.94-4.82 (m, 8H), 4.70 (bs, 4H), 4.63-4.59 (m, 16H), 4.45-4.40 (m, 6H), 4.36-4.15 (m, 16H), 3.99-3.53 (m, 32H).

$^{13}$C NMR (D$_2$O, 100 MHz): 126.38 (2CH, triazole), 126.06 (2CH, triazole), 125.65 (2CH, triazole), 125.12 (2CH, triazole), 103.45 (2C, C-2$_{fructose}$), 99.31, 99.01, 92.45 (2CH, C-1$_{glucose}$), 79.52, 75.53, 74.84, 71.62, 71.42, 70.93, 70.41, 69.80, 69.57, 68.65, 68.03, 67.93, 67.49, 63.14, 62.35, 62.26, 61.89, 52.40, 51.13, 51.04, 50.03, 43.63 (2CH$_2$, C-1$_{fructose}$).

Example 24

Sulfation of Octomer (25)

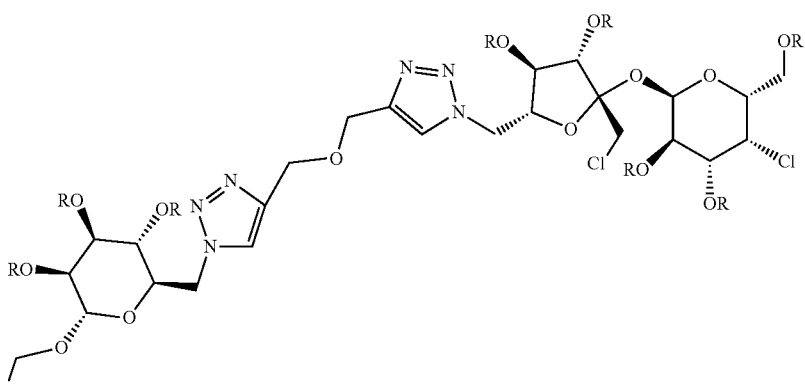

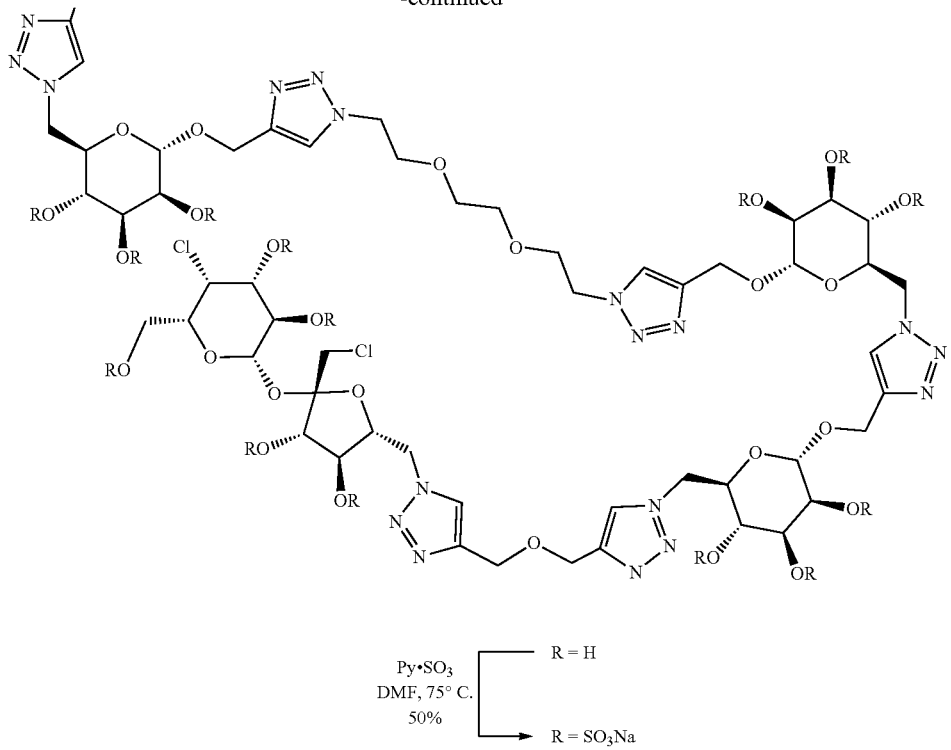

The octomer 24 (51 mg, 2.35×10⁻² mmol) was dissolved in DMF (3 ml) and treated with freshly prepared pyridine sulfur trioxide complex (823 mg, 5.17 mmol, 10 eq per OH group on the octomer). The solution was stirred at 75° C. under nitrogen for 4 days. The solvent was removed by nitrogen stream. The residue was dissolved in water (10 ml) and treated with NaOH (496 mg, 1.24×10⁻² mmol, 2.4 eq. per Py-SO₃). The solution was stirred for 30 minutes under air. It was washed with ethyl acetate (10×10 ml) to remove the excess pyridine. The solvent was removed leaving a yellowish powder that was dried under high vacuum. The dried powder was treated with DMF (15×2 ml). The soluble component was taken up leaving behind the unwanted, insoluble simple salts. The solution was filtered through a cotton wool plug. The DMF was removed and the residue dried under high vacuum. The residue was treated with ACN (20×2 ml). The soluble component was removed. It contained DMF only and was discarded. The insoluble component was dried under high vacuum giving the sulphated octomer 25 as an off-white powder (52 mg, 50%).

¹H NMR (D₂O, 400 MHz): δ=8.25 (s, 2H, H-triazole), 8.13 (s, 2H, H-triazole), 8.08 (s, 2H, H-triazole), 7.93 (s, 2H, H-triazole), 5.82 (d, 2H, J=3.7 Hz), 5.40 (d, 2H, J=7.4 Hz), 5.25 (m, 4H), 5.17-5.07 (m, 6H), 5.05-5.95 (m, 10H), 4.93-4.86 (m, 9H), 4.74 (bs, 6H), 4.70 (m, 3H), 4.68-4.60 (m, 7H), 4.60-4.50 (m, 5H), 4.48-4.31 (m, 10H), 4.30-4.19 (m, 6H), 4.03-3.88 (m, 8H), 3.62 (bs, 4H).

¹³C NMR (1D₂O, 100 MHz): δ=126.45 (2CH, triazole), 126.26 (2CH, triazole), 126.06 (2CH, triazole), 125.27 (2CH, triazole), 103.64 (2C, C-2$_{fructose}$), 96.26, 90.88, 79.49, 79.43, 78.29, 75.14, 75.08, 74.90, 73.49, 72.74, 72.65, 72.37, 71.32, 70.31, 69.62, 68.78, 68, 43, 67.87, 62.41, 60.23, 60.06, 59.89, 52.87, 50.96, 50.94, 50.20, 44.09 (2CH₂, C-1$_{fructose}$).

General Procedure for Click Reaction

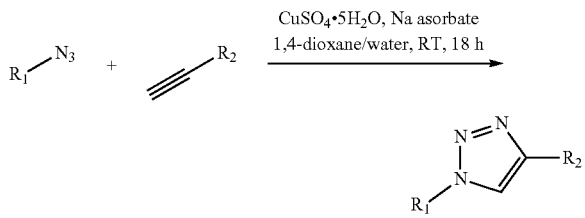

Sodium ascorbate (2 equiv.) and Copper sulphate pentahydrate (1 equiv.) were added to a mixture of azide analogue (1 equiv) and alkyne analogue (1 equiv per N₃) in 1,4-dioxane/H₂O (3:1). The reaction mixture was then stirred at r.t. for 18 h and filtered over a pad of celite. The filtrate was concentrated under reduced pressure and the crude material was dissolved in EtOAc. The organic layer was washed with 1M HCl, sat. NaHCO₃, dried (MgSO₄) and concentrated under reduced pressure. The crude material obtained was purified by flash column chromatography on silica gel to obtain the desired compound.

1-(2,3,3',4'6-penta-O-acetyl-6'-deoxysucralose)-4-(methyl propagyl ether) triazole (26)

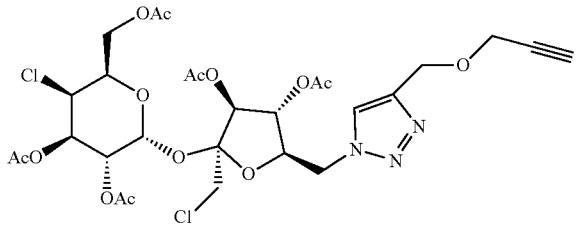 [SMILES: C#CCOCc1cn(C[C@H]2O[C@@](CCl)(O[C@H]3O[C@H](COC(C)=O)[C@H](Cl)[C@H](OC(C)=O)[C@H]3OC(C)=O)[C@@H](OC(C)=O)[C@@H]2OC(C)=O)nn1]

Click reaction of sucralose azide 10 (3.00 g, 4.89 mmol) and propagyl ether (4.00 mL, 42.5 mmol) via the general procedure gave compound 26 (2.56 g, 74%) as a colorless oil; $^1$H NMR (CDCl$_3$, 400 MHz): δ=7.71 (s, 1H, H-7'), 5.59 (d, 1H, J$_{3,4}$=7.3 Hz, H-3'), 5.66-5.64 (m, 1H, H-1), 5.38 (t, 1H, J$_{3',4'}$=J$_{4',5'}$=7.3 Hz, H-4'), 5.32-5.29 (m, 1H, H-2), 4.81 (dd, 1H, J$_{5,6}$=3.5 Hz, J$_{6'a,6'b}$=14.3 Hz, H-6'a), 4.73 (s, 2H, H-9'), 4.67 (dd, 1H, J$_{5',6ab}$=8.8 Hz, J$_{6'a,6'b}$=14.3 Hz, H-6'b), 4.60-4.54 (m, 2H, H-5, H-4), 4.39 (ddd, 1H, J$_{5,6'a}$=3.5 Hz, J$_{4'5'}$=7.3 Hz, J$_{5',6'b}$=8.8 Hz, H-5'), 4.30 (dd, 1H, J$_{5,6a}$=4.5 Hz, J$_{6a,6b}$=11.7 Hz, H-6a), 4.26-4.18 (m, 3H, H-6b, H-10'), 3.61, 3.41 (ABq, 2H, J=12.0 Hz, H-1a, H-1b), 2.47 (t, 1H, J$_{12'10'}$=2.3 Hz, H-12'), 2.13 (s, 3H, CH$_3$), 2.11 (s, 3H, CH$_3$), 2.08 (s, 3H, CH$_3$), 2.07 (s, 3H, CH-3), 2.06 (s, 3H, CH$_3$); $^{13}$C NMR (CDCl$_3$, 100 MHz): δ=170.4, 170.2, 170.1, 170.0, 169.7 (5×COCH$_3$), 104.0 (C-7'), 90.6 (C-1), 79.5 (C-5'), 79.2 (C-12'), 77.2 (C-11'), 75.3 (C-3'), 75.3 (C-4'), 75.1 (C-12'), 68.3 (C-4), 67.8 (C-2), 67.0 (C-3), 64.0 (C-6), 62.8 (C-9'), 58.9 (C-5), 57.6 (C-10'), 52.7 (C-6'), 44.7 (C-1), 20.7, 20.6 (×2), 20.5 (5×COCH$_3$); HRMS (ESI); m/z [M+H]$^+$ calculated for C$_{28}$H$_{35}$Cl$_2$N$_3$O$_{14}$; found 708.1575.

Mannose ethylene Linked Dimer (27)

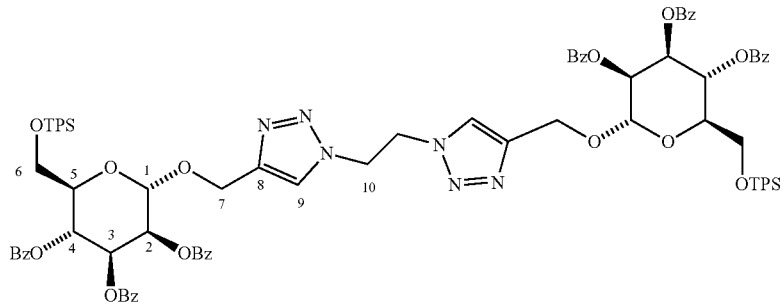

Click reaction of mannopyranoside 5 (1.00 g, 1.2 mmol) and ethylene diazide (70 mg, 0.6 mmol) via the general procedure gave compound 27 (0.55 g, 68%) as a colorless oil; $^1$H NMR (CDCl$_3$, 400 MHz): δ=8.02 (dd, 4H, J=1.1 Hz, J=8.5 Hz, H-OBz), 7.88 (dd, 4H, J=0.8 Hz, J=8.5 Hz, H-OBz), 7.76 (dd, 4H, J=1.1 Hz, J=8.3 Hz, H-OBz), 7.60 (s, 2H, H-9), 7.59-7.53 (m, 1=2H, H-OBz), 7.49-7.15 (m, 18H, H-OBz), 7.10 (s, 4H, Ar-OTPS), 5.87 (dd, 2H, J$_{2,3}$=3.3 Hz, J$_{3,4}$=10.1 Hz, H-3), 5.74 (dd, 2H, J$_{3,4}$=J$_{4,5}$=10.1 Hz, H-4), 5.61 (dd, 2H, J$_{1,2}$=1.8 Hz, J$_{2,3}$=3.3 Hz, H-2), 5.17 (d, 2H, J$_{1,2}$=1.8 Hz, H-2), 5.06-4.93 (m, 4H, H-10), 4.86, 4.79 (ABq, 4H, J=12.6 Hz, H-7), 4.53-4.44 (m, 2H, H-5), 4.27-4.15 (m, 4H, H-6), 4.05 (h, 1H, J=6.9 Hz, J=13.3 Hz, J=20.1 Hz, CH-i-pr), 2.84 (h, 1H, J=6.9 Hz, J=13.3 Hz, J=20.1 Hz, CH-i-pr), 1.20 (s, 3H, CH$_3$), 1.18 (s, 3H, CH$_3$), 1.17 (s, 3H, CH$_3$), 1.16 (s, 3H, CH$_3$), 1.13 (s, 3H, CH$_3$), 1.11 (s, 3H, CH$_3$) ppm; $^{13}$C NMR (CDCl$_3$, 100 MHz): δ=165.5, 165.4, 165.3 (6×C=O), 153.8, 150.9, 133.5, 133.4, 133.5, 133.4, 133.1, 129.9, 129.8, 129.7, 129.1, 129.0, 128.9, 128.7, 128.6, 128.4, 128.3, 128.2, 124.5 (C-9), 123.8 (Ar-OTPS), 96.9 (C-1), 77.2 (C-8), 70.3 (C-2), 69.7 (C-3), 69.4 (C-5), 7.9 (C-6), 67.0 (C-4), 61.1 (C-7), 49.7 (C-10), 34.1 (CH-i-pr), 29.6 (CH-i-pr), 24.7, 24.6, 23.4 (×2) (12×CH$_3$) ppm.

Mannose ethylene Linked Dimer Bisazide (28)

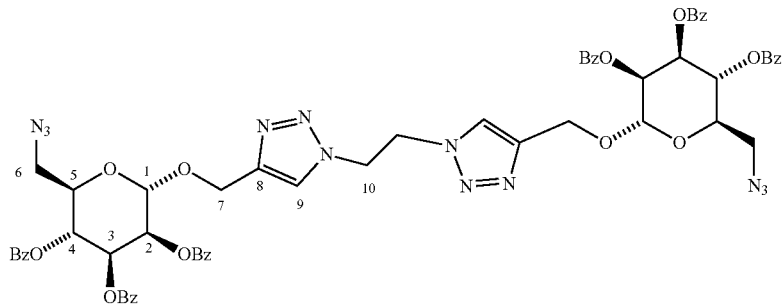

To a solution of 27 (300 mg, 0.23 mmol) in dry DMF (10 mL), sodium azide (0.1 g, 1.5 mmol) was added and the mixture stirred at 80° C. under a nitrogen atmosphere for 18 h. The reaction mixture was then concentrated under reduced pressure and the crude material obtained was suspended in EtOAc (50 mL). The organic layer was washed with HCl (2×50 mL), sat. NaHCO$_3$, dried (MgSO$_4$) and concentrated under reduced pressure to obtain the diazide 28 (0.27 g, 99%) as a yellowish oil. A small portion of this material was then purified by flash column chromatography (EtOAc) on silica gel, to obtain analytical data. $^1$H NMR (CDCl$_3$, 400 MHz): 5=8.04 (dd, 4H, J=1.5 Hz, J=8.1 Hz, H-OBz), 7.92 (dd, 4H, J=1.0 Hz, J=8.0 Hz, H-OBz), 7.77 (dd, 4H, J=1.1 Hz, J=8.3 Hz, H-OBz), 7.61-7.54 (m, 2H, H-OBz), 7.49 (s, 2H, H-9), 7.48-7.28 (m, 12H, H-OBz), 7.23-7.18 (m, 4H, H-OBz), 5.90-5.82 (m, 4H, H-2, H-3), 5.62 (dd, 2H, $J_{1,2}$=1.7 Hz, $J_{2,3}$=1.0 Hz, H-2), 5.18 (d, 2H, $J_{1,2}$=1.7 Hz, H-1), 5.08-4.95 (m, 4H, H-10), 4.93, 4.78 (ABq, 4H, J=12.5 Hz, H-7), 4.37-4.30 (m, 2H, H-5), 4.47 (d, 2H, $J_{5,6}$=4.2 Hz, H-6); $^{13}$C NMR (CDCl$_3$, 100 MHz): δ=171.1, 165.5 (×2), 165.4 (3×C=O), 133.6, 133.5, 133.2, 129.9, 129.8, 129.7, 128.6, 128.5, 128.3, 124.5 (CH-triazole), 96.7 (C-1), 70.5 (C-5), 70.2 (C-2), 69.7 (C-3), 67.6 (C-4), 60.72 (CH$_2$), 51.2 (C-6), 49.7 (H-10).

Mannose diethylene Linked Dimer (29)

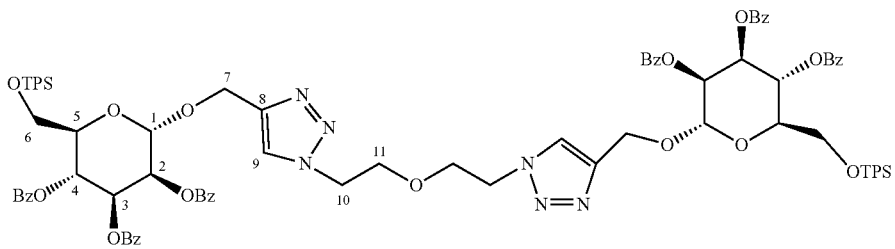

Click reaction of mannopyranoside 5 (1.00 g, 1.30 mmol) and bis(2'-azidoethyl) ether (100 mg, 0.80 mmol) via the general procedure gave 29 (1.0 g, 92%) as a glassy solid. Compound 29 was used in the subsequent step without further purification. $^1$H NMR (CDCl$_3$, 400 MHz): δ=8.03 (dd, 4H, J=1.0 Hz, J=8.1 Hz, H-OBz), 7.90 (dd, 4H, J=1.5 Hz, J=8.0 Hz, H-OBz), 7.84 (s, 2H, H-8), 7.76 (dd, 4H, J=1.1 Hz, J=8.3 Hz, H-OBz), 7.62-7.30 (m, 18H, H-OBz), 7.26-7.18 (m, 2H, H-OBz), 7.13 (s, 4H, Ar-OTPS), 5.88 (dd, 2H, $J_{2,3}$=3.2 Hz, $J_{3,4}$=10.0 Hz, H-3), 5.79 (dd, 2H, $J_{3,4}$=14.3=10.0 Hz, H-4), 5.65 (dd, 2H, $J_{1,2}$=1.8 Hz, $J_{2,3}$=3.2 Hz, H-2), 5.23 (d, 2H, $J_{1,2}$=1.8 Hz, H-2), 4.97, 4.82 (ABq, 4H, J=12.6 Hz, H-7), 4.61 (t, 4H, $J_{10,11}$=5.1 Hz, H-10), 4.55 (ddd, 2H, $J_{5,6}$=2.6 Hz, $J_{5,6b}$=6.0 Hz, $J_{4,5}$=10.0 Hz, H-5), 4.29 (dd, 2H, $J_{5,6b}$=6.0 Hz, $J_{6a,6b}$=11.2 Hz, H-6b), 4.23 (dd, 2H, $J_{5,6a}$=2.6 Hz, $J_{6a,6b}$=11.2 Hz, H-6a),), 4.08 (p, 2H, J=6.3 Hz, J=13.2 Hz, CH-i-pr), 3.92 (t, 4H, $J_{10,11}$=5.1 Hz, H-11), 2.87 (p, 1H, J=6.9 Hz, J=13.7 Hz, CH-i-pr), 1.22 (s, 3H, CH$_3$), 1.21 (s, 6H, CH$_3$), 1.19 (s, 6H, CH$_3$), 1.18 (s, 6H, CH$_3$), 1.16 (s, 6H, CH$_3$), 1.14 (s, 6H, CH$_3$); $^{11}$C NMR (CDCl$_3$, 100 MHz): δ=165.5, 165.4 (6×C=O), 153.8 (Ar-OTPS), 150.9, 143.1, 133.5, 133.2, 129.9, 129.8, 129.7, 129.1 (×2), 129.0, 128.7, 128.6, 128.4, 128.3, 128.9, 124.9 (C-9), 123.8 (Ar-OTPS), 97.1 (C-1), 77.22 (C-8), 70.3 (C-2), 69.8 (C-3), 69.6 (C-5), 69.3 (C-11), 67.9 (C-6), 66.9 (C-4), 61.0 (C-7), 50.6 (C-10), 34.2 (CH-i-pr), 29.7 (CH-i-pr), 24.7 (×2), 23.5 (12×CH$_3$).

Mannose diethylene Linked Dimer (30)

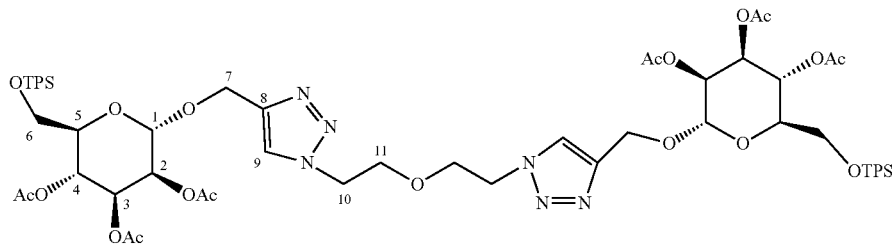

Click reaction of mannopyranoside 8 (1.00 g, 1.70 mmol) and bis(2'-azidoethyl) ether (100 mg, 0.8 mmol) via the general procedure gave 30 (0.7 g, 65%) as a glassy solid; $^1$H NMR (CDCl$_3$, 400 MHz): δ=7.45 (s, 2H, H-9), 6.93 (s, 4H, Ar-OTPS), 5.06 (dd, 2H, J$_{2,3}$=3.4 Hz, J$_{3,4}$=10.0 Hz, H-3), 4.94 (dd, 2H, J$_{1,2}$=1.7 Hz, J$_{2,4}$=3.4 Hz, H-2), 4.89 (t, 2H, J$_{3,4}$=J$_{4,5}$=10.0 Hz, H4), 4.68 (d, 2H, J$_{1,2}$=1.7 Hz, H-1), 4.56, 4.44 (ABq, 4H, J=12.3 Hz, H-7), 4.29 (t, 4H, J$_{10,11}$=5.0 Hz, H-10), 3.99-3.92 (m, 2H, H-5), 3.90-3.80 (m, 4H, H-6a, CH-i-pr), 3.60 (t, 4H, J$_{10,11}$=5.0 Hz, H-11), 2.65 (h, 1H, J=6.9 Hz, J=13.7 Hz, CH-i-pr), 1.83 (s, 6H, OCH$_3$), 1.71 (s, 6H, OCH$_3$), 1.69 (s, 6H, OCH$_3$), 1.01-0.99 (m, 18H, 6×CH$_3$); $^{13}$C NMR (CDCl$_3$, 100 MHz): δ=169.9, 169.8, 169.7 (6×C=O), 154.0, 150.9 (Ar-OTPS), 143.2 (C-8), 129.0 (Ar-OTPS), 124.5 (C-9), 123.9 (Ar-OTPS), 96.9 (C-1), 77.2, 69.4 (C-2), 69.3 (C-11), 69.1 (C-5), 68.8 (C-3), 67.7 (C-6), 66.5 (C-4), 60.8 (C-7), 50.4 (C-10), 34.2 (CH-i-pr), 29.7 (CH-i-pr), 24.7 (×2), 23.5 (6×CH$_3$), 20.8, 20.6 (×2) (6×OCH); HRMS (ESI); m/z [M+H]$^+$ calculated for C$_{64}$H$_{92}$N$_6$O$_{23}$S$_2$; found 1377.5791.

Mannose diethylene Linked Dimer Bisazide (31)

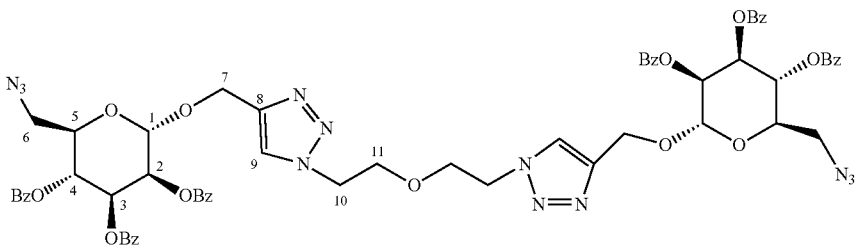

To a solution of tetramer 29 (1.0 g, 0.6 mmol) in dry DMF (15 mL), sodium azide (150 mg, 2.3 mmol) was added and the mixture stirred at 60° C. under a nitrogen atmosphere for 18 h. The reaction mixture was then concentrated under reduced pressure and the crude material obtained was suspended in EtOAc (100 mL). The organic layer was washed with HCl (2×100 mL), sat. NaHCO$_3$, dried (MgSO$_4$) and concentrated. The crude material was purified by flash column chromatography (2:1 EtOAc/Pet.Sp.) on silica gel to obtain the diazide 31 (0.6 g, 76%) as a glassy solid. $^1$H NMR (CDCl$_3$, 400 MHz): δ=8.06 (dd, 4H, J=1.0 Hz, J=8.1 Hz, H-OBz), 7.94 (dd, 4H, J=1.5 Hz, J=8.0 Hz, H-OBz), 7.80-7.75 (m, 5H, C-9, H-OBz), 7.65-7.33 (m, 14H, H-OBz), 7.26-7.19 (m, 5H, H-OBz), 5.95-5.83 (m, 4H, H-3, H4), 5.69 (dd, 2H, J$_{1,2}$=1.8 Hz, J$_{2,3}$=2.9 Hz, H-2), 5.27 (d, 2H, J$_{1,2}$=1.8 Hz, H-2), 5.04, 4.85 (ABq, 4H, J=12.3 Hz, H-7), 4.60 (t, 4H, J$_{10,11}$=5.1 Hz, H-10), 4.44-4.37 (m, 2H, H-5), 3.93 (t, 4H, J$_{10,11}$=5.1 Hz, H-11), 3.54-3.50 (m, 4H, H-6); $^{13}$C NMR (CDCl$_3$, 100 MHz): δ=165.6, 165.5 (×2) (6×C=O), 133.6, 133.5, 133.3, 129.9, 129.7, 129.1, 128.9, 128.8, 128.6, 128.5, 128.3, 125.0 (C-9), 97.0 (C-1), 77.2 (C-8), 70.6 (C-5), 70.2 (C-2), 69.9 (C-3), 69.2 (C-11), 67.4 (C-4), 60.7 (C-7), 51.1 (C-6), 50.8 (C-10).

Mannose diethylene Linked Dimer Bisazide (32)

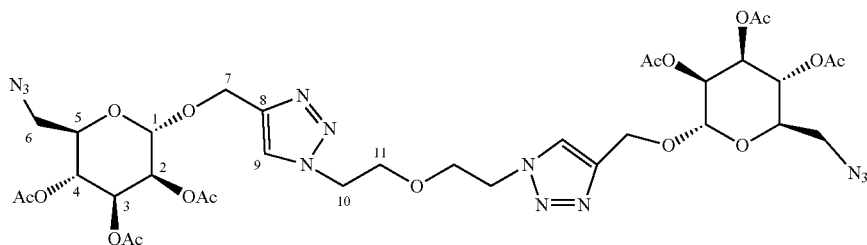 [SMILES: CC(=O)O[C@@H]1[C@H](OC(C)=O)[C@@H](OCc2cn(CCOCCn3cc(CO[C@H]4O[C@H](CN=[N+]=[N-])[C@@H](OC(C)=O)[C@H](OC(C)=O)[C@@H]4OC(C)=O)nn3)nn2)O[C@H](CN=[N+]=[N-])[C@H]1OC(C)=O]

To a solution of tetramer 30 (0.7 g, 0.5 mmol) in dry DMF (10 mL), sodium azide (200 mg, 3.2 mmol) was added and the mixture stirred at 60° C. under a nitrogen atmosphere for 18 h. The reaction mixture was then concentrated under reduced pressure and the crude material obtained was suspended in EtOAc (100 mL). The organic layer was washed with HCl (2×100 mL), sat. NaHCO$_3$, dried (MgSO$_4$) and concentrated to obtain the bisazide 32. Compound 32 was used in the subsequent step without further purification. $^1$H NMR (CDCl$_3$, 400 MHz): δ=7.67 (s, 2H, H-9), 5.33-4.24 (m, 4H, H-3, H-4), 5.23-5.20 (m, 2H, H-2), 4.98 (d, 2H, J$_{1,2}$=1.6 Hz, H-1), 4.90, 4.72 (ABq, 4H, J=12.3 Hz, H-7), 4.54 (t, 4H, J$_{10,11}$=5.0 Hz, H-10), 4.09-4.03 (m, 2H, H-5), 3.86 (t, 4H, J$_{10,11}$=5.0 Hz, H-11), 3.38 (d, 4H, J=4.5 Hz, H-6), 2.15 (s, 6H, OCH$_3$), 2.05 (s, 6H, OCH$_3$), 2.00 (s, 6H, OCH$_3$); $^{13}$C NMR (CDCl$_3$, 100 MHz): δ=170.1, 170.0, 169.6, 124.3 (C-9), 96.6 (C-1), 77.2 (C-8), 70.2 (C-5), 69.4 (C-2), 69.3 (C-11), 68.8 (C-3), 67.0 (C-4), 60.8 (C-7), 51.0 (C-6), 50.3 (C-10), 20.8, 20.7, 20.6 (6×OCH$_3$); HRMS (ESI); m/z [M+H]$^+$ calculated for C$_{34}$H$_{46}$N$_{12}$O$_{17}$; found 895.3179.

Sucralose Mannose Azide (34)

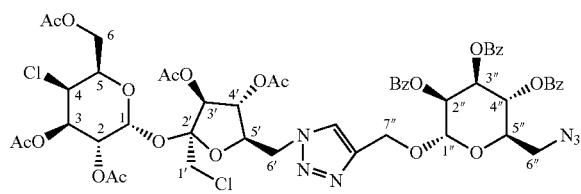

Click reaction of propagyl mannose 5 (2.4 g, 3.00 mmol) and sucralose azide 10 (1.8 g, 2.9 mmol) via the general procedure led to the trisaccharide 33 (3.7 g, 93%). To a solution of trisaccharide (1.0 g, 0.6 mmol) in dry DMF (50 mL), sodium azide (400 mg, 6.30 mmol) was added and the mixture stirred at 60° C. under a nitrogen atmosphere for 18 h. The reaction mixture was then concentrated under reduced pressure and the crude material obtained was suspended in EtOAc (100 mL). The organic layer was washed with HCl (2×100 mL), sat. NaHCO$_3$, dried (MgSO$_4$) and concentrated. The crude material was purified by flash column chromatography (1:1 EtOAc/Pet.Sp.) on silica gel to obtain the azide 34 (1.7 g, 56%) as a glassy solid. $^1$H NMR (CDCl$_3$, 400 MHz): δ=8.11-8.07 (m, 2H, H-Bz), 7.98-7.93 (m, 2H, H-Bz), 7.87 (s, 1H, triazole), 7.83-7.78 (m, 2H, H-Bz), 7.64-7.59 (m, 1H, H-Bz), 7.55-7.34 (m, 6H, H-Bz), 7.28-7.21 (m, 2H, H-Bz), 5.93-5.83 (m, 2H, H-3", H-4"), 5.77-5.71 (m, 2H, H-3, H-1), 5.68 (dd, 1H, J=2.9 Hz, 1.8 Hz, H-3'), 5.42 (t, 1H, J=7.2 Hz, H-4), 5.38-5.32 (m, 2H, H-2, H-2"), 5.25 (d, 1H, J=1.8 Hz, H-1"), 5.04 (d, 1H, J=12.5 Hz, H-7"a), 4.90 (m, 2H, H-7"b, H-6a), 4.77 (dd, 1H, J=14.3 Hz, 9.0 Hz, H-6b), 4.66-4.59 (m, 2H, H-4', H-5'), 4.49 (m, 1H, H-5), 4.41-4.32 (m, 2H, H-5", H-6'b), 4.28 (dd, 1H, J=11.8, 7.0 Hz, H-6'a), 3.65 (d, 1H, J=12.0 Hz, H-1'a), 3.59-3.48 (m, 3H, H-1'b, H-6"a, H-6"b), 2.16-2.01 (5×s, 15H, 5×OAc) ppm; $^{13}$C NMR (CDCl$_3$, 100 MHz): δ=170.63-169.70 (5×C=O), 165.79-165.38 (3× C=O), 143.76 (C, triazole) 133.70 (CH, Bz), 133.70 (CH, Bz), 133.28 (CH, Bz), 130.33-129.58 (CH, Bz), 129.38 (C, Ar), 129.23 (C, Ar), 128.95 (C, Ar), 128.86-128.25 (6CH, Bz), 124.82 (CH, triazole), 104.33 (C, C-2'), 97.06 (CH, C-1"), 90.79 (CH, C-1), 79.71 (CH, C-5), 75.63 (CH), 75.57 (CH), 70.73 (CH, C-5"), 70.46 (CH, C-3'), 69.83 (CH), 68.51 (CH), 67.95 (CH), 67.79 (CH), 67.15 (CH, C-2), 64.17 (CH$_2$, C-6'), 61.28 (CH$_2$, C-7"), 59.09 (CH), 53.01 (CH$_2$, C-6), 51.37 (CH$_2$, C-6"), 44.88 (CH$_2$, C-1'), 20.92-20.61 (CH$_3$) ppm.

Sucralose mannose mannose azide (36)

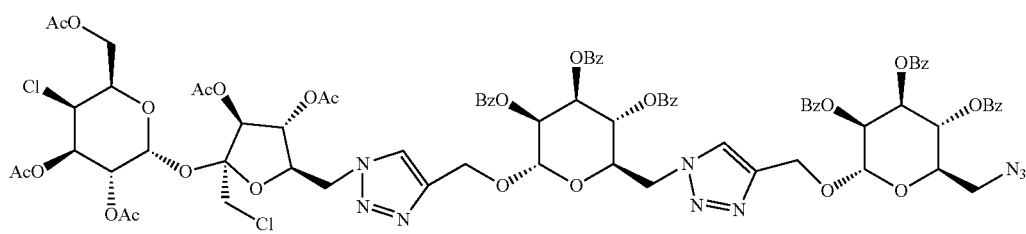

Click reaction of propagyl mannose 5 (600 mg, 0.80 mmol) and azide 34 (900 mg, 0.80 mmol) via the general procedure led to the tetrasaccharide 35 (1.5 g, quant.). The crude material was used without further purification. To a solution of tetrasaccharide (1.5 g, 0.76 mmol) in dry DMF (50 mL), sodium azide (150 mg, 2.3 mmol) was added and the mixture stirred at 60° C. under a nitrogen atmosphere for 18 h. The reaction mixture was then concentrated under reduced pressure and the crude material obtained was suspended in EtOAc (100 mL). The organic layer was washed with HCl (2×100 mL), sat. NaHCO$_3$, dried (MgSO$_4$) and concentrated. The crude material was purified by flash column chromatography (1:1 EtOAc/Pet.Sp.) on silica gel to obtain the azide 36 (1.2 g, 91%) as a glassy solid. $^1$H NMR (CDCl$_3$, 400 MHz): δ=8.09-7.98 (m, 6H), 7.96-7.90 (d, 2H), 7.79 (m, 5H), 7.66-7.58 (m, 2H), 7.50 (m, 7H), 7.45-7.33 (m, 7H), 7.23 (m, 3H), 5.94-5.73 (m, 6H, H-1), 5.66 (dd, 1H, J=3.3, 1.5 Hz), 5.59 (dd, 1H, J=3.3, 1.6 Hz), 5.46-5.30 (m, 3H), 5.22 (s, 2H), 5.00 (d, 1H, J=12.1 Hz), 4.91-4.59 (m, 11H), 4.48 (t, 1H, J=7.2 Hz), 4.34 (m, 2H), 4.30-4.21 (m, 1H), 3.63 (s, 2H), 3.57-3.43 (m, 2H), 2.16 (s, 3H), 2.09 (s, 6H), 2.07 (s, 3H), 1.97 (s, 3H) ppm; $^{13}$C NMR (CDCl$_3$, 100 MHz): S=170.6, 170.3, 170.3, 167.0, 169.8, 166.0, 165.7, 165.5 (×3), 165.4, 134.0-133.60, 133.30, 130.3-129.7, 129.3, 129.2, 129.0-128.5, 128.4, 125.4, 125.0, 104.3, 97.1, 96.8, 90.9, 79.6 (×3), 70.6, 70.4, 69.89, 69.9, 69.7, 68.4 (×2), 68.1, 67.7, 67.0, 64.2, 61.4, 60.8, 59.2, 53.0, 51.4 (×2), 44.9, 21.2-20.2 ppm.

Sucralose mannose (36)

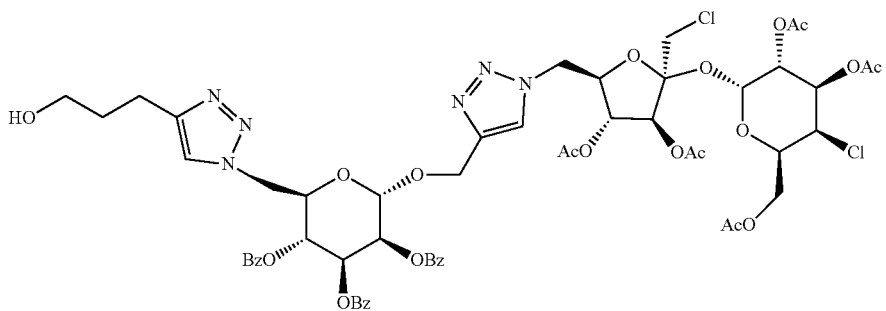

Click reaction of trisaccharide 34 (540 mg, 0.46 mmol) and 4-pentyn-1-ol (110 mg, 0.46 mmol) via the general procedure led to the trisaccharide 36 (370 mg, 58%). $^1$H NMR (CDCl$_3$, 400 MHz): S=7.98 (dd, 4H, J=7.1 Hz, J=16.4 Hz), 7.78 (s, 1H, H-triazole), 7.77 (d, 2H, J=8.5 Hz), 7.63 (s, 1H, H-triazole), 7.62-7.56 (m, 1H), 7.54-7.42 (m, 3H), 7.42-7.33 (m, 3H), 7.21 (m, 2H), 5.86 (dd, 1H, J=3.2 Hz, J=9.9 Hz), 5.80 (d, 1H, J=2.8 Hz), 5.77-5.70 (m, 2H), 5.62-5.58 (m, 1H), 5.38 (t, 1H, J=7.1 Hz), 5.36-5.32 (m, 2H), 5.14-5.11 (m, 1H), 4.87 (dd, 1H, J=3.6 Hz, J=14.3 Hz), 4.79-4.67 (m, 2H), 4.66-4.41 (m, 8H), 4.32 (dd, 11H, J=4.5 Hz, J=11.9 Hz), 4.25 (dd, 1H, J=7.3 Hz, J=11.9 Hz), 3.74-3.52 (m, 4H), 2.79 (br-t, 2H, J=7.1 Hz), 2.13 (s, 3H), 2.08 (s, 3H), 2.07 (s, 3H), 2.05 (s, 3H), 1.92 (s, 3H), 1.87 (br-t, 2H, J=6.5 Hz); $^{13}$C NMR (CDCl$_3$, 100 MHz): S=171.03, 170.3, 170.1 (×2), 169.7, 169.6, 165.7, 165.3, 165.1, 143.3, 133.6, 133.5, 133.1, 129.8, 129.7, 129.6, 129.0, 128.8, 128.5, 128.4, 128.1, 124.5, 122.8, 104.1, 96.1, 90.6, 79.4, 74.4, 75.3, 70.3, 69.7, 69.4, 68.2, 68.0, 67.8, 66.7, 64.0, 61.1, 58.9, 52.7, 50.8, 44.5, 31.6, 21.7, 20.9, 20.6, 20.5 (×2), 20.4 (×2).

Sucralose mannose (37)

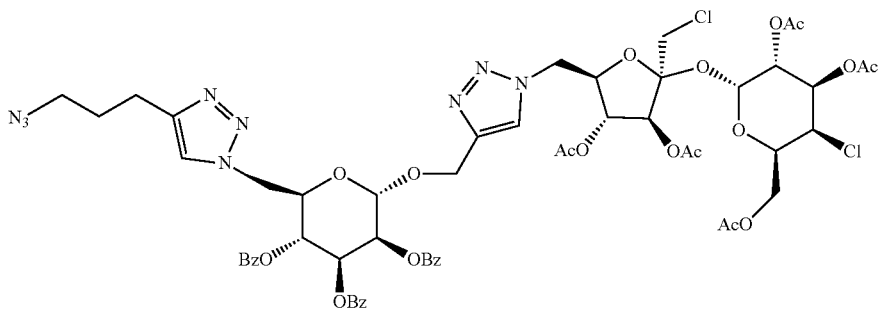

To a solution of the alcohol 36 (370 mg, 0.30 mmol) in anhydrous DCM (20 mL), triethylamine (140 mg, 1.40 mmol) and methanesulfonyl chloride (40 mg, 0.35 mmol) were added and stirred at r.t. for 18 h. The reaction mixture was washed with 1 M HCl (2×30 mL), sat. NaHCO$_3$ (30 mL), dried (MgSO$_4$) and concentrated under reduced pressure. To a solution of the crude material in anhydrous DMF (20 mL), NaN$_3$ (60 mg, 1.00 mmol) was added and stirred at 60° C. for 18 h. The reaction mixture was concentrated under reduced pressure and the crude material was dissolved in EtOAc (100 mL) and washed with 1 M HCl (50 mL), sat. NaHCO$_3$ (50 mL), dried (MgSO$_4$) and concentrated under reduced pressure. The crude material was purified by flash column chromatography (1.5:1 EtOAc/Pet.Sp to EtOAc) to obtain the azide 37 (250 mg, 60%). $^1$H NMR (CDCl$_3$, 400 MHz): δ=8.02-7.93 (m, 4H), 7.79-7.74 (m, 3H), 7.64 (s, 1H), 7.63-7.57 (m, 1H), 7.52-7.43 (m, 4H), 7.42-7.34 (m, 3H), 7.21 (t, 2H, J=8.1 Hz), 5.85 (dd, 1H, J=3.3 Hz, J=10.0 Hz), 5.82 (d, 1H, J=3.4 Hz), 5.77-5.68 (m, 2H), 5.60 (dd, 1H, J=1.7 Hz, J=3.4 Hz), 5.41 (t, 1H, J=7.3 Hz), 5.34 (dd, 1H, J=3.3 Hz, J=9.6 Hz), 5.16 (d, 1H, J=1.6 Hz), 4.88 (dd, 1H, J=3.5 Hz, J=14.3 Hz), 4.76 (d, 1H, J=9.2 Hz), 4.70 (d, 1H, J=11.8 Hz), 4.65-4.52 (m, 6H), 4.50-4.42 (m, 1H), 4.32 (dd, 1H, J=4.2 Hz, J=11.8 Hz), 4.24 (dd, 1H, J=7.0 Hz, J=11.9 Hz), 3.63 (d, 2H, J=3.7 Hz), 3.27 (t, 2H, J=6.8 Hz), 2.76 (ddd, 2H, J=3.1 Hz, J 7.4 Hz, J=10.4 Hz), 2.14 (s, 3H), 2.10 (s, 3H), 2.08 (s, 3H), 2.06 (s, 3H), 1.95 (s, 3H), 1.91 (t, 2H, J=7.0 Hz); $^{13}$C NMR (CDCl$_3$, 100 MHz): δ=170.3, 170.1, 170.0, 169.7, 169.6, 165.6, 165.2, 165.1, 146.6, 143.2, 133.6, 133.5, 133.1, 129.8, 129.7, 129.6, 129.0, 128.8, 128.5 (×2), 128.4, 128.1, 125.6, 122.7, 104.0, 96.3, 90.6, 79.4, 77.2, 75.4, 75.2, 70.3, 69.5, 68.2, 67.9, 67.8, 66.8, 64.0, 60.4, 58.9, 52.7, 50.8, 50.5, 44.6, 42.7, 28.3, 22.5, 22.6 (×2), 20.5 (×2), 20.4.

Mannose ethylene Linked Tetramer (38)

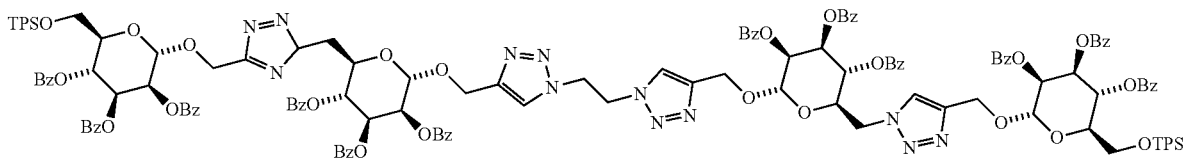

Click reaction of diazide 28 (400 mg, 0.40 mmol) and mannopyranoside 5 (600 mg, 0.80 mmol) via the general procedure gave 38 (600 mg, 65%) as a glassy solid; $^1$H NMR (CDCl$_3$, 400 MHz): δ=8.06 (s, 2H, H-9, H-9'), 8.02-7.93 (m, 12H, OBz), 7.87 (dd, 4H, J=1.3 Hz, J=8.3 Hz, OBz), 7.77 (dd, 8H, J=0.9 Hz, J=8.3 Hz, OBz), 7.73 (dd, 4H, J=1.3 Hz, J=8.1 Hz, OBz), 7.62-7.51 (m, 4H, OBz), 7.51-7.14 (m, 34H, OBz), 7.10 (s, 4H, Ar-OTPS), 5.94 (dd, 2H, J$_{2,3}$=3.5 Hz, J$_{3,4}$=10.1 Hz, H-3'), 5.81-5.70 (m, 6H, H-3, H4'', H4), 5.64 (dd, 2H, J$_{1',2}$=1.6 Hz, J$_{2',3}$=3.4 Hz, H-2'), 5.57-5.53 (m, 2H, H-2), 5.22, 5.16 (m, 4H, H-1', H-1), 4.94-4.63 (m, 12H, H-6', H-10', H-5, H-7), 4.60, 4.54 (Abq, 4H, J=12.6 Hz, H-7'), 4.51-4.44 (m, 2H, H-5'), 4.29-4.16 (m, 4H, H-6),), 4.06 (p, 2H, J=6.9 Hz, J=13.8 Hz, CH-i-pr), 2.84 (p, 1H, J=6.9 Hz, J=13.7 Hz, CH-i-pr), 1.20 (s, 3H, CH$_3$), 1.18 (s, 3H, CH$_3$), 1.16 (s, 3H, CH$_3$), 1.14 (s, 3H, CH$_3$), 1.13 (s, 3H, CH$_3$), 1.11 (s, 3H, CH$_3$); $^{13}$C NMR (CDCl$_3$, 100 MHz): S=165.8, 165.4, 165.3 (×2), 165.2 (×2) (12×C=O), 153.7, 150.9 (Ar-OTPS), 143.5, 143.2 (C-8, C-8'), 133.6, 133.5, 133.1, 129.9 (×2), 129.8, 129.7, 129.6, 129.1 (×2), 129.0, 128.9, 128.7, 128.6 (×2), 128.5 (×2), 128.4, 128.3, 125.2, 128.6 (C-9, C-9'), 123.8 (Ar-OTPS), 96.9, 96.4 (C-1, C-1'), 70.3 (C-2), 70.1 (C-2'), 69.8 (C-3), 69.7 (C-3'), 69.4 (×2) (C-5, C-5'), 68.2 (C-4'), 67.8 (C-6), 66.9 (C-4), 61.1 (C- 7), 60.3 (C-7'), 51.2 (C-6'), 49.5 (C-10'), 34.2 (CH-i-pr), 29.6 (CH-i-pr), 24.7, 24.6, 23.5 (12×CH$_3$).

Mannose ethylene Linked Tetramer Bisazide (39)

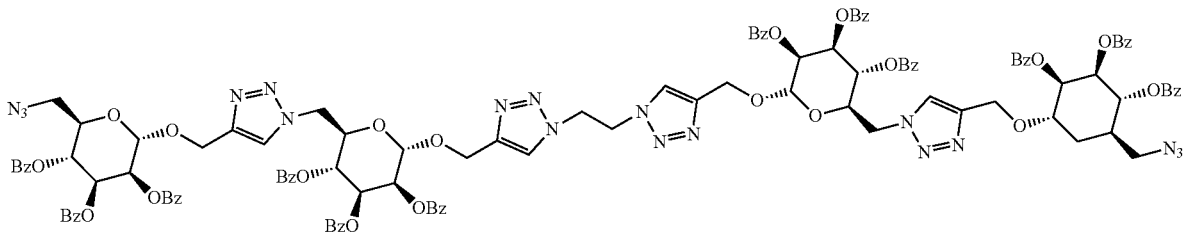

To a solution of tetramer 38 (600 mg, 0.20 mmol) in dry DMF (10 mL), sodium azide (60 mg, 0.9 mmol) was added and the mixture stirred at 60° C. under a nitrogen atmosphere for 18 h. The reaction mixture was then concentrated under reduced pressure and the crude material obtained was suspended in EtOAc (50 mL). The organic layer was washed with HCl (2×50 mL), sat. NaHCO$_3$, dried (MgSO$_4$) and concentrated under reduced pressure to obtain the diazide 39 as a yellow oil. The crude material was used without further purification. $^1$H NMR (CDCl$_3$, 400 MHz): δ=8.13 (s, 2H, H-9), 8.09-7.88 (m, 16H, H-OBz), 7.84-7.72 (m, 8H, H-OBz), 7.65-7.16 (m, 44H, H-OBz, H-9'), 5.98 (dd, 2H, J$_{2',3'}$=3.4 Hz, J$_{3',4'}$=10.0 Hz, H-3'), 5.86 (dd, 2H, J$_{3,4}$=J$_{4,5}$=10.1 Hz, H-4), 5.82-5.74 (m, 4H, H-3, H-4'), 5.64 (dd, 2H, J$_{1',2'}$=1.6 Hz, J$_{2',3'}$=3.4 Hz, H-2'), 5.60 (dd, 2H, J$_{1,2}$=1.6 Hz, J$_{2,3}$=3.2 Hz, H-2), 5.23 (d, 2H, J$_{1',2'}$=1.6 Hz, H-1'), 5.19 (d, 2H, J$_{1,2}$=1.6 Hz, H-1), 4.98, 4.82 (ABq, 4H, J=12.6 Hz, H-7'), 4.87-4.64 (m, 10H, H-6', H-7, H-5'), 4.60, 4.34 (ABq, 4H, J=12.7 Hz, H-10'), 4.35 (ddd, 2H, J$_{5,6}$=2.7 Hz, J$_{5,6}$=5.4 Hz, J$_{4,5}$=10.0 Hz, H-5), 3.52 (dd, 2H, J$_{5,6a}$=2.7 Hz, J$_{6a,6b}$=13.4 Hz, H-6a), 3.46 (dd, 2H, J$_{5,6b}$=5.4 Hz, J$_{6a,6b}$=13.4 Hz, H-6b); $^{13}$C NMR (CDCl$_3$, 100 MHz): δ=165.9, 165.5, 165.4 (×3), 165.3, 148.6, 148.4, 143.4, 143.2, 133.7, 133.6, 133.5, 133.2, 130.0, 129.9 (×3), 129.7 (×2), 129.2, 129.1, 129.0, 128.9, 128.8, 128.6 (×2), 128.5 (×2), 128.3, 125.5 (C-9), 124.9 (C-9'), 97.1 (C-1'), 96.3 (C-1), 77.2 (C-8, C-8'), 70.4 (×2) (C-5, C-2'), 70.1 (C-2), 69.8 (C-3), 69.7 (C-3'), 69.4 (C-5'), 68.2 (C-4'), 67.5 (C-4), 61.0 (C-7'), 60.1 (C-10'), 51.5 (C-6'), 51.1 (C-6), 49.7 (C-7).

Mannose diethylene Linked Tetramer (40)

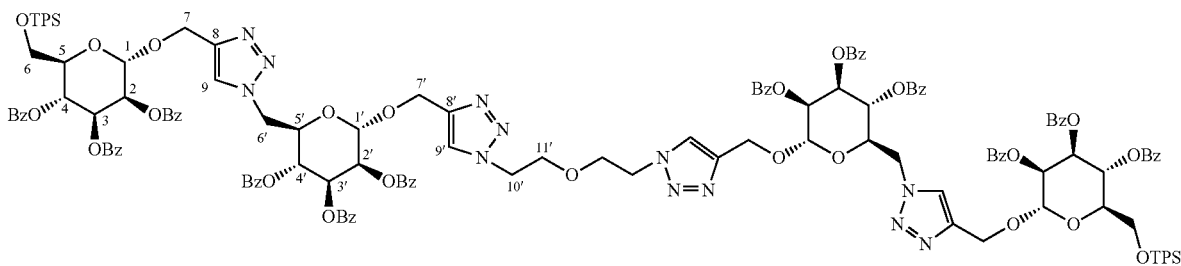

Click reaction of diazide 32 (500 mg, 0.40 mmol) and mannopyranoside 5 (600 mg, 0.80 mmol) via the general procedure gave 40 (900 mg, 99%) as a glassy solid; $^1$H NMR (CDCl$_3$, 400 MHz): δ=8.11 (s, 2H, H-9), 8.09-7.84 (m, 16H, H-OBz), 7.84-7.66 (m, 8H, H-OBz), 7.66-7.16 (m, 36H, H-OBz), 7.11 (s, 4H, Ar-OTPS), 5.90 (dd, 2H, J$_{2,3}$=3.5 Hz, J$_{3',4'}$=10.0 Hz, H-3'), 5.82-5.72 (m, 6H, H-3, H-4, H-4'), 5.68 (dd, 2H, J$_{1',2'}$=1.7 Hz, J$_{2',3}$=3.5 Hz, H-2'), 5.58-5.54 (m, 2H, H-2), 5.24 (d, 2H, J$_{1',2'}$=1.7 Hz, H-1'), 5.19 (d, 2H, J$_{1,2}$=1.7 Hz, H-1), 4.91, 4.79 (ABq, 4H, J=12.3 Hz, H-7'), 4.85-4.57 (m, 10H, H-5', H-6, H-7), 4.57-4.45 (m, 6H, H-10', H-5), 4.26 (dd, 2H, J$_{5,6a}$=6.0, J$_{6a,6b}$=11.1 Hz, H-6a), 4.20 (dd, 2H, J$_{5,6b}$=2.7 Hz, J$_{6a,6b}$=11.1 Hz, H-6b), 4.07 (p, 2H, J=6.3 Hz, J=13.2 Hz, CH-i-pr), 3.83 (t, 4H, J$_{10',11'}$=5.2 Hz, H-11'), 2.85 (p, 1H, J=6.9 Hz, J=13.7 Hz, CH-i-pr), 1.22 (s, 6H, CH$_3$), 1.20 (s, 6H, CH$_3$), 1.17 (s, 6H, CH$_3$), 1.15 (s, 6H, CH$_3$), 1.14 (s, 6H, CH$_3$), 1.12 (s, 6H, CH$_3$); $^{13}$C NMR (CDCl$_3$, 100 MHz): δ=165.8, 165.4, 165.3, 153.8, 150.9, 143.4, 133.6, 133.5, 133.2, 129.9, 129.8 (×3), 129.7 (×2), 129.1, 128.9 (×2), 128.7, 128.6, 128.5, 128.4, 128.3, 123.8, 96.9, 96.8, 77.2, 70.2, 70.1, 69.9, 69.7, 69.5, 69.4, 68.1, 67.8, 66.8, 61.0, 60.4, 51.3, 34.2, 29.6, 24.7, 24.6, 23.5.

Mannose diethylene Linked Tetramer Bisazide (41)

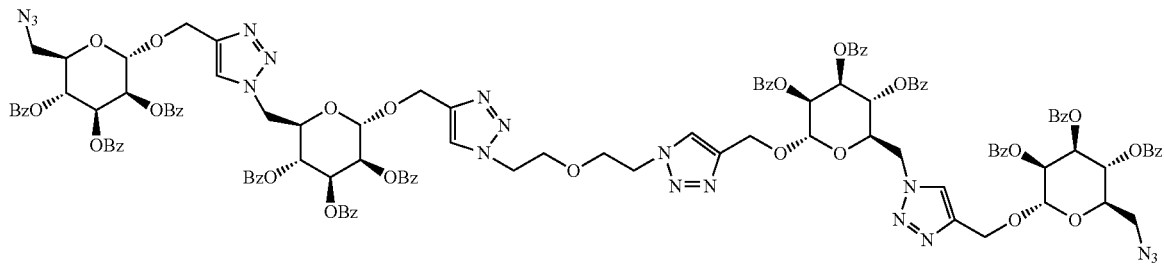

To a solution of tetramer 40 (0.9 g, 0.4 mmol) in dry DMF (10 mL), sodium azide (100 mg, 1.6 mmol) was added and the mixture stirred at 60° C. under a nitrogen atmosphere for 18 h. The reaction mixture was then concentrated under reduced pressure and the crude material obtained was suspended in EtOAc (75 mL). The organic layer was washed with HCl (2×75 mL), sat. NaHCO$_3$, dried (MgSO$_4$) and concentrated to obtain the diazide 41. This material was used in the subsequent step without further purification. $^1$H NMR (CDCl$_3$, 400 MHz): δ=8.21 (s, 2H, H-triazole), 8.11-7.69 (m, 28H, H-OBz, H-triazole), 7.65-7.15 (m, 38H, H-OBz), 5.94-5.83 (m, 4H), 5.82-5.72 (m, 4H), 5.70-5.66 (m, 2H), 5.60-5.54 (m, 2H), 5.27-5.19 (m, 4H), 5.04-5.96 (m, 2H), 4.82-4.36 (m, 16H), 4.30-4.32 (m, 2H), 3.94-3.76 (m, 4H), 3.61-3.41 (m, 4H); $^{13}$C NMR (CDCl$_3$, 100 MHz): δ=165.6, 165.5 (×2), 133.6 (×2), 133.3, 129.9, 129.8, 129.7, 129.1, 128.9, 128.8, 128.6, 128.5, 128.3, 125.0, 97.0, 77.2, 70.6, 70.2, 69.9, 67.4, 60.7, 51.2, 50.8.

Ethylene Linked Hexamer (42)

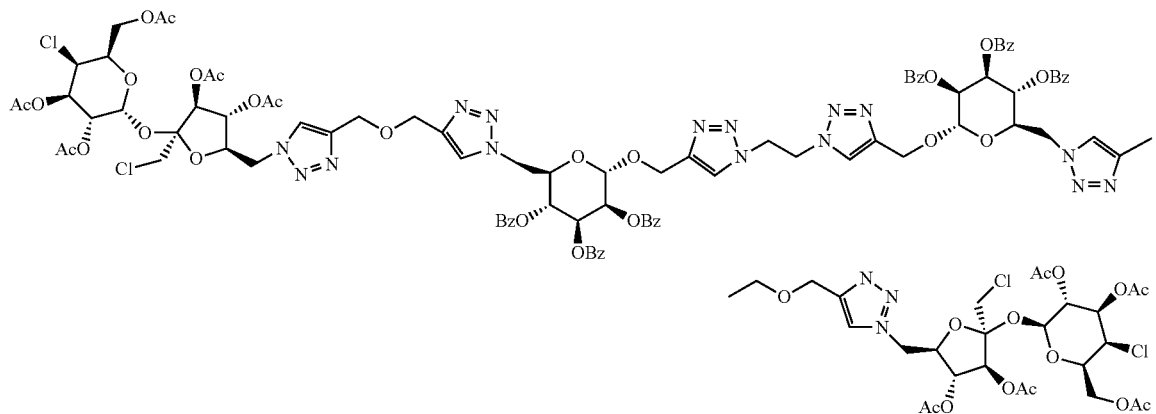

Click reaction of diazide 28 (270 mg, 0.20 mmol) and triazole 26 (300 mg, 0.40 mmol) via the general procedure gave 26 (222 mg, 38%) as a glassy solid; $^1$H NMR (CDCl$_3$, 400 MHz): δ=7.91 (dd, 8H, J=1.3 Hz, J=8.3 Hz, OBz), 7.86 (s, 2H, H-triazole), 7.74-7.64 (m, 6H, OBz, H-triazole), 7.57-7.22 (m, 14H, OBz), 7.16 (t, 4H, OBz), 5.85 (dd, 2H, J$_{2,3}$=3.4 Hz, J$_{3,4}$=10.1 Hz, H-c), 5.70-5.61 (m, 6H, H-1, H-3', H-d), 5.45 (dd, 2H, J$_{1,2}$=1.7 Hz, J$_{2,3}$=3.4 Hz, H-b), 5.33 (t, 2H, J=7.2 Hz, H-4'), 5.28-5.24 (m, 4H, H-2, H-3), 5.05 (d, 2H, J=1.2 Hz, H-a), 4.98-4.81 (m, 4H, H-16'), 4.81-4.50 (m, 20H, H-4, H-5, H-6', H-9', H-10', H-e, H-f), 4.47, 4.40 (ABq, 4H, J=12.1 Hz, H-13'), 4.22 (dd, 2H, J$_{5,6a}$=4.6 Hz, J$_{6a,6b}$=11.8 Hz, H-6a), 4.16 (dd, 2H, J$_{5,6b}$=6.9 Hz, J$_{6a,6b}$=11.8 Hz, H-6b), 3.57, 3.49 (ABq, 4H, J=12.1 Hz, H-1'), 2.07 (s, 6H, OCH$_3$), 2.04 (s, 6H, OCH$_3$), 2.01 (s, 6H, OCH$_3$), 2.00 (s, 6H, OCH$_3$), 1.99 (s, 6H, OCH$_3$); $^{13}$C NMR (CDCl$_3$, 100 MHz): δ=206.9, 171.1, 170.4, 170.1 (×2), 169.9, 169.6, 165.8, 165.3, 165.2, 133.6, 133.2, 129.9, 129.6, 129.1, 128.9, 128.6, 128.5 (×2), 128.3, 104.7, 96.3, 90.6, 75.3, 70.3, 69.6, 68.2, 67.8, 66.8, 63.9, 60.3, 59.0, 44.7, 21.0, 20.7, 20.6, 20.4.

Diethylene Linked Hexamer (43)

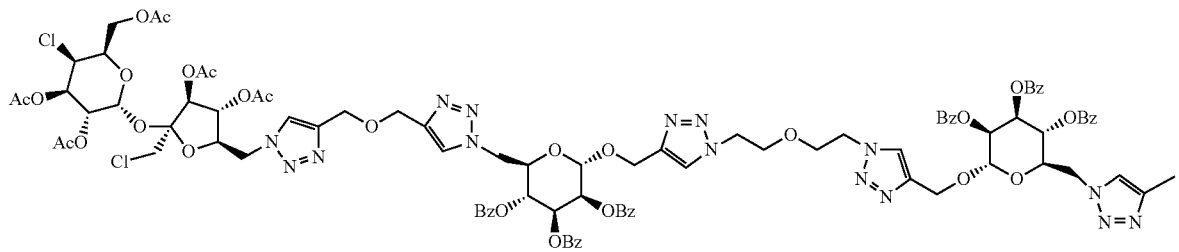

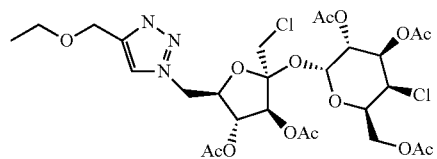

Click reaction of diazide 32 (500 mg, 0.50 mmol) and triazole 26 (700 mg, 1.00 mmol) via the general procedure gave 43 (200 mg, 20%) as a glassy solid; $^1$H NMR (CDCl$_3$, 400 MHz): δ=7.86, 7.70, 7.57 (3×(s, 2H, H-triazole)), 5.69-5.64 (s, 4H, H-3", H-3'), 5.33 (t, 2H, J=7.3 Hz, H-4"), 5.29-5.26 (m, 4H, H-1', H-4'), 5.24 (dd, 2H, J=3.3 Hz, J=10.0 Hz, H-3), 5.13 (dd, 2H, J=1.7 Hz, J=3.3 Hz, H-2), 5.07 (t, 2H, J=10.0 Hz, H-4), 4.86-4.81 (m, 2H, H-1), 4.77 (dd, 2H, J=3.5 Hz, J=14.3 Hz), 4.71-4.29 (m, 28H, H-5', H-5, H-6", H-6', H-7, H-10, H-14, H-15), 4.20-4.12 (m, 6H, H-6, H-5"), 3.82-3.73 (m, 4H, H-11), 3.58, 3.51 (ABq, 4H, J=12.1 Hz, H-1"); $^{13}$C NMR (CDCl$_3$, 100 MHz): δ=170.4, 170.2, 170.1, 170.0, 169.9, 169.8, 169.7, 169.6, 144.1, 142.4, 125.3, 124.9, 124.8, 104.1, 96.6, 90.7, 79.4, 77.2, 75.4, 75.3, 69.3, 69.2, 68.7, 68.3, 67.8, 67.4, 66.9, 64.0, 63.1, 63.0, 60.4, 60.1, 59.0, 53.0, 51.2, 50.4, 44.7, 20.8, 20.7, 20.6 (×3), 20.5.

Ethylene Linked Octomer (44)

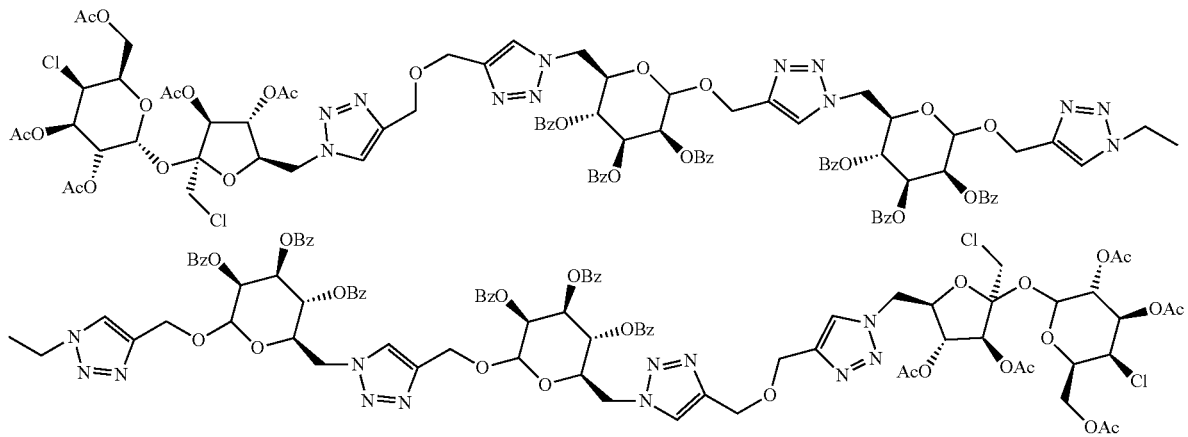

Click reaction of diazide 39 (500 mg, 0.20 mmol) and triazole 26 (300 mg, 0.40 mmol) via the general procedure gave 44 (500 mg, 74%) as a glassy solid; $^1$H NMR (CDCl$_3$, 400 MHz): δ=8.06-7.89 (m, 20H, H-OBz), 7.82-7.69 (m, 12H, H-OBz, H-triazole), 7.66-7.16 (m, 52H, H-OBz, H-triazole), 5.97 (dd, 2H, J=3.3 Hz, J=9.9 Hz, H-3'), 5.82-5.75 (m, 4H, H-3, H-1"), 5.74-5.66 (m, 6H, H-4, H-4', H-3'''), 5.64 (dd, 2H, J=1.7 Hz, J=3.3 Hz, H-2'), 5.55 (dd, 2H, J=1.6 Hz, J=3.3 Hz, H-2), 5.39 (t, 2H, J=7.1 Hz, H-4'''), 5.35-5.31 (m, 4H, H-3", H-4"), 5.21-5.16 (m, 4H, H-1', H-1), 4.90-4.47 (m, 40H, H-5, H-5', H-5", H-6''', H-6', H-6, H-7, H-7', H-9, H-9''', H-10'), 4.45-4.37 (m, 2H, H-5"), 4.29 (dd, 2H, J=4.6 Hz, J=11.8 Hz, H-6"a), 4.21 (dd, 2H, J=6.8 Hz, J=11.8 Hz, H-6"b), 3.62, 3.53 (ABq, 4H, J=12.1 Hz, H-1'''), 2.13 (s, 6H, OCH$_3$), 2.10 (s, 6H, OCH$_3$), 2.06 (s, 6H, OCH$_3$), 2.05 (s, 6H, OCH$_3$), 2.05 (s, 6H, OCH$_3$); $^{13}$C NMR (CDCl$_3$, 100 MHz): δ=170.4, 170.2, 170.0, 169.4, 169.7, 165.4, 165.3 (×2), 165.2 (×2), 143.2, 143.1, 133.7, 133.2, 129.9 (×2), 129.8, 129.7, 128.9, 128.6, 128.5, 128.3, 104.2, 96.8, 90.7, 79.5, 75.3, 70.2, 69.6, 69.4, 68.3, 68.0, 67.8, 66.9, 64.0, 63.3, 63.2, 59.0, 44.8, 20.7, 20.6, 20.5.

Diethylene Linked Octamer (45)

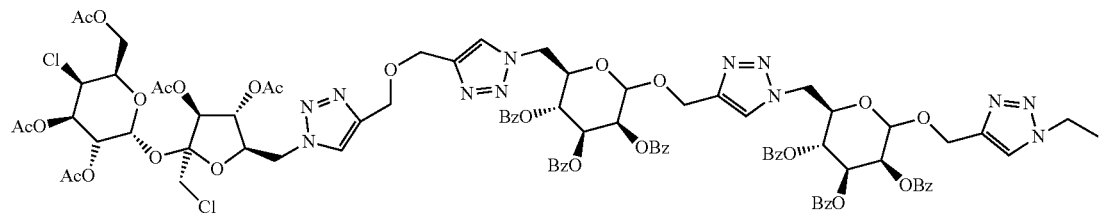

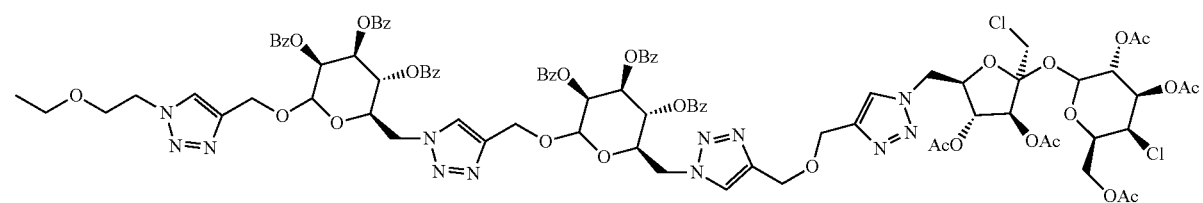

Click reaction of diazide 41 (900 mg, 0.40 mmol) and triazole 26 (500 mg, 0.80 mmol) via the general procedure gave 45 (800 mg, 57%) as a glassy solid; $^1$H NMR (CDCl$_3$, 400 MHz): δ=8.14-7.86 (m, 18H, H-OBz, H-triazole), 7.83-7.68 (m, 10H, H-OBz), 7.65-7.12 (m, 64H, H-OBz, H-triazole), 5.90 (dd, 2H, J=3.1 Hz, J=10.0 Hz), 5.83-5.63 (m, 10H), 5.58-5.54 (m, 2H), 5.39 (t, 2H, J 7.1 Hz), 5.34-5.32 (d, 4H), 5.23 (br-s, 2H), 5.18 (br-s, 2H), 4.88-4.35 (m, 40H), 4.29 (dd, 2H, J=4.6 Hz, J=11.6 Hz), 4.22 (dd, 2H, J=6.8 Hz, J=11.6 Hz), 3.91-3.74 (m, 4H), 3.63, 3.53 (ABq, J=12.0 Hz), 2.14, 2.11, 2.07, 2.06, 2.05 (10×(s, 3H)).

Hexasaccharide (46)

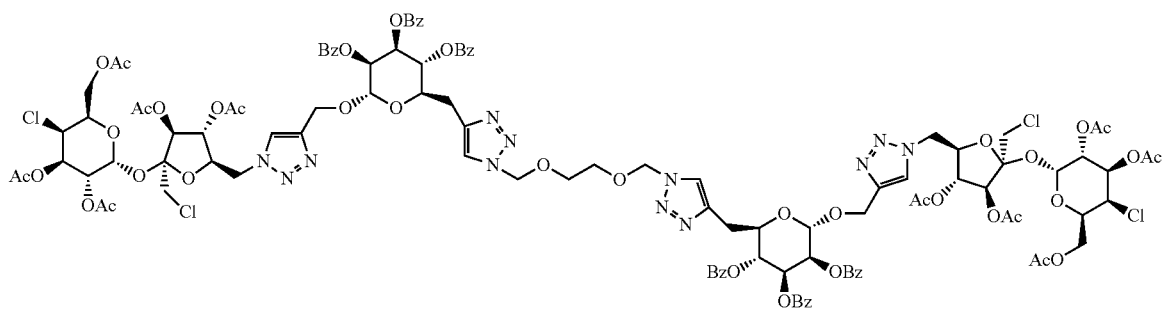

Click reaction of sucralose mannose azide 34 (410 mg, 0.35 mmol) and bispropagyl glycol linker (24 mg, 0.18 mmol) via the general procedure gave hexasaccharide 46 (90 mg, 20/6) as an oil; $^1$H NMR (CDCl$_3$, 400 MHz): δ=8.09-7.92 (m, 8H), 7.89 (s, 2H), 7.82-7.72 (m, 6H), 7.66-7.56 (m, 2H), 7.56-7.44 (m, 6H), 7.44-7.34 (m, 6H), 7.26-7.18 (m, 4H), 5.91-5.68 (m, 8H), 5.62 (br-s, 2H), 5.46-5.30 (m, 6H), 5.17 (s, 2H), 4.97-4.41 (m, 24H), 4.38-4.20 (m, 4H), 3.87-3.40 (m, 10H), 2.15 (s, 6H), 2.10 (s, 6H), 2.09 (s, 6H), 2.07, 2.06 (s, 6H) ppm; $^{13}$C NMR (CDCl$_3$, 100 MHz): δ=170.4, 170.2, 170.1, 169.8, 169.7, 165.7, 165.3, 165.2, 143.2, 133.7 (×2), 133.1, 129.9, 129.8, 129.7, 129.1, 128.9, 128.6, 128.5, 128.2, 124.7, 104.2, 96.6, 90.7, 79.4, 77.2, 75.4, 75.3, 70.3, 69.5, 68.3, 67.9, 66.8, 64.1, 60.7, 60.3, 59.0, 52.8, 51.2, 44.6, 20.7 (×2), 20.6 (×3) ppm.

Octasaccharide (47)
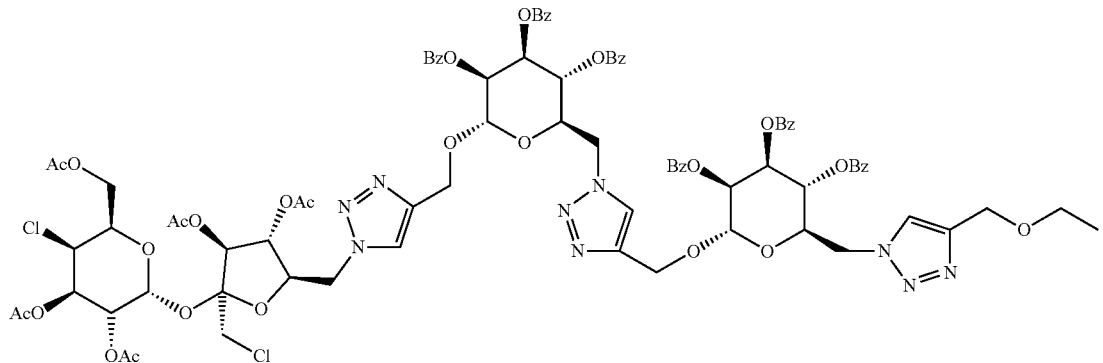
Click reaction of azide 36 (800 mg, 0.46 mmol) and propagyl ether (22 mg, 0.23 mmol) via the general procedure gave octasaccharide 47 (350 mg, 43%) as an oil; $^1$H NMR (CDCl$_3$, 400 MHz): δ=8.09-7.84 (m, 18H), 7.83-7.68 (m, 8H), 7.66-7.29 (m, 24H), 7.25-7.16 (m, 6H), 5.95-5.82 (m, 4H), 5.81-70 (m, 4H), 5.69-5.61 (m, 4H), 5.58-5.52 (m, 2H), 5.46-5.29 (m, 6H), 5.21 (s, 2H), 5.16 (s, 2H), 4.93-4.39 (m, 30H), 4.40-4.19 (m, 4H), 3.73-3.57 (m, 4H), 2.15 (s, 6H), 2.10 (s, 12H), 2.05 (s, 6H), 1.95 (s, 6H) ppm; $^{13}$C NMR (CDCl$_3$, 100 MHz): δ=171.1, 170.4, 170.1, 169.8, 169.7, 165.7, 165.6, 165.3, 165.2, 165.1 (×2), 144.3, 143.1, 133.6, 133.1, 129.9, 129.8 (×2), 129.7 (×2), 129.6, 129.1, 129.0, 128.9 (×2), 128.6, 128.5 (×2), 128.2, 125.3, 125.0, 124.7, 104.1, 96.7, 96.6, 90.6, 79.3, 77.2, 75.3, 70.3, 70.1, 69.5, 69.3, 68.2, 68.1, 68.0, 67.9, 66.7, 64.0, 60.3, 59.0, 52.7, 51.1, 44.7, 20.7, 20.6 (×2), 20.5 ppm.
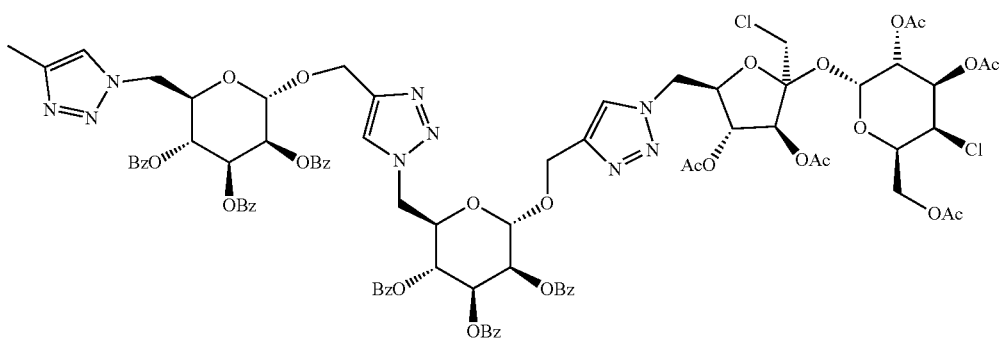
Octasaccharide (48)
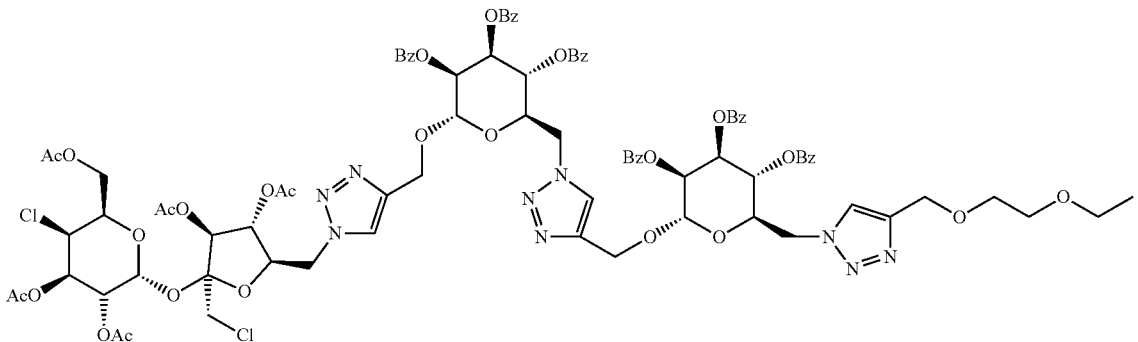

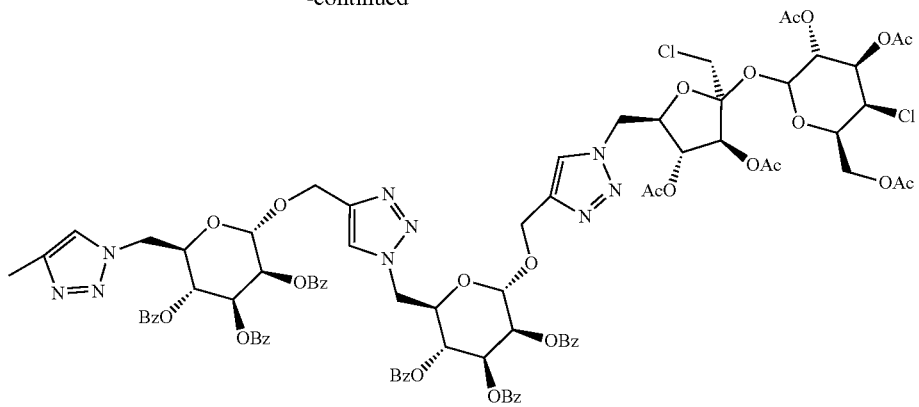

Click reaction of azide 36 (400 mg, 0.23 mmol) and bis propagyl ethylene linker (16 mg, 0.11 mmol) via the general procedure gave octasaccharide 48 (150 mg, 38%) as an oil; $^1$H NMR (CDCl$_3$, 400 MHz): δ=8.09-7.83 (m, 20H), 7.83-70 (m, 10H), 7.66-7.55 (m, 4H), 7.55-7.43 (m, 12H), 7.42-7.31 (m, 12H), 7.26-7.17 (m, 8H), 5.89 (dd, 2H, J=3.3 Hz, J=10.0 Hz), 5.85 (d, 2H, J=3.5 Hz), 5.81-5.69 (m, 6H), 5.69-5.61 (m, 4H), 5.54 (dd, 2H, J=1.7 Hz, J=3.2 Hz), 5.42 (t, 2H, J=7.3 Hz), 5.39 (dd, 2H, J=3.6 Hz, J=10.8 Hz), 5.32 (dd, 2H, J=3.3 Hz, J=10.8 Hz), 5.21 (d, 2H, J=1.5 Hz), 5.16 (d, 2H, J=1.5 Hz), 4.84 (dd, 2H, J=3.6 Hz, J=14.4 Hz), 4.78-4.39 (m, 32H), 4.33 (dd, 2H, J=4.4 Hz, J=11.7 Hz), 4.25 (dd, 2H, J=7.1 Hz, J=11.9 Hz), 3.72-3.52 (m, 8H), 2.15 (s, 6H), 2.07 (s×2, 12H), 5.56 (s, 6H); $^{13}$C NMR (CDCl$_3$, 100 MHz): δ=170.4, 170.1, 169.8, 169.7, 165.8, 165.6, 165.3, 165.2, 165.1, 144.6, 143.1 (×2), 133.7, 133.6, 133.1, 129.9 (×2), 129.8 (×2), 129.7, 129.6, 129.1, 129.0 (×2), 128.9, 128.6, 128.5 (×2), 128.2, 125.3, 124.8, 124.7, 104.1, 96.7, 96.6, 90.6, 79.3, 77.2, 75.4, 75.3, 70.3, 70.2, 69.6, 69.3, 68.3, 68.1, 68.0, 67.9, 67.0, 66.7, 64.0, 59.0, 52.7, 51.1, 44.7, 21.0, 20.7, 20.6 (×2), 20.5 ppm.

Ethylene Linked Dimaltotriose (49)

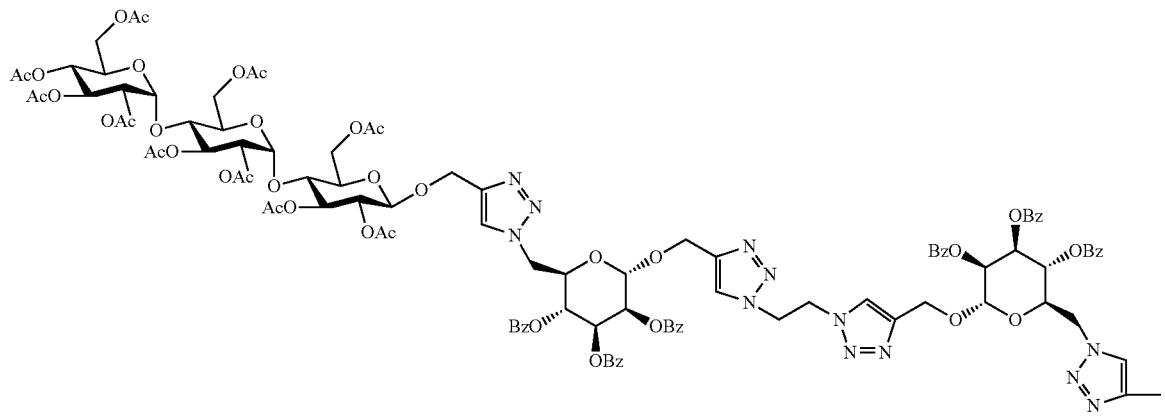

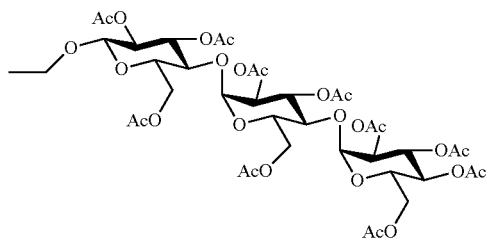

Click reaction of azide 28 (160 mg, 0.13 mmol) and propagyl maltotriose 13 (250 mg, 0.25 mmol) via the general procedure gave oligosaccharide 49 (235 mg, 57%) as a glassy solid; $^1$H NMR (CDCl$_3$, 400 MHz): δ=8.07-7.89 (m, 5H), 7.83-7.73 (m, 1H), 7.66-7.56 (m, 1H), 7.54-7.29 (m, 6H), 7.25-7.16 (m, 2H), 6.09 (dd, 1H, J=3.2 Hz, J=9.9 Hz), 5.76 (t, 1H, J=9.9 Hz), 5.66-5.56 (m, 1H), 5.43-5.30 (m, 3H), 5.20 (d, 1H, J=4.1 Hz), 5.14 (s, 1H), 5.05 (t, 2H, J=10.0 Hz), 4.98-4.68 (m, 9H), 4.67-4.31 (m, 6H), 4.31-4.11 (m, 3H), 4.09-3.83 (m, 5H), 3.77-3.59 (m, 1H), 2.16-1.78 (10×s, 30H, 10×OAc) ppm; $^{13}$C NMR (CDCl$_3$, 100 MHz): δ=170.5, 170.3, 169.9, 169.8, 169.7, 169.6, 169.4, 165.8, 165.4, 165.2, 143.8, 143.2, 133.7, 133.5, 133.2, 129.8 (×2), 129.6, 129.0, 128.8, 128.6 (×2), 128.4, 128.3, 125.4, 124.9, 98.8, 95.8, 95.6, 95.4, 77.2, 74.9, 73.9, 72.5, 71.9, 71.6, 70.4, 70.0, 69.8, 69.3 (×2), 68.9, 68.5, 68.1, 67.9, 62.8, 62.3, 62.2, 61.3, 59.2, 51.1, 50.3, 20.8, 20.7, 20.6, 20.5.

Diethylene Linked Dimaltotriose (50)

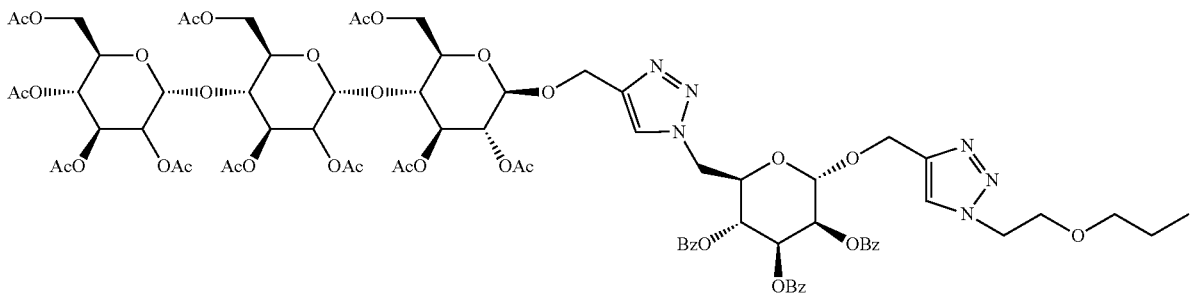

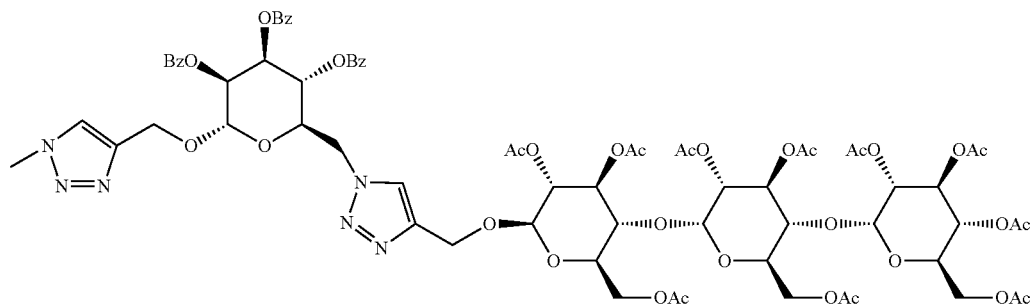

Click reaction of azide 32 (260 mg, 0.21 mmol) and acetylated propagyl maltotriose 13 (400 mg, 0.42 mmol) via the general procedure gave oligosaccharide 50 (205 mg, 31%) as a glassy solid; $^1$H NMR (CDCl$_3$, 400 MHz): δ=8.02-7.89 (m, 9H), 7.87 (s, 2H), 7.77-7.69 (m, 6H), 7.63-7.56 (m, 2H), 7.53-7.42 (m, 6H), 7.41-7.30 (m, 6H), 7.24-7.16 (m, 4H), 5.91-5.82 (m, 2H), 5.76-5.67 (m, 3H), 5.65-5.58 (m, 2H), 5.41-5.29 (m, 6H), 5.25-5.20 (m, 2H), 5.19-5.16 (m, 2H), 5.13 (t, 2H, J=9.2 Hz), 5.04 (t, 2H, J=10.0 Hz), 4.92-4.38 (m, 34H), 4.29-4.12 (m, 6H), 4.06-3.99 (m, 2H), 3.98-3.83 (m, 14H), 3.70-3.62 (m, 2H), 2.16-1.88 (10×s, 30H, 10×OAc) ppm; $^{13}$C NMR (CDCl$_3$, 100 MHz): δ=171.02, 170.5 (×2), 170.4 (×2), 170.3, 169.9, 169.7, 169.6 (×2), 169.3, 165.6, 165.2 (×2), 144.0, 142.9, 133.6 (×2), 133.2, 129.8, 129.7, 129.6, 129.0, 128.8, 128.6, 128.5, 128.4, 128.2, 124.7, 124.5, 99.1, 96.3, 95.6 (×2), 77.2, 75.1, 73.7, 72.5, 72.0, 71.9, 71.6, 70.4, 70.2, 70.0, 69.6, 69.3 (×2), 68.8, 68.4, 67.9 (×2), 62.5, 62.2, 61.3, 60.5, 60.3, 50.9, 50.2, 20.9 (×2), 20.8, 20.7 (×2), 20.6, 20.4.

Sucralose-Acarbose (51)

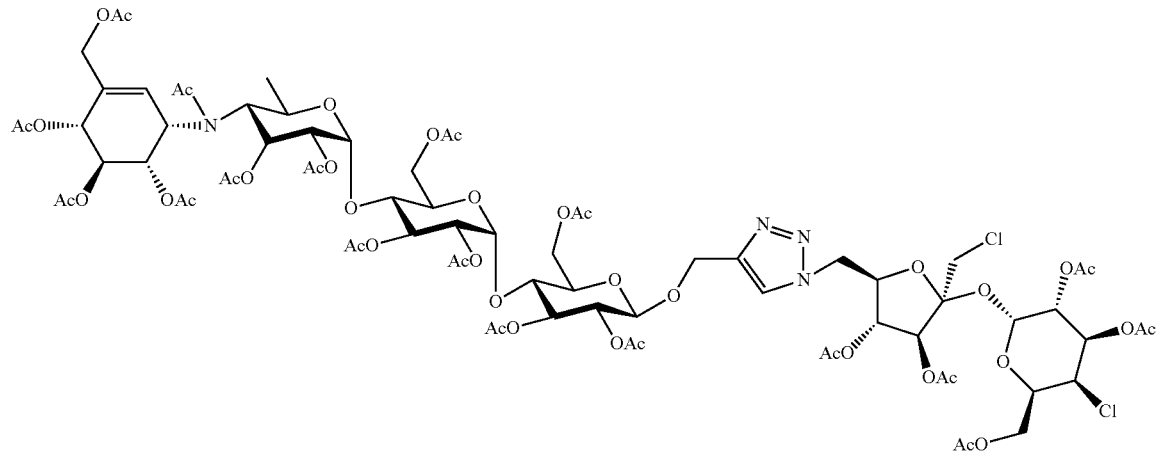

Click reaction of sucralose azide 10 (105 mg, 0.17 mmol) and acetylated propagyl acarbose 14 (400 mg, 0.42 mmol) via the general procedure gave oligosaccharide 51 (100 mg, 33%) as a glassy solid; $^1$H NMR (CDCl$_3$, 400 MHz): δ=7.65 (s, 1H), 5.93 (d, 1H, J=5.4 Hz), 5.73-5.64 (m, 2H), 5.59-5.48 (m, 2H), 5.40-5.28 (m, 3H), 5.26-5.16 (m, 3H), 5.07 (t, 2H, J=10.1 Hz), 4.93-4.86 (m, 2H), 4.85-4.54 (m, 9H), 4.54-4.11 (m, 8H), 3.96 (t, 1H, J=9.2 Hz), 3.92-3.85 (m, 2H), 3.77-3.65 (m, 2H), 3.62, 3.49 (ABq, 2H, J=12.1 Hz), 3.54-3.45 (m, 1H), 2.36 (t, 1H, J=9.9 Hz), 2.14 (s, 3H), 2.12 (2, 3H), 2.11 (s, 3H), 2.10 (s, 3H), 2.07 (s, 6H), 2.06 (s, 3H), 2.05 (s, 3H), 2.02 (s, 3H), 2.00 (s, 3H), 1.97 (×2) (s, 9H), 1.95 (×2) (s, 6H), 1.93 (s, 3H), 1.17 (d, 3H, J=6.1 Hz) ppm; $^{13}$C NMR (CDCl$_3$, 100 MHz): δ=171.0, 170.9, 170.7, 170.6, 170.5, 170.3 (×2), 170.2, 170.1 (×2), 170.0, 169.8, 169.6 (×2), 169.5, 133.8, 127.9, 124.2, 104.1, 99.2, 95.8, 95.6, 90.5, 79.5, 77.2, 75.3, 75.2, 75.1, 73.4, 72.1 (×2), 71.9, 71.8, 71.0, 70.8, 70.6, 70.4, 70.0, 69.7, 69.0, 68.2, 67.7, 66.8, 63.9, 63.0, 62.7, 62.6, 62.2, 61.1, 58.9, 52.5, 52.1, 20.9, 20.8 (×2), 20.6 (×2), 20.5 (×2), 20.4, 18.1 ppm.

Sucralose-Acarbose (52)

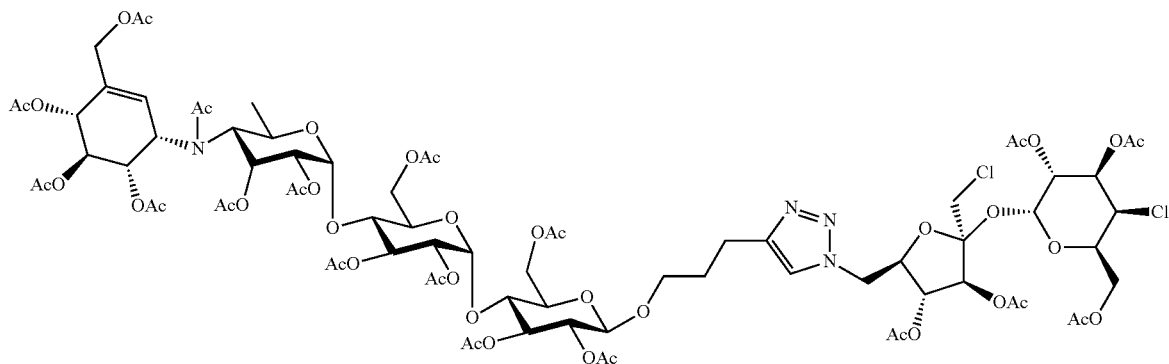

Click reaction of sucralose azide 10 (75 mg, 0.12 mmol) and propagyl acarbose 15 (146 mg, 0.12 mmol) via the general procedure gave oligosaccharide 36 (90 mg, 41%) as a glassy solid; $^1$H NMR (CDCl$_3$, 400 MHz): 5=7.51-7.40 (m, 1H), 5.94 (d, 1H, J=5.4 Hz), 5.71-5.66 (m, 1H), 5.60-5.49 (m, 2H), 5.42-5.18 (m, 6H), 5.08 (t, 1H, J=10.2 Hz), 4.90 (dd, 1H, J=4.2 Hz, J=10.1 Hz), 4.83-4.13 (m, 16H), 3.99-3.84 (m, 3H), 3.74-3.66 (m, 2H), 3.62, 3.49 (ABq, 2H, J=12.2 Hz), 3.58-3.46 (m, 1H); $^{13}$C NMR (CDCl$_3$, 100 MHz): δ=171.1, 170.9, 170.7 (×2), 170.6, 170.5, 170.3 (×2), 170.2, 170.1 (×3), 170.0 (×2), 169.8, 169.7, 169.6 (×2), 147.0, 133.9, 127.9, 122.7, 122.4, 104.0, 100.2, 95.8, 95.6, 90.5, 79.5, 77.2, 75.3 (×2), 75.2, 73.5, 72.2, 72.1 (×2), 71.8, 71.0, 70.8, 70.6, 70.4, 70.0, 69.7, 69.1, 68.2, 67.7, 66.9, 63.9, 63.0, 62.8, 62.2, 61.1, 60.3, 60.0, 52.1, 44.8, 20.96-20.57, 18.1.

Sucralose-Mannose-Acarbose (53)

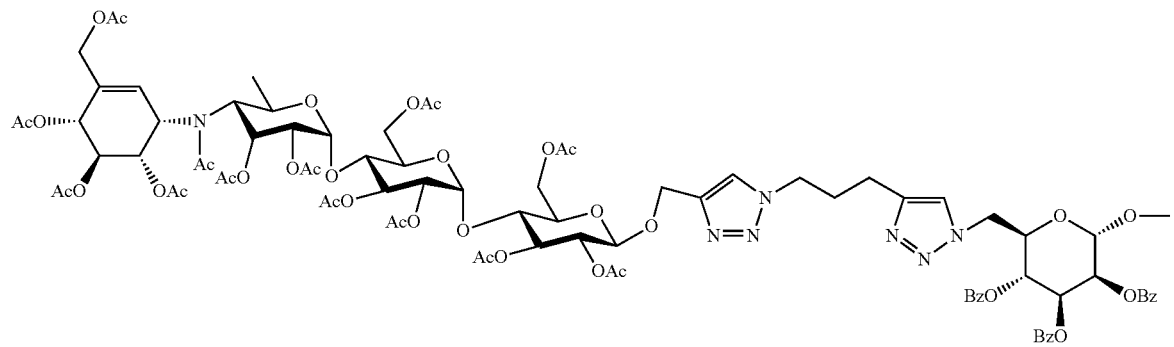

Click reaction of acetylated propagyl acarbose 14 (280 mg, 0.24 mmol) and azide 37 (310 mg, 0.24 mmol) via the general procedure gave compound 53 (340 mg, 58%) as a glassy solid; $^1$H NMR (CDCl$_3$, 400 MHz): δ=7.97-7.85 (m, 4H), 7.74 (s, 1H), 7.72-7.66 (m, 2H), 7.62 (s, 1H), 7.59-7.50 (m, 2H), 7.48-7.36 (m, 3H), 7.36-7.27 (m, 3H), 7.15 (t, 2H, J=7.7 Hz), 5.89 (d, 1H, J=5.1 Hz), 5.78 (dd, 1H, J=3.3 Hz, J=10.0 Hz), 5.75 (d, 1H, J=2.9 Hz), 5.68 (d, 1H, J=7.8 Hz), 5.64 (t, 1H, J=9.7 Hz), 5.56-5.43 (m, 4H), 5.34 (t, 1H, J=7.1 Hz), 5.32-5.23 (m, 3H), 5.21-5.11 (m, 4H), 5.10 (s, 1H), 5.03 (t, 1H, J=10.1 Hz), 4.90-4.07 (m, 34H), 3.91 (t, 1H, J=9.2 Hz), 3.88-3.80 (m, 2H), 3.73-3.52 (m, 5H), 3.50-3.40 (m, 1H), 2.62 (br-t, 2H, J=6.5 Hz), 2.32 (t, 1H, J=9.8 Hz), 2.17 (t, 2H, J=6.7 Hz), 2.08-1.85 (15×s, 51H), 1.17 (d, 3H, J=6.1 Hz) ppm; $^{13}$C NMR (CDCl$_3$, 100 MHz): δ=170.7, 170.5, 170.4, 170.3, 170.2 (×2), 170.1 (×2), 170.0, 169.9, 169.8, 169.7, 169.6, 169.4 (×2), 165.5, 165.1, 165.0, 145.8, 143.6, 143.1, 133.6, 133.5, 133.0, 129.6, 129.5, 129.4, 128.9, 128.7, 128.4 (×2), 128.3, 128.0, 127.8, 124.5, 123.1, 123.0, 103.9, 99.1, 96.2, 95.6, 95.4, 90.4, 79.3, 75.3, 75.1, 75.0, 73.2, 72.0, 71.9, 71.8, 71.6, 70.9, 70.7, 70.5, 70.3, 70.1, 69.8, 69.6, 69.3, 68.9, 68.1, 67.8, 67.7, 66.5, 63.9, 62.8, 62.5 (×2), 62.0, 60.9, 60.3, 58.9, 52.5, 51.9, 50.6, 49.0, 44.5, 29.4, 21.9, 20.7-20.2, 17.9 ppm.

Ethylene Linked Diacarbose (54)

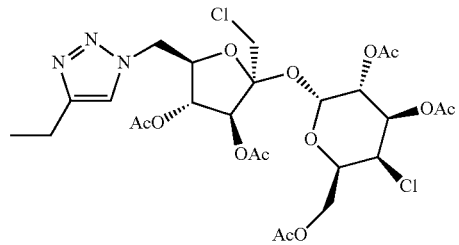

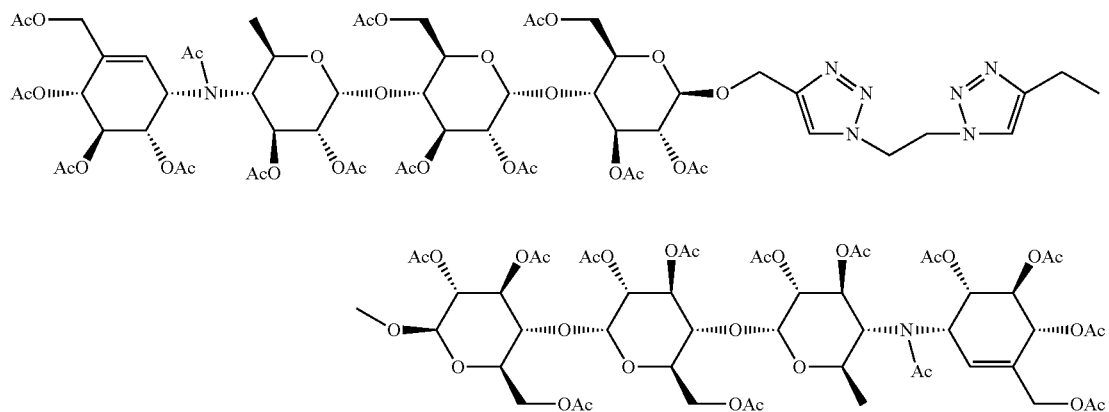

Click reaction of acetylated propagyl acarbose 14 (40 mg, 0.20 mmol) and ethylene diazide (6.70 mg, 60 µmol) via the general procedure gave diacrbose 54 (93 mg, 81%) as a solid; $^1$H NMR (CDCl$_3$, 400 MHz): δ=7.39 (s, 1H), 5.94 (d, J=5.2 Hz), 5.60-5.50 (m, 2H), 5.37-5.30 (m, 1H), 5.27-5.17 (m, 4H), 5.09 (t, 1H, J=10.3 Hz), 4.95-4.87 (m, 3H), 4.86-4.67 (m, 6H), 4.66-4.58 (m, 2H), 4.51 (dd, 1H, J=2.6 Hz, J=12.3 Hz), 4.43 (d, 1H, J=12.2 Hz), 4.34 (d, 1H, J=13.2 Hz), 4.23 (dd, 1H, J=3.9 Hz, J=12.1 Hz), 3.95 (t, 1H, J=9.2 Hz), 3.91-3.86 (m, 2H), 3.71-3.62 (m, 2H), 3.48 (ddd, 1H, J=6.0 Hz, J=12.2 Hz, J=16.0 Hz); $^{13}$C NMR (CDCl$_3$, 100 MHz): δ=171.0, 170.7, 170.6, 170.5, 170.3, 170.2 (×2), 170.0, 169.9, 169.6 (×2), 133.9, 127.9, 124.1, 99.7, 95.8, 95.6, 77.2, 75.1, 73.2, 72.3, 72.1, 72.0, 71.8, 71.0, 70.8, 70.6, 70.5, 70.0, 69.1, 63.0 (×2), 62.6, 62.4, 62.2, 61.1, 60.3, 52.1, 49.3.

Butylene Linked Diacarbose (55)

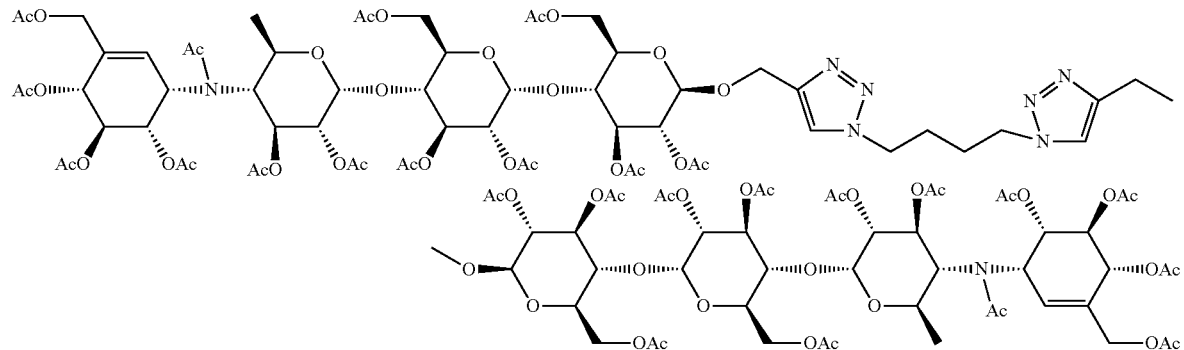

Click reaction of acetylated propagyl acarbose 14 (1.00 g, 0.90 mmol) and 1,4-diazidobutane (60 mg, 0.42 mmol) via the general procedure gave diacarbose 55 (0.7 g, 70%) as a solid; $^1$H NMR (CDCl$_3$, 400 MHz): δ=7.47 (s, 2H), 5.87 (d, 2H, J=5.3 Hz), 5.53-5.43 (m, 4H), 5.32-5.24 (m, 2H), 5.21-5.12 (m, 6H), 5.02 (t, 1H, J=10.3 Hz), 4.88-4.53 (m, 18H), 4.51-4.16 (m, 12H), 4.14-4.06 (m, 2H), 3.91 (t, 2H, J=9.3 Hz), 3.87-3.82 (m, 4H), 3.69-3.59 (m, 4H), 3.44-3.39 (m, 2H), 2.31 (t, 2H, J=9.9 Hz), 2.10 (s, 6H), 2.06 (s, 6H), 2.02 (s, 6H), 1.97-1.86 (m, 54H) 1.12 (d, 6H, J=6.2 Hz); $^{13}$C NMR (CDCl$_3$, 100 MHz): δ=170.8, 170.6, 170.5, 170.3, 170.2 (×2), 170.1, 170.0, 169.9, 169.7, 169.5 (×2), 144.1, 133.8, 127.8, 122.9, 99.4, 95.7, 95.5, 77.2, 75.1, 73.1, 72.1, 72.0, 71.9, 71.7, 70.9, 70.7, 70.5, 70.3, 69.9, 69.6, 69.0, 63.0, 62.9, 62.5, 62.1, 61.0, 52.0, 49.2, 26.9, 20.8, 20.7, 20.5 (×2), 20.4, 18.0.

Diethylene Ether Linked Diacarbose (56)

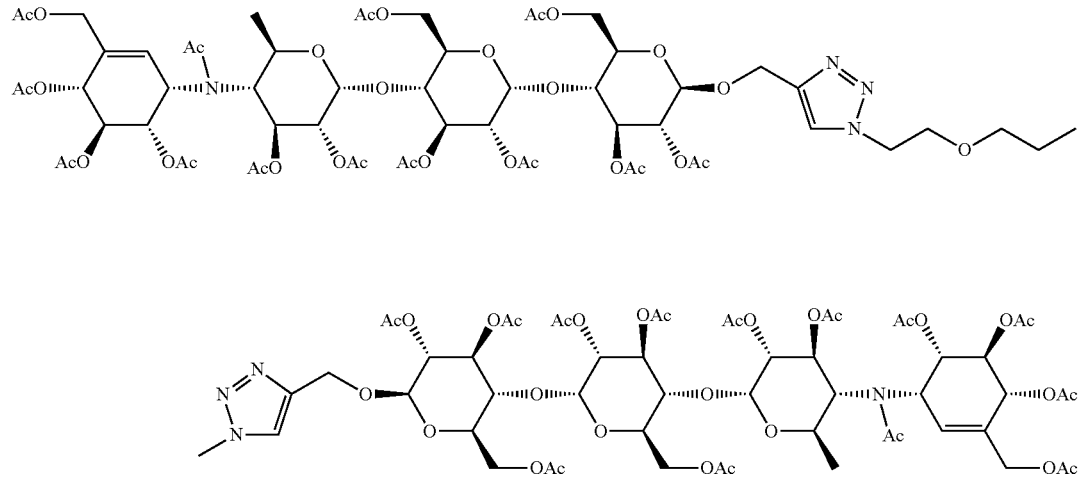

Click reaction of propagyl acarbose 14 (100 mg, 0.09 mmol) and bis(2-azidoethyl) ether (6.60 mg, 0.04 mmol) via the general procedure gave diacarbose 56 (80 mg, 74%) as a solid; $^1$H NMR (CDCl$_3$, 400 MHz): δ=7.55 (s, 2H), 5.94 (d, 2H, J=4.7 Hz), 5.59-5.49 (m, 4H), 5.39-5.29 (m, 1H), 5.27-5.19 (m, 6H), 5.09 (t, 1H, J=10.2 Hz), 4.96-4.85 (m, 4H), 4.84-4.12 (m, 32H), 3.98 (t, 2H, J=9.4 Hz), 3.94-3.66 (m, 12H), 3.57-3.47 (m, 2H), 2.45-2.33 (m, 2H), 2.15 (s, 6H), 2.12 (s, 6H), 2.09 (s, 6H), 2.04-1.93 (m, 54H), 1.19 (d, 6H, J=6.0 Hz).

Triethylene Ether Linked Diacarbose (57)

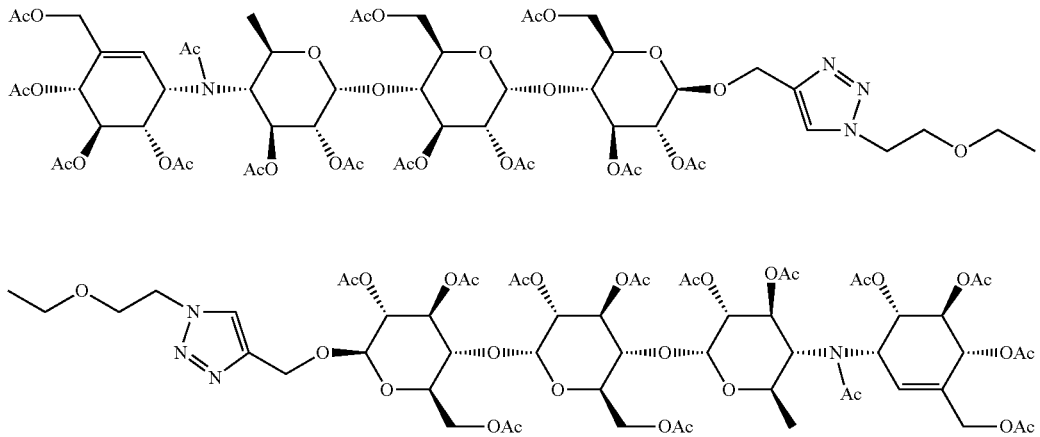

Click reaction of propagyl acarbose 14 (350 mg, 0.30 mmol) and 1,2-bis(2-azidoethoxy)ethane (30 mg, 0.13 mmol) via the general procedure gave diacarbose 57 (235 mg, 71%) as a solid; $^1$H NMR (CDCl$_3$, 400 MHz): δ=7.62 (s, 2H), 5.93 (d, 2H, J=5.2 Hz), 5.59-5.49 (m, 4H), 5.37-5.29 (m, 2H), 5.26-5.17 (m, 6H), 5.07 (t, 2H, J=10.2 Hz), 4.93-4.86 (m, 4H), 4.83-4.58 (, 12H), 4.56-4.40 (m, 8H), 4.38-4.22 (m, 4H), 4.19-4.11 (m, 2H), 4.00-3.79 (m. 10H), 3.74-3.65 (m, 4H), 3.54-3.44 (m, 4H), 2.36 (t, 2H, J=10.0 Hz), 2.14 (s, 6H), 2.12 (s, 6H), 2.10 (s, 6H), 2.04-1.91 (m, 54H), 1.18 (d, 6H, J=6.2 Hz); $^{13}$C NMR (CDCl$_3$, 100 MHz): δ=171.0, 170.7, 170.6, 170.4, 170.3 (×2), 170.2, 170.0, 169.9, 169.7, 169.6, 143.8, 133.9, 128.0, 124.0, 99.44, 95.8, 95.6, 77.2, 75.3, 73.4, 72.2 (×2), 72.0, 71.9, 71.0, 70.9, 70.7, 70.5, 70.4, 70.1, 69.8, 69.4, 69.1, 63.0, 62.9, 62.7, 62.2, 61.1, 52.1, 50.2, 20.9, 20.8, 20.7, 20.6 (×2), 20.5, 18.1.

Tetraethylene Ether Linked Diacarbose (58)

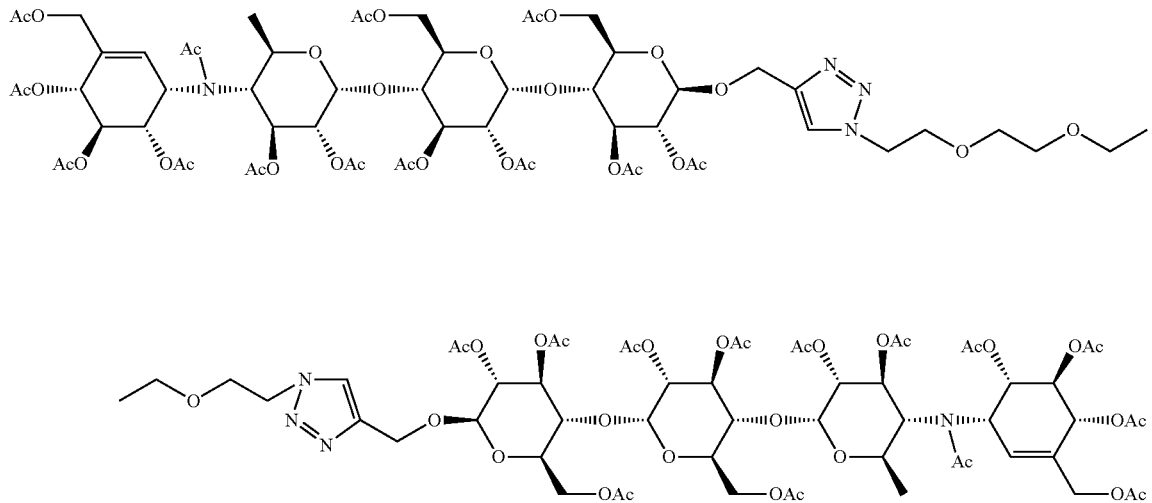

Click reaction of propagyl acarbose 14 (1.00 g, 0.85 mmol) and bis(2'-azidoethoxyethane) ether (0.09 mL, 0.43 mmol) via the general procedure gave diacarbose 58 (980 mg, 88%) as a solid; $^1$H NMR (CDCl$_3$, 400 MHz): δ=7.63 (s, 2H), 5.89 (s, 2H, J=5.4 Hz), 5.54-5.45 (m, 4H), 5.32-5.25 (m, 2H), 5.21-5.13 (m, 6H), 5.04 (t, 2H, J=10.2 Hz), 4.90-4.53 (m, 16H), 4.50-4.36 (m, 8H), 4.34-4.18 (m, 4ll), 4.16-4.08 (m, 2ll), 3.92 (t, 2H, J=9.3 Hz), 3.88-3.77 (m, 8H), 3.71-3.61 (m, 4H), 3.56-3.40 (m, 12H), 2.31 (t, 2H, J=9.9 Hz), 2.11 (s, 6H), 2.08 (s, 6H), 2.04 (s, 6H), 1.99-1.86 (m, 54H), 1.14 (d, 3H, J=6.2 Hz); $^{13}$C NMR (CDCl$_3$, 100 MHz): δ=170.9, 170.7, 170.6 (×2), 170.4, 170.3 (×2), 170.2, 170.1, 170.0, 169.9, 169.6 (×2), 143.6, 133.8, 128.0, 124.0, 99.2, 95.7, 95.5, 77.2, 75.2, 73.3, 72.1, 72.0, 71.8, 71.0, 70.8, 70.6, 70.4, 70.3, 70.0, 69.7, 69.2, 69.0, 62.9, 62.7 (×2), 62.1, 61.0, 60.3, 52.0, 50.1, 20.8, 20.7, 20.6 (×2), 20.5, (×2), 20.4, 18.0.

Pentaethylene Ether Linked Diacarbose (59)

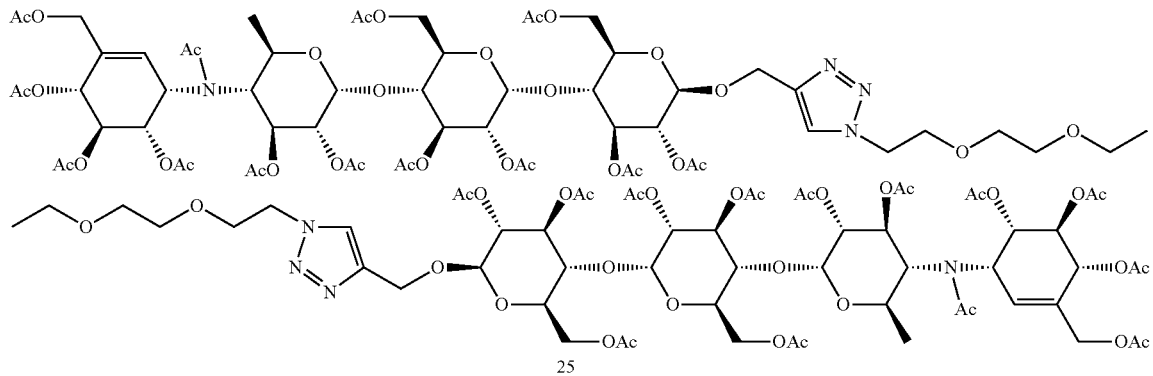

Click reaction of propagyl acarbose 14 (1.00 g, 0.85 mmol) and 1,2-bis(2"-azido-2'-ethoxyethoxy)ethane (0.12 g, 0.43 mmol) via the general procedure gave diacarbose 59 (980 mg, 88%) as a solid; $^1$H NMR (CDCl$_3$, 400 MHz): δ=7.61 (s, 2H), 5.85 (d, 2ll, J=5.1 Hz), 5.49-5.40 (m, 4H), 5.28-5.20 (m, 2ll), 5.17-5.08 (m, 6H), 4.99 (t, 2ll, J=10.3 Hz), 4.83-4.75 (m, 4H), 4.73-4.50 (m, 12H), 4.46-4.30 (m, 8H), 4.29-4.23 (m, 2H), 4.18 (dd, 2H, J=3.9 Hz, J=12.1 Hz), 4.10-4.03 (m, 2H), 3.87 (t, 2H, J=9.2 Hz), 3.83-3.72 (m, 8H), 3.66-3.57 (m, 4H), 3.57-3.36 (m, 16H), 2.27 (t, 2H, J=10.0 Hz), 2.06 (s, 6H), 2.03 (s, 6H), 1.99 (s, 6H), 1.95-1.80 (m, 54H), 1.09 (d, 3H, J=6.2 Hz); $^{13}$C NMR (CDCl$_3$, 100 MHz): δ=170.8 (×2), 170.5, 170.4, 170.3 (×2), 170.2, 170.1 (×2), 170.0, 169.8, 169.7, 169.4 (×2), 143.4, 133.6, 127.8, 123.9, 99.0, 95.6, 95.4, 77.2, 75.1, 73.2, 72.0, 71.8, 71.6, 70.9, 70.7, 70.5, 70.2, 70.1, 69.8, 69.6, 69.1, 68.9, 62.8, 62.6, 62.5, 62.0, 60.9, 60.1, 51.9, 50.0, 20.7, 20.6 (×2), 20.4 (×3), 20.3 (×2), 17.9.

General Procedure for Acetate and Bezoyl Ester Hydrolysis

A solution of 30% aq. NH$_3$ (3-5 mL) and oligosaccharide in methanol (20 mL) was stirred at r.t. for 48 h. The reaction mixture was concentrated under reduced pressure and the crude material was dissolved in ultra-pure water (5-10 mL) and washed with EtOAc (5×10 mL). The aqueous layer was concentrated to obtain the pure compound.

Ethylene Linked Hexamer (60)

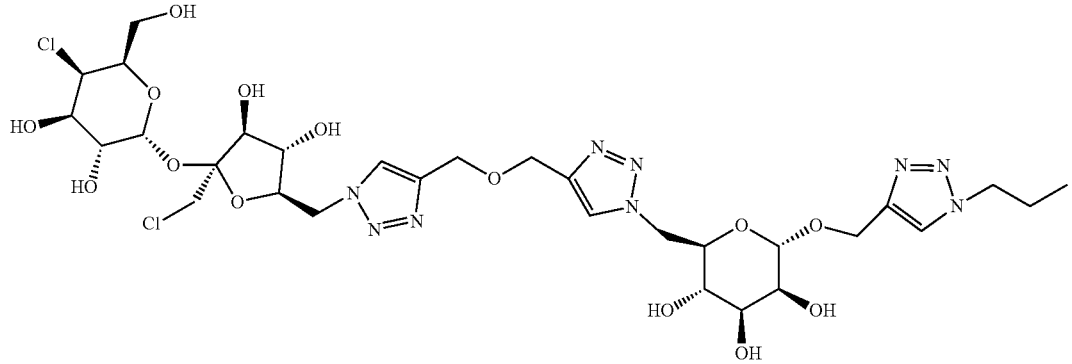

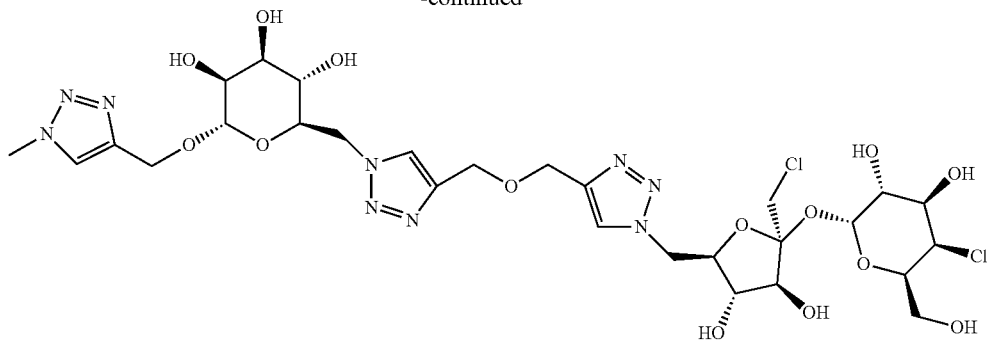

Acetate and benzoyl ester hydrolysis of compound 42 (150 mg, 0.06 mmol) according to the general procedure gave the oligosaccharide 60 (% mg, 98%); $^1$H NMR (D$_2$O, 400 MHz): δ=8.07 (s, 2H), 7.92 (s, 2H), 7.48 (s, 2H), 5.26 (d, 2H, J=3.9 Hz), 4.90-4.60 (m, 16H), 4.59-4.44 (m, 8H), 4.41-4.31 (m, 4H), 4.23-4.07 (m, 10H), 3.94-3.60 (m, 18H), 3.59-3.50 (m, 2H); $^{13}$C NMR (D$_2$O, 400 MHz); δ=103.5, 99.0, 92.4, 79.5, 75.5, 74.8, 71.6, 70.9, 70.4, 69.8, 68.0, 67.5, 63.1, 62.4, 61.9, 51.2, 43.6.

Diethylene Linked Hexamer (61)

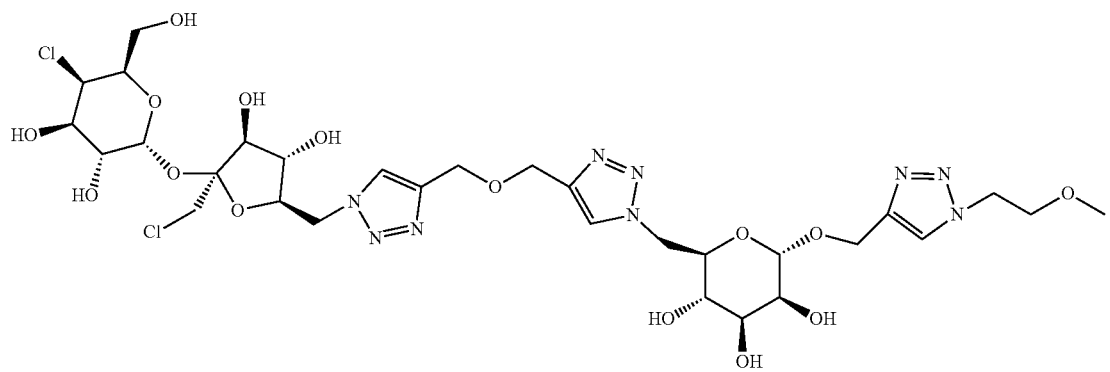

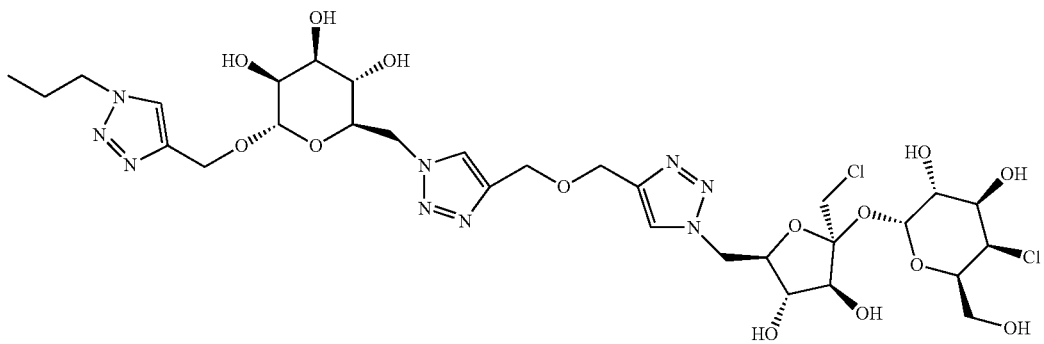

Acetate and benzoyl ester hydrolysis of compound 43 (240 mg, 0.09 mmol) according to the general procedure gave the oligosaccharide 61 (150 mg, 81%); $^1$H NMR (D$_2$O, 400 MHz): δ=8.09 (s, 2H, H-triazole), 7.91 (s, 2H, H-triazole), 7.51 (s, 2H, H-triazole), 5.37 (d, 2H, J=4.3 Hz), 4.87-4.74 (m, 10H), 4.68-4.63 (m, 12H), 4.58-4.45 (m, 10H), 4.43-4.32 (m, 10H), 4.30-4.98 (m, 14H), 4.00-3.51 (m, 26H); $^{13}$C NMR (D$_2$O, 100 MHz): δ=143.8, 142.8, 126.3, 125.6, 124.9, 103.5, 99.2, 92.4, 79.5, 75.5, 74.8, 71.6, 70.9, 70.4, 69.8, 68.5, 68.0, 67.9, 67.5, 63.1, 62.4, 62.3, 61.9, 59.3, 52.4, 51.1, 49.9, 43.6.

Ethylene Linked Octomer (62)

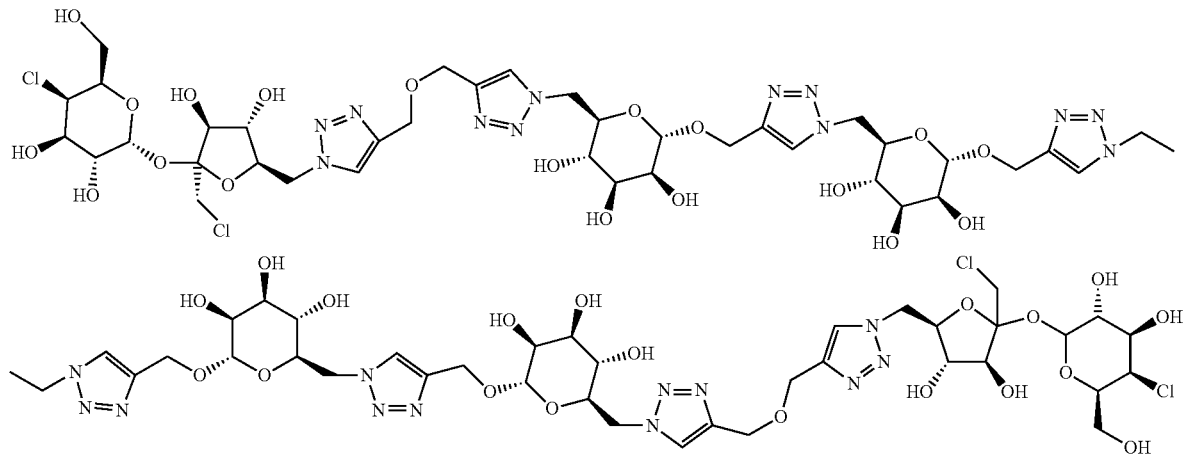

Acetate and benzoyl ester hydrolysis of compound 44 (344 mg, 0.09 mmol) according to the general procedure gave the oligosaccharide 62 (150 mg, 81%); $^1$H NMR (D$_2$O, 400 MHz): δ=8.10 (s, 2H, H-triazole), 7.90 (s, 2H, H-triazole), 7.59 (s, 2H, H-triazole), 5.37 (di, 2H, J=4.0 Hz), 4.92-4.61 (m, 22H), 4.57-4.43 (m, 10H), 4.40-4.32 (m, 4H), 4.28-4.07 (m, 14H), 3.92-3.47 (m, 28H); $^{13}$C NMR (D$_2$O, 100 MHz): δ=143.8, 143.4, 142.9, 126.3, 126.0, 125.6, 125.0, 103.5, 99.1, 99.0, 79.5, 75.5, 74.9, 71.6, 71.4, 70.9, 70.4, 69.8, 68.0, 67.9, 67.5, 63.2, 62.4, 62.3, 61.9, 59.1, 52.4, 51.1, 51.0, 49.9, 43.6.

Diethylene Linked Octamer (63)

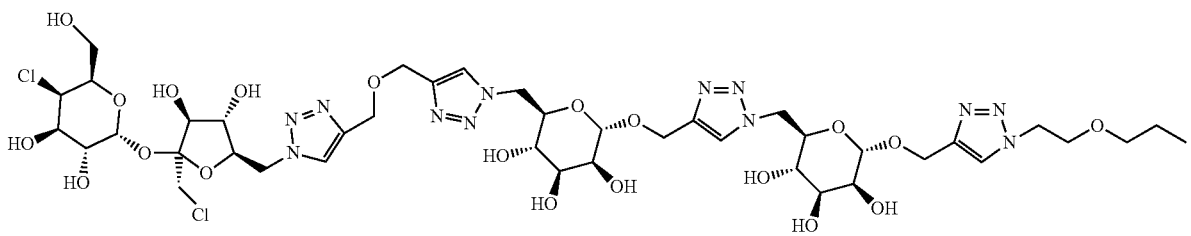

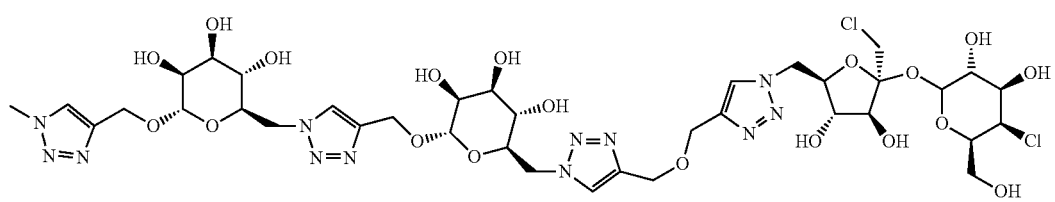

Acetate and benzoyl ester hydrolysis of compound 45 (800 mg, 0.20 mmol) according to the general procedure gave the oligosaccharide 63 (400 mg, 94%); $^1$H NMR (D$_2$O, 400 MHz): δ=8.18, 7.99, 7.92, 7.67 (8×H-triazole), 5.46 (d, 2H, J=4.1 Hz), 4.99-4.81 (m, 12H), 4.77-4.68 (m, 6H), 4.67-4.9 (m, 16H), 4.48-4.40 (m, 4H), 4.39-4.16 (m, 14H), 4.02-3.55 (m, 32H); $^{13}$C NMR (D$_2$O, 100 MHz): δ=143.8, 143.0 (×2), 126.3, 126.0, 125.6, 124.9, 103.5, 99.4, 99.0, 92.5, 79.5, 75.5, 74.9, 71.6, 71.4, 70.9, 70.4, 69.8 (×2), 68.6, 68.0, 67.9 (×2), 67.5, 63.2, 62.4, 62.3, 61.9, 59.1, 52.4, 51.1, 50.0, 43.6.

Triethylene Linked Hexamer (64)
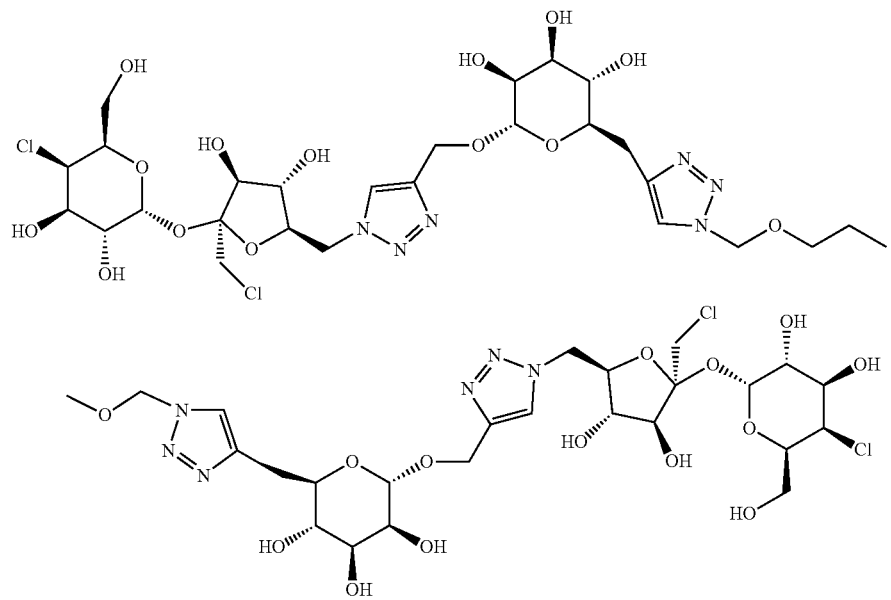
Acetate and benzoyl ester hydrolysis of compound 46 (90 mg, 0.04 mmol) according to the general procedure gave the oligosaccharide 64 (44 mg, 85%); $^1$H NMR (D$_2$O, 400 MHz): δ=8.02 (s, 2H), 7.87 (s, 2H), 5.39 (d, 2H, J=3.8 Hz), 4.88-4.73 (m, 8H), 4.60-4.45 (m, 10H), 4.43-4.32 (m, 6H), 4.20-4.08 (m, 8H), 3.97-3.79 (m, 8H), 3.78-3.68 (m, 8H), 3.66-3.60 (m, 4H), 3.57-3.49 (m, 4H); $^{13}$C NMR (CDCl$_3$, 100 MHz): δ=143.9, 143.2, 126.1, 125.6, 103.5, 99.4, 92.4, 79.6, 75.5, 74.9, 71.5, 71.0, 70.4, 69.8, 68.6, 68.0, 67.9, 67.5, 63.1, 63.0, 61.9, 60.3, 59.5, 52.5, 51.0, 43.6.
Compound (65)
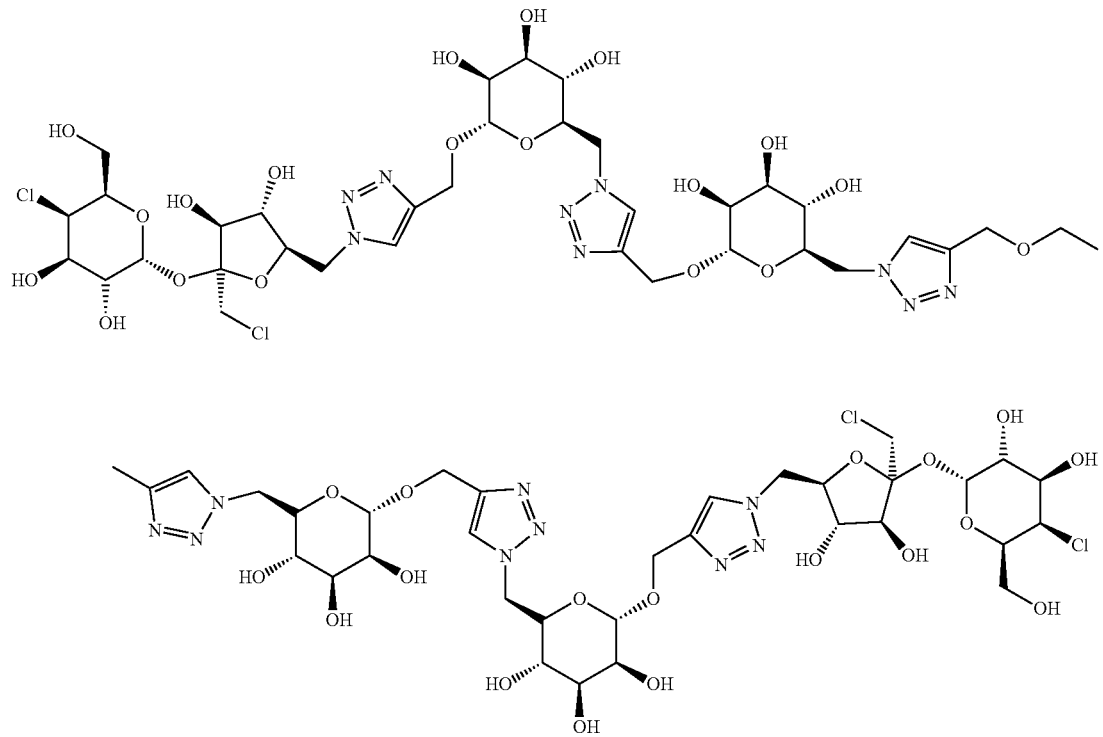

Acetate and benzoyl ester hydrolysis of compound 47 (350 mg, 0.10 mmol) according to the general procedure gave the oligosaccharide 65 (120 mg, 65%); $^1$H NMR (D$_2$O, 400 MHz): δ=8.00 (s, 2H), 7.85 (×2), (s, 4H), 5.40 (d, 2H, J=4.02 Hz), 4.91-4.74 (m, 10H), 4.59-4.44 (m, 10H), 4.41-4.09 (m, 20H), 3.96-3.67 (m, 20H), 3.67-3.58 (m, 6H), 3.56-3.46 (m, 4H); $^{13}$C NMR (CDCl$_3$, 100 MHz): δ=143.7, 143.3, 143.0, 126.0 (×2), 125.6, 103.5, 99.5, 98.9, 92.4, 79.6, 75.4, 74.9, 71.5, 71.4, 71.0, 70.4, 69.8, 68.0, 67.9, 67.8, 67.5, 63.2, 62.2, 61.9, 59.5, 59.1, 52.6, 51.1, 51.0, 43.6.

Compound 66

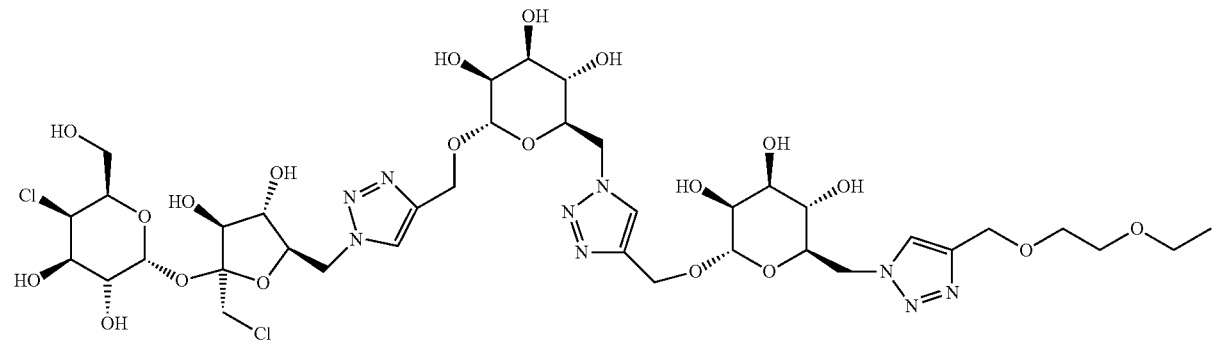

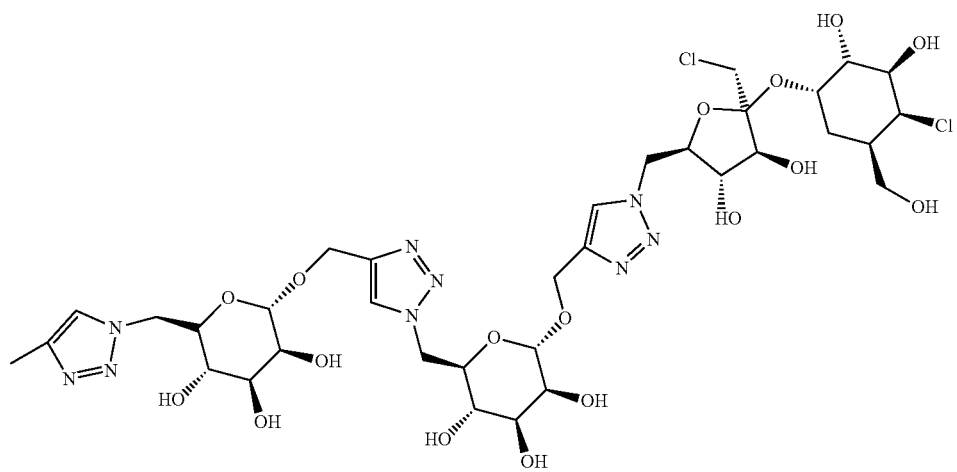

Acetate and benzoyl ester hydrolysis of compound 48 (150 mg, 0.04 mmol) according to the general procedure gave the oligosaccharide 66 (47 mg, 59%); $^1$H NMR (D$_2$O, 400 MHz): δ=8.03 (s, 2H), 7.90 (s, 2H), 7.89 (s, 2H), 5.40 (d, 2H, J=3.9 Hz), 4.91-4.08 (m, 12H), 4.58-4.44 (m, 30H), 3.97-3.40 (m, 32H); $^{13}$C NMR (CDCl$_3$, 100 MHz): δ=126.0, 125.7, 103.5, 99.5, 98.9, 92.5, 79.6, 75.4, 71.5, 71.4, 71.0, 70.4, 69.8, 68.7, 68.0, 67.9, 67.8, 67.5, 63.2, 63.0, 61.9, 59.5, 59.1, 52.6, 51.1, 51.0, 43.6.

Ethylene Linked Dimaltotriose (67)
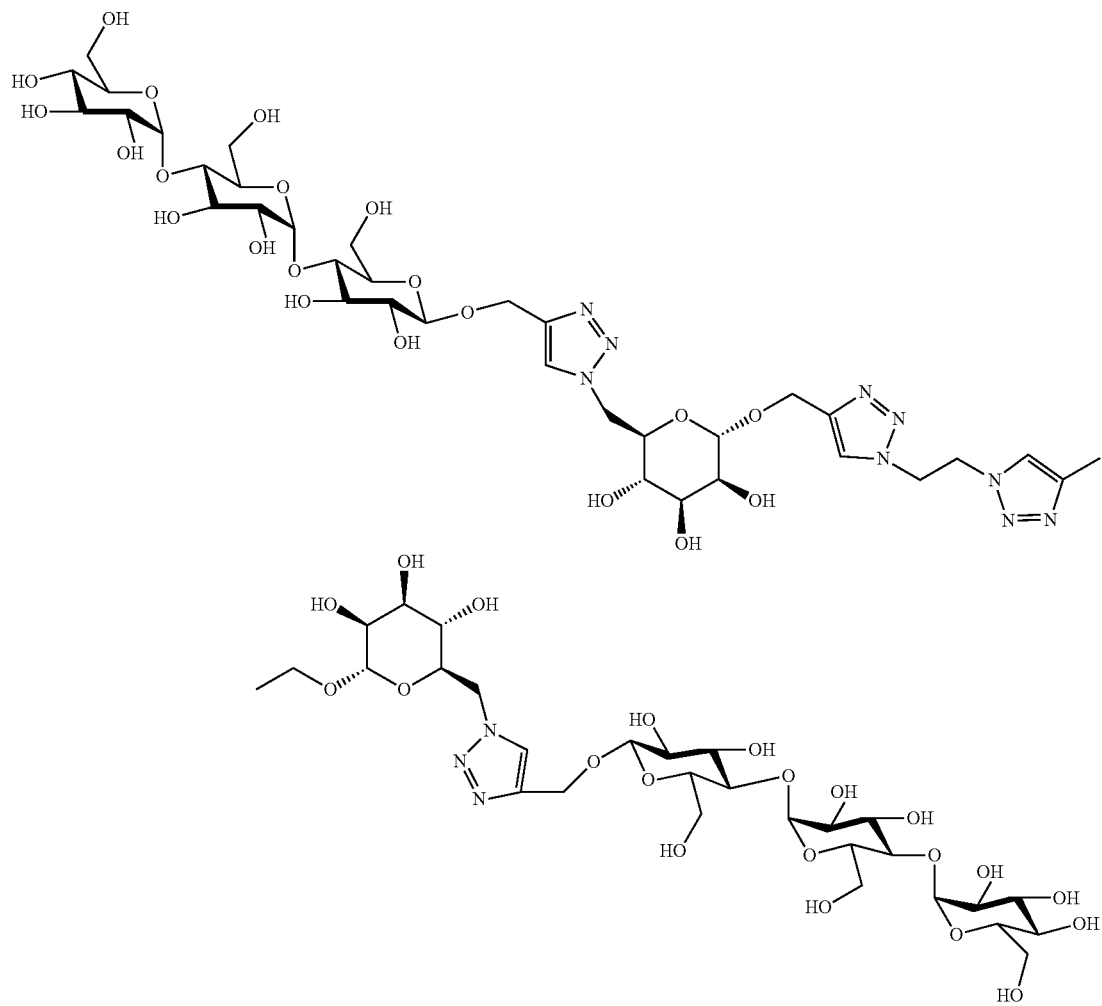
Acetate and benzoyl ester hydrolysis of compound 49 (235 mg, 0.07 mmol) according to the general procedure gave the oligosaccharide 67 (129 mg, 98%); $^1$H NMR (D$_2$O, 400 MHz): δ=8.20 (s, 2H), 7.72 (s, 2H), 5.46-5.36 (m, 6H), 5.09-4.84 (m, 16H), 4.70-4.61 (m, 4H), 4.56 (d, J=7.9 Hz, 4H), 4.41 (s, 4H), 4.05-3.54 (m, 66H), 3.47 (t, 2H, J=9.3 Hz), 3.33 (t, 2H, J=8.3 Hz); $^{13}$C NMR (CDCl$_3$, 100 MHz): δ=143.6, 143.5, 126.6, 125.1, 101.2, 99.8, 99.6, 99.1, 77.2, 76.8, 76.1, 75.9, 74.6, 73.3, 72.9, 72.8, 72.7, 71.8, 71.5, 71.4, 71.2, 70.4, 69.8, 69.3, 67.9, 62.0, 61.7, 60.7, 60.5, 60.2, 59.3, 51.1, 50.0.
Diethylene Linked Dimaltotriose (68)
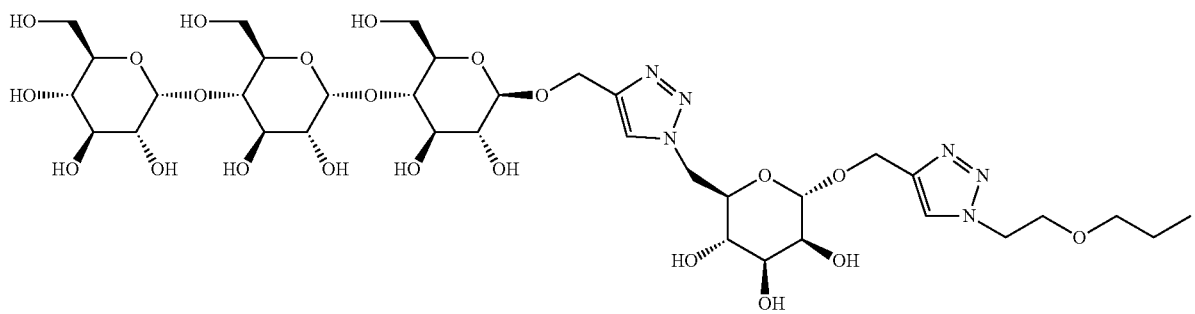

-continued

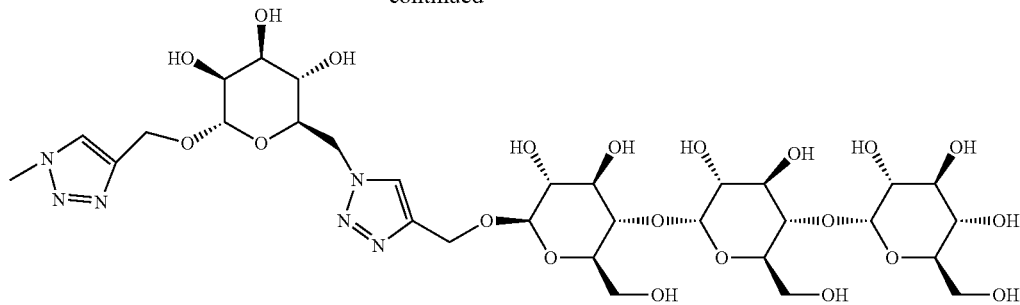

Acetate and benzoyl ester hydrolysis of compound 50 (150 mg, 0.05 mmol) according to the general procedure gave the oligosaccharide 68 (70 mg, 86%); $^1$H NMR (D$_2$O, 400 MHz): δ=8.20 (s, 2H), 7.71 (s, 2H), 5.44 (d, 2H, J=3.9 Hz), 5.40 (d, 2H, J 4.0 Hz), 5.03, 4.91 (ABq, 4H, J=12.8 Hz), 4.96-4.85 (m, 4H), 4.66 (dd, 2H, J=8.4 Hz, J=14.6 Hz), 4.62-4.54 (m, 6H), 4.43 (ABq, 4H, J=12.7 Hz), 4.03-3.55 (m, 50H), 3.47 (t, 2H, J=9.5 Hz), 3.33 (dd, 2H, J=8.0 Hz, J=9.3 Hz); C NMR (CDCl$_3$, 100 MHz): δ=143.5, 143.2, 126.5, 124.9, 101.2, 99.8, 99.6, 99.5, 77.2, 76.8, 76.1, 74.6, 73.3, 72.9, 72.8, 72.7, 71.8, 71.5, 71.4, 71.2, 70.4, 69.8, 69.3, 68.5, 67.9, 61.7, 60.7, 60.5, 59.7, 51.1, 50.0.

Compound (69)

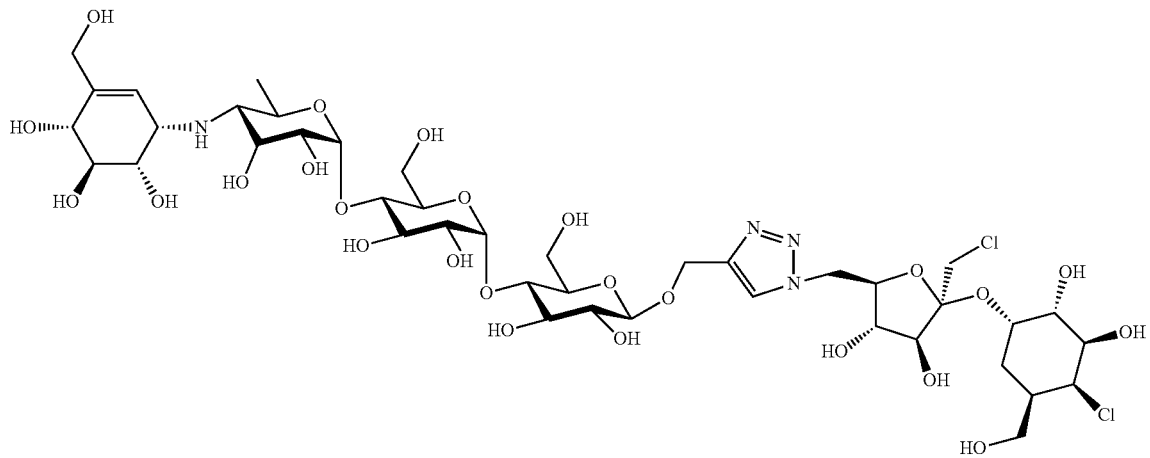

Acetate ester hydrolysis of compound 51 (150 mg, 0.08 mmol) according to the general procedure gave the oligosaccharide 69 (86 mg, 96%); $^1$H NMR (D$_2$O, 400 MHz): 8.05 (s, 1H), 5.88-5.81 (m, 1H), 5.42 (d, 1H, J=4.1 Hz), 5.31 (d, 1H, J=3.9 Hz), 5.26 (d, 1H, J=3.9 Hz), 4.93, 4.85 (ABq, 2H, J=12.7 Hz), 4.49 (dd, 1H, J=0.9 Hz, J=3.9 Hz), 4.48-4.35 (m, 3H), 4.23-4.07 (m, 5H), 4.05-4.00 (m, 1H), 3.94-3.82 (m, 4H), 3.82-3.63 (m, 12H), 3.63-3.45 (m, 5H), 3.28 (dd, 1H, J=8.1 Hz, J=9.4 Hz), 2.70 (t, 1H, J=10.1 Hz), 1.31 (d, 3H, J=6.3 Hz);); $^{13}$C NMR (D$_2$O, 100 MHz): δ=143.4, 141.8, 126.4, 120.5, 103.5, 100.9, 99.9, 99.6, 92.5, 79.5, 77.4, 77.1, 76.2, 75.6, 74.9, 74.6, 73.3, 72.8, 72.6, 72.5, 71.5, 71.3, 71.2, 71.0, 70.9, 69.3, 69.0, 67.8, 67.5, 64.2, 63.1, 61.9, 61.7, 61.4, 60.7, 60.5, 56.1, 52.5, 43.6, 17.3.

Compound (70)

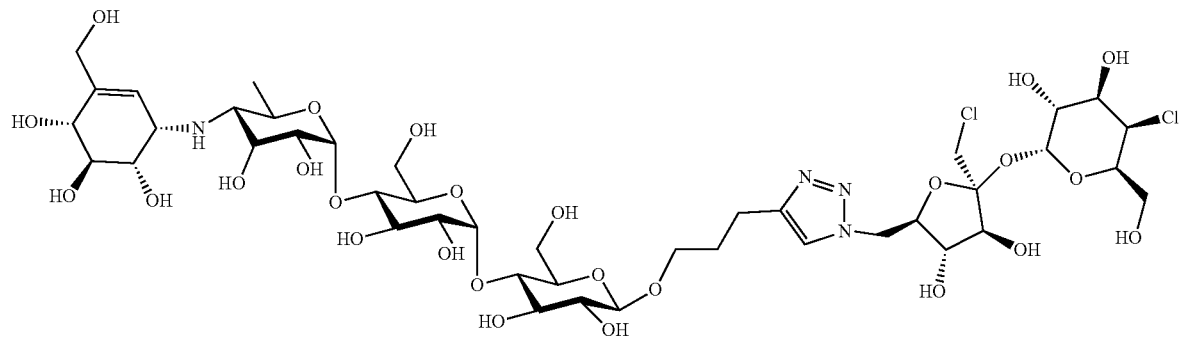

Acetate ester hydrolysis of compound 52 (150 mg, 0.08 mmol) according to the general procedure gave the oligosaccharide 70 (86 mg, 96%); $^1$H NMR (D$_2$O, 400 MHz): δ=7.79 (s, 1H), 5.88-5.81 (m, 1H), 5.38 (d, 1H, J=4.1 Hz), 5.33 (d, 1H, J=4.0 Hz), 5.29 (d, 1H, J=3.8 Hz), 4.52-4.46 (m, 1H), 4.42-4.33 (m, 3H), 4.24-4.00 (m, 6H), 3.99-3.42 (m, 25H), 3.33-3.20 (m, 1H), 2.88-2.71 (m, 2H), 1.33 (d, 3H, J=6.2 Hz).

Compound (71)

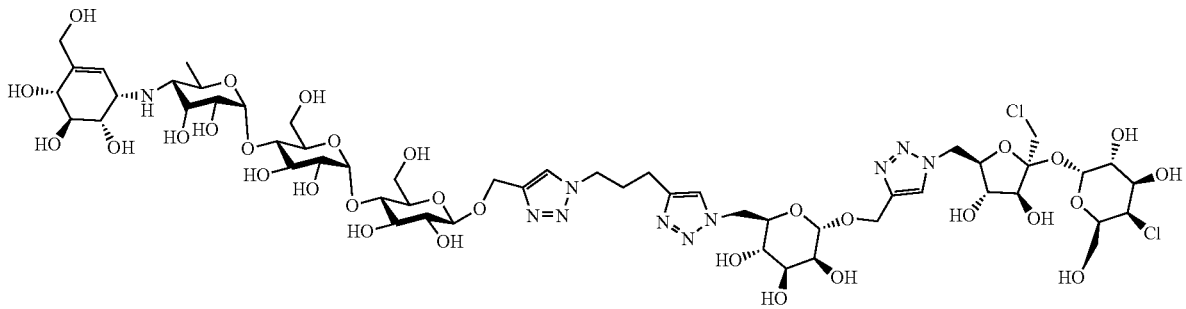

Acetate ester hydrolysis of compound 53 (340 mg, 0.14 mmol) according to the general procedure gave the oligosaccharide 71 (quat.); $^1$H NMR (D$_2$O, 400 MHz): δ=7.89 (s, 1H), 7.87 (s, 1H), 7.79 (s, 1H), 5.85-5.80 (m, 1H), 5.33 (d, 1H, J=3.9 Hz), 5.30 (d, 1H, J=3.9 Hz), 5.25 (d, 1H, J=3.8 Hz), 4.93-4.76 (m, 3H), 4.53-4.43 (m, 3H), 4.40-4.23 (m, 6H), 4.21-4.04 (m, 5H), 4.04-3.95 (m, 1H), 3.94-3.40 (m, 26H), 3.28 (dd, 1H, J=8.2 Hz, J=9.2 Hz), 2.70-2.58 (m, 3H), 2.15 (t, 1H, J=7.0 Hz), 1.29 (d, 3H, J=6.2 Hz); $^{13}$C NMR (D$_2$O, 100 MHz): δ=146.6, 143.5, 143.3, 141.4, 125.5, 125.1, 124.3, 120.8, 103.5, 101.4, 99.9, 99.6, 99.4, 92.4, 79.6, 77.3, 77.2, 76.1, 75.5, 74.9, 74.6, 73.3, 72.9, 72.6, 72.5, 71.5, 71.2, 70.9, 70.5, 69.8, 69.5, 68.0, 67.9, 67.5, 64.3, 63.2, 61.9, 61.5, 60.7, 60.5, 59.5, 56.2, 52.5, 50.9, 49.4, 43.7, 17.4.

Ethylene Linked Diacarbose (72)

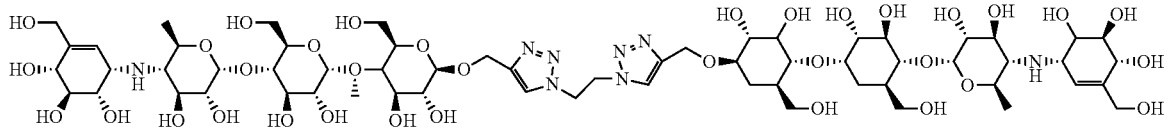

Acetate hydrolysis of compound 54 (93 mg, 37.9 μmol) according to the general procedure 1 gave diacarbose compound 72 (42 mg, 73%). $^1$H NMR (D$_2$O, 400 MHz): δ=7.93 (s, 2H), 5.93 (s, 2H), 5.44-5.36 (m, 4H), 5.07-4.84 (, 8H), 4.51 (di, 2H, J=8.0 Hz) 4.35-3.50 (m, 42H), 3.35 (t, 2H, J=8.6 Hz), 3.23 (t, 2H, J=10.2 Hz), 2.21, 2.14 (m, 2H), 1.45 (di, 6H, 6.1 Hz); $^{13}$C NMR (D$_2$O, 100 MHz): δ=146.0, 145.0, 143.8, 129.5, 125.6, 125.5, 115.4, 101.1, 99.6 (×2), 77.4, 77.1, 76.1, 74.5, 73.2, 72.9, 72.3, 71.7, 71.5, 71.1, 70.5, 68.7, 67.0, 65.0, 63.0, 61.7, 61.2, 60.6, 60.5, 56.4, 50.0, 17.4.

Compound (73)

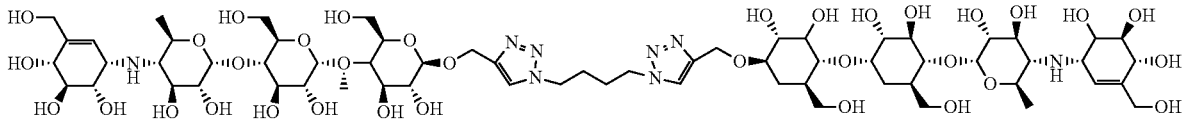

Acetate hydrolysis of compound 55 (0.56 g, 0.22 mmol) according to the general procedure 2 gave diacarbose compound 73 (0.33 mg, 99%). $^1$H NMR (D$_2$O, 400 MHz): δ=8.05 (s, 1H), 5.94-5.88 (m, 1H), 5.39 (d, 1H, J=3.9 Hz), 5.33 (d, 1H, J=3.7 Hz), 4.99, 4.87 (ABquat. 2H, J=12.6 Hz), 4.57 (d, 1H, J=8.1 Hz), 4.50-4.40 (m, 1H), 4.25, 4.17 (ABquat. 2H, J=14.1 Hz), 4.08 (d, 1H, J=6.3 Hz), 4.00-3.55 (m, 17H), 3.35 (t, 1H, J=8.5 Hz), 2.66 (t, 1H, J=9.9 Hz), 1.38 (d, 1H, J=6.4 Hz); $^{13}$C NMR (D$_2$O, 100 MHz): δ=143.6, 140.8, 125.2, 121.5, 101.4, 100.0, 99.6, 77.4, 77.2, 76.1, 74.6, 73.3, 72.9, 72.6, 71.9, 71.5, 71.2, 71.0, 69.9, 68.4, 64.5, 62.0, 61.5, 60.7, 60.6, 56.2, 49.7, 17.4.

Compound (74)

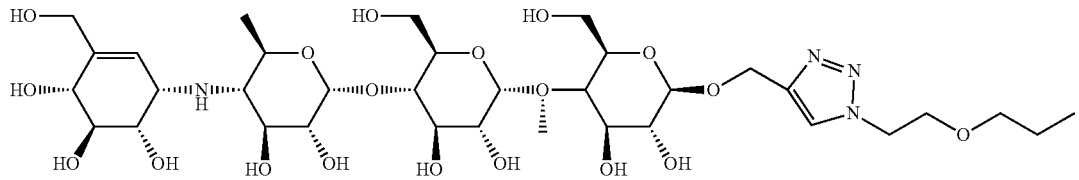

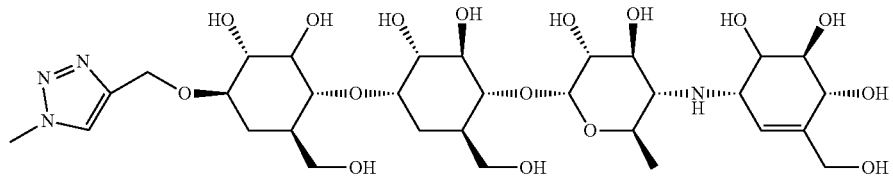

Acetate hydrolysis of compound 56 (60 mg, 24 μmol) according to the general procedure 1 gave diacarbose compound 74 (22 mg, 61%). $^1$H NMR (D$_2$O, 400 MHz): δ=7.12 (s, 1H), 5.16-5.12 (m, 1H), 4.62 (d, 1H, J=4.0 Hz), 4.56 (d, 1H, J=3.6 Hz), 4.21, 4.08 (ABquat. 2H, J=12.7 Hz), 3.83-3.76 (m, 3H), 3.48, 3.38 (ABquat. 2H, J=14.2 Hz), 3.30 (d, 1H, J=6.6 Hz), 3.22-2.79 (m, 22H), 2.58 (dd, 1H, J=8.0 Hz, J=9.4 Hz), 1.85 (t, 1H, J=9.7 Hz), 1.37 (d, 3H, J=6.4 Hz); $^{13}$C NMR (D$_2$O, 100 MHz): δ=143.4, 140.4, 125.5, 122.1, 101.4, 99.9, 99.5, 77.2, 77.1, 76.1, 74.6, 73.3, 72.9, 72.7, 72.6, 72.1, 71.55, 71.2, 71.0, 70.0, 68.7, 68.5, 64.6, 61.9, 61.5, 60.7, 60.5, 56.1, 50.0, 30.3, 17.3.

Compound (75)

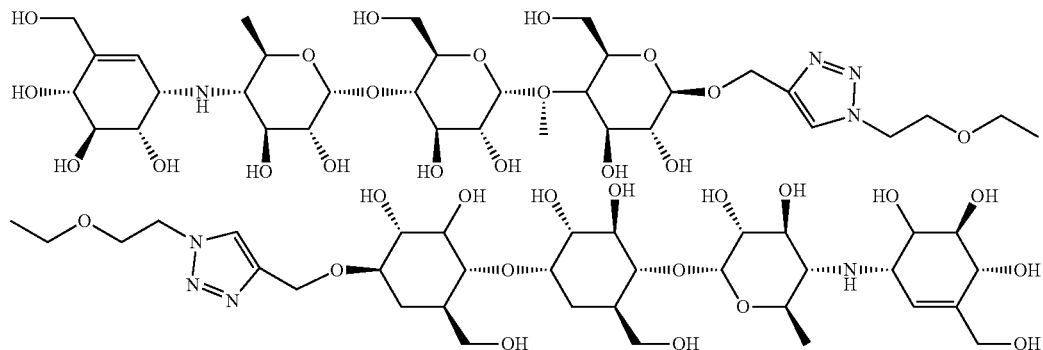

Acetate hydrolysis of compound 57 (0.24 g, 94 μmol) according to the general procedure 1 gave diacarbose compound 75 (0.15 mg, 99%). $^1$H NMR (D$_2$O, 400 MHz): δ=8.00 (s, 1H), 5.86-5.82 (m, 1H), 5.32 (d, 1H, J=3.8 Hz), 5.25 (d, 1H, J=3.4 Hz), 4.92, 4.80 (ABquat. 2H), 4.56-4.47 (m, 2H), 4.17, 4.06 (ABquat., 2H, J=13.7 Hz), 3.98 (di, 1H, J=6.9 Hz), 3.91-3.43 (m, 22H), 3.26 (dd, 1H, J=8.0 Hz, J=9.4 Hz), 2.41 (t, 1H, J=9.5 Hz), 1.28 (d, 3H, J=6.3 Hz);

$^{13}$C NMR (D$_2$O, 100 MHz): δ=143.5, 138.9, 125.7, 123.8, 101.3, 100.0, 99.5, 77.1, 77.0, 74.6, 73.3, 73.0, 72.9 (×2), 72.7, 71.4, 71.2 (×2), 70.8, 69.6, 68.7, 64.9, 61.9, 61.6, 60.7, 60.5, 56.0, 50.1, 17.3.

Compound (76)

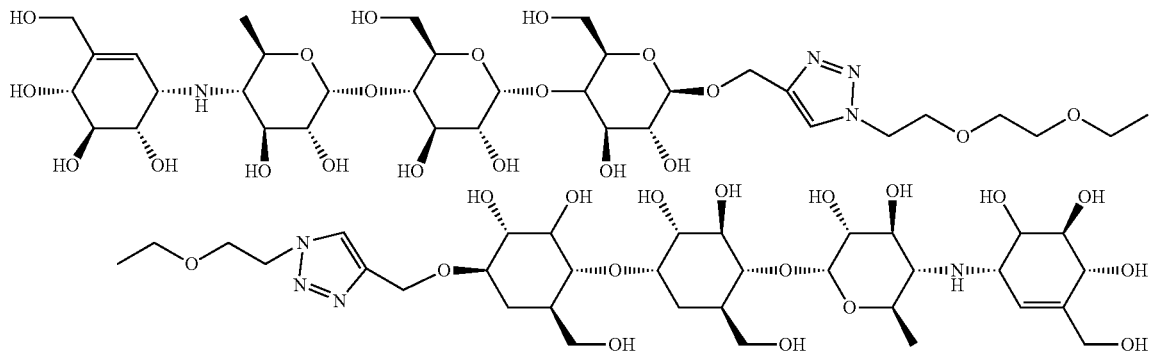

Acetate hydrolysis of compound 58 (0.44 g, 170 μmol) according to the general procedure 2 gave diacarbose compound 76 (0.26 g, 99%). $^1$H NMR (D$_2$O, 400 MHz): δ=8.13 (s, 1H), 5.96-5.92 (m, 1H), 5.42 (d, 1H, J=3.9 Hz), 5.36 (d, 1H, J=3.8 Hz), 5.01, 4.88 (ABquat. 2H, J=12.7 Hz), 4.69-4.63 (m, 2H), 4.60 (d, 1H, J=7.9 Hz), 4.28, 4.19 (ABquat. 2H, J=14.2 Hz), 4.11 (d, 1H, J=6.1 Hz), 4.05-3.56 (m, 24H), 3.36 (dd, 1H, J=8.0 Hz, J=9.4 Hz), 2.67 (t, 1H, J=9.7 Hz), 1.40 (d, 3H, J=6.2 Hz); $^{13}$C NMR (D$_2$O, 100 MHz): δ=143.5, 140.7, 125.7, 121.7, 101.3, 99.9, 99.6, 77.2, 77.1, 74.6, 73.3, 72.9, 72.6, 72.0, 71.5, 71.2, 71.0, 69.9, 69.7, 69.6, 69.4, 68.7, 68.5, 64.5, 61.9, 61.5, 60.7, 60.5, 56.1, 50.1, 17.4.

Compound (77)

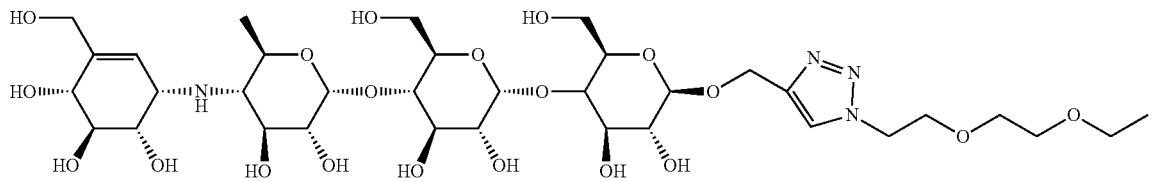

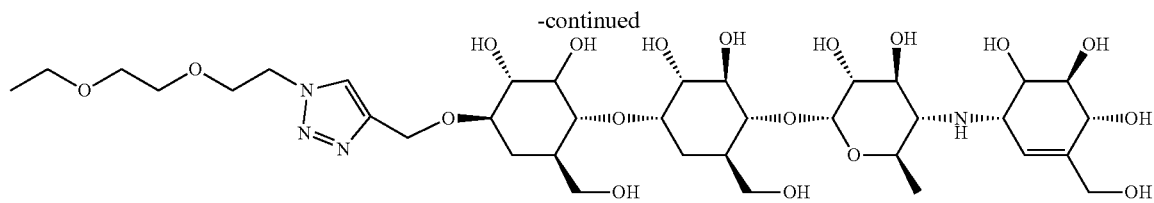

Acetate hydrolysis of compound 59 (0.84 g, 319 μmol) according to the general procedure 2 gave diacarbose compound 77 (0.26 g, 99%). $^1$H NMR (D$_2$O, 400 MHz): δ=8.15 (s, 1H), 5.96-5.92 (m, 1H), 5.42 (d, 1H, J=4.0 Hz), 5.36 (d, 1H, J=3.7 Hz), 5.03, 5.90 (ABquat. 2H, J=12.5 Hz), 4.70-4.65 (m, 2H), 4.60 (d, 1H, J=8.0 Hz), 4.28, 4.18 (ABquat. 2H, J=14.3 Hz), 4.10 (d, 1H, J=6.2 Hz), 4.06-3.56 (m, 25H), 3.37 (dd, 1H, J=8.0 Hz, J=9.4 Hz), 2.66 (t, 1H, J=9.7 Hz), 1.40 (d, 3H, J=6.3 Hz); $^{13}$C NMR (D$_2$O, 100 MHz): δ=143.5, 140.5, 125.7, 121.9, 101.3, 99.9, 99.6, 66.2, 77.1, 76.1, 74.6, 73.3, 72.9, 72.7, 72.1, 71.5, 71.2, 71.0, 70.0, 69.7, 69.6, 69.5, 69.2, 68.7, 68.6, 64.6, 61.9, 61.5, 60.7, 60.5, 56.1, 50.0, 17.4.

Procedure for Synthesis of SO$_3$·Py

To a solution of pyridine (4 mL) in DCM (20 mL) at 0° C., chlorosulfonic acid (1.6 mL) was added dropwise and the mixture stirred for 30 min. The reaction mixture was then filtered and the precipitate was washed with ice cold water (3×20 mL), ice cold sat. NaHCO$_3$ (2×10 mL), ice cold water (2×10 mL) (till the pH of the filtrate was 7), cold EtOH (2×20 mL), cold toluene (10 mL) and cold DCM (10 mL). The precipitated SO$_3$·Py was then thoroughly dried under high vacuum and used within 24 h.

General Procedure 1 for Sulfation

Freshly prepared SO$_3$·Py (10 eq. per OH) complex was added to a solution of the starting material in dry DMF (10 mL) kept under nitrogen atmosphere. The reaction mixture was stirred at r.t. for 2 days and made basic using 5 M NaOH (2 equiv. per SO$_3$·Py). The mixture was then concentrated under reduced pressure and the crude material was dissolved in ultra-pure water (10-20 mL) and dialysed according to the general procedure.

General Procedure 2 for Sulfation

Freshly prepared SO$_3$·Py (10 eq. per OH) complex was added to a solution of the starting material in dry DMF (10 mL) kept under nitrogen atmosphere. The reaction mixture was stirred at r.t. for 2 days. The DMF was then decanted from the reaction mixture and the precipitated material was dissolved in ultra-pure water (10 mL) and made basic using 5 M NaOH (PH=9-11). The solution was then dialysed according to the general procedure.

General Procedure for Dialysis

Commercially available Cellulose membrane dialysis tubing with MWCO of 0.5 KD, 1KD and 2 KD were used for dialysis. The dialysis tubing was washed with miliQ water before use (approximately 5-10 mins of washing). One end of the dialysis tube was knotted and the sample was loaded into the tube. The tube was then closed using a clip, leaving little room for bubbles. A 3 L flask equipped with a stirrer bar was filled with miliQ water and placed on a magnetic stirring plate at room temperature. The stirring was set such that the dialysis bag slowly float around the top of the solution in the flask. After 2h, the water was replaced with fresh miliQ water and dialysis continued for 2 days with the dialysis water being changed after every 18 h. The dialysis bag was then removed from the flask and the content of the bag was collected and freeze dried.

Sulfated Ethylene Linked Hexamer (78)

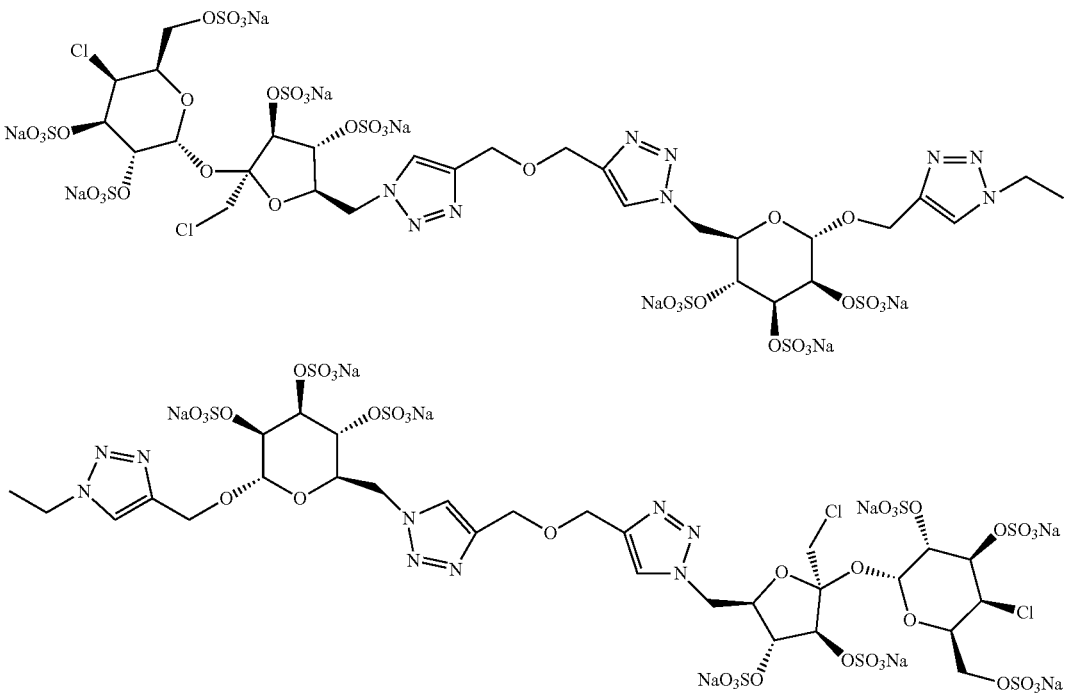

Sulfation of the deprotected hexamer 60 (60 mg, 0.04 mmol) according to the general procedure 1 followed by dialysis gave the hexamer 78 (46 mg, 51%) as a white powder; $^1$H NMR (D$_2$O, 400 MHz): δ=8.17 (s, 1H), 8.06 (s, 2H), 7.66 (s, 2H), 5.75 (d, 2H, J=3.6 Hz), 5.33 (d, 2H, J=7.6 Hz), 5.16-5.11 (m, 2H), 5.09-5.01 (m, 4H), 5.00-5.78 (m, 20H), 4.77-4.56 (m), 4.53-4.44 (m, 4H), 4.39-4.10 (m, 12H), 3.94, 3.85 (ABq, 4H, J=12.5 Hz); $^{13}$C NMR (D$_2$O, 100 MHz): δ=143.8, 143.2, 126.2, 125.6, 125.2, 103.6, 96.3, 90.9, 79.5 (×2), 78.3, 75.1, 73.5, 72.7, 72.4, 71.4, 70.6, 70.3, 68.5, 67.9, 62.4, 60.3, 60.0, 52.8, 51.0, 49.8, 43.9.

Sulfated Diethylene Linked Hexamer (79)

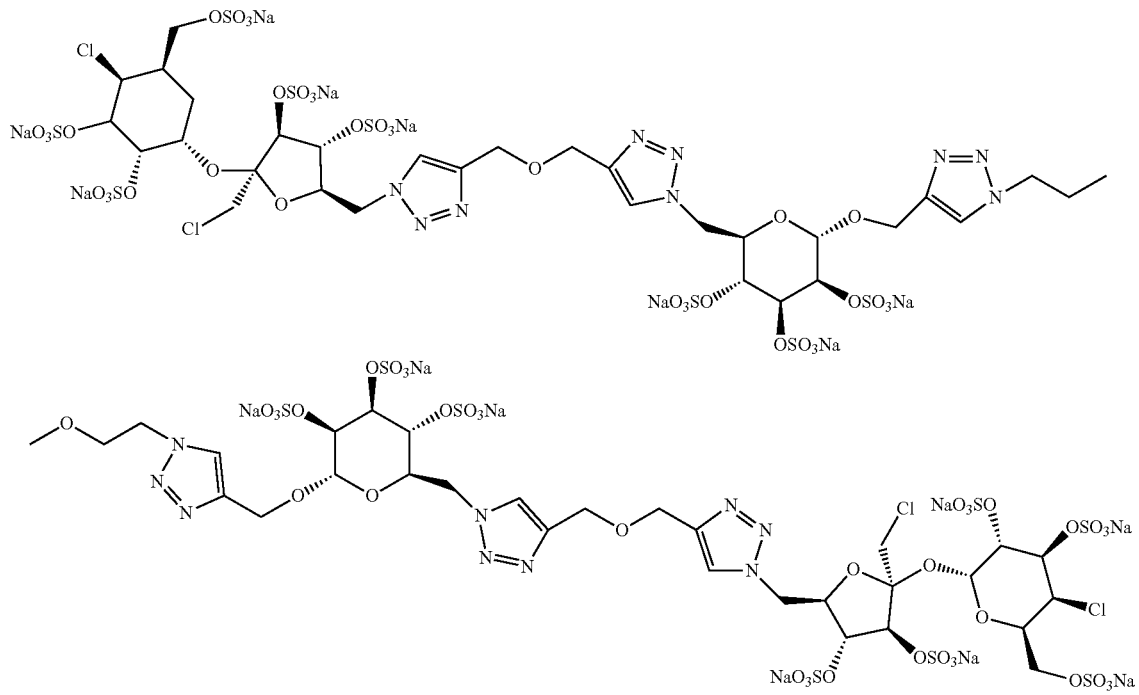

Sulfation of the deprotected hexamer 61 (80 mg, 0.05 mmol) according to the general procedure 1 followed by dialysis gave the hexamer 79 (90 mg, 60%) as a white powder; $^1$H NMR (D$_2$O, 400 MHz): δ=8.22 (s, 2H), 8.08 (s, 2H), 7.86 (s, 2H), 5.74 (d, 2H, J=3.6 Hz), 5.74 (d, 2H, J=3.6 Hz), 5.29 (d, 2H, J=7.6 Hz), 5.18-5.14 (m, 2H), 5.10-5.96 (m, 4H), 4.96-4.84 (m, 8H), 4.83-4.54 (m), 4.54-4.41 (m, 8H), 4.37 (s, 4H), 4.29-4.09 (m, 6H), 3.91, 3.82 (ABq, 4H, J=12.8 Hz), 3.83-3.72 (m, 4H).

Sulfated Ethylene Linked OCTOMER (80)

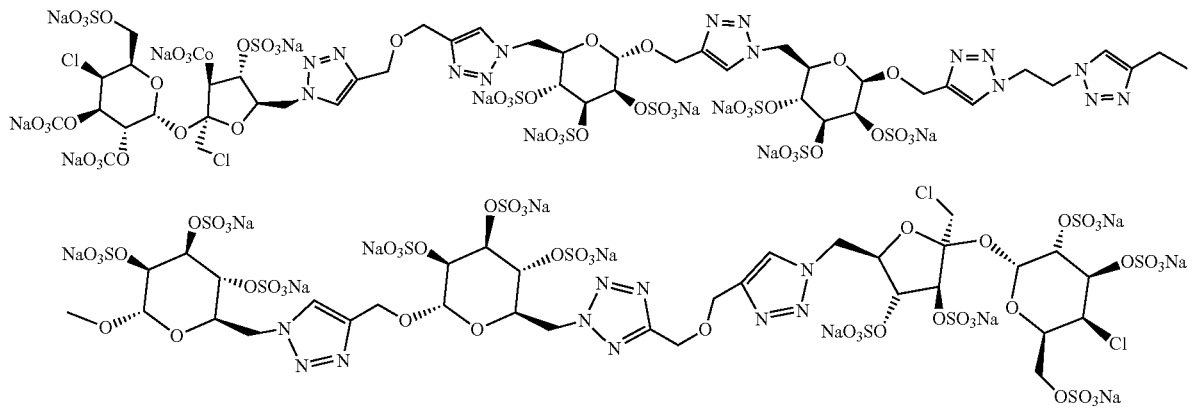

Sulfation of the deprotected octomer 62 (50 mg, 0.02 mmol) according to the general procedure 1 followed by dialysis gave the octamer 80 (56 mg, 59%) as a white powder; $^1$H NMR (1D$_2$O, 400 MHz): δ=8.26 (s, 2H), 8.13 (s, 2H), 8.08 (s, 2H), 7.92 (s, 2H), 5.82 (d, 2H, J=3.5 Hz), 5.39 (d, 2H, J=7.6 Hz), 5.29-5.16 (m, 8H), 5.15-5.04 (m, 10H), 5.04-4.93 (m, 18H), 4.93-4.59 (m), 4.59-4.13 (m, 30H), 3.99, 3.91 (ABq, 4H, J=12.6 Hz).

Sulfated Diethylene Linked Octomer (81)

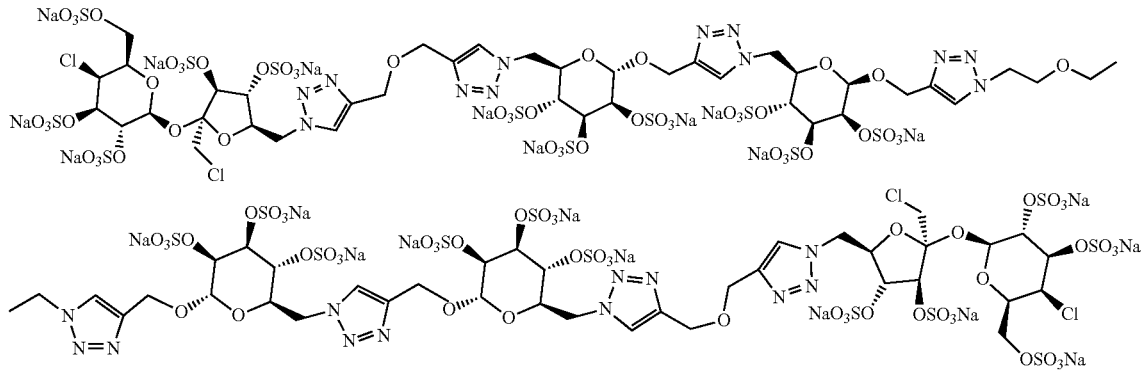

Sulfation of the deprotected octomer 63 (20 mg, 0.01 mmol) according to the general procedure 1 followed by dialysis gave the hexamer 81 (36 mg, 91%) as a white powder; $^1$H NMR (D$_2$O, 400 MHz): δ=8.22 (s, 2H), 8.07 (2×s, 4H), 7.92 (s, 2H), 5.79 (s, 2H), 5.34 (d, 2H, J=7.4 Hz), 5.21 (s, 4H), 5.13-4.12 (m, 72H), 3.91, 3.82 (ABq, 4H, J=12.6 Hz), 3.87-3.82 (n, 4H).

Compound (82)

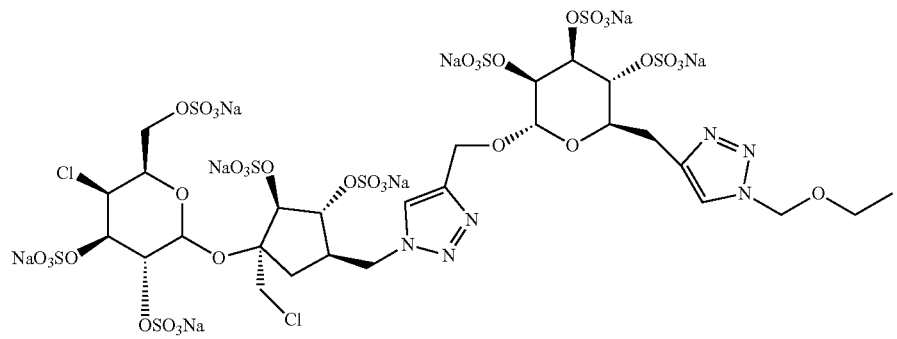

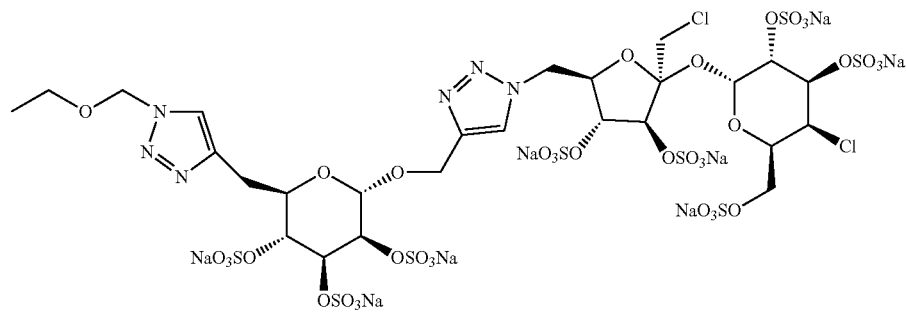

Sulfation of the deprotected hexamer 64 (30 mg, 0.02 mmol) according to the general procedure 1 followed by dialysis gave the hexamer 82 (37 mg, 64%) as a white powder; $^1$H NMR (D$_2$O, 400 MHz): δ=8.28 (s, 2H), 8.05 (s, 2H), 5.85 (d, 2H, J=3.5 Hz), 5.38 (d, 2H, J=7.8 Hz), 5.31-5.27 (m, 2H), 5.16-4.84 (m, 20H), 4.84-4.74 (m), 4.74-4.60 (s, 10H), 4.54 (t, 2H, J=9.5 Hz), 4.45 (s, 4H), 4.38-4.30 (m, 4H), 4.26 (dd, 2H, J=4.5 Hz, =10.6 Hz), 3.99, 3.91 (ABq, 4H, J=12.4 Hz), 3.71 (s, 4H); $^{13}$C NMR (D$_2$O, 100 MHz): δ=125.9, 103.4, 96.6, 90.8, 79.4, 79.3, 78.1, 75.1, 73.5, 72.7, 72.4, 71.3, 70.0, 68.8, 68.3, 67.7, 63.0, 60.2, 60.0, 52.9, 50.8, 43.8.

Compound (83)

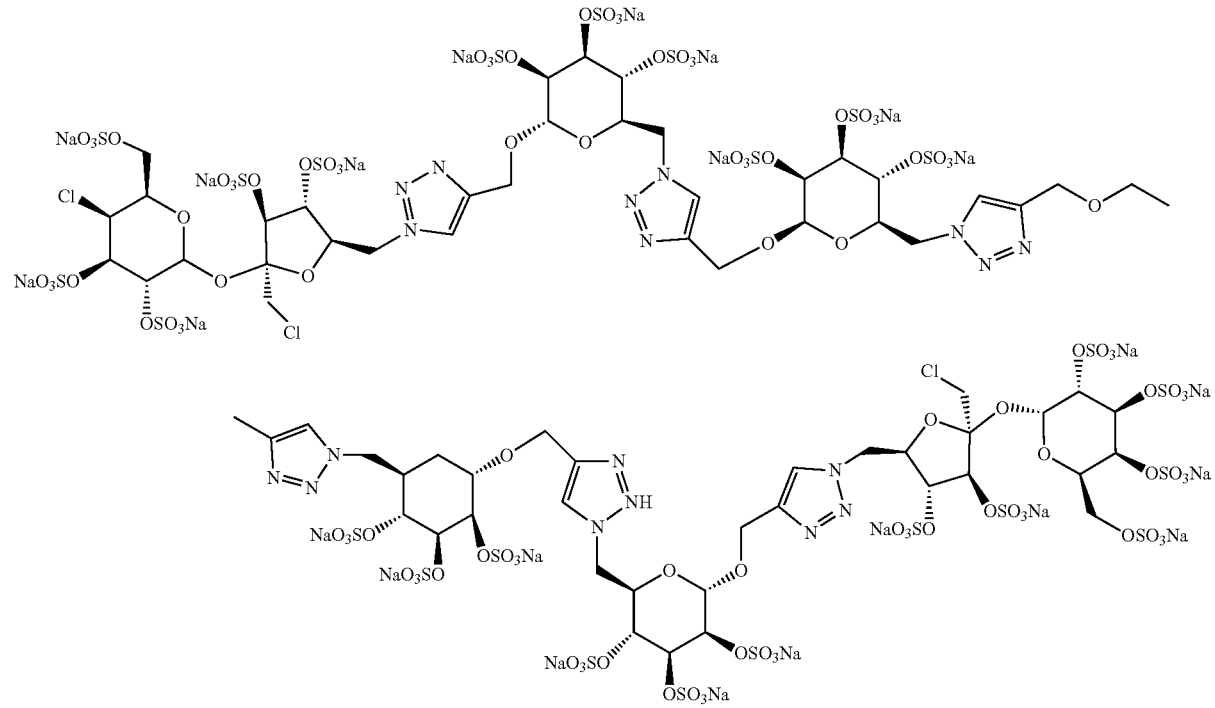

Sulfation of the deprotected hexamer 65 (68 mg, 0.04 mmol) according to the general procedure 1 followed by dialysis gave the hexamer 83 (21 mg, 16%) as a white powder; $^1$H NMR (D$_2$O, 400 MHz): δ=8.23 (s, 2H), 8.17 (s, 2H), 8.06 (s, 2H), 5.87 (s, 2H, J=3.6 Hz), 5.38 (d, 2H, J=7.8 Hz), 5.30 (d, 2H, J=1.5 Hz), 5.26 (d, 2H, J=1.8 Hz), 5.16-4.86 (m, 22H), 5.86-4.62 (m), 4.61-4.49 (m, 8H), 4.46 (s, 4H), 4.42-4.22 (m, 8H), 4.00, 3.92 (ABq, 4H, J=12.4 Hz); $^{13}$C NMR (D$_2$O, 100 MHz): δ=143.6, 143.1, 143.0, 126.5, 126.3, 125.8, 103.4, 96.5, 96.4, 90.8, 79.4, 79.3, 78.1, 75.1, 73.5, 72.7, 72.6, 72.5, 71.3, 69.9, 68.3, 67.6, 62.4, 60.4, 60.2, 60.0, 52.9, 50.8, 50.6, 43.8.

Compound (84)

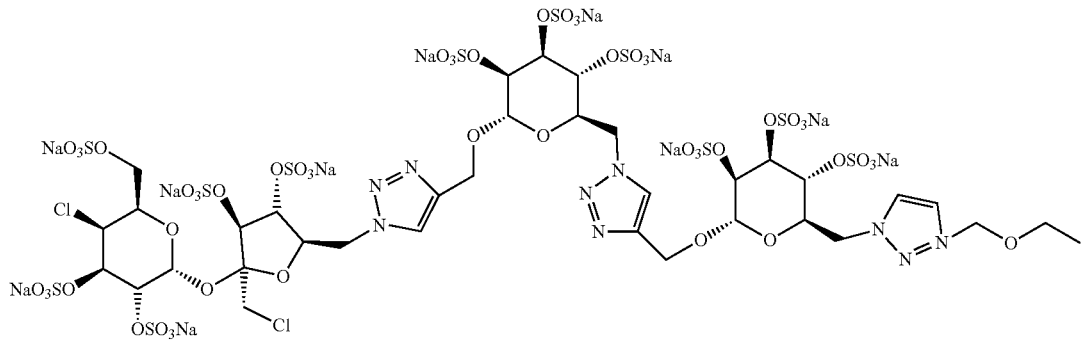

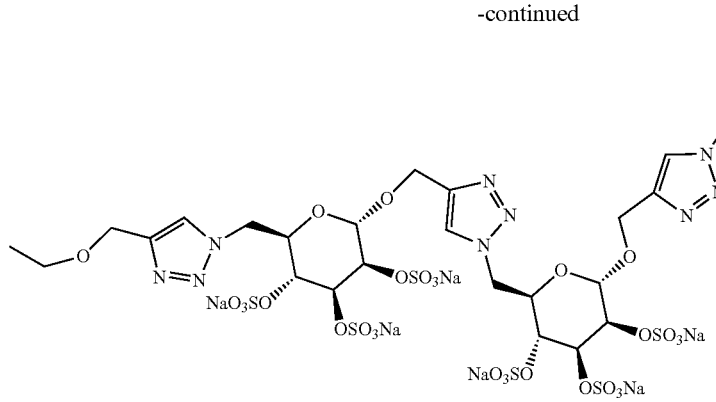
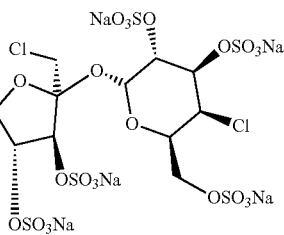

Sulfation of the deprotected hexamer 66 (30 mg, 0.02 mmol) according to the general procedure 1 followed by dialysis gave the hexamer 84 (25 mg, 41%) as a white powder, ¹H NMR (D₂O, 400 MHz): δ=8.24 (br s, 2H), 8.15 (s, 2H), 8.05 (s, 2H), 5.86 (d, 2H, J=3.6 Hz), 5.38 (d, 2H, J=7.8 Hz), 5.31-5.28 (m, 2H), 5.26-5.22 (m, 1H), 5.17-4.83 (m, 30H), 4.83-4.74 (m), 4.75-4.61 (m, 12H), 4.60-4.48 (m, 8H), 4.47-4.40 (4H), 4.39-4.22 (m, 10H), 4.00, 3.92 (ABq, 4H, J=12.4 Hz), 3.75 (s, 4H).

Sulfated Ethylene Linked Dimaltotriose (85)

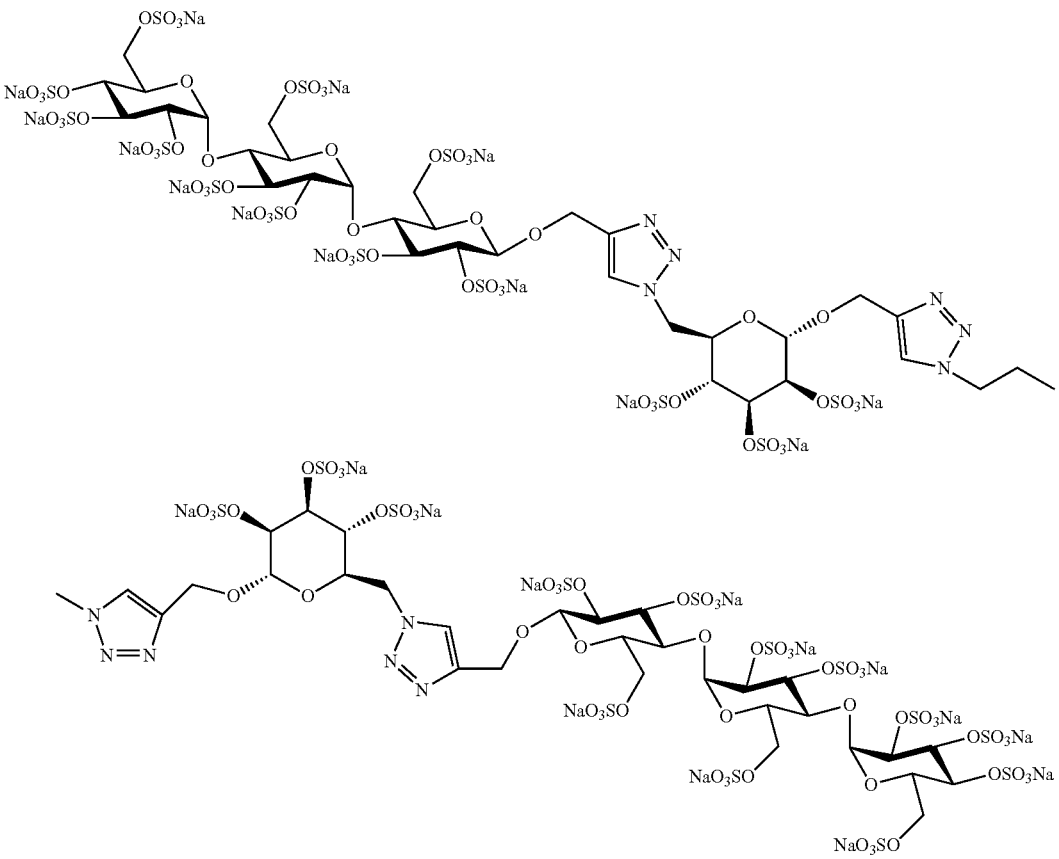

Sulfation of the deprotected hexamer 67 (100 mg, 0.06 mmol) according to the general procedure 1 followed by dialysis gave the hexamer 85 (70 mg, 27%) as a white powder, ¹H NMR (D₂O, 400 MHz): δ=8.30 (s, 2H), 7.94 (s, 2H), 5.74-5.67 (m, 2H), 5.64-5.56 (m, 2H), 5.32-4.88 (m, 25H), 4.67-4.10 (m, 40H); ¹³C NMR (CDCl₃, 100 MHz): δ=126.9, 125.3, 99.4, 96.4, 94.4, 93.8, 76.2, 75.1, 74.8, 73.5, 73.0, 72.8, 72.6, 71.8, 71.7, 70.3, 69.9, 67.8, 66.5, 66.0, 61.9, 61.2, 51.0, 49.8.

Sulfated Diethylene Linked Dimaltotriose (86)

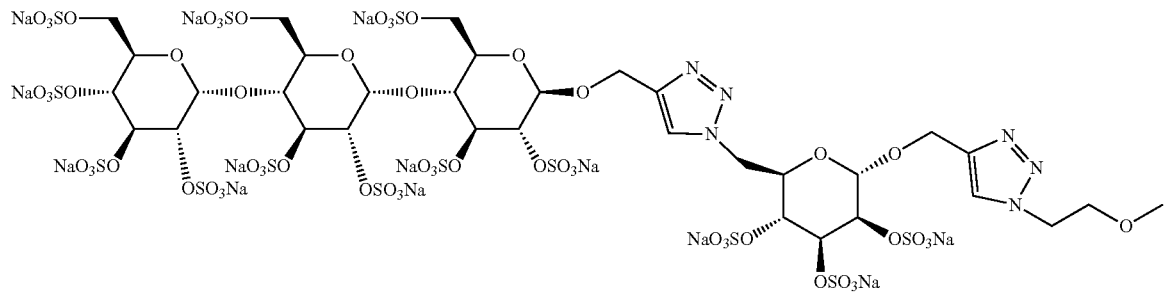

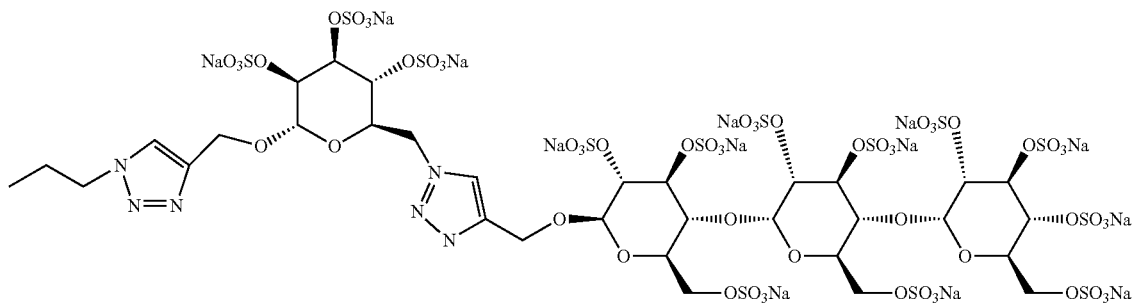

Sulfation of the deprotected hexamer 68 (70 mg, 0.04 mmol) according to the general procedure 1 followed by dialysis gave the hexamer 86 (40 mg, 23%) as a white powder; $^1$H NMR (D$_2$O, 400 MHz): δ=8.32 (s, 2H), 8.02 (s, 2H), 5.70 (d, 2H, J=3.2 Hz), 5.61 (d, 2H, J=3.6 Hz), 5.26 (s, 2H), 5.21-5.04 (m, 6H), 5.03-4.67 (20H), 4.67-4.08 (m, 40H); $^{13}$C NMR (CDCl$_3$, 100 MHz): δ=127.0, 125.6, 99.4, 96.3, 94.3, 93.5, 76.3, 75.1, 74.6, 73.5, 72.9, 72.7, 72.5, 71.5, 71.4, 70.3, 69.7, 68.9, 67.8, 66.5, 65.9, 61.8, 60.0, 57.4, 51.2, 50.3.

Sulfated Pentamer (87)

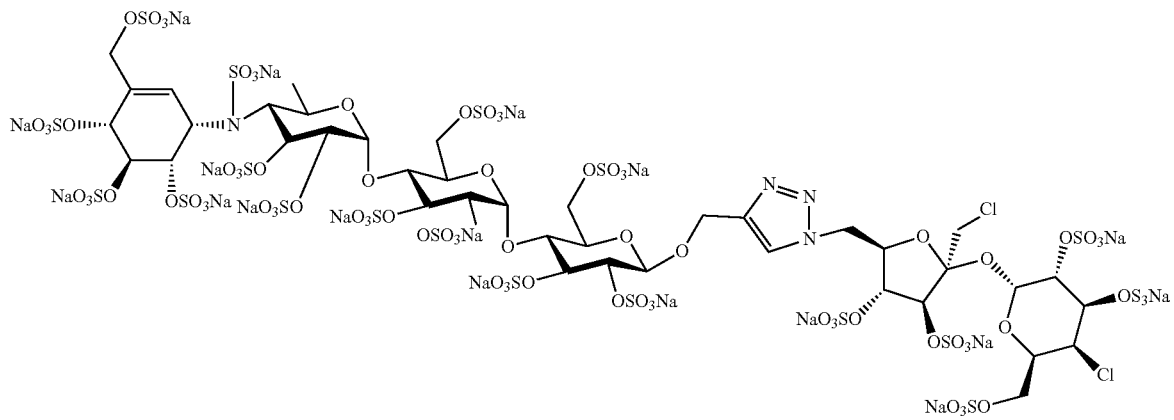

Sulfation of the deprotected pentamer 69 (41 mg, 0.04 mmol) according to the general procedure 1 followed by dialysis gave the pentamer 87 (63 mg, 59%) as a white powder, $^1$H NMR (D$_2$O, 400 MHz): 5-8.17 (s, 1H), 6.15 (s, 1H), 5.89 (d, 1H, J=3.6 Hz), 5.72-5.52 (m, 3H), 5.40 (d, 1H, J=7.8 Hz), 5.26-4.86 (m, 16H), 4.74-4.58 (m, 5H), 4.57-4.06 (m, 16H), 4.00, 3.93 (ABq, 2H, J=12.2 Hz), 1.55 (d, 3H, J=6.2 Hz).

Compound (88)

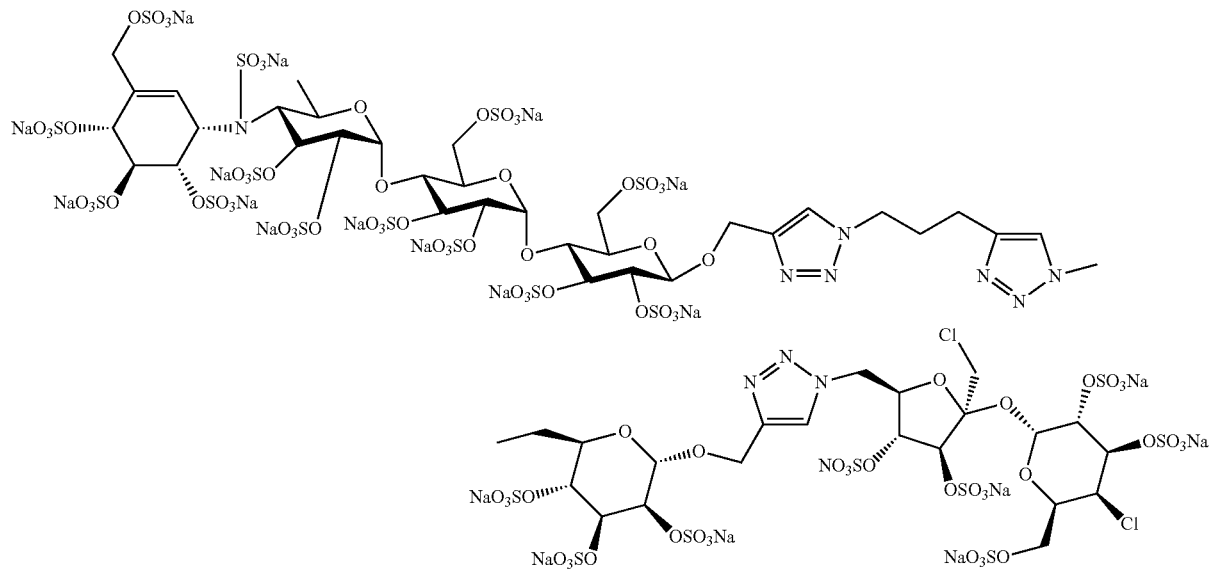

Sulfation of the deprotected pentamer 71 (210 mg, 0.15 mmol) according to the general procedure 1 followed by dialysis gave the pentamer 88 (70 mg, 20%) as a white powder; $^1$H NMR (D$_2$O, 400 MHz): δ=8.13 (s, 1H), 8.04 (s, 1H), 8.03 (s, 1H), 6.19 (s, 1H), 5.86 (d, 1H, J=3.6 Hz), 5.70 (d, 1H, J=2.7 Hz), 5.64-5.57 (m, 2H), 5.39 (d, 1H, J=7.8 Hz), 5.35-5.27 (m, 2H), 5.17-4.85 (m, 16H), 4.86-4.60 (m), 4.62-4.08 (m, 20H), 4.01, 3.93 (ABq, 2H), 3.93-3.83 (m, 1H), 2.84-2.74 (m, 2H), 2.32 (t, 2H, J=7.1 Hz), 1.64 (d, 3H, J=6.2 Hz); $^{13}$C NMR (CDCl$_3$, 100 MHz): δ=146.8, 143.6, 142.9, 134.2, 125.8, 125.5, 124.5, 120.9, 103.4, 99.3, 96.6, 94.3, 93.7, 90.9, 79.4, 78.1, 76.2, 75.8, 75.2, 73.6, 73.4, 72.7, 72.4, 72.3, 71.5, 71.3, 70.1, 70.0, 69.8, 68.4, 67.8, 67.6, 67.4, 66.3, 62.0, 60.3, 60.0, 52.9, 52.7, 50.7, 49.6, 43.9, 29.0, 21.6, 18.1.

Sulfated Ethylene Linked Diacarbose (89)

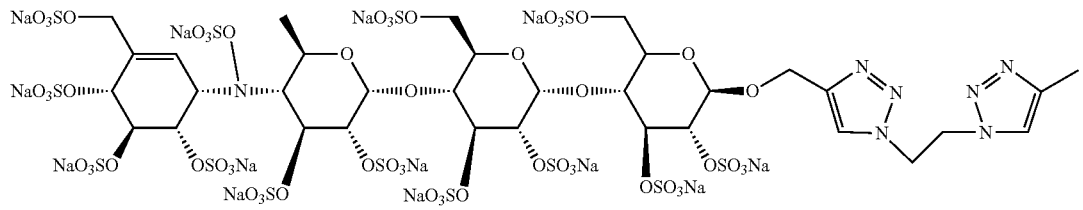

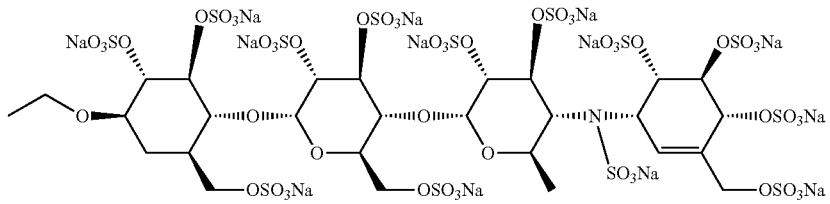

Sulfation of the deprotected octomer 72 (110 mg, 0.07 mmol) according to the general procedure 2 followed by dialysis gave the hexamer 89 (69 mg, 25%) as a white powder, $^1$H NMR (D$_2$O, 400 MHz): δ=8.15 (s, 2H), 6.18 (S, 2H), 5.68 (s, 2H), 5.59 (s, 4H), 5.32 (s, 2H), 5.20-4.57 (m), 4.59-4.07 (m, 20H), 4.03-3.92 (m, 2H), 1.63 (d, 6H, J=6.2 Hz).

Sulfated Diacarbose (90)

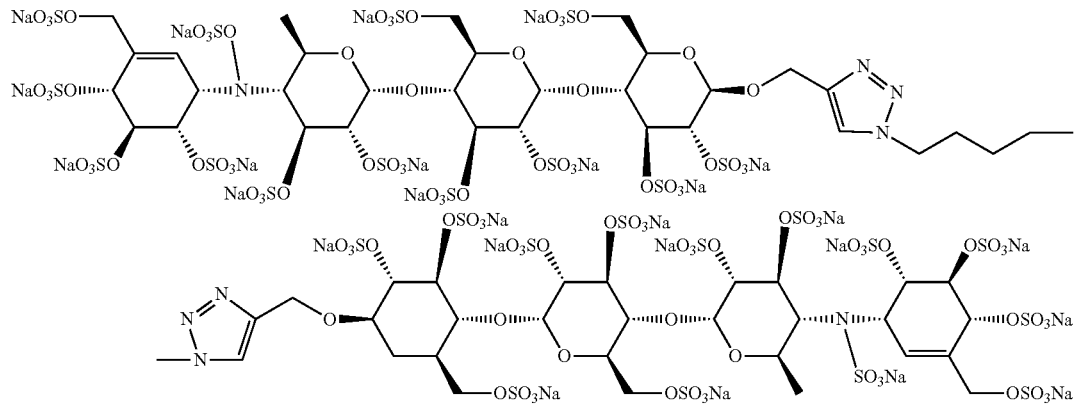

Sulfation of the deprotected octomer 73 (10 mg, 0.007 mmol) according to the general procedure 1 followed by dialysis gave the hexamer 90 (20 mg, 74%) as a white powder; $^1$H NMR (D$_2$O, 400 MHz): δ=8.18 (s, 2H), 6.16 (s, 2H), 5.69 (d, 2H, J=3.7 Hz), 5.62 (d, 2H, J=3.7 Hz), 5.58 (dd, 2H, J=1.6 Hz, I=4.2 Hz), 5.22-5.15 (m, 2H), 5.12-4.94 (m, 10H), 4.93-4.66 (m), 4.66-4.59 (m, 2H), 4.59-4.42 (m, 12H), 4.40-4.22 (m, 8H), 4.22-4.10 (m, 4H), 4.07-3.95 (m, 2H), 3.20 (t, 2H, J=8.7 Hz), 1.53 (di, 6H, J=6.2 Hz); $^{13}$C NMR (CDCl$_3$, 100 MHz): δ=143.8, 129.5, 125.6, 99.3, 94.3, 94.1, 78.6, 76.7, 76.3, 75.5, 74.8, 73.1, 72.6, 72.5, 71.9, 71.6, 70.9, 70.1, 69.9, 69.4, 68.3, 67.7, 66.5, 62.2, 59.3, 50.1, 49.8, 18.6.

Sulfated Diethylene Linked Diacarbose (91)

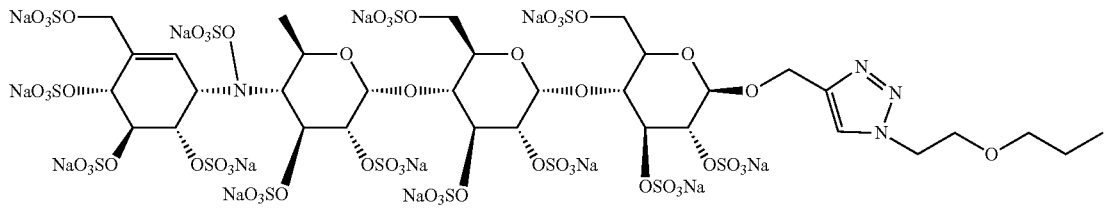

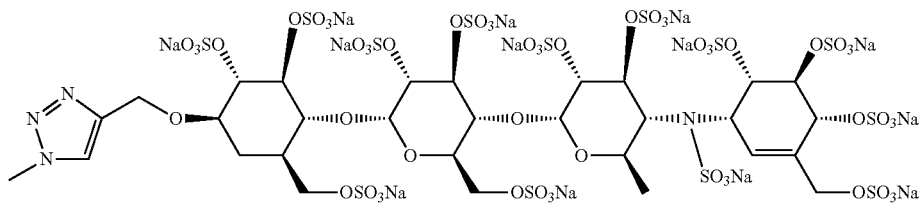

Sulfation of the deprotected octomer 74 (55 mg, 0.04 mmol) according to the general procedure 1 followed by dialysis gave the hexamer 91 (47 mg, 30%) as a white powder; $^1$H NMR (D$_2$O, 400 MHz): 5=8.13 (s, 2H), 6.15 (s, 2H), 5.67 (d, 2H, J=3.7 Hz), 5.61 (d, 2H, J=3.3 Hz), 5.57 (d, 2H, J=3.7 Hz), 5.2-5.12 (m, 2H), 5.11-4.94 (m, 12H), 4.92-4.55 (m), 4.54-4.40 (m, 8H), 4.38-4.18 (m, 8H), 4.17-4.06 (m, 4H), 4.03-3.90 (m, 6H), 3.11 (t, 2H, J=9.0 Hz), 1.51 (d, 6H, J=6.0 Hz); $^{13}$C NMR (CDCl$_3$, 100 MHz): 5=143.8, 130.6, 129.0, 125.8, 99.4, 94.4, 94.1, 78.7, 76.7, 75.4, 74.9, 72.9, 72.6, 72.4, 71.9, 71.6, 71.0, 70.1, 69.7, 68.8, 68.4, 67.7, 66.6, 62.2, 59.4, 18.6.

Sulfated Diacarbose (92)

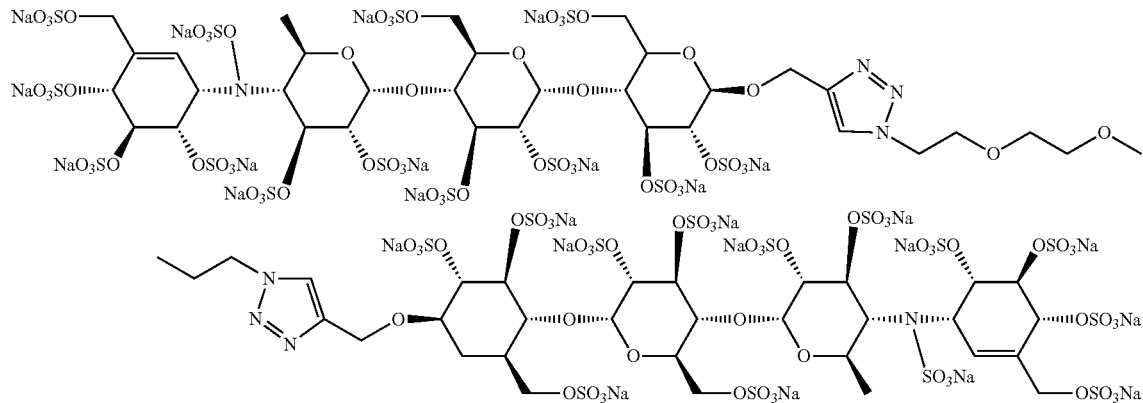

Sulfation of the deprotected octomer 75 (50 mg, 0.03 mmol) according to the general procedure 1 followed by dialysis gave the hexamer 92 (60 mg, 53%) as a white powder; $^1$H NMR (D$_2$O, 400 MHz): δ=8.18 (s, 2H), 6.14 (s, 2H), 5.67 (d, 2H, J=3.1 Hz), 5.59 (d, 2H, J=2.7 Hz), 5.57-5.52 (m, 2H), 5.22-5.14 (m, 2H), 5.14-5.55 (m), 4.55-4.38 (m, 6H), 4.37-4.18 (m, 8H), 4.18-4.04 (m, 4H), 4.02-3.90 (m 4H), 3.74-3.57 (m, 4H), 3.45-3.27 (m, 2H), 1.54 (d, 6H, J=6.0 Hz).

Sulfated Diacarbose (93)

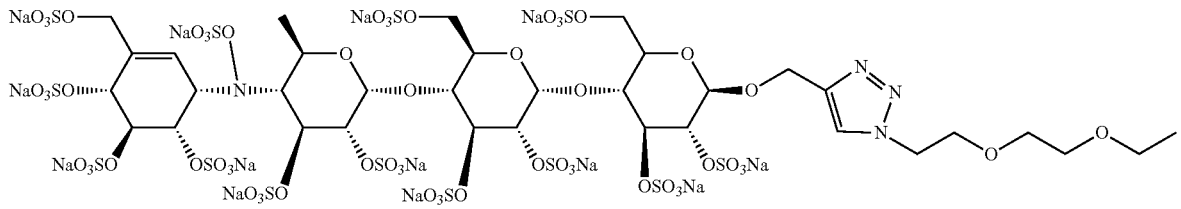

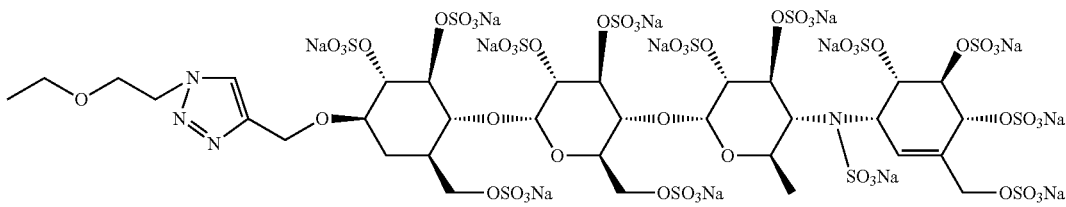

Sulfation of the deprotected octomer 76 (170 mg, 0.11 mmol) according to the general procedure 2 followed by dialysis gave the hexamer 93 (142 mg, 32%) as a white powder, $^1$H NMR (D$_2$O, 400 MHz): δ=8.22 (s, 2H), 6.22 (s, 2H), 5.72-5.57 (s, 4H), 5.41-5.31 (m, 2H), 5.22-4.95 (10H), 4.63-4.49 (m, 6H), 4.49-4.14 (m, 12H), 4.11-3.93 (m, 4H), 3.74-3.58 (m, 6H), 1.67 (d, 3H, J=6.3 Hz); $^{13}$C NMR (CDCl$_3$, 100 MHz): δ=143.8, 134.8, 127.5, 125.9, 120.0, 99.00, 94.3, 94.1, 99.01, 94.3, 94.1, 77.7, 76.2, 75.9, 73.8, 73.5, 73.3, 72.8, 72.3, 71.5, 71.4, 70.1, 69.7, 69.4, 68.8, 67.6, 67.3, 66.3, 66.0, 61.8, 53.1, 50.2, 18.1.

Sulfated Diacarbose (94)

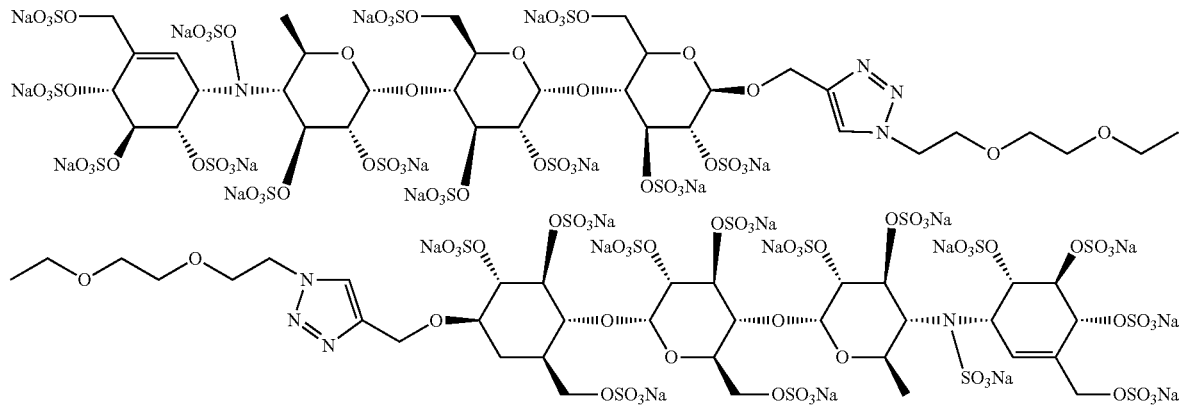

Sulfation of the deprotected octomer 77 (250 mg, 0.16 mmol) according to the general procedure 2 followed by dialysis gave the hexamer 94 (390 mg, 60%) as a white powder; $^1$H NMR (1D$_2$O, 400 MHz): δ=8.20 (s, 2H), 6.15 (s, 2H), 5.66 (d, 2H, J=3.3 Hz), 5.59 (d, 2H, J=3.4 Hz), 5.58-5.54 (m, 2H), 5.23-5.13 (m, 2H), 5.13-4.92 (m, 12H), 4.55-4.38 (m, 9H), 4.38-3.93 (m, 20H), 3.78-3.57 (m, 12H), 3.47-3.26 (m, 2H), 1.55 (d, 6H, J=6.1 Hz);); $^{13}$C NMR (CDCl$_3$, 100 MHz): δ=143.9, 130.8, 125.8, 99.3, 94.1, 76.5, 75.6, 74.4, 73.1, 72.4, 72.3, 71.6, 70.6, 70.0, 69.6, 69.5, 69.4, 69.2, 68.8, 68.5, 68.0, 67.7, 66.4, 62.1, 59.1, 50.8, 50.0, 18.4.

Example 25

BIAcore Screening Assay

The optical phenomenon of surface plasmon resonance is used to monitor physical interactions between molecules. Passing a solution of a potential protein ligand (e.g. IL-4, IL-5, IL-6, IL-13, eotaxin-1, eotaxin-2, IL-8 or MCP-1) over a sensor surface to which a target (e.g. heparin) is coupled monitors the real-time binding of protein ligands to the immobilized target. Detection is achieved by measuring refractive index changes very close to the sensor surface. When the refractive index is altered, the angle at which plasmon resonance occurs changes and this change directly correlates with the amount of protein interacting with the surface. A BIAcore T200 is conveniently used. It is very sensitive and its microfluidics ensures that only small amounts of material are required.

Biotinylated heparin is immobilized on the biosensor chip. Biotinylation occurs via amino groups, or reducing termini modified with ammonia by reductive amination, using sulfo-NHS-biotin. Solutions containing potential protein ligands of interest are injected over the sensor chip surface, and the binding is measured in real time (Fernig, In: Proteoglycan protocols, Ed. R. V. Iozzo, Humana Press, Totowa, NJ, USA, 2001). Baculovirus expressed recombinant human IL-5 (rhIL-5) readily bind to heparin immobilized by this method (see PCT/AU2005/000551). Similarly, binding is specific, as there is little interaction of IL-5 with sensor chips that lack heparin.

Example 26

Functional Analyses of Simplified Sulfated Glycoconjugates on the Asthma Target Protein, IL-13

The various simplified sulphated glycoconjugates inhibited the proliferation of an IL-13 responsive cell line to differing degrees. This occurs at very low doses and is believed not to be due to a toxic effect of the glycoconjugates because other, similarly sulfated polysaccharides (e.g. sucrose octasulfate), at the same concentrations of IL-13 and polysaccharide have no effect. These experiments utilize the TF-1 cells that are grown in 2 ng/ml recombinant human (rh) GM-CSF. TF-1 cells were originally established from a bone marrow sample from a male with severe pancytopenia. These cells are dependent on IL-3 or GM-CSF for long term growth and are responsive to a variety of human cytokines including IL-13.

Briefly, proliferation assays were carried out in 96-well microplates suitable for such assays. Routinely, the cells were cultured in low dose rhGM-CSF (0.1 ng/ml) for 24 hours before the assay. Cells were washed to remove any cytokine in the growth medium and then resuspended in RPMI/5% w/v FCS and routinely 2.5×10$^4$ cells were added to microplate wells that contain either no rhIL-13 (negative control) or various dilutions of rhIL-13. Routinely rhIL-13 is titrated from a starting concentration of 25 ng/ml. When the effect of the different simplified sulfated glycoconjugates was measured, the wells also contained various concentrations of these molecules (10 µg/ml and 2.5 µg/ml) and the rhIL-13 concentration was held constant at 4 ng/ml. The cells proliferated for 48 hours, after which the number of cells present was quantified by staining with 20 µL per well of the CellTiter 96 Aqueous One reagent was incubated with TF1 cells for the last 3.5 to 4 hours of culture and then absorbance was read at 490 nm on an Enspire Multimode plate reader (PerkinElmer). These data are in FIG. 1. It is clear from these data that the different glycoconjugate structures inhibit IL-13 stimulated cell proliferation to different extents.

Figure 8:
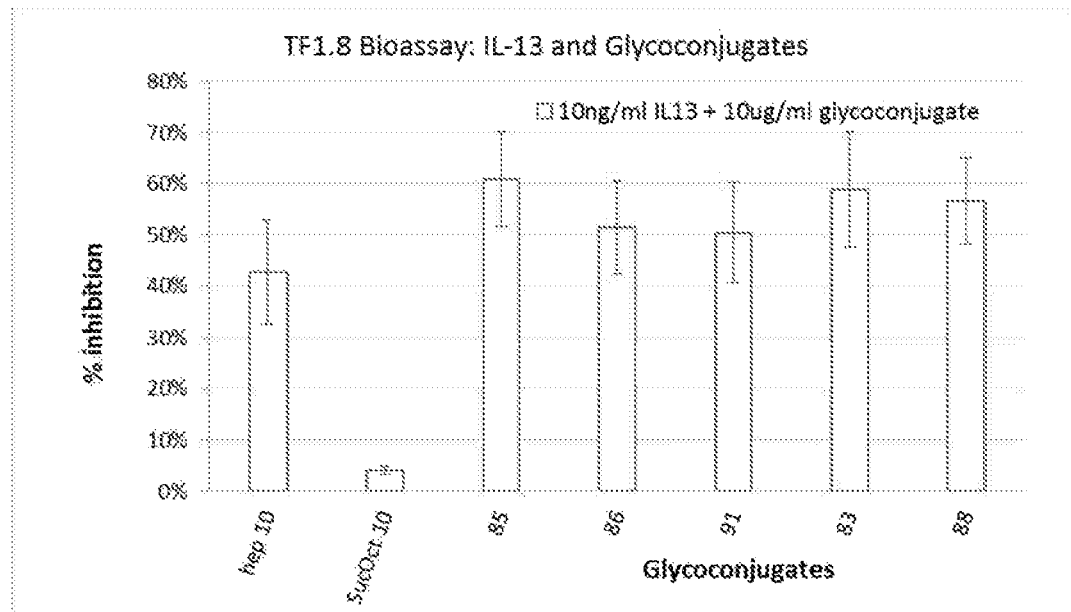
FIG. 8 is a graphical representation showing a TF1.8 bioassay with recombinant human IL-13. Data from at least 3 replicates are displayed as an average of the % inhibition of cell proliferation at 10 ng/ml IL-13 and 10 μg/ml of inhibitor. The inhibitors were A: heparin, sucrose octasulfate and glycoconjugates 83, 85, 86, 88 and 91, B: heparin and glycoconjugates 78-84 and 87-94. Mean and standard deviation are shown.
Figure 8:
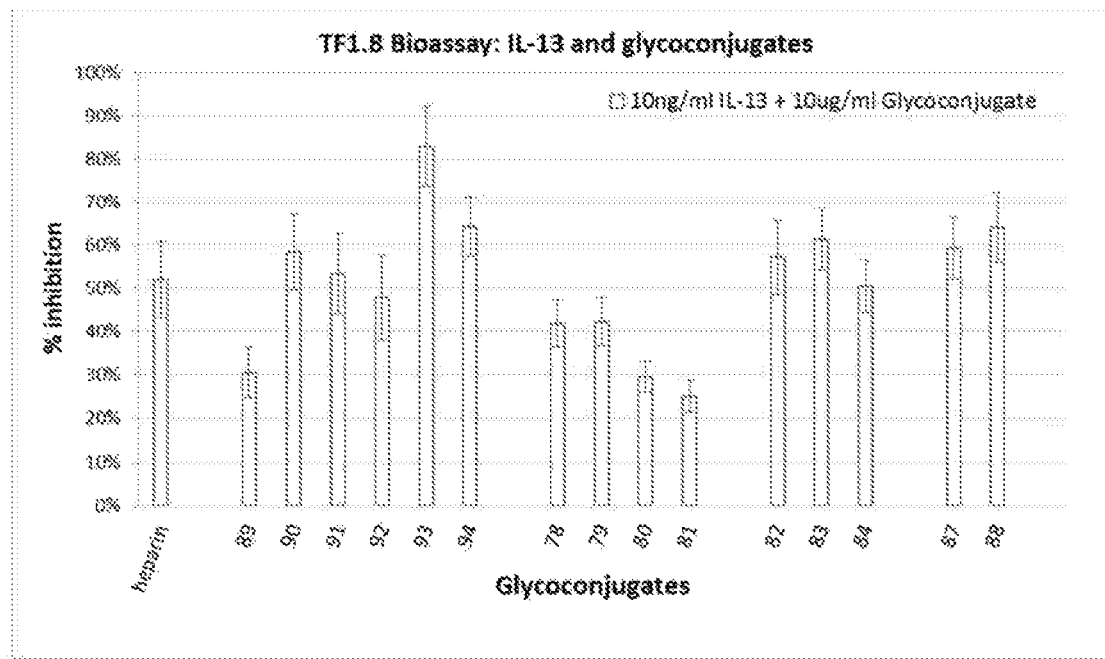

It is also possible to do these experiments with TF-1.8 cells. TF-1.8 cells are a subclone of the TF-1 cells that have been selected for growth in IL-4 or IL-5. TF-1.8 cells have been transfected with the firefly luciferase gene contained in the expression vector, pPGK-puromycin-luciferase (Coombe et al. (1998) *Journal of Immunological Methods* 215:145-150). The positive transfectants are cloned to produce a line with good luciferase expression. The proliferation assays are carried out in 96-well microplates suitable for such assays (Falcon). The wells are flat bottomed, with white sides and a clear bottom. The assay is as described for TF1 cells and IL-13 except that 10 ng/ml of rhIL-13 is used and cell number after 48 hours of proliferation is quantified by measuring luciferase activity. Luciferase activity is measured by the addition of 50 µl of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on an Enspire Multimode plate reader (PerkinElmer). The data for this assay are shown in FIG. 8 and from this figure it is clear that selected glycoconjugates are very effective inhibitors of IL-13 stimulated cell proliferation, whereas glycoconjugates of a different structure are less effective.

Example 27

Functional Analysis of Simplified Sulfated Glycoconjugates on the Asthma and Allergic Rhinitis Target Protein, IL-5

The various simplified sulfated glycoconjugates inhibited the proliferation of an IL-5 responsive cell line to differing degrees. This occurs at very low doses and is not due to a toxic effect of the glycoconjugate as other similarly sulfated polysaccharides have no effect in this assay. These experiments are performed with the IL-5 responsive cells, Ba/F-IL-5. The Ba/F-IL-5 cells were derived from the Ba/F3 cell line. The Ba/F3 cell line was transformed to be both IL-5 dependent and to express luciferase by co-transfection of the cells with pGL3 control vector (Promega, USA) and pEE6hcmv-IL-5Ra. The control vector, pGL3 expresses a modified luciferase under the direct control of the SV40 promoter and enhancer, but contains no selectable marker. To prepare pEE6hcmv-hIL-5Ra a full length human IL-5 receptor a chain (hIL-5R-a) was cloned by RT PCR from HL60 cells. The preparation of the Ba/F-IL-5 cells has been described by Coombe et al, (1998) supra. The Ba/F-IL-5 cells may be further modified by co-transfection with pPGK-puromycin-luciferase, a vector containing luciferase under the control of the SV40 promotor with the selectable marker puromycin.

After transfection, positive transfectants are selected in 3 µg/mL puromycin. The positive transfectants are then cloned to produce a line with detectable luciferase expression. The proliferation assays are carried out in 96-well microplates suitable for such assays. The wells are flat bottomed, with white sides and a clear bottom. Cells are washed to remove any cytokine in the growth medium and then resuspended in RPMI/S % w/v FCS. The cells are counted with a Coulter Z2 Particle Counter and Size Analyzer (Coulter Electronics, England) and routinely $1.6 \times 10^4$ cells are added to microplate wells that contain either no rhIL-5 (negative control) or various dilutions of rhIL-5. When the effect of sulphated glycoconjugates, or other sulfated polysaccharides is to be measured, the wells also contain various concentrations of these molecules.

Figure 2:
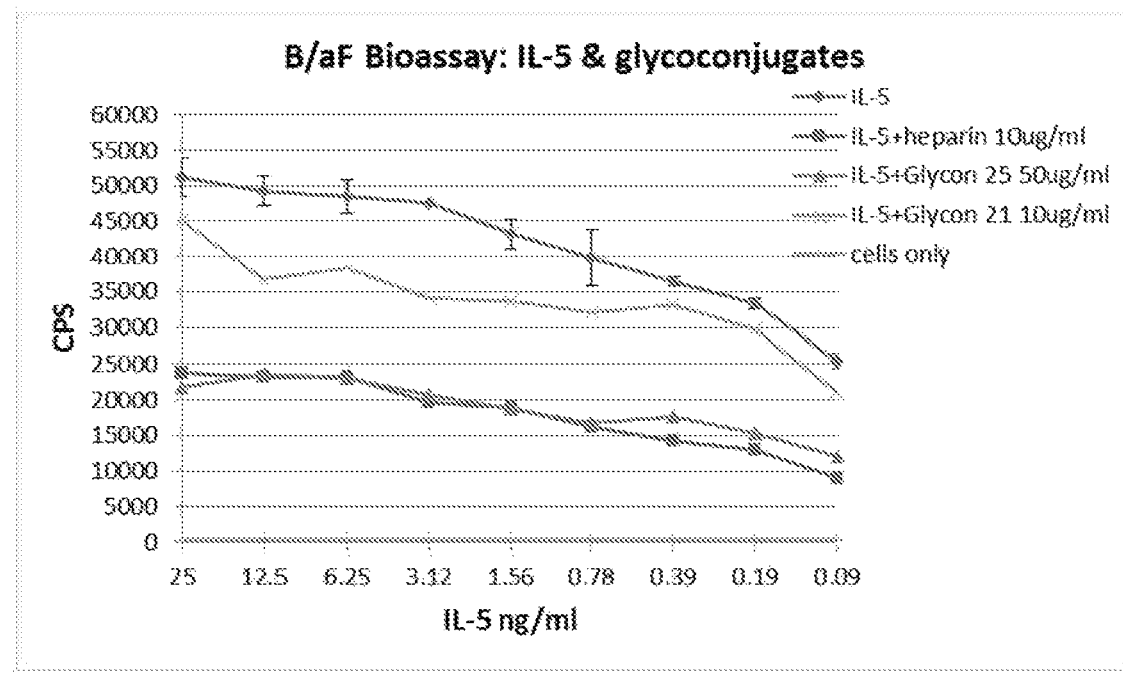
FIG. 2 is a graphical representation showing a Ba/F-IL-5 bioassay with recombinant human IL-5. A: IL-5 is titrated from 25 ng/ml-0.9 ng/ml and the inhibitors: heparin, sulphated glycoconjugates: 21 and sucrose octasulfate are held at 10 µg/ml, but glycoconjugate 25 was used at 50 µg/ml. The IL-5 dependent cell proliferation is shown as luminescence counts/second. B: data from 3 independent experiments are displayed as an average of the % inhibition of cell proliferation at 1.6 ng/ml IL-5 and either 2.5 µg/ml or 10 µg/ml of inhibitor for heparin, sucrose octasulfate and glycoconjugate 21, glycoconjugate 25 was used at 12.5 µg/ml. Mean and standard deviation are shown.
Figure 2:
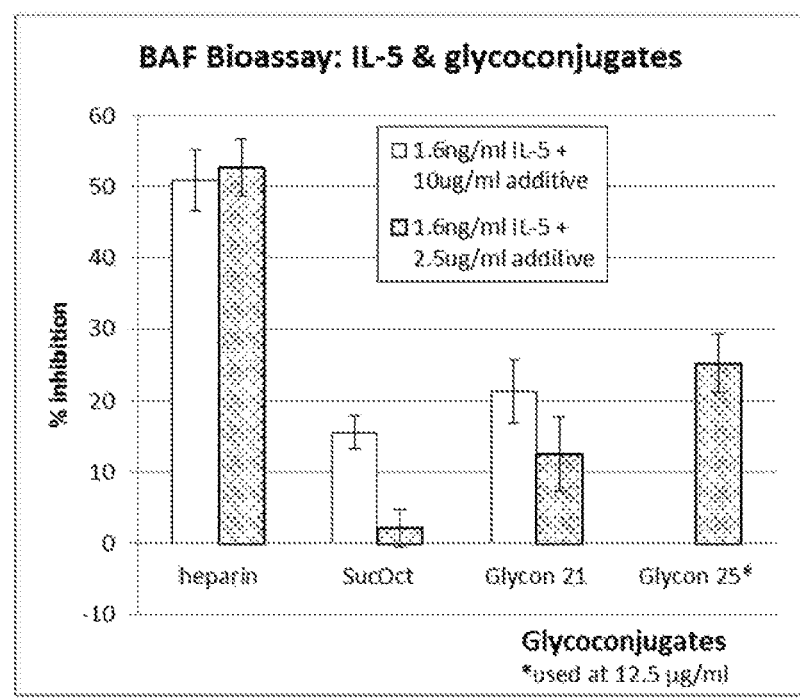
Figure 9:
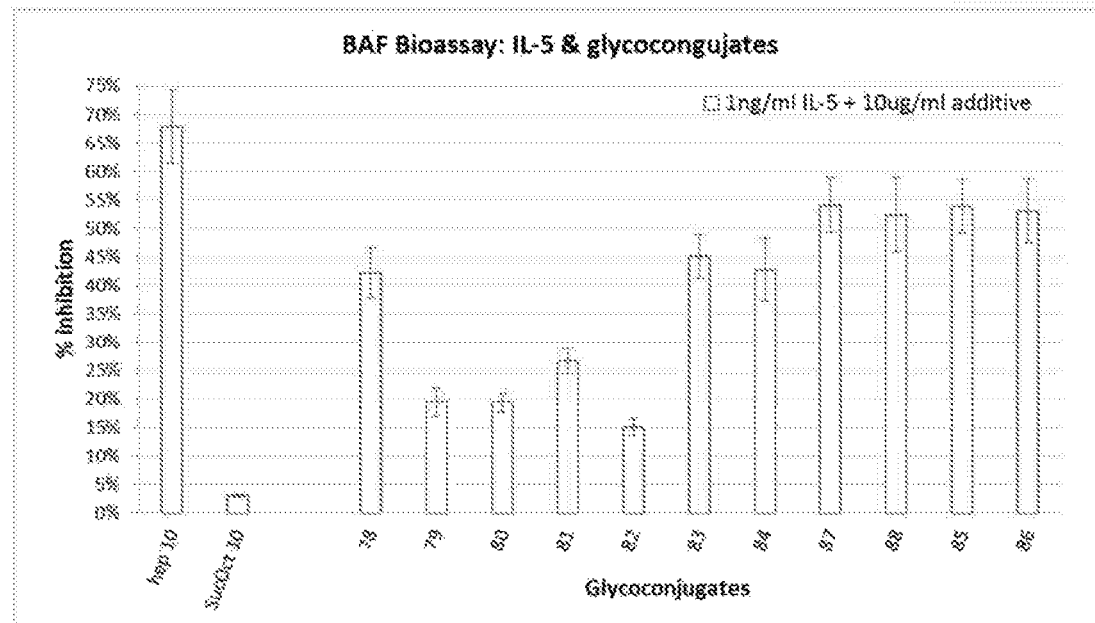
FIG. 9 is a graphical representation showing a Ba/F-IL-5 bioassay with recombinant human IL-5. Data from at least 3 replicates are displayed as an average of the % inhibition of cell proliferation at 1 ng/ml IL-5 and 10 μg/ml of inhibitor. The inhibitors were A: heparin, sucrose octasulfate and glycoconjugates 78-88, B: heparin, sucrose octasulfate and glycoconjugates 89-94. Mean and standard deviation are shown.
Figure 9:
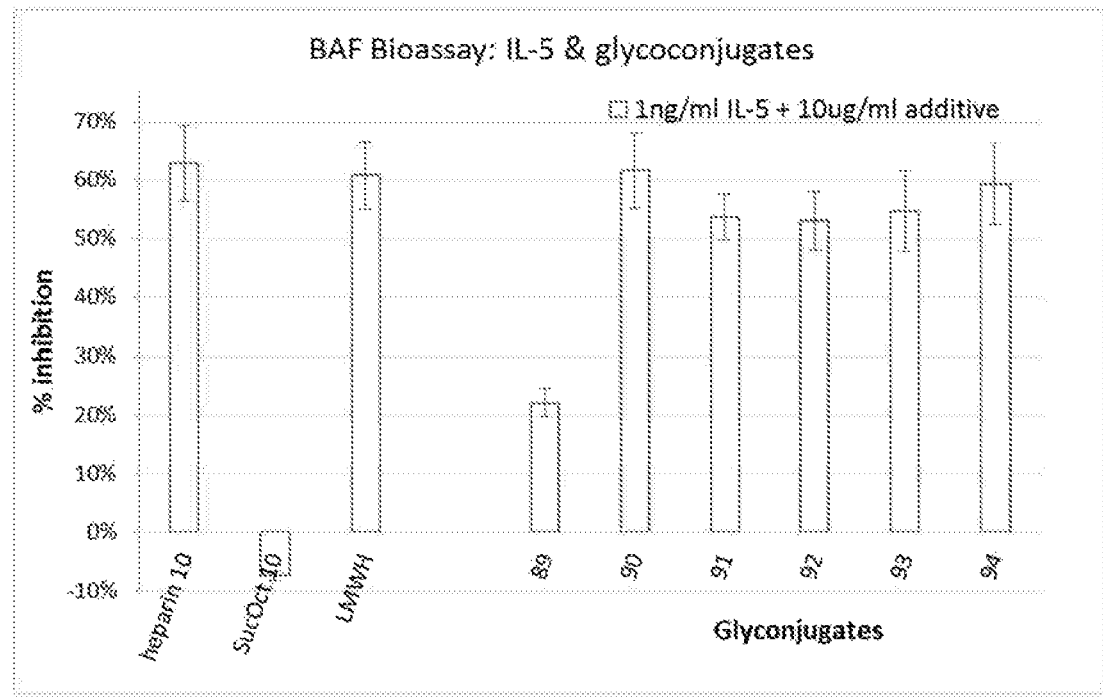

The cells proliferate for 24 hours at 37° C. in a humidified atmosphere, after which the luciferase activity is measured by the addition of 50 µl of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on an Enspire Multimode plate reader (PerkinElmer). Using this assay it has been demonstrated that some of the simplified sulphated glycoconjugates are very effective inhibitors of rhIL-5 dependent Ba/F-IL-5 cell proliferation whereas others are less effective. These data are in FIGS. 2 and 9. Heparin and sucrose octasulfate were used as positive and negative controls, respectively.

Example 28

Functional Analyses of Simplified Sulfated Glycoconjugates on the Asthma and COPD Target Protein, IL-4

The various simplified sulphated glycoconjugates inhibited the proliferation of an IL-4 responsive cell line to differing degrees. This occurs at very low doses and is not due to a toxic effect of the glycoconjugate because other, similarly sulfated polysaccharides (sucrose octasulfate), at the same concentrations of IL-4 and polysaccharide have no effect. These experiments utilize the TF-1 cells that are grown in 2 ng/ml recombinant human (rh) GM-CSF. TF-1 cells were originally established from a bone marrow sample from a male with severe pancytopenia. These cells are dependent on IL-3 or GM-CSF for long term growth and are responsive to a variety of human cytokines including human IL-4.

Briefly, proliferation assays were carried out in 96-well microplates suitable for such assays. Routinely, the cells were cultured in low dose rhGM-CSF (0.1 ng/ml) for 24 hours before the assay. Cells were washed to remove any cytokine in the growth medium and then resuspended in RPMI/5% w/v FCS and routinely $2.5 \times 10^4$ cells were added to microplate wells that contain either no rhIL-4 (negative control) or various dilutions of rhIL-4. Routinely rhIL-4 is titrated from a starting concentration of 25 ng/ml. When the effect of the different simplified sulfated glycoconjugates was measured, the wells also contained various concentrations of these molecules (10 µg/ml and 2.5 µg/ml) and the rhIL-4 concentration was held constant at 4 ng/ml. The cells proliferated for 48 hours, after which the number of cells present was quantified by staining with 20 µL per well of the CellTiter 96 Aqueous One reagent was incubated with TF1 cells for the last 3.5 to 4 hours of culture and then absorbance was read at 490 nm on an Enspire Multimode plate reader (PerkinElmer).

Figure 3:
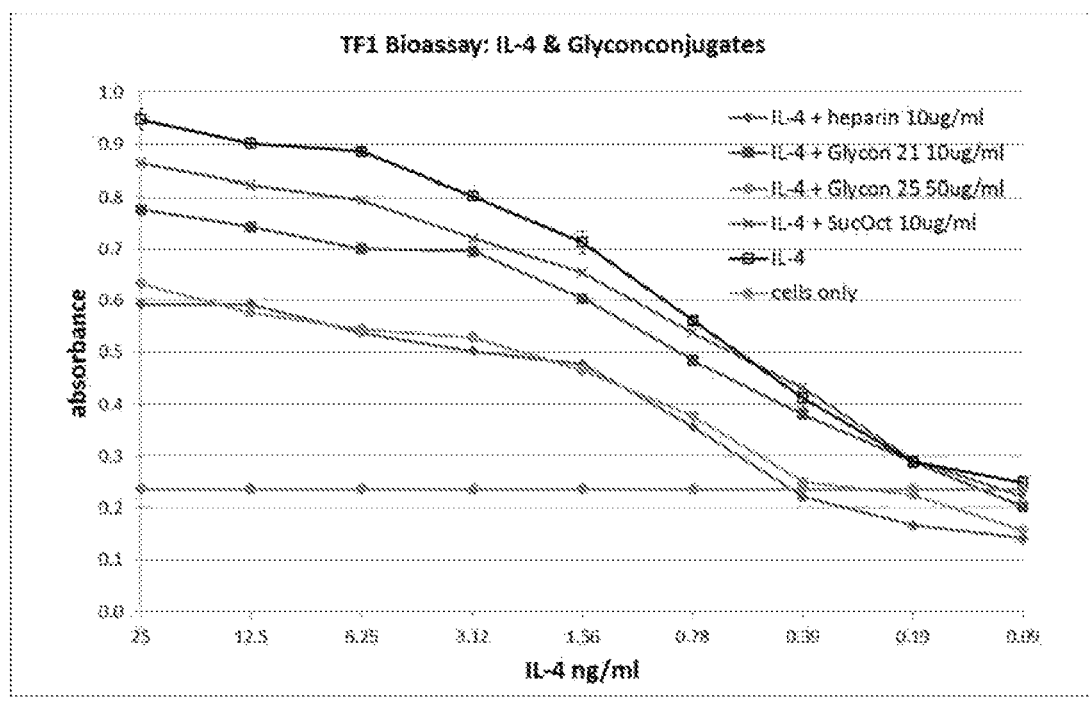
FIG. 3 is a graphical representation showing a TF1 bioassay with recombinant human (rh) IL-4. A: IL-4 is titrated from 25 ng/ml-0.9 ng/ml and the inhibitors: heparin, sulphated glycoconjugates: 21, and sucrose octasulfate are held at 10 µg/ml, but glycoconjugate 25 was used at 50 µg/ml. The IL-4 dependent cell proliferation is shown as absorbance at 490 nm. B: data from 3 independent experiments are displayed as an average of the % inhibition of cell proliferation at 4 ng/ml IL-4 and either 2.5 µg/ml or 10 µg/ml of inhibitor for heparin, sucrose octasulfate and glycoconjugate 21, glycoconjugate 25 was used at 12.5 µg/ml. Mean and standard deviation are shown.
Figure 3:
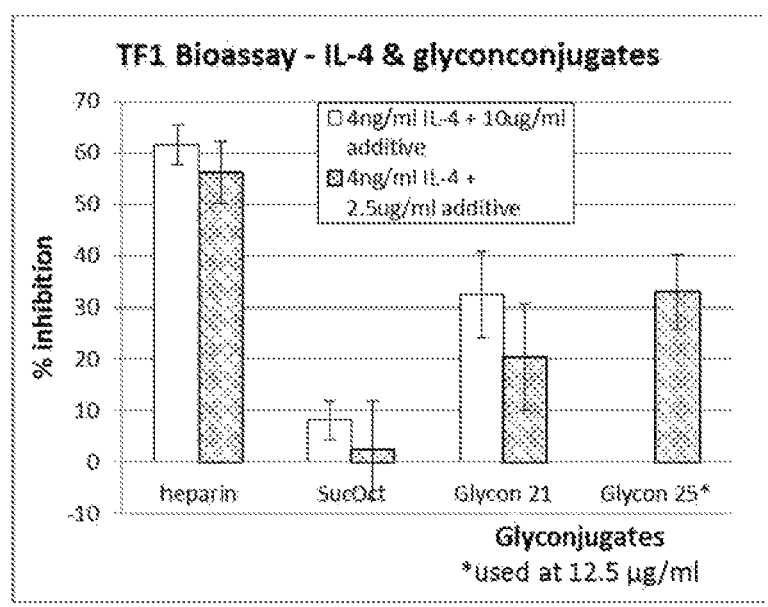

Of the two glycoconjugates in the example shown in FIG. 3 one was a more effective inhibitor than the other; the less active glycoconjugate requiring a higher concentration for good activity.

Figure 10:
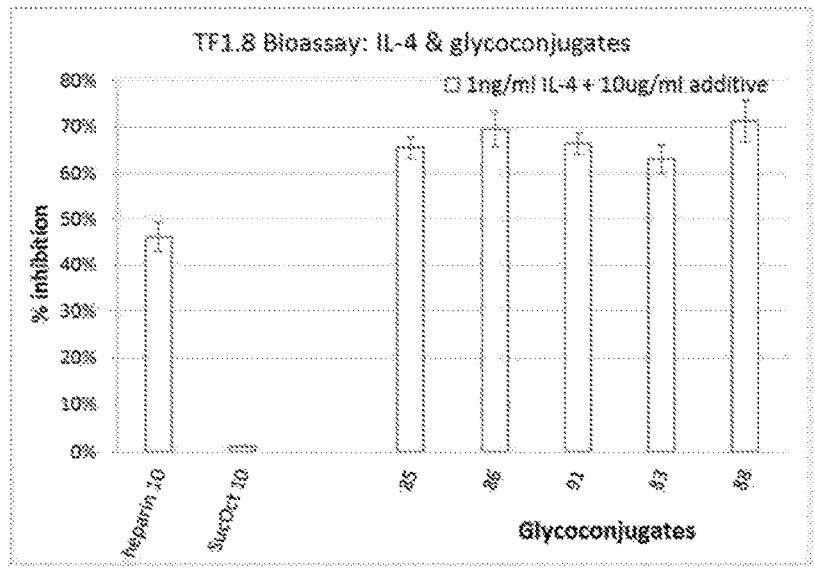
FIG. 10 is a graphical representation showing a TF1.8 bioassay with recombinant human IL-4. Data from at least 3 replicates are displayed as an average of the % inhibition of cell proliferation at 1 ng/ml IL-4 and 10 μg/ml of inhibitor. The inhibitors were A: heparin, sucrose octasulfate and glycoconjugates 83, 85, 86, 88 and 91, B: heparin and glycoconjugates 78-84 and 87-94. Mean and standard deviation are shown.
Figure 10:
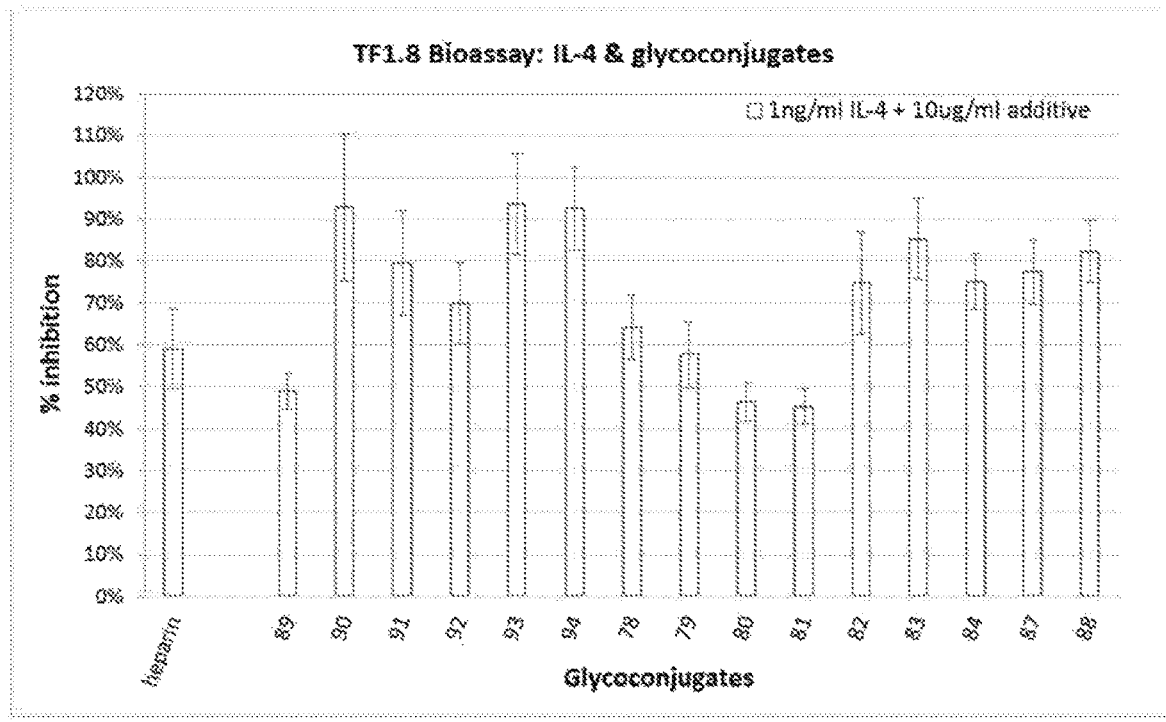

It is also possible to do these experiments with TF-1.8 cells. TF-1.8 cells are a subclone of the TF-1 cells that have been selected for growth in IL-4 or IL-5. TF-1.8 cells have been transfected with the firefly luciferase gene contained in the expression vector, pPGK-puromycin-luciferase (Coombe et al. (1998) supra). The positive transfectants are cloned to produce a line with good luciferase expression. The proliferation assays are carried out in 96-well microplates suitable for such assays (Falcon). The wells are flat bottomed, with white sides and a clear bottom. The assay is as described for TF1 cells and IL-4 except that 1 ng/ml of rhIL-4 is used and cell number after 48 hours of proliferation is quantified by measuring luciferase activity. Luciferase activity is measured by the addition of 50 μl of luciferase substrate buffer (50 mM Tris-HCl, pH 7.8, 15 mM MgSO$_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on an Enspire Multimode plate reader (PerkinElmer). The data for this assay are shown in FIG. 10 and from this Figure it is clear that some of the glycoconjugates were very effective inhibitors of IL-4 stimulated cell proliferation, where as glycoconjugates of a different structure were less effective.

Example 29

Functional Analyses of Simplified Sulfated Glycoconjugates on the Osteoarthritis and COPD and ARDS Target Proteins, IL-1β and IL-6

The various simplified sulphated glycoconjugates inhibited the proliferation of an IL-1β responsive cell line to differing degrees, however, little inhibition of the activity of IL-6 was detected. The inhibition of IL-1β activity occurs at very low doses and is believed not to be due to a toxic effect of the glycoconjugate because other, similarly sulfated polysaccharides, at the same concentrations of IL-1β and polysaccharide have no effect. These experiments utilize the TF-1 cells that are grown in 2 ng/ml rhGM-CSF. TF-1 cells were originally established from a bone marrow sample from a male with severe pancytopenia. These cells are dependent on IL-3 or GM-CSF for long term growth and are responsive to a variety of cytokines including human IL-1β and human IL-6.

Briefly, proliferation assays were carried out in 96-well microplates suitable for such assays. Routinely, the cells were cultured in low dose rhGM-CSF (0.1 ng/ml) for 24 hours before the assay. Cells were washed to remove any cytokine in the growth medium and then resuspended in RPMI/5% w/v FCS and routinely 2.5×10$^4$ cells were added to microplate wells that contain either no cytokine (IL-10 or IL-6 (negative control)) or various dilutions of these cytokines. Routinely these cytokines are titrated from a starting concentration of 25 ng/ml. When the effect of the different simplified sulfated glycoconjugates was measured, the wells also contained various concentrations of these molecules and the cytokine concentration was held constant. The rhIL-1β concentration was held constant at 2 ng/ml. The cells proliferated for 48 hours, after which the number of cells present was quantified by staining with 20 μL per well of the CellTiter 96 AQueous One reagent was incubated with TF1 cells for the last 3.5 to 4 hours of culture and then absorbance was read at 490 nm on an Enspire Multimode plate reader (PerkinElmer).

Figure 4:
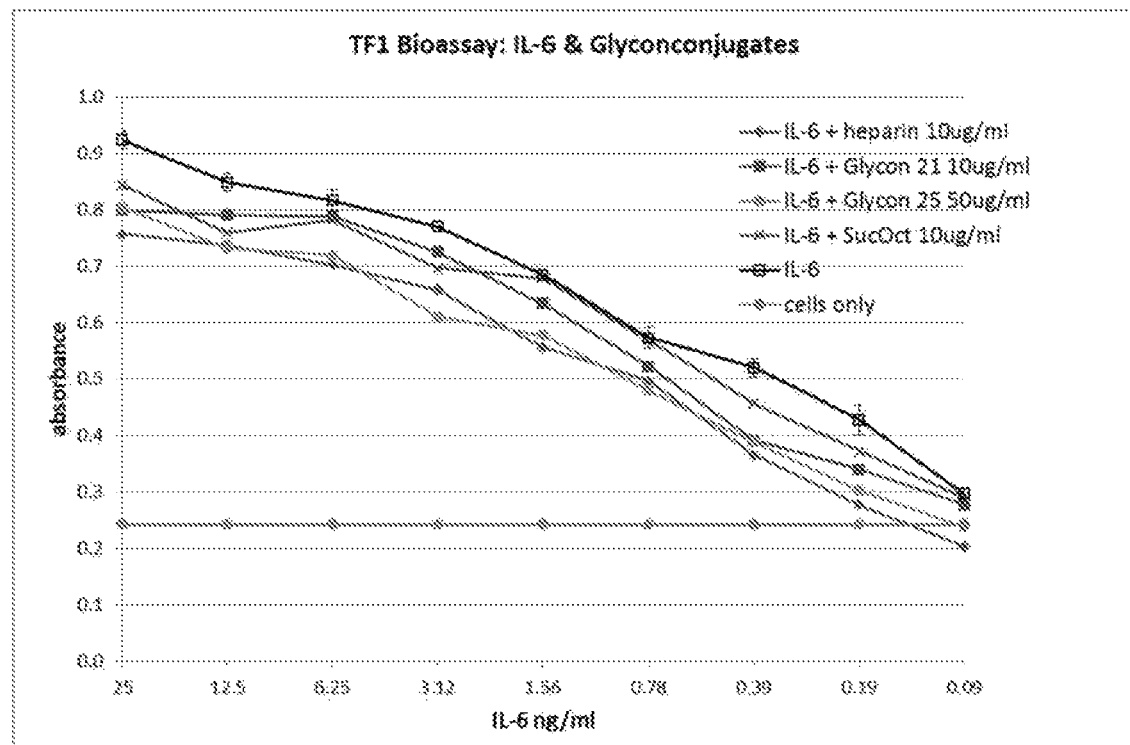
FIG. 4 is a graphical representation showing a TF1 bioassay with recombinant human (rh) IL-6. IL-6 is titrated from 25 ng/ml-0.9 ng/ml and the inhibitors: heparin, sulphated glycoconjugates: 21 and sucrose octasulfate are held at 10 μg/ml, but glycoconjugate 25 was used at 50 μg/ml. The IL-6 dependent cell proliferation is shown as absorbance at 490 nm.
Figure 5:
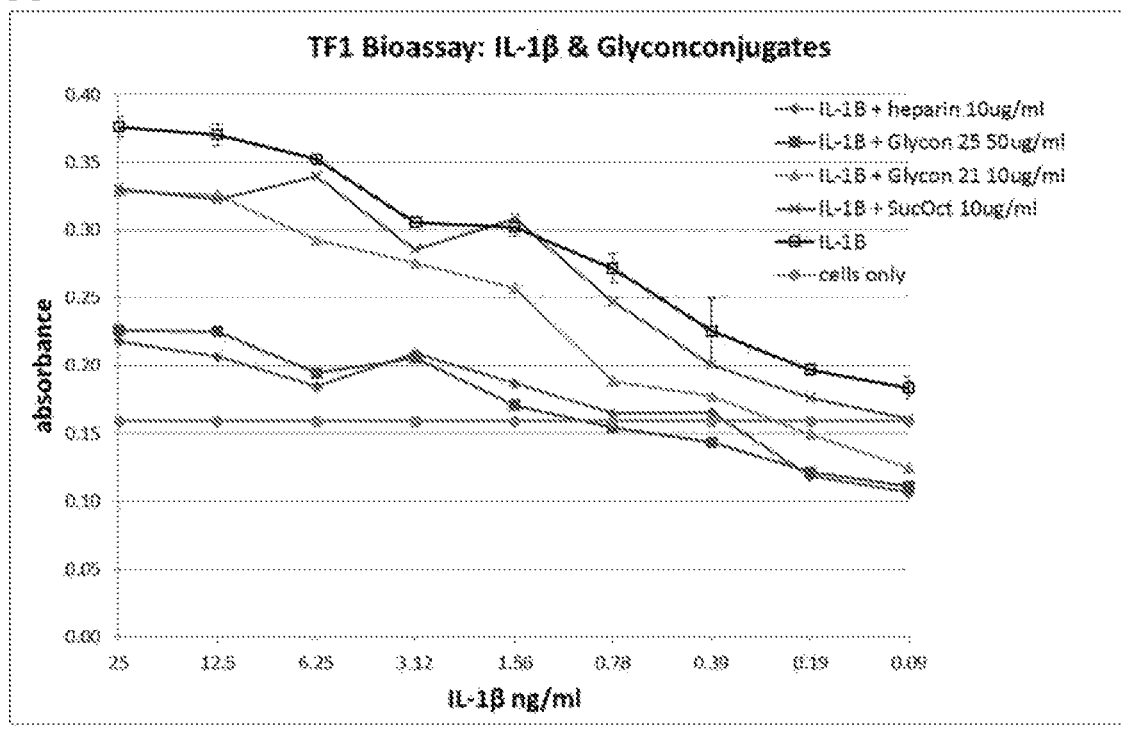
FIG. 5 is a graphical representation showing a TF1 bioassay with recombinant human (rh) IL-1β. A: rhIL-1β is titrated from 25 ng/ml-0.9 ng/ml and the inhibitors: heparin, sulphated glycoconjugates: 21 and sucrose octasulfate are held at 10 μg/ml, but glycoconjugate 25 was used at 50 μg/ml. The IL-1β dependent cell proliferation is shown as absorbance at 490 nm. B: data from 4 independent experiments are displayed as an average of the % inhibition of cell proliferation at 2 ng/ml IL-1p and either 2.5 μg/ml or 10 μg/ml of inhibitor for heparin, sucrose octasulfate and glycoconjugate 21, glycoconjugate 25 was used at 12.5 μg/ml. Mean and standard deviation are shown.
Figure 5:
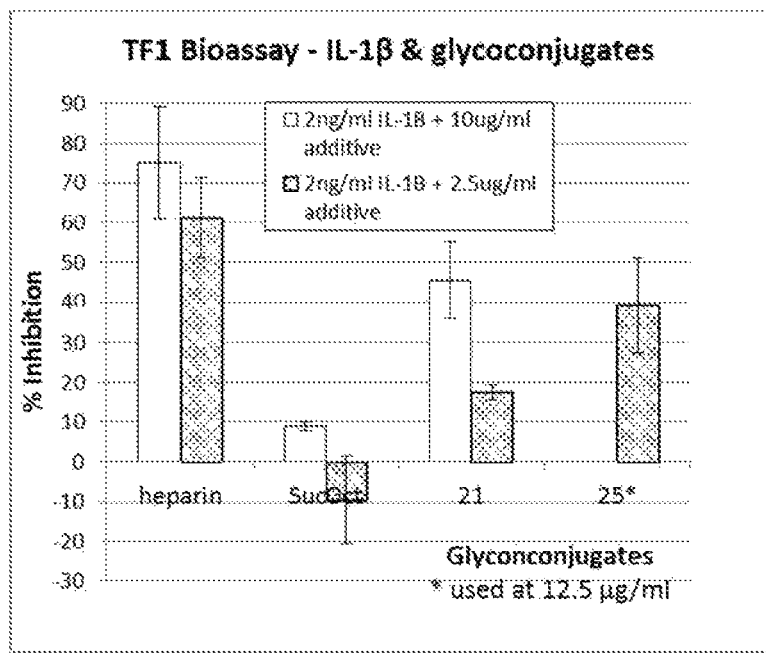

Of the two glycoconjugates in the example one was a more effective inhibitor of rhIL-1β than the other, and neither glycoconjugate convincingly inhibited rhIL-6 induced cell proliferation. These data are shown in FIGS. 4 and 5. These experiments indicate that the sulphated glycoconjugates with different structure bind differently, or have different levels of activity, with different cytokines. The fact that the rhIL-6 was not inhibited (FIG. 4) also indicates that the sulphated glycoconjugates tested are not toxic to these cells.

Example 30

Functional Analyses of Simplified Sulphated Glycoconjugates on the Pro-Inflammatory Cytokine, TNF-α

TNF-α is a pro-inflammatory cytokine and is involved in COPD, ARDS as well as osteoarthritis and other inflammatory diseases. The various simplified sulphated glycoconjugates inhibited hTNFα induced apoptosis of the myelomonocytic leukemia cell line U937. Apoptosis was monitored by the Apo-ONE Homogenous Caspase-3/7 assay kit (Promega). The kit measures the activities of caspase-3 and -7. These are members of the cysteine aspartic acid-specific protease (caspase) family and play key effector roles in apoptosis in mammalian cells. The kit consists of a buffer and substrate that is combined on the day of use. The buffer rapidly and efficiently lyses cultured cells and supports optimal caspase-3/7 enzymatic activity. A non-fluorescent substrate Z-DEVD-R110 (rhodamine 110) is cleaved by caspase-3/7, removing the DEVD peptide to create a fluorescent rhodamine 110.

The U937 cells are cultured in phenol red free RPMI 1640 containing 10% heat inactivated foetal bovine serum (FBS). They are sub-cultured at least 7 hours before use to synchronize the cells and reduce variability. Recombinant human TNFα is preincubated for 3 hours at room temperature with the diluted inhibitors in the wells of a 96-welled plate (total volume of 25 μl). Then 25 μl of U937 cells [cell number 2×104] are added to the wells, and 25 μl media to the media only well, giving a total volume of 50 μl in all wells and incubate for 16 hours at 37° C. Prepared Apo-ONE substrate (diluted ¹⁄₂₅₀) in buffer provided in the Apo-ONE kit. Add 50 μl Apo-ONE substrate in buffer to all wells, mix and incubate for 30 min at room temperature. Read fluorescence signal on EnSpire multimode plate reader at 485/535 nm. The media only signal is subtracted before any further calculations are performed. Data are presented as % inhibition of apoptosis.

Figure 6:
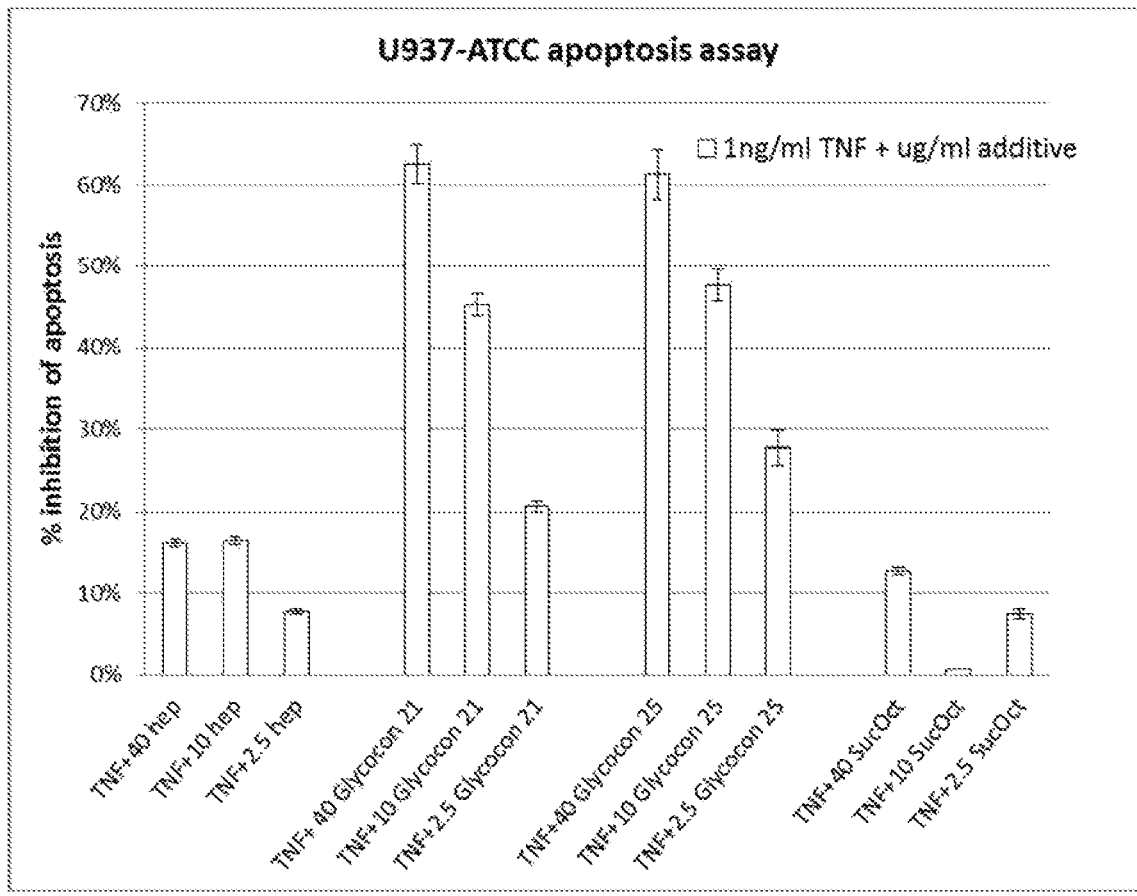
FIG. 6 is a graphical representation showing a U937 cell apoptosis TNF-α bioassay. The TNF-α is used at 1 ng/ml throughout and the inhibitors: heparin, two of the sulphated glycoconjugates and sucrose octasulfate were used at either 40, 10 or 2.5 μg/ml. Average and standard error are shown of 4 replicates.

The two simplified sulphated glycoconjugates tested were consistently superior to heparin and to the specificity control of sucrose octasulfate (FIG. 6). In this assay both sulphated glycoconjugates were equally effective in inhibiting TNF-α apoptosis of U937 cells.

Example 31

Functional Analyses of Simplified Sulphated Glycoconjugates on Chemokines Implicated in Inflammation Associated with COPD Chemokines known to play an important role in mediating the inflammation associated with COPD include IL-8, MCP-1 and MIP-1α (Barnes (2004) supra). Various simplified sulphated glycoconjugates were shown to block cell migration triggered by IL-8. These experiments were performed using DMSO treated human promyelocytic HL-60 cells. These cells were derived from a patient with acute promyelocytic leukemia. The cells were treated with DMSO (1.2% w/v) for 4 days before being used in the experiments. The chemotaxis assays were performed in 96-well Costar chemotaxis plates consisting of a bottom chamber to which was added the human IL-8 (+/−inhibitor) and then cells in RPMI and 1% v/v FCS were added to a top chamber and the plate was incubated at 37° C. for 1 hour to allow cells to move from the top chamber into the bottom. The number of cells migrating into the bottom chamber was quantified by labeling with CellTiter 96 AQueous One reagent for 1.75 hours and then absorbance was read at 490 nm on an Enspire Multimode plate reader (PerkinElmer).

To examine whether the various glycoconjugates were effective inhibitors of the chemokine MCP-1 the human monocytic cell line THP-1 was used. These cells were originally derived from the peripheral blood of a patient with acute monocytic leukaemia. The assay was very similar to that described above, except that the cells were placed in 1% foetal calf serum for 20 hour prior to the assay commencing. The chemotaxis assays were performed in 96-well Costar chemotaxis plates and human MCP-1 (+/−inhibitor) was added to the bottom chamber and the THP-1 cells in RPMI/1% FCS were added to the top chamber and the plate was incubated at 37° C. for 2.5 hour to allow cells to move from the top chamber into the bottom. The number of cells migrating into the bottom chamber was quantified by labelling with CellTiter 96 AQueous One reagent for 1.75 hours and then absorbance was read at 490 nm on an Enspire Multimode plate reader (PerkinElmer).

Example 32

Functional Analyses of Simplified Sulfated Glycoconjugates on Cell Proliferation Target IL-2

The murine cytotoxic T lymphocytic line (CTLL) is a subclone of T cells derived from a C57bl/6 mouse. These cells require interleukin-2 (IL-2) for growth and are used to assay for its presence in conditioned media. The cells are responsive to both murine and human IL-2. CTLL cells have been transfected with the firefly luciferase gene contained in the expression vector, pPGK-puromycin-luciferase (Coombe et al. (1998) supra). The positive transfectants are cloned to produce a line with good luciferase expression and these cells are called CTL-Luc. The proliferation assays are carried out in 96-well microplates suitable for such assays (Falcon). The wells are flat bottomed, with white sides and a clear bottom. Cells are washed to remove any cytokine in the growth medium and then resuspended in RPMI/5% w/v FCS. The cells are counted with a Coulter Z2 Particle Counter and Size Analyzer (Coulter Electronics, England) and routinely $1.6 \times 10^4$ cells are added to microplate wells that contain either no recombinant human IL-2 (rhIL-2) (negative control) or various dilutions of rhIL-2. When the effect of glycoconjugates, or other sulfated polysaccharides is to be measured, the wells also contain various concentrations of these molecules.

The CTL-Luc cells proliferate for 24 hours at 37° C. in a humidified atmosphere, after which the luciferase activity is measured by the addition of 50 μL of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on an Enspire Multimode plate reader (PerkinElmer).

Figure 7:
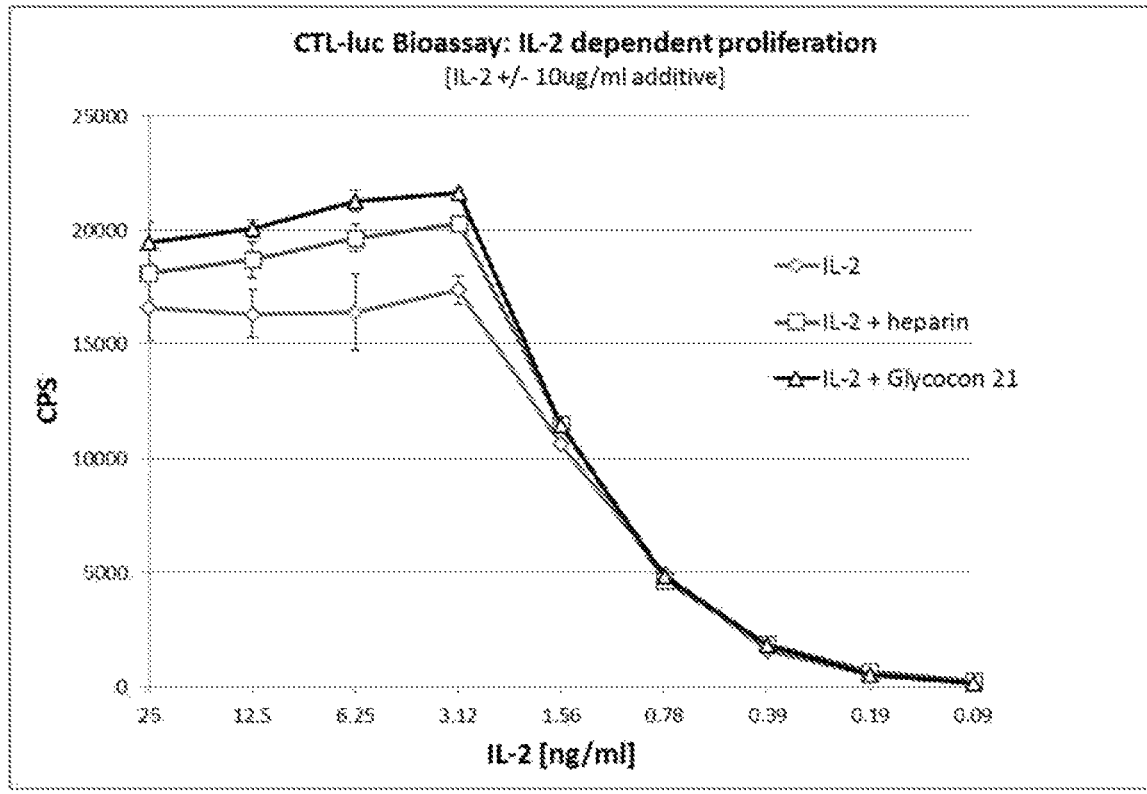
FIG. 7 is a graphical representation showing a CTL-luc bioassay with recombinant human IL-2. IL-2 is titrated from 25 ng/ml-0.09 ng/ml and the inhibitors: heparin, sulphated glycoconjugate: 21 are held at 10 sg/ml. The IL-2 dependent cell proliferation is shown as luminescence counts/second.

The results of these experiments with the IL-2 responsive cell lines indicate that the sulphated glycoconjugate tested does not affect the proliferative activity of IL-2 (FIG. 7). The results of these experiments also suggest that the sulphated glycoconjugate tested is not toxic to cytokine dependent lymphocytic cell lines. This example shows that while the tested glycoconjugates of the present invention may bind to a cytokine, not all cytokines are inhibited in their activity. The sulphated glycoconjugates are therefore specific for certain cytokines.

Example 33

Functional Analyses of the Binding of the Simplified Sulfated Glycoconjugates to IL-4, as Measured in a BIAcore Assay The optical phenomenon of surface plasmon resonance is used to monitor physical interactions between molecules. Passing a solution of a potential protein ligand (e.g. IL-4, IL-5, or MCP-1) over a sensor surface to which a target (e.g. heparin) is coupled monitors the real-time binding of protein ligands to the immobilized target. Detection is achieved by measuring refractive index changes very close to the sensor surface. When the refractive index is altered, the angle at which plasmon resonance occurs changes and this change directly correlates with the amount of protein interacting with the surface. A BIAcore T200 is conveniently used. It is very sensitive and its microfluidics ensures that only small amounts of material are required.

The optical phenomenon of surface plasmon resonance is used to monitor physical interactions between molecules. Passing a solution of a potential protein ligand (e.g. IL-4, IL-5, or MCP-1) over a sensor surface to which a target (e.g. heparin) is coupled monitors the real-time binding of protein ligands to the immobilized target. Detection is achieved by measuring refractive index changes very close to the sensor surface. When the refractive index is altered, the angle at which plasmon resonance occurs changes and this change directly correlates with the amount of protein interacting with the surface. A BIAcore T200 is conveniently used. It is very sensitive and its microfluidics ensures that only small amounts of material are required.

Biotinylated heparin is immobilized on the biosensor chip. Biotinylation occurs via amino groups, or reducing termini modified with ammonia by reductive amination, using sulfo-NHS-biotin. Solutions containing potential protein ligands of interest are injected over the sensor chip surface, and the binding is measured in real time (Femig (2001) supra). Baculovirus expressed recombinant human IL-4 (rhIL-4) readily bind to heparin immobilized by this method (see PCT/AU2005/000551). Binding is specific, as there is little interaction of IL-4 with sensor chips that lack heparin.

Figure 11:
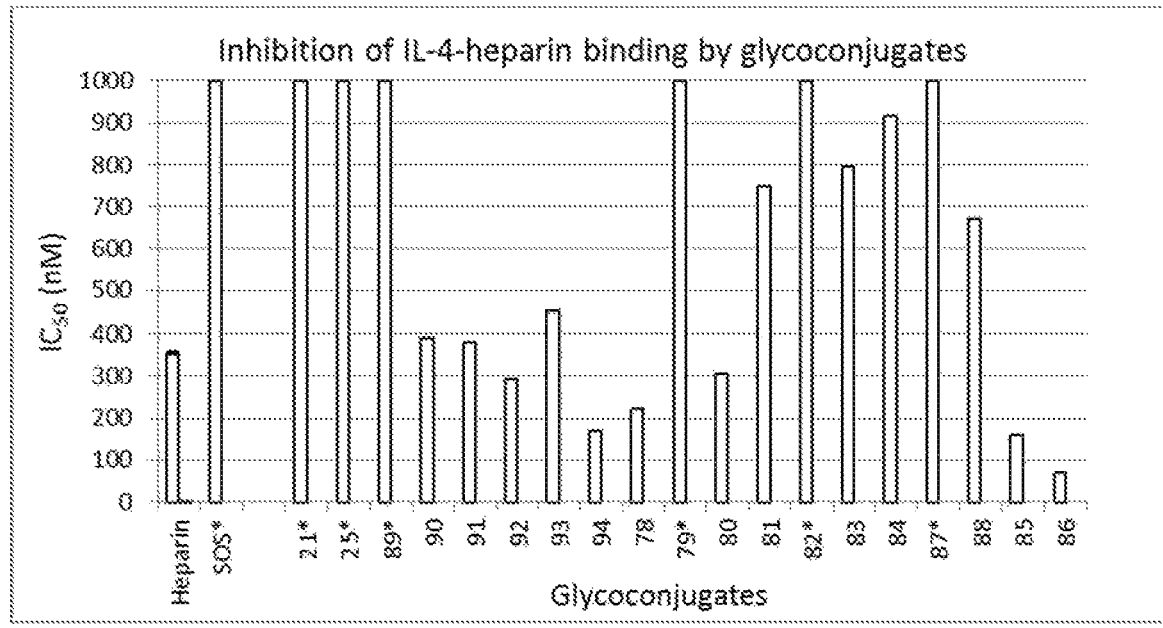
FIG. 11 is a graphical representation showing BIAcore data of the $IC_{50}$ concentration required for the various glycoconjugates to inhibit by 50% the binding of 100 nM of recombinant human IL-4 to heparin immobilized on a BIAcore biosensor chip. The inhibitors were heparin, sucrose octasulfate and the glycoconjugates 21, 25, 78-94.

Preparations of the various anionic oligosaccharide conjugates of sulfated oligosaccharides inhibit the binding of IL-4 to heparin immobilized on the BIAcore chip surface. It is clear from the data shown in FIG. 11 of the concentrations of the different glycoconjugates required to inhibit 100 nM IL-4 binding by 50% ($IC_{50}$), that some glycoconjugates were more effective in this regard than others.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Adcock and Ito (2005) *Proc. Am. Thorac. Soc.* 2:313-319
Ballantyne (2007) *J. Allergy Clin. Immunol.* 120:1324-1331

Barnes (2004) *Pharmacol. Rev.* 56:515-548
Boyle et al. (2014) *Expert. Opin. Biol. Ther.*, 14:969-981
Caramori et al. (2014) *Internat. J. COPD* 9:397-412
Cardona (2010) *Archiv Immunol Et Therap Experimental.* 58:7-14
Cepkova and Matthay (2006) *J. Intensive Care Med.*, 21:119-143
Conrad (1998) Heparin binding proteins. Academic Press, San Diego
Coombe et al. (1998) *Journal of Immunological Methods* 215:145-150
El-Shanawany et al. (2008) *Clin. Exp. Immunol.* 153:1-9
Fernig (2001) In: Proteoglycan protocols, Ed. R. V. Iozzo, Humana Press, Totowa, NJ, USA
Gelfand (2004) *J. Allergy Clin. Immunol,* 114:513S-138
Greene and Wuts (1991) "Protective Groups in Organic Synthesis" 2nd Ed., John Wiley and Sons, N.Y
Golden (2007) *Curr. Opin. Allergy Clin. Immunol.,* 7:331-336
Han and Mallampalli (2015) *J. Immunol.* 194:855-860
Lander and Selleck (2000) *J. Cell Biol.* 148(2):227-232
Lloyd (2015) *Curr Opin Immunol.* 34:52-58
Mabey and Honsawek (2015) *World J Orthop.* 6:95-105
MacLaren and Stringer (2007) *Pharmacotherapy.* 27:860-873
MacNee (2005) *Proc. Am. Thorac. Soc.* 2:258-266
Martinez-Gonalez et al. (2015) *Trends Immunol.* 36:189-195
Marzo et al. (2014) *Tuberculosis* 94:55-64
Matsushita et al. (2015) *Allergol. Internat.* 64:235e240
Nabe (2014) *J. Pharmacol. Sci.* 126:85-91
Nasi et al. (2015) *Ann Rheum Dis* doi:10.1136/annrheumdis-2015-207487
Nouailles et al. (2014) *J. Clin. Invest.* 124:1268-1282
Ogamo et al. (1989) *Carbohydr. Res.* 193:165-172
Ogawa and Grant (2007) *Immunol. Allergy Clin. N. Am.,* 27:249-260
Passalacqua et al. (2004) *Curr. Opin. Allergy Clin. Immunol.* 4:177-183
Peavy and Metcalfe (2008) *Curr. Opin. Allergy Clin. Immunol.,* 8:310-314
Pethe et al. (2001) *Nature* 412:190-4
Remington's Pharmaceutical Sciences (1990) 18th Ed., Mack Publishing, Company
Shen et al. (2011) *Expert. Opin. Biol. Ther.* 5:107-114
Simons (2008) *J. Allergy Clin. Immunol.* 121:S402-7
Solleiro-Villavicencio et al. (2015) *Clin Immunol.* doi: 10.1016/j.clim.2015.07.009
Sutherland and Martin (2003) *J Allergy Clin. Immunol.* 112:819-27
Wildhagen et al. (2014) *Blood* 123:1098-1101
Wojdasiewicz (2014) *Mediators Inflamm.* 561459 doi: 10.1155/2014/561459
Wygrecka et al. (2008) *Thromb. Haemost.* 99:494-501
Yoshimoto (2014) *Allergol. Internat.* 63 Suppl 1:3-11

The invention claimed is:
1. A compound selected from the group consisting of:

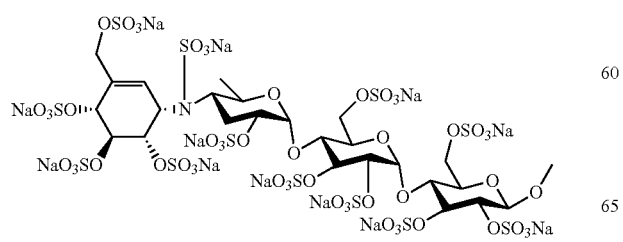

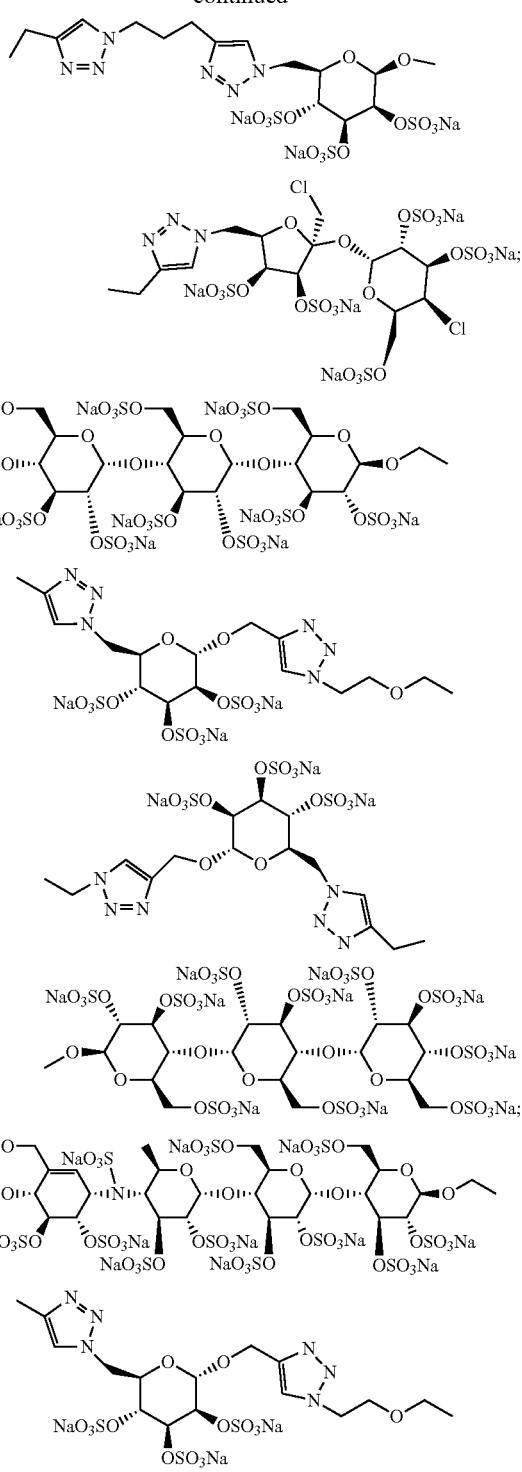

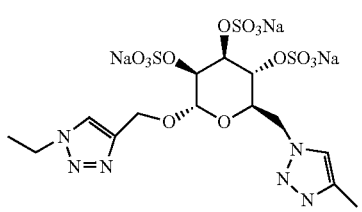

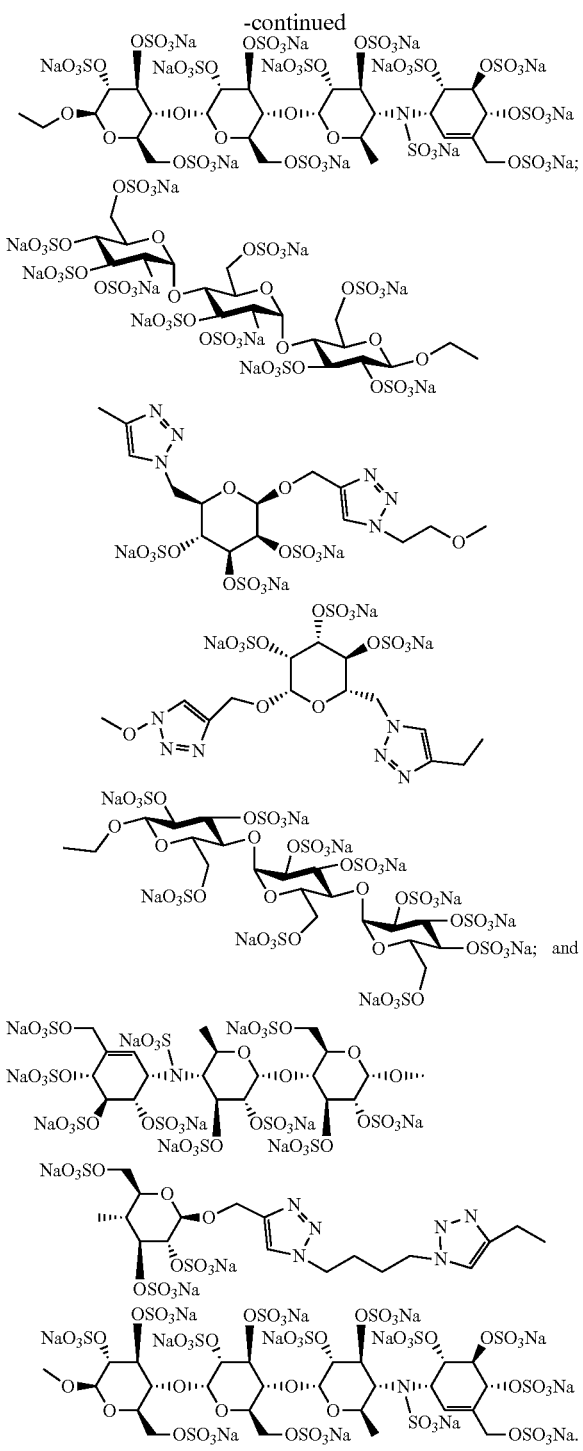

2. A process for the preparation of a compound according to claim 1, comprising:
  i) providing a divalent linker; and
  ii) conjugating at least two equivalents of a capping sugar via the divalent linker;
  to form the compound.

3. A process for the preparation of a compound according to claim 1, comprising:
  (i) providing a divalent linker;
  (ii) conjugating at least two equivalents of a connecting sugar via the divalent linker to form a conjugate intermediate; and
  (iii) conjugating with at least two equivalents of a capping sugar via the conjugate intermediate;
  to form the compound.

4. The process according to claim 3, wherein at least 2 or more additional equivalents of a connecting sugar are conjugated with the conjugate intermediate of step (ii) prior to step (iii).

5. A process for the preparation of a compound according to claim 1, comprising:
  (i) providing a capping sugar;
  (ii) conjugating the capping sugar with a connecting sugar to form a conjugate intermediate; and
  (iii) conjugating with at least two equivalents of the conjugate intermediate via a divalent linker;
  to form the compound.

6. The process according to claim 5, wherein at least 2 or more additional equivalents of a connecting sugar are conjugated with the conjugate intermediate of step (ii) prior to step (iii),
  to form the compound.

7. A method of treating an inflammatory disease comprising administering to a person in need thereof a therapeutically effective amount of a compound according to claim 1.

8. The method according to claim 7, wherein the inflammatory disease is selected from the group consisting of asthma, allergic respiratory disease, allergic rhinitis, subepithelial fibrosis in airway hyperresponsiveness, chronic sinusitis, perennial allergic rhinitis, allergic bronchopulmonary aspergillosis in cystic fibrosis patients, COPD, eosinophilic bronchitis, bronchiectasis, bronchospasm, bronchial constriction, bronchial hyperreactivity, and bronchial hypertrophy.

9. The method according to claim 7, wherein the inflammatory disease is asthma.

10. The method according to claim 7, wherein the inflammatory disease is allergic respiratory disease.

11. The method according to claim 7, wherein the inflammatory disease is allergic rhinitis.

12. The method according to claim 7, wherein the inflammatory disease is perennial allergic rhinitis.

13. The method according to claim 7, wherein the inflammatory disease is chronic sinusitis.

* * * * *

UNITED STATES PATENT AND TRADEMARK OFFICE
CERTIFICATE OF CORRECTION

PATENT NO. : 11,903,958 B2  
APPLICATION NO. : 16/341777  
DATED : February 20, 2024  
INVENTOR(S) : Alan David Payne et al.

Page 1 of 8

It is certified that error appears in the above-identified patent and that said Letters Patent is hereby corrected as shown below:

In the Claims

Columns 163, Line 58 through Column 164, Line 15:

"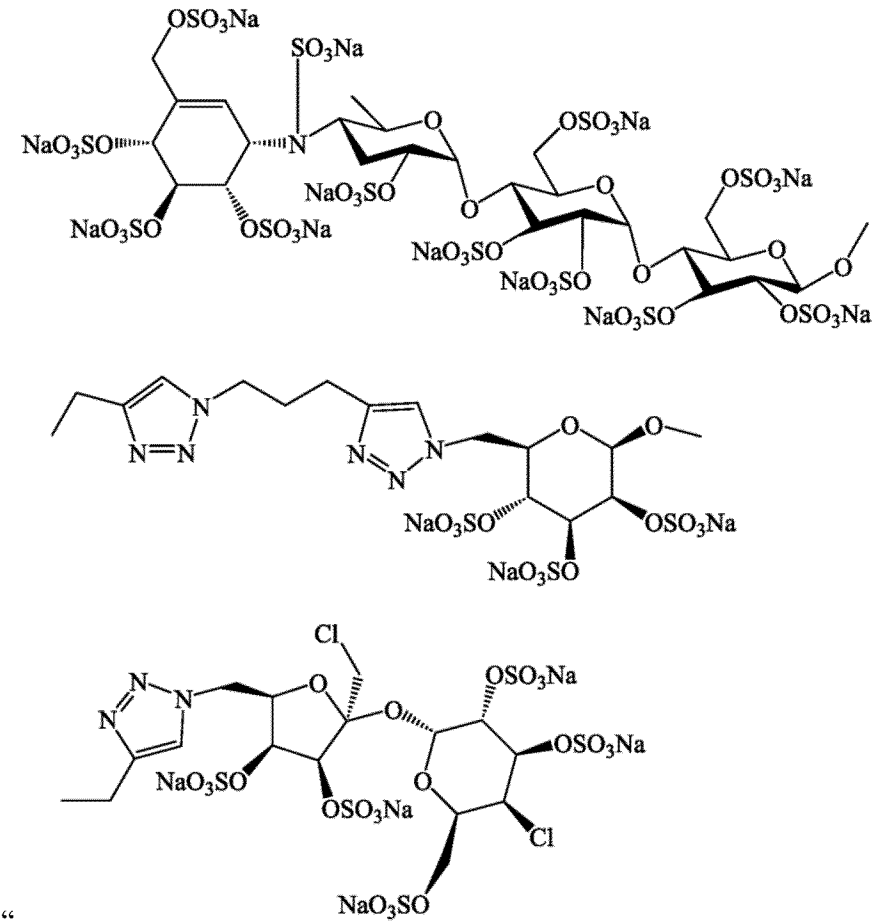"

Signed and Sealed this  
Twenty-ninth Day of July, 2025

Coke Morgan Stewart  
*Acting Director of the United States Patent and Trademark Office*

CERTIFICATE OF CORRECTION (continued)
U.S. Pat. No. 11,903,958 B2

Should read:

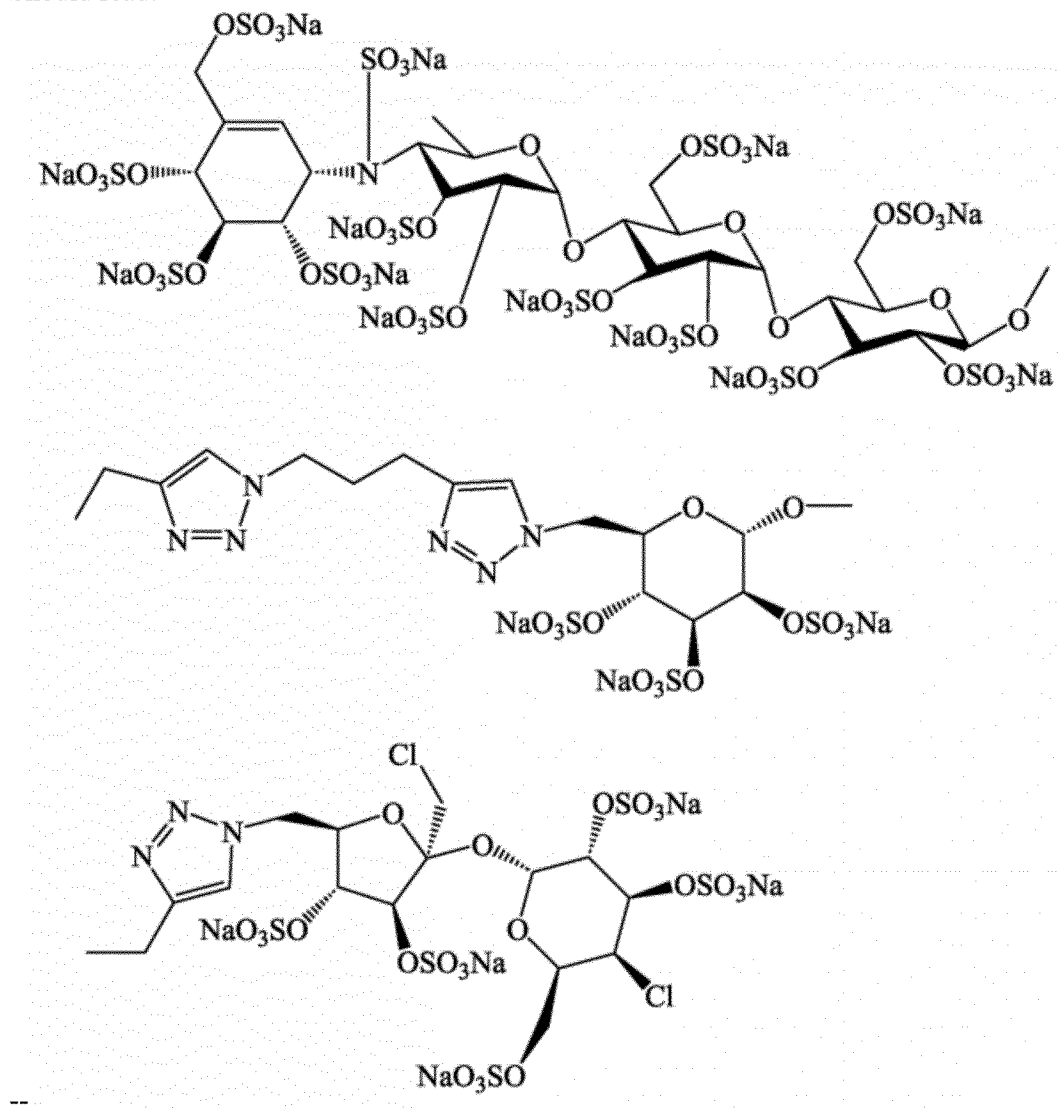

-- --.

CERTIFICATE OF CORRECTION (continued)
U.S. Pat. No. 11,903,958 B2

Column 164, Claim 1, Lines 16-43:

"

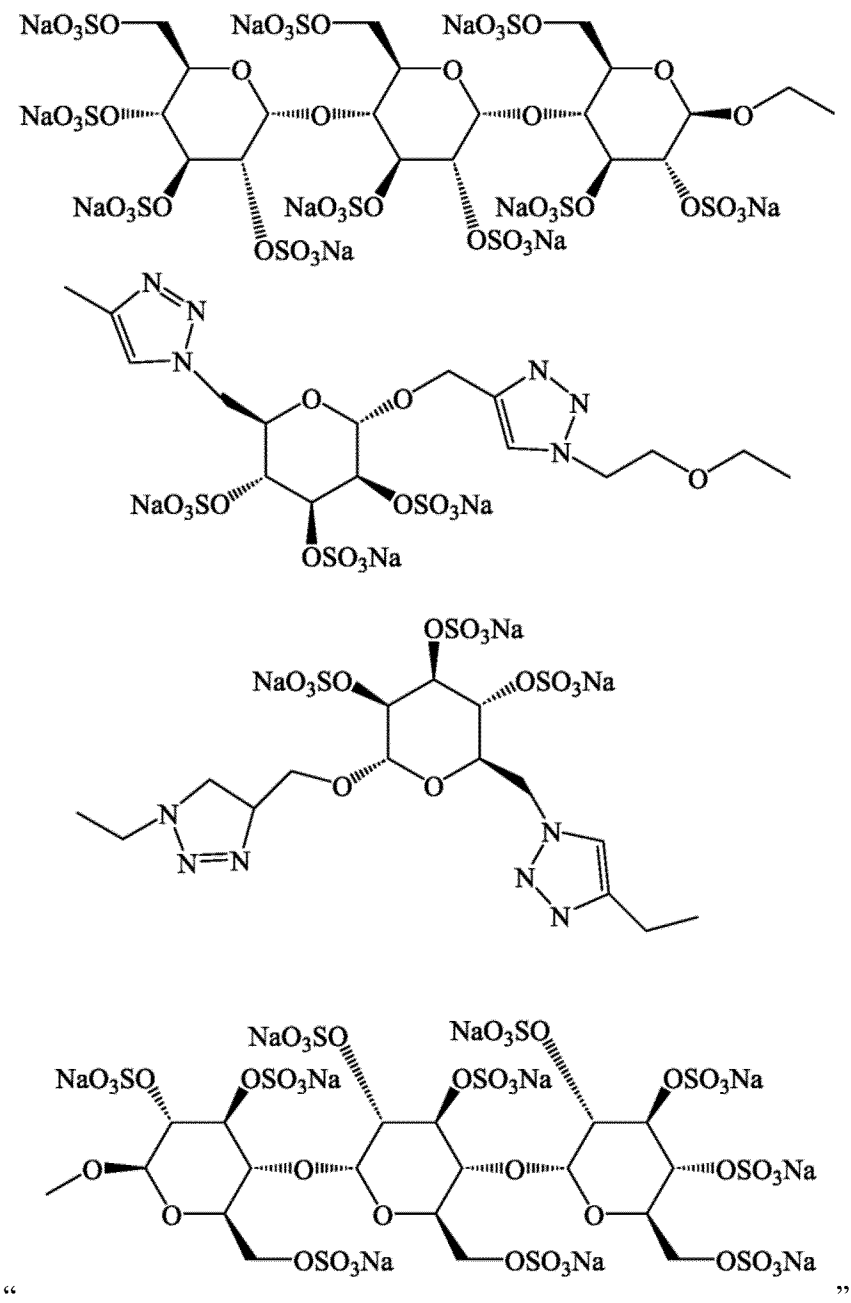

"

CERTIFICATE OF CORRECTION (continued)
U.S. Pat. No. 11,903,958 B2

Should read:

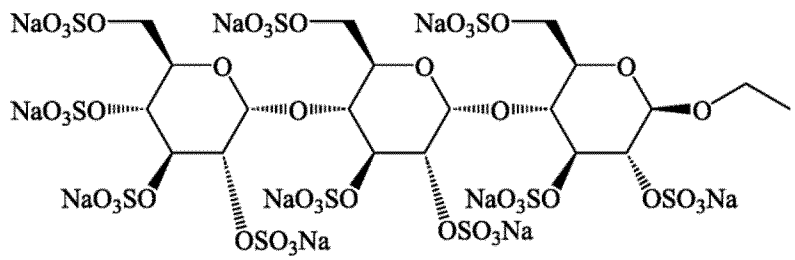

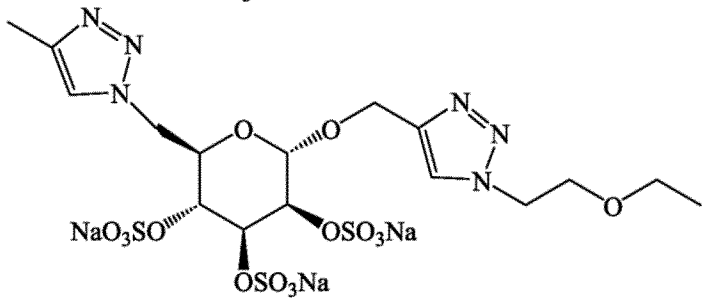

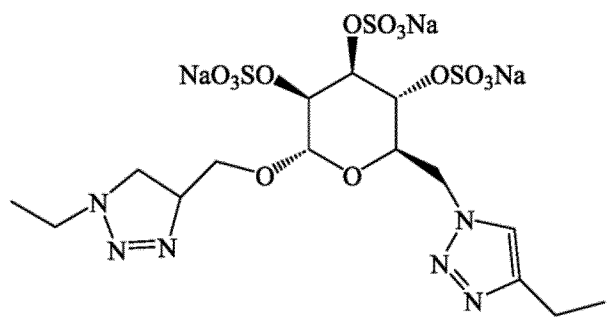

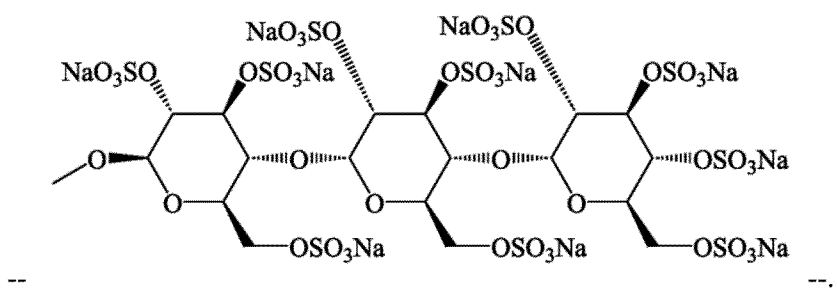

-- --.

Column 164, Claim 1, Lines 44 through Column 165, Lines 6:

CERTIFICATE OF CORRECTION (continued)
U.S. Pat. No. 11,903,958 B2

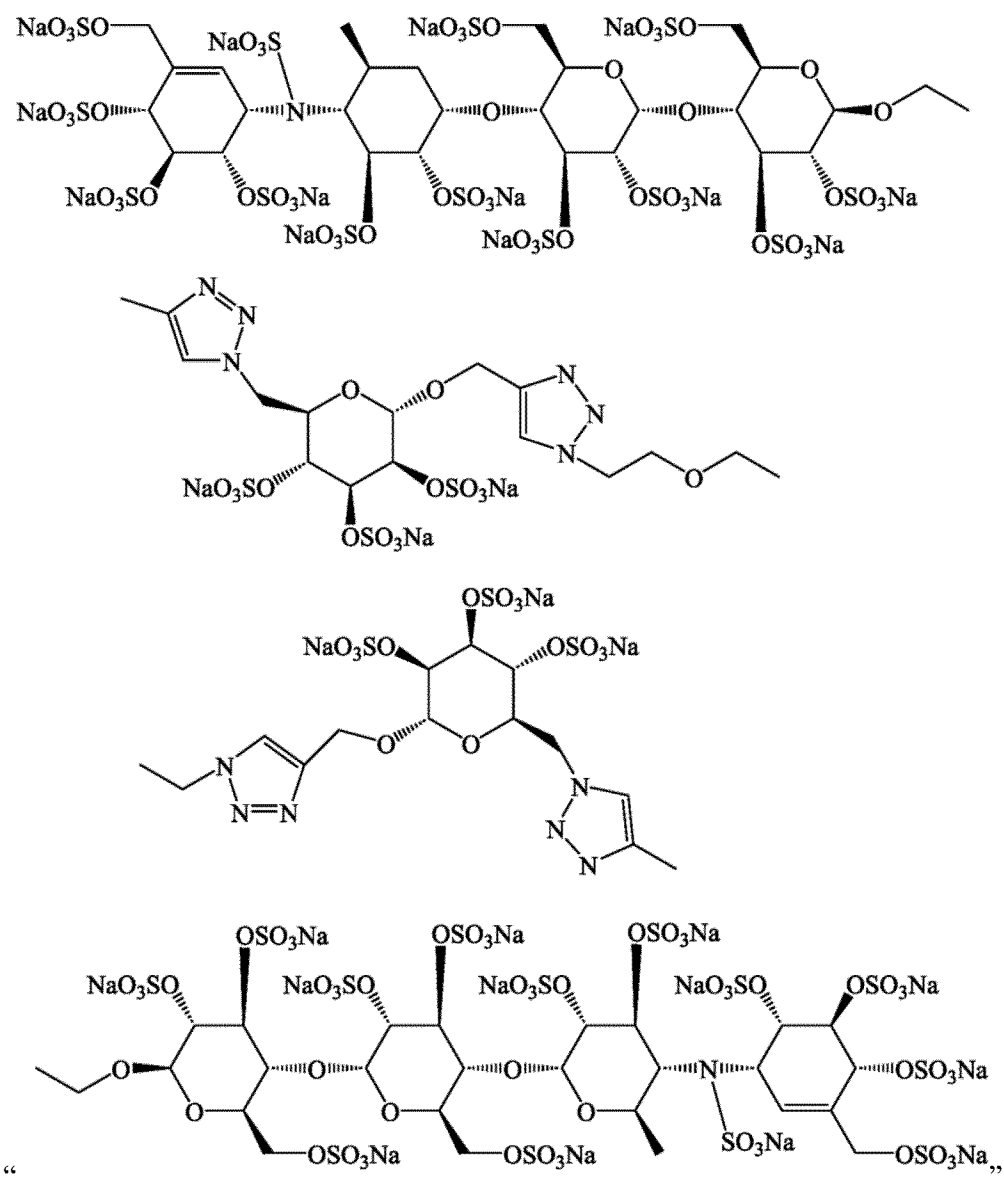

"

Should read:

CERTIFICATE OF CORRECTION (continued)
U.S. Pat. No. 11,903,958 B2

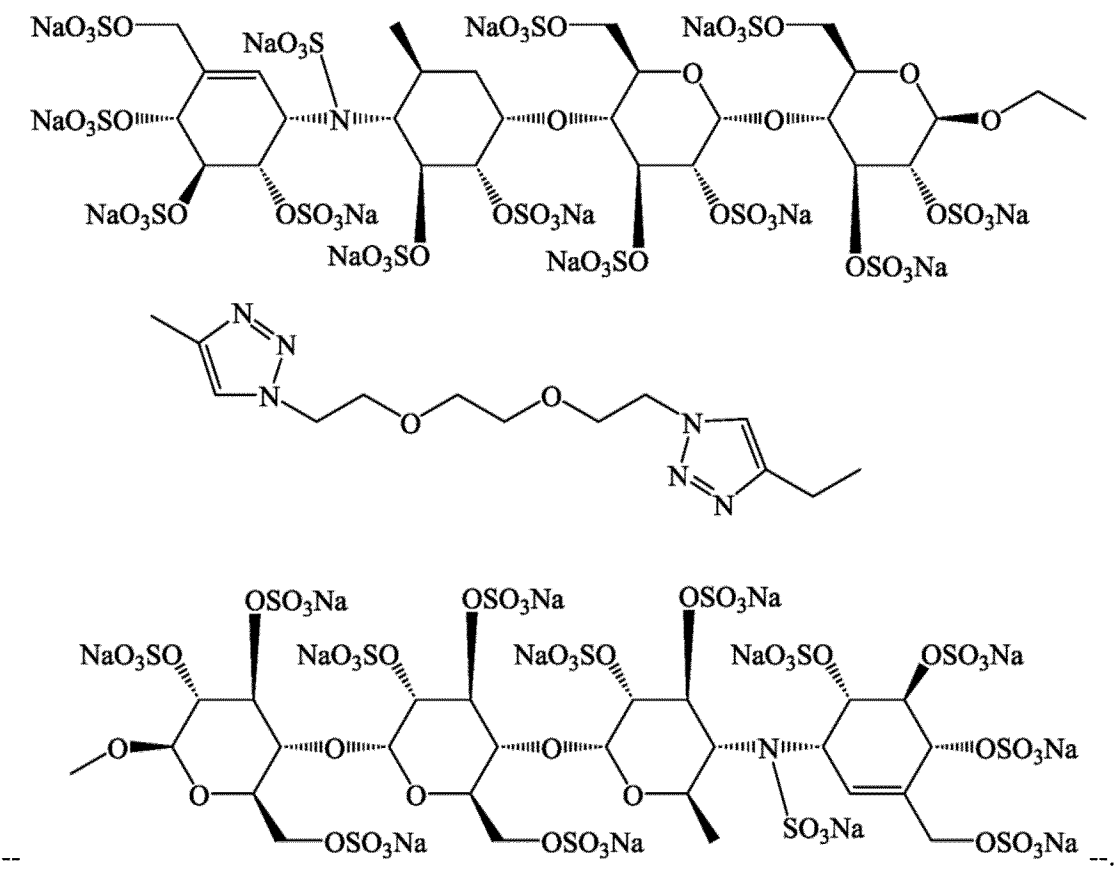

Column 165, Claim 1, Lines 7-38:

CERTIFICATE OF CORRECTION (continued)
U.S. Pat. No. 11,903,958 B2

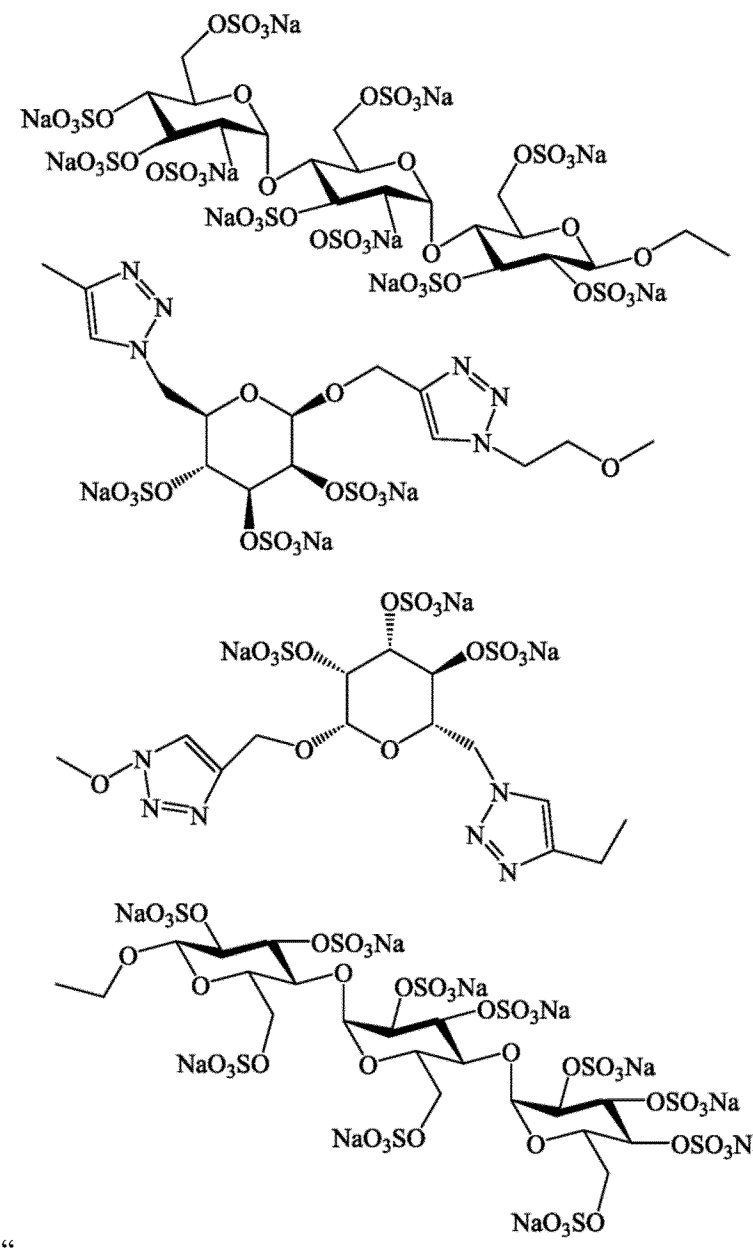

"                                                         "

Should read:

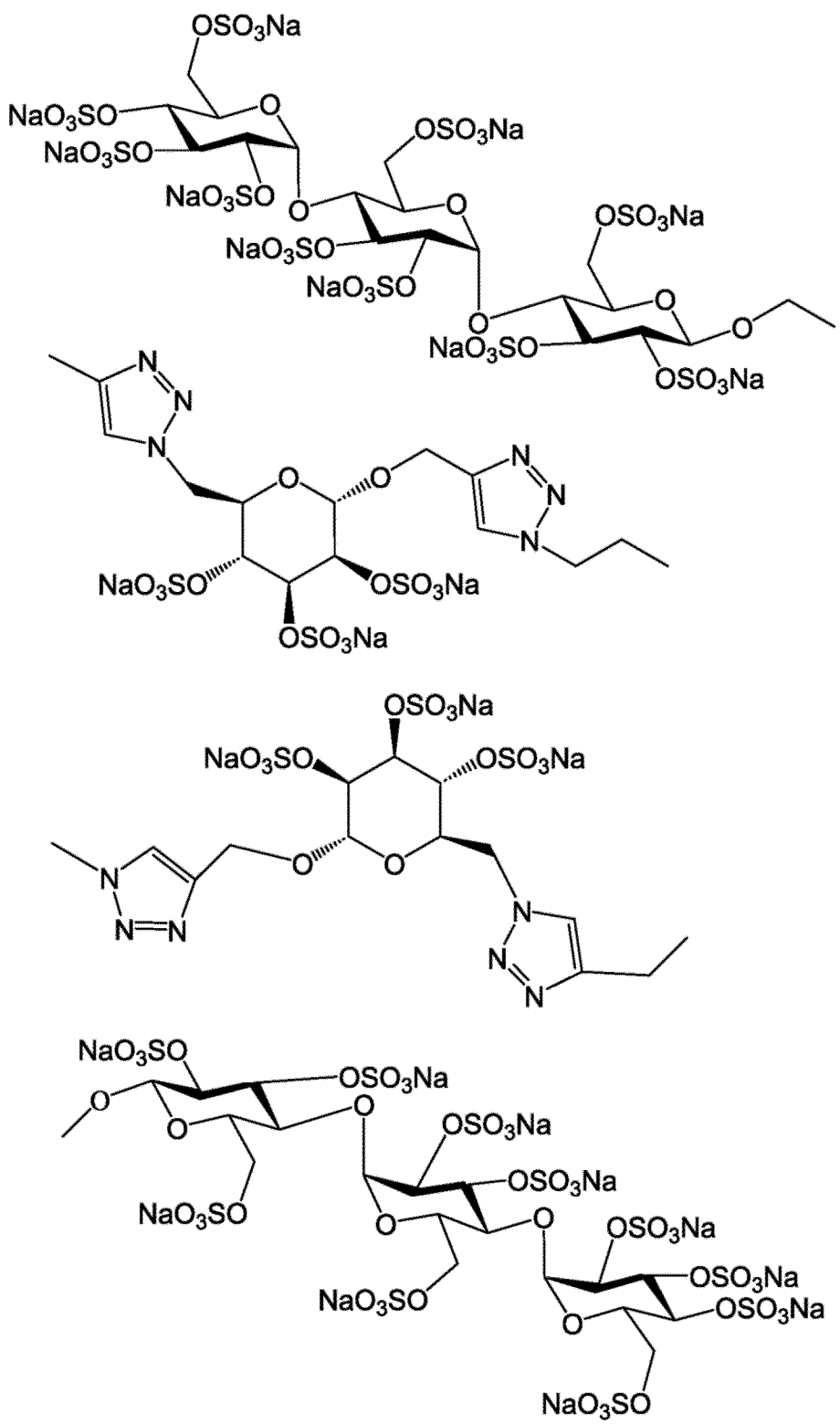
--                                                                    --.